(12) United States Patent
Frank et al.

(10) Patent No.: US 11,903,680 B2
(45) Date of Patent: Feb. 20, 2024

(54) WEARABLE-BASED HEALTH STATE VERIFICATION FOR PHYSICAL ACCESS AUTHORIZATION

(71) Applicant: Facense Ltd., Kiryat Tivon (IL)

(72) Inventors: Ari M Frank, Haifa (IL); Arie Tzvieli, Berkeley, CA (US); Ori Tzvieli, Berkeley, CA (US); Gil Thieberger, Kiryat Tivon (IL)

(73) Assignee: Facense Ltd., Kiryat Tivon (IL)

( * ) Notice: Subject to any disclaimer, the term of this patent is extended or adjusted under 35 U.S.C. 154(b) by 415 days.

(21) Appl. No.: 17/319,634

(22) Filed: May 13, 2021

(65) Prior Publication Data

US 2021/0275034 A1   Sep. 9, 2021

Related U.S. Application Data

(63) Continuation-in-part of application No. 16/689,929, filed on Nov. 20, 2019, now Pat. No. 11,064,892, (Continued)

(51) Int. Cl.
*A61B 5/01*      (2006.01)
*A61B 5/16*      (2006.01)
(Continued)

(52) U.S. Cl.
CPC ............ *A61B 5/015* (2013.01); *A61B 5/0075* (2013.01); *A61B 5/165* (2013.01); *A61B 5/6803* (2013.01);
(Continued)

(58) Field of Classification Search
CPC .... A61B 2562/0271; A61B 2562/0276; A61B 2576/00; A61B 5/0075; A61B 5/0077;
(Continued)

(56) References Cited

U.S. PATENT DOCUMENTS 7,031,483 B2   4/2006   Boone et al.
7,447,333 B1   11/2008  Masticola et al.
(Continued)

FOREIGN PATENT DOCUMENTS

EP    3238612 A1    11/2017
EP    3375362       9/2018
WO    WO2011005224  1/2011

OTHER PUBLICATIONS

Nima Karimian, "Evolving Authentication Design Considerations for the Internet of Biometric Things (IoBT)," Oct. 1-7, 2016, CODES/ISSS '16, Oct. 1-7, 2016, Pittsburgh, PA, USA, pp. 1-8.*
(Continued)

*Primary Examiner* — Omar S Ismail
(74) *Attorney, Agent, or Firm* — Active Knowledge Ltd.

(57) ABSTRACT

Embodiments disclosed herein involve a wearable-based system that can help determine in a privacy-preserving manner whether a user is healthy (and thus poses low risk of contagiousness), and use determinations of this nature to grant passage through a doorway. In one embodiment, a wearable device takes measurements of a user comprising a photoplethysmogram signal (PPG signal) and a temperature measurement. A computer calculates a health score based on a difference between baseline measurements of the user, measured one or more days earlier, and more current measurements of the user. Additionally, the computer calculates an extent of similarity between characteristics of the PPG signal in the current measurements and characteristics of the PPG signal in the baseline measurements. The computer authorizes the user's passage through the doorway responsive to the health score reaching a first threshold and the extent of the similarity reaching a second threshold.

20 Claims, 36 Drawing Sheets

Related U.S. Application Data which is a continuation-in-part of application No. 16/551,654, filed on Aug. 26, 2019, now Pat. No. 10,638,938, which is a continuation-in-part of application No. 16/453,993, filed on Jun. 26, 2019, now Pat. No. 10,667,697, which is a continuation-in-part of application No. 16/375,841, filed on Apr. 4, 2019, now Pat. No. 10,376,153, which is a continuation-in-part of application No. 16/156,493, filed on Oct. 10, 2018, now Pat. No. 10,524,667, said application No. 16/689,929 is a continuation-in-part of application No. 16/156,586, filed on Oct. 10, 2018, said application No. 16/453,993 is a continuation of application No. 62/722,655, filed on Aug. 24, 2018, and a continuation-in-part of application No. 15/859,772, filed on Jan. 2, 2018, now Pat. No. 10,159,411, which is a continuation-in-part of application No. 15/832,855, filed on Dec. 6, 2017, now Pat. No. 10,130,308, which is a continuation-in-part of application No. 16/147,695, filed on Sep. 29, 2018, said application No. 16/156,493 is a continuation-in-part of application No. 15/833,115, filed on Dec. 6, 2017, now Pat. No. 10,130,261, said application No. 15/832,815 is a continuation of application No. 62/456,105, filed on Feb. 7, 2017, which is a continuation-in-part of application No. 15/722,434, filed on Oct. 2, 2017, now Pat. No. 10,523,852, said application No. 15/833,115 is a continuation-in-part of application No. 15/635,178, filed on Jun. 27, 2017, now Pat. No. 10,136,856, which is a continuation-in-part of application No. 15/284,528, filed on Oct. 3, 2016, which is a continuation-in-part of application No. 15/284,528, filed on Oct. 3, 2016, now Pat. No. 10,113,913, which is a continuation-in-part of application No. 15/231,276, filed on Aug. 8, 2016, said application No. 16/156,493 is a continuation-in-part of application No. 15/635,178, filed on Jun. 27, 2017, now Pat. No. 10,136,856, which is a continuation-in-part of application No. 15/182,592, filed on Jun. 14, 2016, now Pat. No. 10,165,949, which is a continuation-in-part of application No. 15/231,276, filed on Aug. 8, 2016, which is a continuation of application No. 15/182,566, filed on Jun. 14, 2016, now Pat. No. 9,867,546.

(60) Provisional application No. 63/140,453, filed on Jan. 22, 2021, provisional application No. 63/122,961, filed on Dec. 9, 2020, provisional application No. 63/113,846, filed on Nov. 14, 2020, provisional application No. 63/048,638, filed on Jul. 6, 2020, provisional application No. 63/024,471, filed on May 13, 2020, provisional application No. 62/928,726, filed on Oct. 31, 2019, provisional application No. 62/874,430, filed on Jul. 15, 2019, provisional application No. 62/667,453, filed on May 5, 2018, provisional application No. 62/652,348, filed on Apr. 4, 2018, provisional application No. 62/566,572, filed on Oct. 2, 2017, provisional application No. 62/480,496, filed on Apr. 2, 2017, provisional application No. 62/372,063, filed on Aug. 8, 2016, provisional application No. 62/354,833, filed on Jun. 27, 2016, provisional application No. 62/236,868, filed on Oct. 3, 2015, provisional application No. 62/202,808, filed on Aug. 8, 2015, provisional application No. 62/175,319, filed on Jun. 14, 2015.

(51) Int. Cl.
| | | |
|---|---|---|
| *G01J 5/12* | (2006.01) | |
| *G01J 5/02* | (2022.01) | |
| *G01J 5/48* | (2022.01) | |
| *A61B 5/00* | (2006.01) | |
| *G01J 5/00* | (2022.01) | |

(52) U.S. Cl.
CPC .......... *A61B 5/6814* (2013.01); *A61B 5/7282* (2013.01); *A61B 5/748* (2013.01); *G01J 5/0265* (2013.01); *G01J 5/12* (2013.01); *A61B 5/0077* (2013.01); *A61B 2562/0271* (2013.01); *A61B 2562/0276* (2013.01); *A61B 2576/00* (2013.01); *G01J 5/485* (2022.01); *G01J 2005/0077* (2013.01)

(58) Field of Classification Search
CPC ..... A61B 5/015; A61B 5/0205; A61B 5/1455; A61B 5/165; A61B 5/6803; A61B 5/6814; A61B 5/7282; A61B 5/748; G01J 2005/0077; G01J 5/0025; G01J 5/025; G01J 5/0265; G01J 5/07; G01J 5/12; G01J 5/20; G01J 5/34; G01J 5/485
See application file for complete search history.

(56) References Cited

U.S. PATENT DOCUMENTS

| | | | |
|---|---|---|---|
| 7,609,842 B2 | 10/2009 | Sipkema et al. | |
| 7,817,046 B2 | 10/2010 | Coveley et al. | |
| 8,225,380 B2 | 7/2012 | Moshir | |
| 8,392,152 B2 | 3/2013 | Rao | |
| 8,684,900 B2 | 4/2014 | Tran | |
| 9,075,909 B2 | 7/2015 | Almogy et al. | |
| 9,152,769 B2 | 10/2015 | Baudino et al. | |
| 9,349,235 B2 | 5/2016 | Agrafioti et al. | |
| 9,367,975 B2 | 6/2016 | Robertson et al. | |
| 9,396,643 B2 | 7/2016 | He et al. | |
| 9,460,263 B2 | 10/2016 | Holmes et al. | |
| 9,524,598 B2 | 12/2016 | Jang | |
| 9,558,336 B2 * | 1/2017 | Lee .................... | G06F 1/3231 |
| 9,563,998 B2 | 2/2017 | Hoyos et al. | |
| 9,646,261 B2 | 5/2017 | Agrafioti et al. | |
| 9,727,697 B1 | 8/2017 | Sundar et al. | |
| 9,762,581 B1 | 9/2017 | Wang et al. | |
| 9,811,648 B2 | 11/2017 | Choi et al. | |
| 9,905,107 B2 | 2/2018 | Chong et al. | |
| 9,946,942 B2 * | 4/2018 | Wang .................. | G06F 18/22 |
| 9,990,785 B2 | 6/2018 | God et al. | |
| 10,154,818 B2 | 12/2018 | Zhang et al. | |
| 10,178,969 B2 | 1/2019 | Negi | |
| 10,186,097 B2 | 1/2019 | Tehranchi et al. | |
| 10,475,260 B2 | 11/2019 | Yoo et al. | |
| 10,629,015 B1 | 4/2020 | Le Burge et al. | |
| 10,885,530 B2 | 1/2021 | Mercury et al. | |
| 2007/0222554 A1 | 9/2007 | Hart | |
| 2009/0203972 A1 * | 8/2009 | Heneghan ........... | A61B 5/0205 |
| | | | 600/301 |
| 2011/0112969 A1 | 5/2011 | Zaid | |
| 2015/0112606 A1 * | 4/2015 | He ..................... | A61B 5/02055 |
| | | | 702/19 |
| 2015/0126824 A1 | 5/2015 | LeBoeuf et al. | |
| 2015/0135310 A1 * | 5/2015 | Lee .................... | H04W 12/065 |
| | | | 726/20 |
| 2015/0164351 A1 * | 6/2015 | He ..................... | A61B 5/0285 |
| | | | 702/19 |
| 2015/0366518 A1 * | 12/2015 | Sampson ............ | A61B 5/7264 |
| | | | 600/509 |
| 2016/0058376 A1 * | 3/2016 | Baek .................. | A61B 5/0205 |
| | | | 340/870.07 |
| 2016/0081572 A1 * | 3/2016 | Hong ................. | A61B 5/14542 |
| | | | 600/301 |
| 2016/0140834 A1 | 5/2016 | Tran | |
| 2016/0224773 A1 | 8/2016 | Ramaci | |

(56) References Cited

U.S. PATENT DOCUMENTS

| | | | |
|---|---|---|---|
| 2017/0000359 A1 | 1/2017 | Kohli et al. | |
| 2017/0038848 A1 | 2/2017 | Yuen et al. | |
| 2017/0071551 A1* | 3/2017 | Jain | A61B 5/02416 |
| 2017/0103178 A1 | 4/2017 | Heinrich et al. | |
| 2017/0118640 A1* | 4/2017 | Lee | G06Q 20/40145 |
| 2017/0187710 A1 | 6/2017 | Outwater et al. | |
| 2017/0302641 A1 | 10/2017 | Ramatchandirane et al. | |
| 2017/0347895 A1* | 12/2017 | Wei | A61B 5/7207 |
| 2018/0049675 A1* | 2/2018 | Kerber | A61B 5/1112 |
| 2018/0054710 A1 | 2/2018 | Gum | |
| 2018/0078187 A1 | 3/2018 | Anwar et al. | |
| 2018/0103859 A1* | 4/2018 | Provenzano | A61B 5/681 |
| 2018/0192893 A1 | 7/2018 | Magi | |
| 2018/0247713 A1* | 8/2018 | Rothman | A61B 5/02055 |
| 2018/0276672 A1 | 9/2018 | Breed et al. | |
| 2018/0317846 A1 | 11/2018 | Moyerman et al. | |
| 2018/0325385 A1* | 11/2018 | Deterding | A61B 5/14551 |
| 2019/0029563 A1 | 1/2019 | Sels et al. | |
| 2019/0209022 A1* | 7/2019 | Sobol | A61B 5/0022 |
| 2019/0246902 A1 | 8/2019 | Chang et al. | |
| 2019/0251238 A1* | 8/2019 | Venkatraman | G06Q 20/40145 |
| 2020/0185100 A1* | 6/2020 | Francois | G06Q 10/0631 |
| 2020/0281518 A1 | 9/2020 | Salorinne | |
| 2020/0302452 A1 | 9/2020 | Platt et al. | |
| 2020/0327755 A1 | 10/2020 | Burris et al. | |
| 2021/0012871 A1 | 1/2021 | Hagen et al. | |

OTHER PUBLICATIONS

A.Anbarasi, "Design and Implementation of Smart Home Using Sensor Network," Jan. 27, 2017, Proceedings of International Conference on Optical Imaging Sensor and Security, Coimbatore, Tamil Nadu, India, Jul. 2-3, 2013, pp. 1-5.*

Numan Celik, "Evaluation of a Behind-the-Ear ECG Device for Smartphone based Integrated Multiple Smart Sensor System in Health Applications,", 2016, International Journal of Advanced Computer Science and Applications (IJACSA), 7(7): (2016), pp. 1-6.*

H. Harry Asada, "Mobile Monitoring with Wearable Photoplethysmographic Biosensors," Jul. 22, 2003,IEEE Engineering in Medicine and Biology Magazine, May/Jun. 2013, pp. 28-37.*

Melanie Swan, "Sensor Mania! The Internet of Things, Wearable Computing, Objective Metrics, and the Quantified Self 2.0," Nov. 8, 2012, J. Sens. Actuator Netw. 2012, 1, 217-253; doi:10.3390/jsan1030217,pp. 217-233.*

Dimitrios I. Fotiadis, "Wearable Medical Devices," Apr. 14, 2006,Wiley Encyclopedia of Biomedical Engineering, pp. 3816-3026.*

Thieberger, Gil. Facense smartglasses for early detection of COVID-19 disease, Apr. 8, 2020 [online], [retrieved on Aug. 15, 2021]. Retrieved from <https://www.linkedin.com/pulse/facense-smartglasses-early-detection-covid-19-disease-gil-thieberger>. Gil Thieberger Apr. 8, 2020 (Apr. 8, 2020).

International search report, PCT/IB2021/054072, dated Aug. 17, 2021.

Written opinion of the international searching authority, PCT/IB2021/054072, dated Aug. 17, 2021.

Occupational Safety and Health Administration. "Guidance on preparing workplaces for an influenza pandemic." (2007) U.S. Department of Labor Occupational Safety and Health Administration OSHA 3327-02N 2007.

* cited by examiner

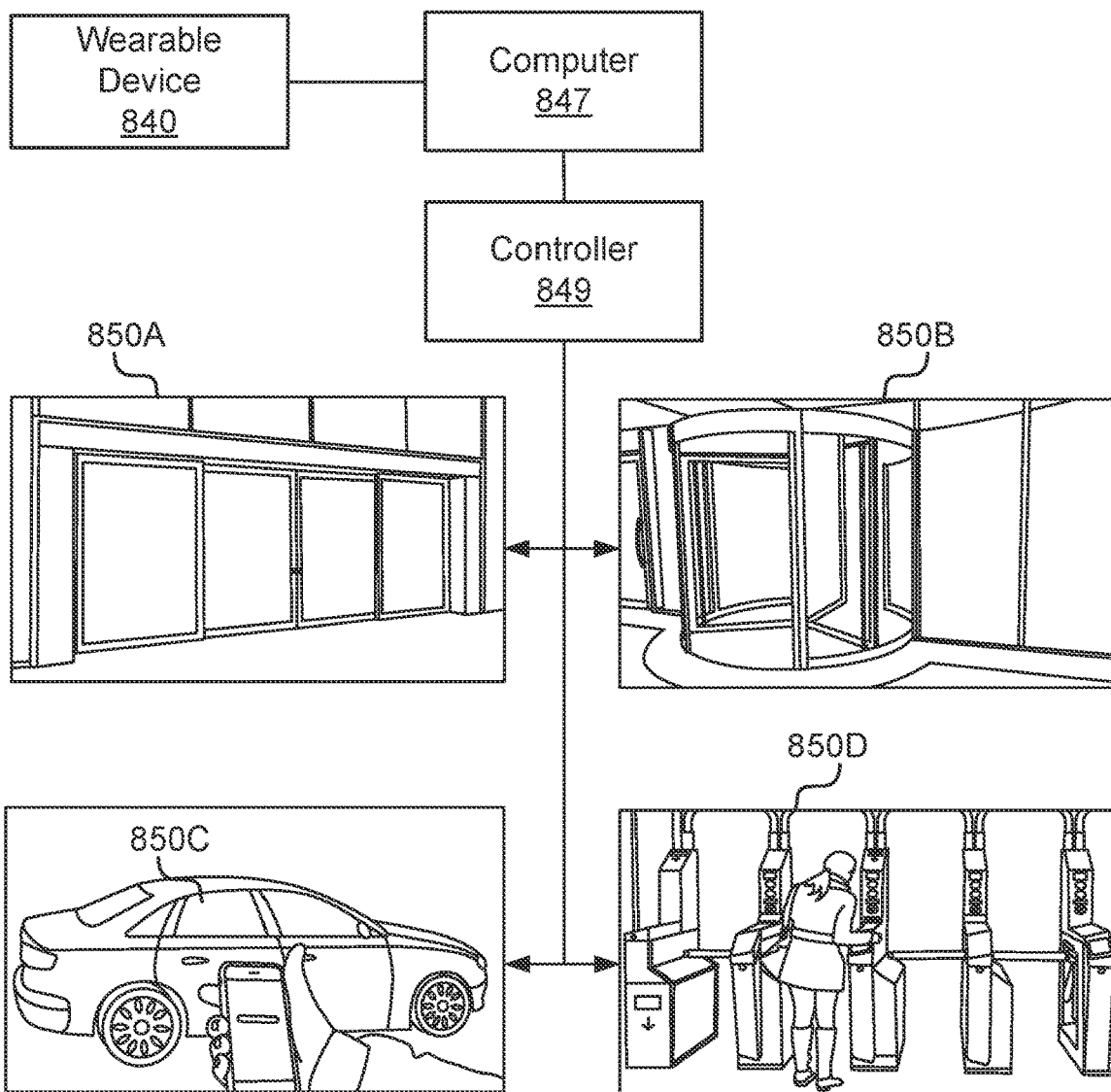
FIG. 3
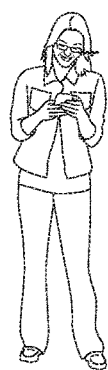 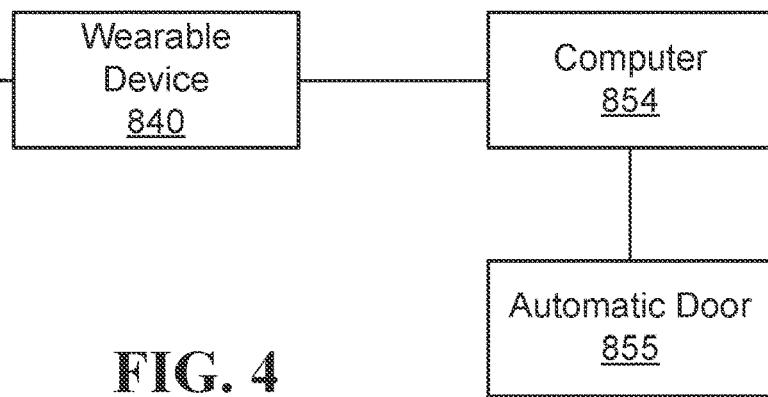
FIG. 4

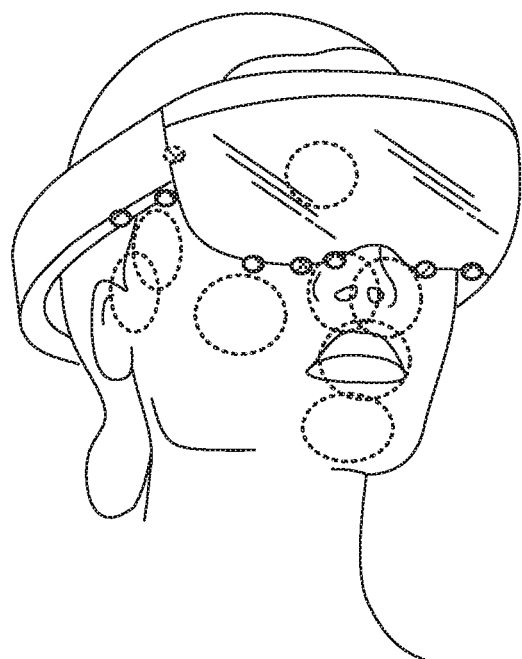 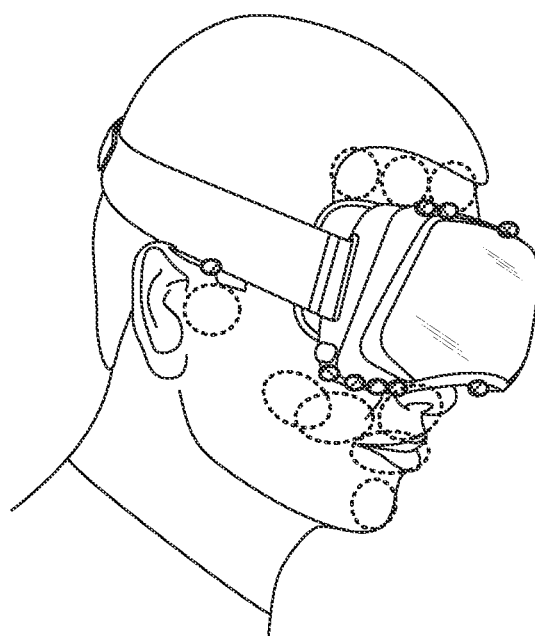
FIG. 17       FIG. 18
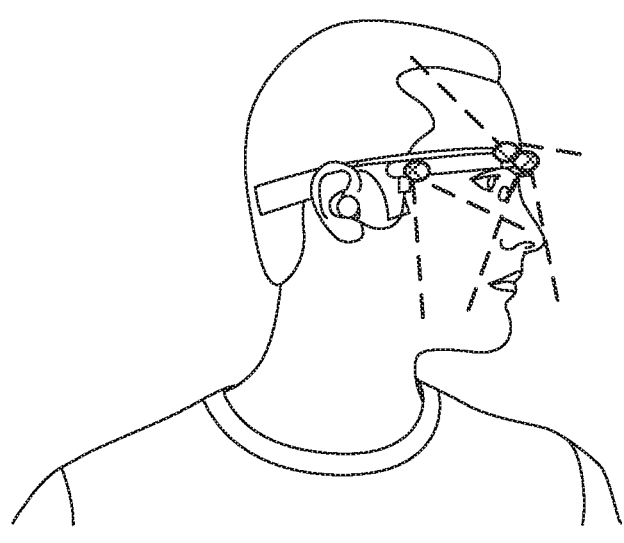 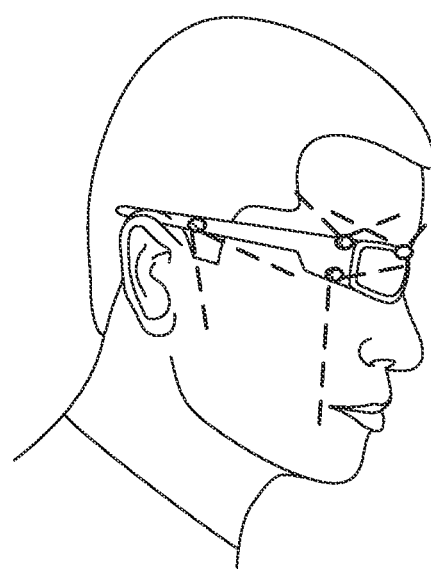
FIG. 19       FIG. 20

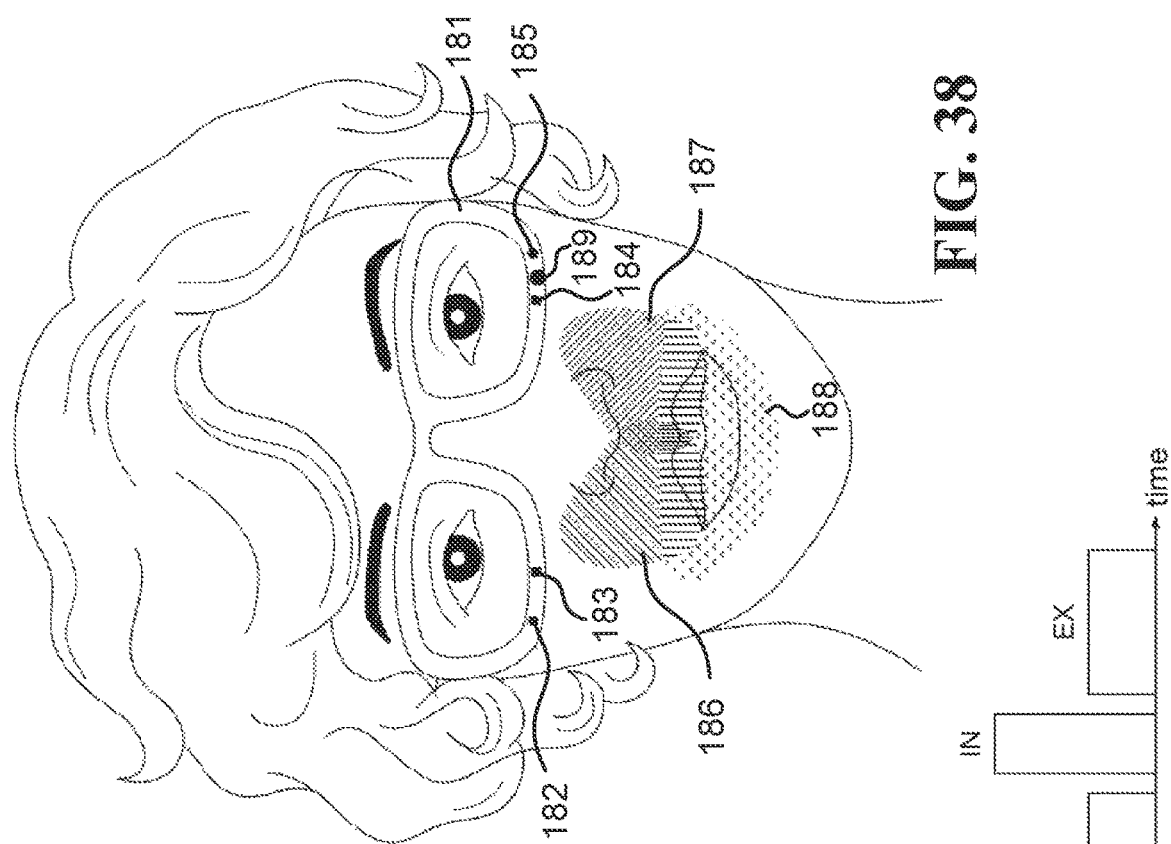
FIG. 38
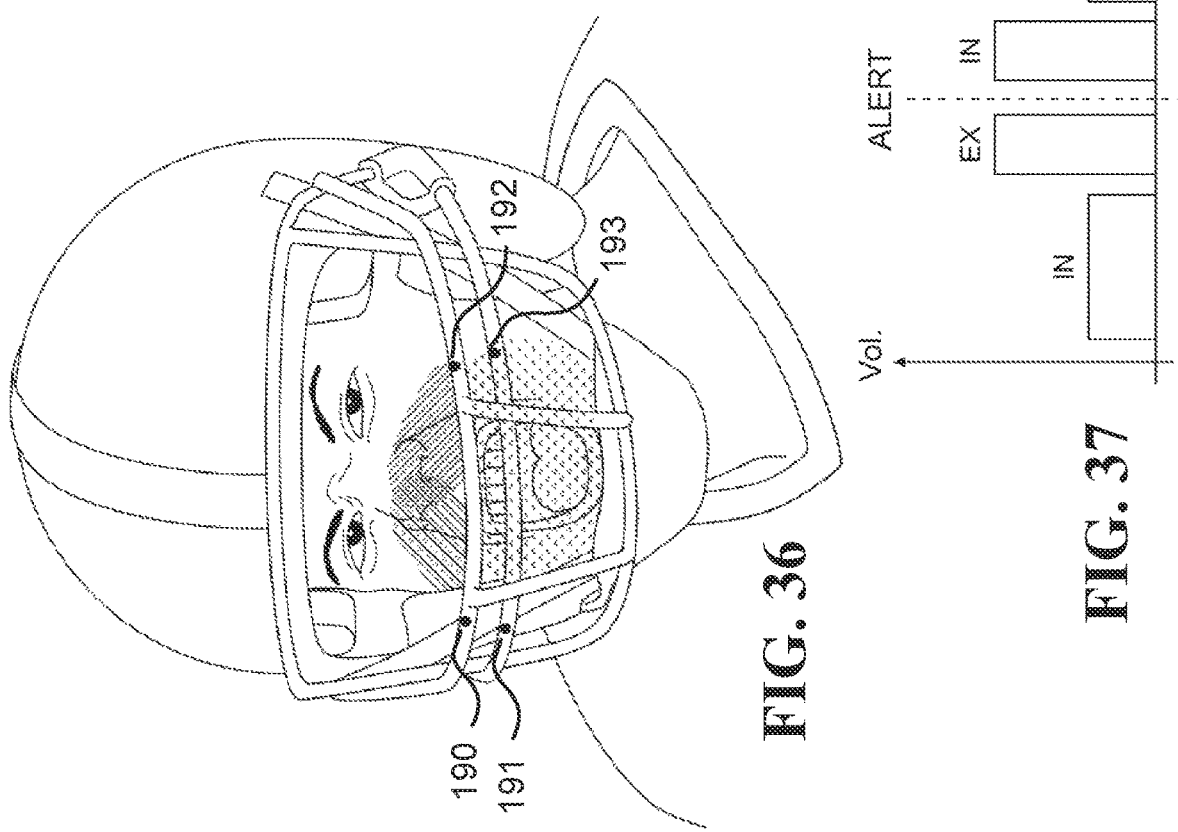
FIG. 36
FIG. 37

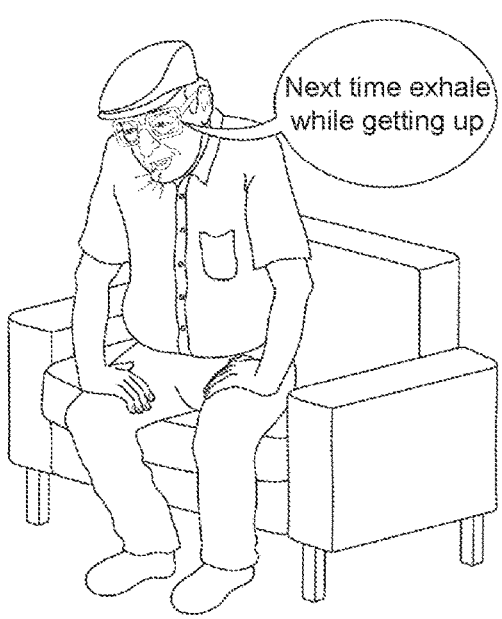 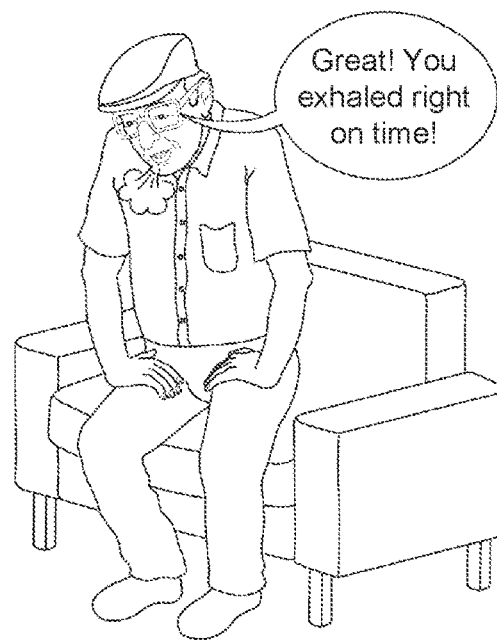
FIG. 39A  FIG. 39B
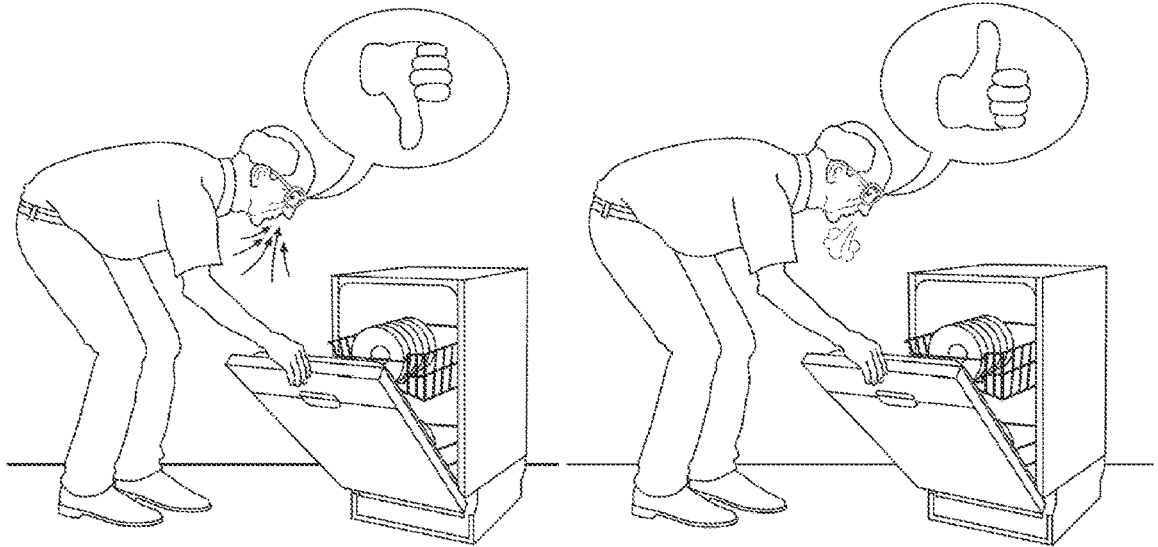
FIG. 40A  FIG. 40B
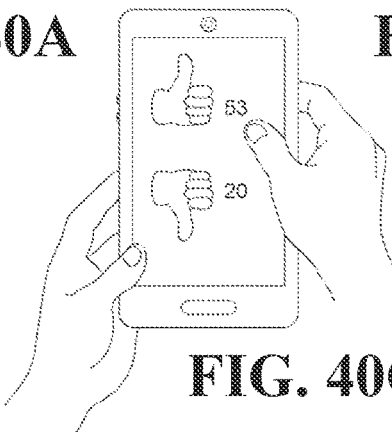
FIG. 40C

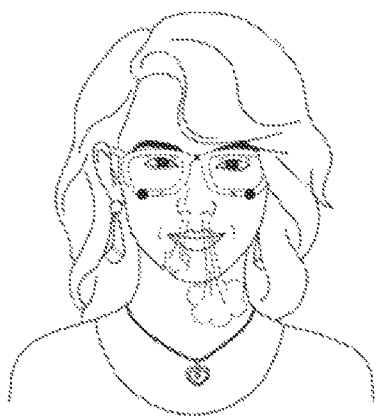
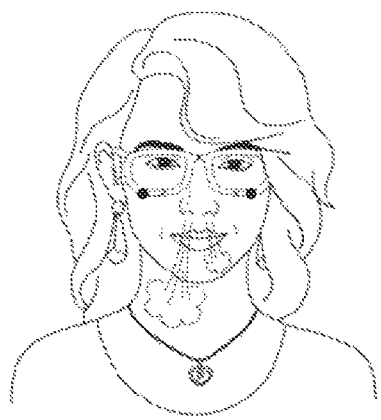
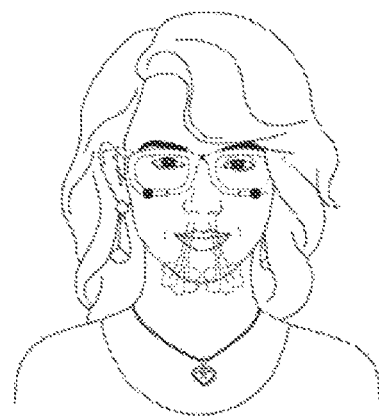
FIG. 47A   FIG. 47B   FIG. 47C
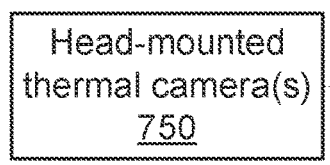
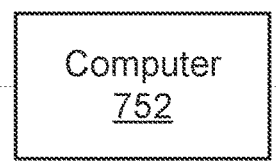
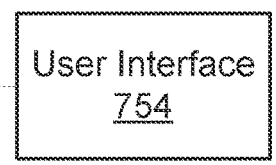
Head-mounted thermal camera(s) 750 — Computer 752 — User Interface 754
FIG. 48
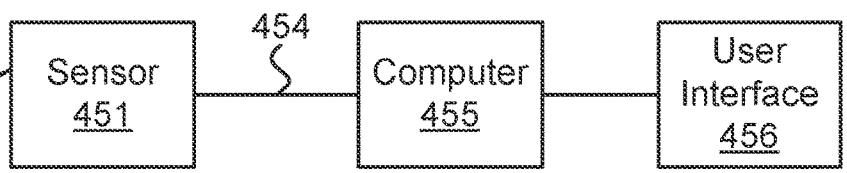
Sensor 451 — 454 — Computer 455 — User Interface 456
FIG. 49A
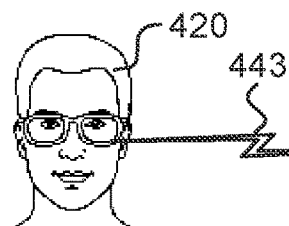
420, 443, Computer 445, Model 442, Sensor 435, $m_{move}$ 450, Value 447, User Interface 448
FIG. 49B

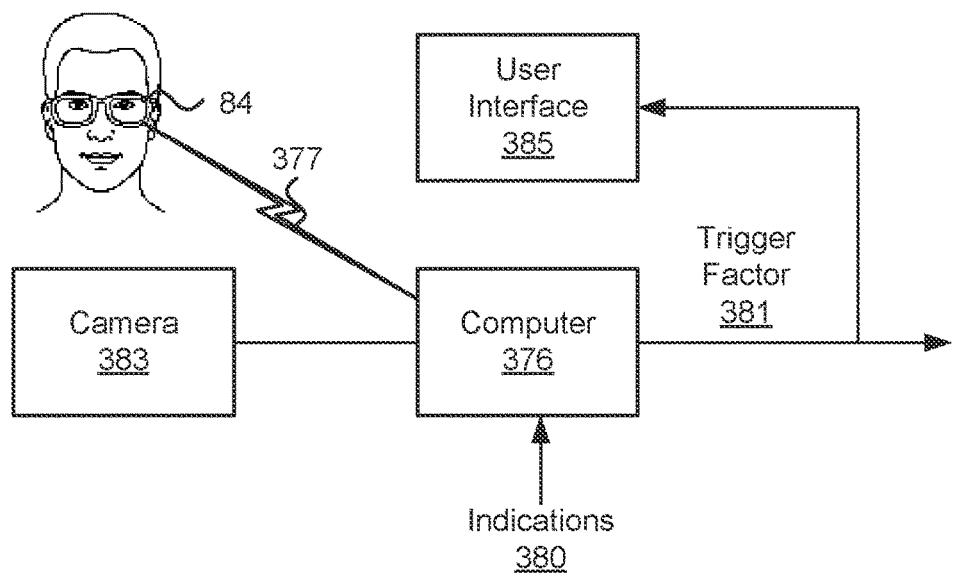
FIG. 53
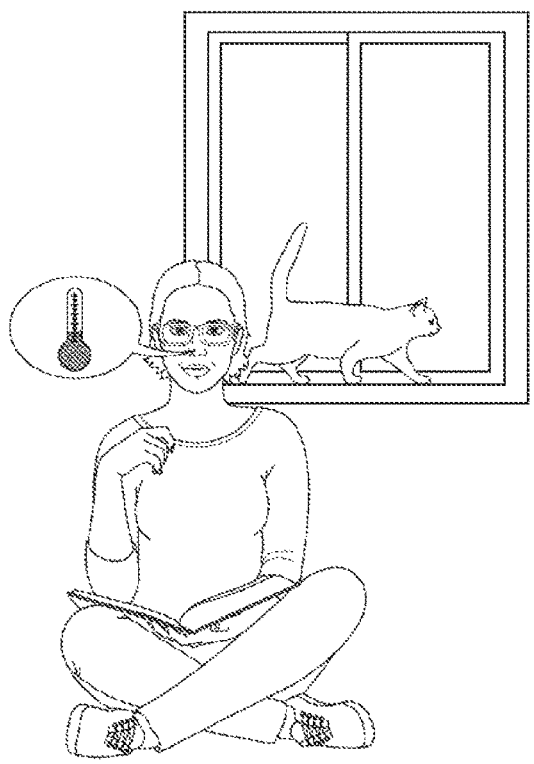
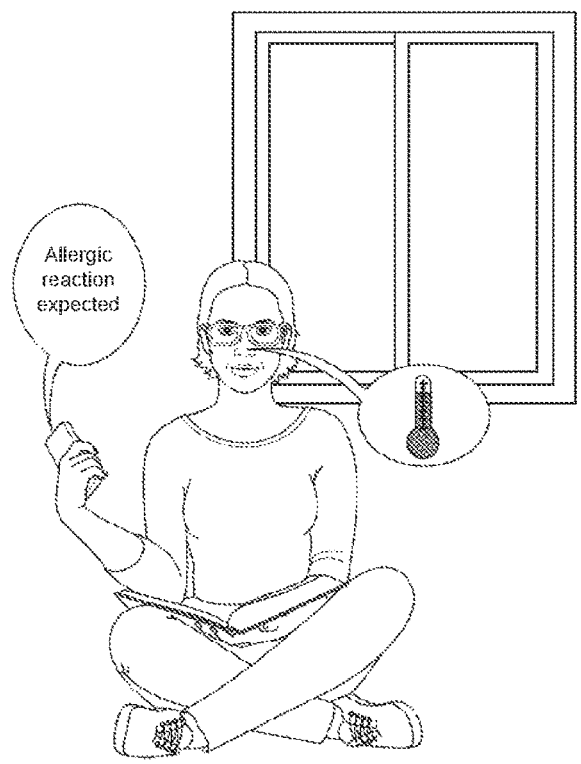
FIG. 54A          FIG. 54B

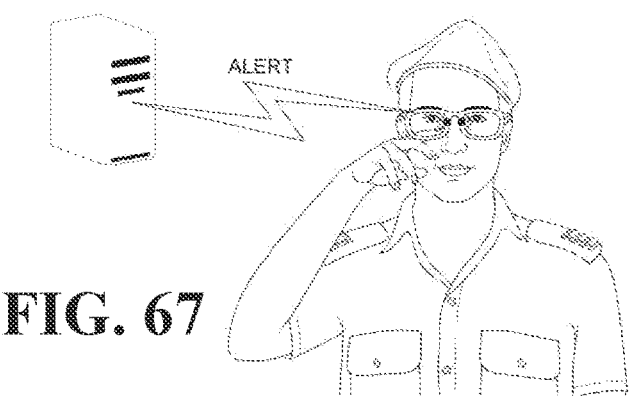
FIG. 67
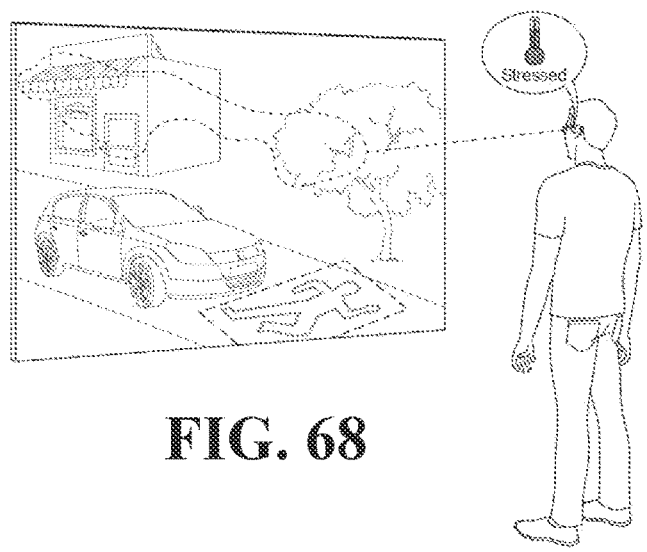
FIG. 68
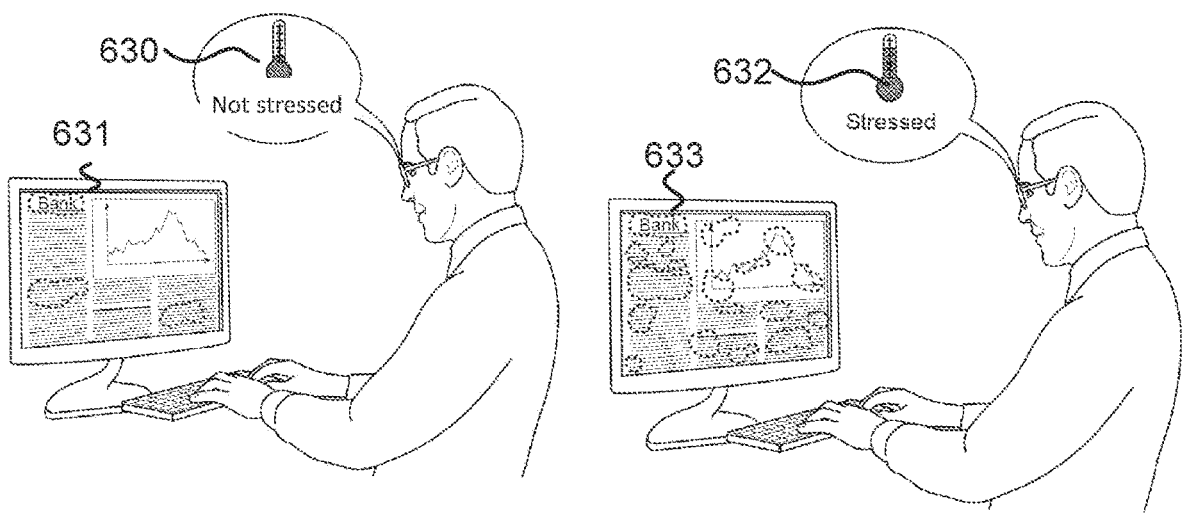
FIG. 69A   FIG. 69B

WEARABLE-BASED HEALTH STATE VERIFICATION FOR PHYSICAL ACCESS AUTHORIZATION

CROSS-REFERENCE TO RELATED APPLICATIONS

This Application claims priority to U.S. Provisional Patent Application No. 63/024,471, filed May 13, 2020, U.S. Provisional Patent Application No. 63/048,638, filed Jul. 6, 2020, U.S. Provisional Patent Application No. 63/113,846, filed Nov. 14, 2020, U.S. Provisional Patent Application No. 63/122,961, filed Dec. 9, 2020, and U.S. Provisional Patent Application No. 63/140,453 filed Jan. 22, 2021.

This Application is a Continuation-In-Part of U.S. Ser. No. 16/689,929, filed Nov. 20, 2019, which claims priority to U.S. Provisional Patent Application No. 62/874,430, filed Jul. 15, 2019, and U.S. Provisional Patent Application No. 62/928,726, filed Oct. 31, 2019.

U.S. Ser. No. 16/689,929 is a Continuation-In-Part of U.S. Ser. No. 16/156,586, filed Oct. 10, 2018, that is a Continuation-In-Part of U.S. application Ser. No. 15/832,815, filed Dec. 6, 2017, which claims priority to U.S. Provisional Patent Application No. 62/456,105, filed Feb. 7, 2017, and U.S. Provisional Patent Application No. 62/480,496, filed Apr. 2, 2017, and U.S. Provisional Patent Application No. 62/566,572, filed Oct. 2, 2017. U.S. Ser. No. 16/156,586 is also a Continuation-In-Part of U.S. application Ser. No. 15/859,772 Jan. 2, 2018, now U.S. Pat. No. 10,159,411.

U.S. Ser. No. 16/689,929 is also a Continuation-in-Part of U.S. application Ser. No. 16/453,993, filed Jun. 26, 2019. U.S. Ser. No. 16/453,993 is a Continuation-in-Part of U.S. application Ser. No. 16/375,841, filed Apr. 4, 2019. U.S. Ser. No. 16/375,841 is a Continuation-In-Part of U.S. application Ser. No. 16/156,493, filed Oct. 10, 2018. U.S. Ser. No. 16/156,493, is a Continuation-In-Part of U.S. application Ser. No. 15/635,178, filed Jun. 27, 2017, now U.S. Pat. No. 10,136,856, which claims priority to U.S. Provisional Patent Application No. 62/354,833, filed Jun. 27, 2016, and U.S. Provisional Patent Application No. 62/372,063, filed Aug. 8, 2016.

U.S. Ser. No. 16/156,493 is also a Continuation-In-Part of U.S. application Ser. No. 15/231,276, filed Aug. 8, 2016, which claims priority to U.S. Provisional Patent Application No. 62/202,808, filed Aug. 8, 2015, and U.S. Provisional Patent Application No. 62/236,868, filed Oct. 3, 2015.

U.S. Ser. No. 16/156,493 is also a Continuation-In-Part of U.S. application Ser. No. 15/832,855, filed Dec. 6, 2017, now U.S. Pat. No. 10,130,308, which claims priority to U.S. Provisional Patent Application No. 62/456,105, filed Feb. 7, 2017, and U.S. Provisional Patent Application No. 62/480, 496, filed Apr. 2, 2017, and U.S. Provisional Patent Application No. 62/566,572, filed Oct. 2, 2017. U.S. Ser. No. 15/832,855 is a Continuation-In-Part of U.S. application Ser. No. 15/182,592, filed Jun. 14, 2016, now U.S. Pat. No. 10,165,949, a Continuation-In-Part of U.S. application Ser. No. 15/231,276, filed Aug. 8, 2016, a Continuation-In-Part of U.S. application Ser. No. 15/284,528, filed Oct. 3, 2016, now U.S. Pat. No. 10,113,913, a Continuation-In-Part of U.S. application Ser. No. 15/635,178, filed Jun. 27, 2017, now U.S. Pat. No. 10,136,856, and a Continuation-In-Part of U.S. application Ser. No. 15/722,434, filed Oct. 2, 2017.

U.S. Ser. No. 15/832,855 is a Continuation-In-Part of U.S. application Ser. No. 15/182,566, filed Jun. 14, 2016, now U.S. Pat. No. 9,867,546, which claims priority to U.S. Provisional Patent Application No. 62/175,319, filed Jun. 14, 2015, and U.S. Provisional Patent Application No. 62/202,808, filed Aug. 8, 2015.

U.S. Ser. No. 15/182,592 claims priority to U.S. Provisional Patent Application No. 62/175,319, filed Jun. 14, 2015, and U.S. Provisional Patent Application No. 62/202, 808, filed Aug. 8, 2015.

U.S. Ser. No. 15/284,528 claims priority to U.S. Provisional Patent Application No. 62/236,868, filed Oct. 3, 2015, and U.S. Provisional Patent Application No. 62/354,833, filed Jun. 27, 2016, and U.S. Provisional Patent Application No. 62/372,063, filed Aug. 8, 2016.

U.S. Ser. No. 16/156,493 is also a Continuation-In-Part of U.S. application Ser. No. 15/833,115, filed Dec. 6, 2017, now U.S. Pat. No. 10,130,261. U.S. Ser. No. 15/833,115 is a Continuation-In-Part of U.S. application Ser. No. 15/182, 592, a Continuation-In-Part of U.S. application Ser. No. 15/231,276, filed Aug. 8, 2016, a Continuation-In-Part of U.S. application Ser. No. 15/284,528, a Continuation-In-Part of U.S. application Ser. No. 15/635,178, and a Continuation-In-Part of U.S. application Ser. No. 15/722,434, filed Oct. 2, 2017.

U.S. Ser. No. 16/453,993 is also a Continuation-In-Part of U.S. application Ser. No. 16/147,695, filed Sep. 29, 2018. U.S. Ser. No. 16/147,695 is a Continuation of U.S. application Ser. No. 15/182,592, filed Jun. 14, 2016, which claims priority to U.S. Provisional Patent Application No. 62/175, 319, filed Jun. 14, 2015, and U.S. Provisional Patent Application No. 62/202,808, filed Aug. 8, 2015.

BACKGROUND

Pandemics and epidemics involving communicable diseases such as the flu and COVID-19 pose a great risk to society, both due to the great toll in human life they can exact and the potential wide-scale disruption to the economy. Combating the spread of communicable diseases is often done with extreme measures such as restrictions on peoples' movements and blanket orders for quarantines. The reason such extreme measures are often used is that it is difficult to determine, on a population-wide scale, who are the symptomatic people who pose a risk of spreading the communicable disease (and limit restrictions to those people). Thus, for practical reasons, often whole populations are treated as if they all pose a risk, and are subject to many restrictions, even though the majority of these people are not symptomatic and cannot spread the disease.

Wearable devices with sensors capable of measuring physiological signals of their wearers have been suggested as possible tools that can be used to combat the spread of communicable diseases. However, so far, very few practical applications of these devices have been suggested that go beyond reporting to users their physiological state. Additionally, various challenges concerning user privacy that emerge when data from wearable devices of users is used by external applications are mostly unanswered. Thus, there is a need for ways to utilize wearable devices to better manage steps employed for curbing the spread of communicable diseases, while doing so in a privacy-minded manner.

SUMMARY

One aspect of this disclosure is a wearable-based system that can help determine in a privacy-preserving manner whether a user is healthy (and thus poses low risk of contagiousness). A health score generated by the wearable device can be used to provide a verified health status for the user, granting the user with greater freedom of movement, e.g., via automatic opening of certain doors that are closed to people who cannot provide furnish such a verified health status.

Some aspects of this disclosure involve utilization of wearable devices with sensors that measure physiological signals of their wearers. An example of such a wearable device are smartglasses with embedded sensors. For example, the smartglasses may include some of the following sensors: a photoplethysmogram (PPG) sensor that measures blood flow and blood oxygen saturation at a region on the face, a thermal sensor that measures temperature at region on the face, an acoustic sensor that takes audio recordings indicative of voice, respiration, and/or coughing, a movement sensor, and more.

One aspect of this disclosure involves utilization of measurements taken by a wearable device worn by a user to calculate a health score for the user. Some examples of physiological signals that may be used to calculate the health score include one or more of the following: heart rate, blood oxygen saturation, respiration rate, skin and/or core body temperature, blood pressure, and extent of coughing. In some embodiments, the health score of a user may be indicative of the extent to which a user is healthy and/or non-contagious. Optionally, a health score may refer to an extent to which a user displays symptoms of a certain disease certain disease (e.g., the flu, COVID-19, or some other communicable disease) and/or is considered contagious with respect to the certain disease. Additionally or alternatively, a health score may refer to an extent to which a user is considered healthy according to general wellness considerations that involve one or more of the user's vital signs (e.g., whether the core body temperature is elevated, blood oxygen saturation is in a normal range, etc.)

In some embodiments described herein, health scores for users are calculated based on differences between current measurements of users (which in some examples are measurements up to 3 hours old) and baseline measurements of the users (which in some examples are at least 10 hours old, or even several days old). Differences between the current measurements and the baseline measurements are used to detect deviation from a baseline state that may be indicative of a change in the health state of the user. For example, a rise in estimated core body temperature compared to a baseline estimated core body temperature and a drop in blood oxygen saturation ($SpO_2$) compared to a baseline $SpO_2$ may be indications that the user is becoming ill.

Another aspect of this disclosure involves utilization of measurements taken by a wearable device worn by a user to authenticate the user and/or determine whether current measurements and baseline measurements are of the same user. In some embodiments, this involves detecting biometric similarities between patterns in the current measurements and the baseline measurements. For example, this similarities may be ascertained by calculating an extent of similarity between characteristics of a PPG signal in the current measurements and characteristics of a PPG signal in the baseline measurements. Optionally, additional physiological signals such as characteristics of gait and/or spectral properties of voice.

Similarities between current measurements and baseline measurements may be used to establish, with a certain degree of certainty, that the baseline measurements and the current measurements are of the same person. This form of biometric identification/verification can help reduce the likelihood of mistakes and/or deceptive behavior when the wearable device is used for various applications related to granting access or privilege based on a wearable-based health state. For example, this can help reduce occurrence of cases that involve measuring a first user (who is healthy) and then providing the wearable device to a second user, who poses as the first user, in order to trick the system.

One aspect of this disclosure is a system configured to grant passage through a doorway based on health state. In one embodiment the system includes a wearable device and a computer. The wearable device comprising: a first sensor configured to measure a signal indicative of a photoplethysmogram signal (PPG signal) of a user, and a second sensor configured to measure a temperature of the user. The computer receives current measurements of the user, taken with the wearable device, as well as baseline measurements of the user, taken with the wearable device on one or more earlier days. Optionally, the current measurements are taken over a duration of at least five minutes. The computer calculates a health score based on a difference between the baseline measurements and the current measurements, and calculates an extent of similarity between characteristics of the PPG signal in the current measurements and characteristics of the PPG signal in the baseline measurements. The computer transmits an authorization signal responsive to the health score reaching a first threshold and the extent of the similarity reaching a second threshold; whereby transmission of the authorization signal indicates a health state of the user permits passage through the doorway. Optionally, the authorization signal does not include information identifying the user.

In some embodiments, the system includes a controller that commands an automatic door to open and/or unlock, permitting the passage through the doorway, responsive to receiving the authorization signal. Optionally, the automatic door includes a barrier that restricts the passage through the doorway when the automatic door is in a closed and/or locked position. Optionally, the controller commands the automatic door to close and/or remain shut, thereby restricting the passage through the doorway, responsive to detecting that the user has passed through the doorway and/or not receiving an additional transmission of the authorization signal within a predetermined time.

In one example, the automatic door belongs to a vehicle, and commanding the automatic door to open unlocks the door and/or moves the door to an open position, enabling the user to enter the cabin of the vehicle.

In another example, the automatic door is an entrance door to a room and/or building, and commanding the automatic door to open unlocks the door and/or moves the door to an open position, enabling the user to enter the interior of the room and/or building.

In yet another example, the automatic door is a gate comprising a turnstile or a revolving door, and commanding the automatic door to open enables the turnstile or the revolving door to revolve and/or revolving the turnstile or the revolving door, enabling the user to pass through the gate.

In one embodiment, the computer transmits a second signal responsive to the health score not reaching the first threshold and/or the extent of the similarity not reaching the second threshold. Optionally, the system includes a controller configured to command an automatic door to close and/or remain shut, thereby restricting the passage through the doorway, responsive to receiving the second signal.

In one embodiment, calculation of the health score by the computer involves the following: calculating, based on the baseline measurements, an expected value of a physiological signal of the user, calculating, based on the current measurements, a current value of the physiological signal; and calculating the health score based on a difference between the expected value and the currant value. In one example, the physiological signal is body temperature, and the calculating of the health score utilizes a function that returns a value that is below the first threshold when a current body temperature is greater than an expected body temperature by at least a certain margin; and wherein the certain margin is at least 0.4° C. In one embodiment, calculating the current value of the physiological signal comprises: generating feature values based on the current measurements, and utilizing a model to calculate, based on the feature values, the current value of the physiological signal; and wherein the model was generated from training data comprising: previous measurements of the user taken with the wearable device, and values of the physiological signal obtained utilizing a sensor that is not part of the wearable device. In one embodiment, the system includes a movement sensor, physically coupled to the wearable device, configured to measure a signal indicative of movements of the user. Optionally, calculating the current value of the physiological signal comprises: generating feature values based on the current measurements and the signal indicative of movements of the user, and utilizing a model to calculate the current value of the physiological signal; and wherein one or more of the feature values are indicative of an extent of movements of the user while the current measurements were taken.

In one embodiment, the computer determines, based on the measurements taken with the wearable device, whether the wearable device was removed from the user's body while the current measurements were taken or after the current measurements were taken, and responsive to making a determination that he wearable device has been removed, to refrain from transmitting the authorization signal. Optionally, the computer performs the following steps responsive to making the determination that the wearable device was removed: receiving additional measurements of the user, taken at most three hours after the current measurements were taken; calculating an additional similarity between characteristics of the PPG signal in the current measurements and characteristics of the PPG signal in the additional measurements; and transmitting the authorization signal responsive to the health score reaching the first threshold and the additional similarity reaching the second threshold; whereby the additional similarity reaching the second threshold is indicative of a probability that the current measurements and the additional measurements are of the same person is above a predetermined threshold.

In one embodiment, the computer receives additional measurements of the user and calculates an additional extent of similarity between characteristics of the PPG signal in the additional measurements and characteristics of the PPG signal in the baseline measurements. The computer also calculates an additional health score based on a difference between the baseline measurements and the additional measurements. And responsive to the extent of similarity reaching the second threshold, reports the additional health score to the user and/or providing the user with an indication of whether the health state of the user permits passage through the doorway.

In one embodiment, the computer generates feature values based on data comprising the current measurements and the baseline measurements, and utilized a model to calculate, based on the feature values, the health score. Optionally, the model is generated based on training data comprising a first set of training measurements of a plurality of users taken while the plurality of users were healthy and a second set of training measurements of the plurality of users taken while the plurality of users were not healthy.

BRIEF DESCRIPTION OF THE DRAWINGS

The embodiments are herein described by way of example only, with reference to the following drawings:

FIG. 3 illustrates examples of automatic doors;

FIG. 4 illustrates components of an embodiment of a system configured to manage access using reservations and wearable-based health state verifications;

FIG. 17 illustrates inward-facing head-mounted cameras coupled to an augmented reality device;

FIG. 18 illustrates head-mounted cameras coupled to a virtual reality device;

FIG. 19 illustrates a side view of head-mounted cameras coupled to an augmented reality device;

FIG. 20 illustrates a side view of head-mounted cameras coupled to a sunglasses frame;

FIG. 36 illustrates an embodiment of a system that collects thermal measurements related to respiration, in which four inward-facing head-mounted thermal cameras (CAMs) are coupled to a football helmet;

FIG. 37 illustrates a situation in which an alert is issued to a user when it is detected that the ratio the duration of exhaling and inhaling is too low;

FIG. 38 illustrates an embodiment of a system that collects thermal measurements related to respiration, in which four CAMs are coupled to the bottom of an eyeglasses frame;

FIG. 39A, FIG. 39B, FIG. 40A, FIG. 40B and FIG. 40C illustrate how embodiments described herein may help train an elderly user to exhale during effort;

FIG. 47A is a schematic illustration of a left dominant nostril.

FIG. 47B is a schematic illustration of a right dominant nostril;

FIG. 47C is a schematic illustration of balanced breathing;

FIG. 48 is a schematic illustration of an embodiment of a system that identifies the dominant nostril;

FIG. 49A illustrates an embodiment of a system that suggests activities according to the dominant nostril;

FIG. 49B illustrates an embodiment of a system for calculating a respiratory parameter;

FIG. 53 illustrates an embodiment of a system configured to select a trigger of an allergic reaction of a user;

FIG. 54A and FIG. 54B illustrate a scenario in which a user is alerted about an expected allergic reaction;

FIG. 67 illustrates triggering an alert when the user moves the HMD and touches the CAM;

FIG. 68 illustrates a scenario that identifies that a user is agitated from viewing a video;

FIG. 69A and FIG. 69B illustrate scenarios in which stress levels and gaze patterns are utilized do detect atypical user behavior.

DETAILED DESCRIPTION

Figure 1:
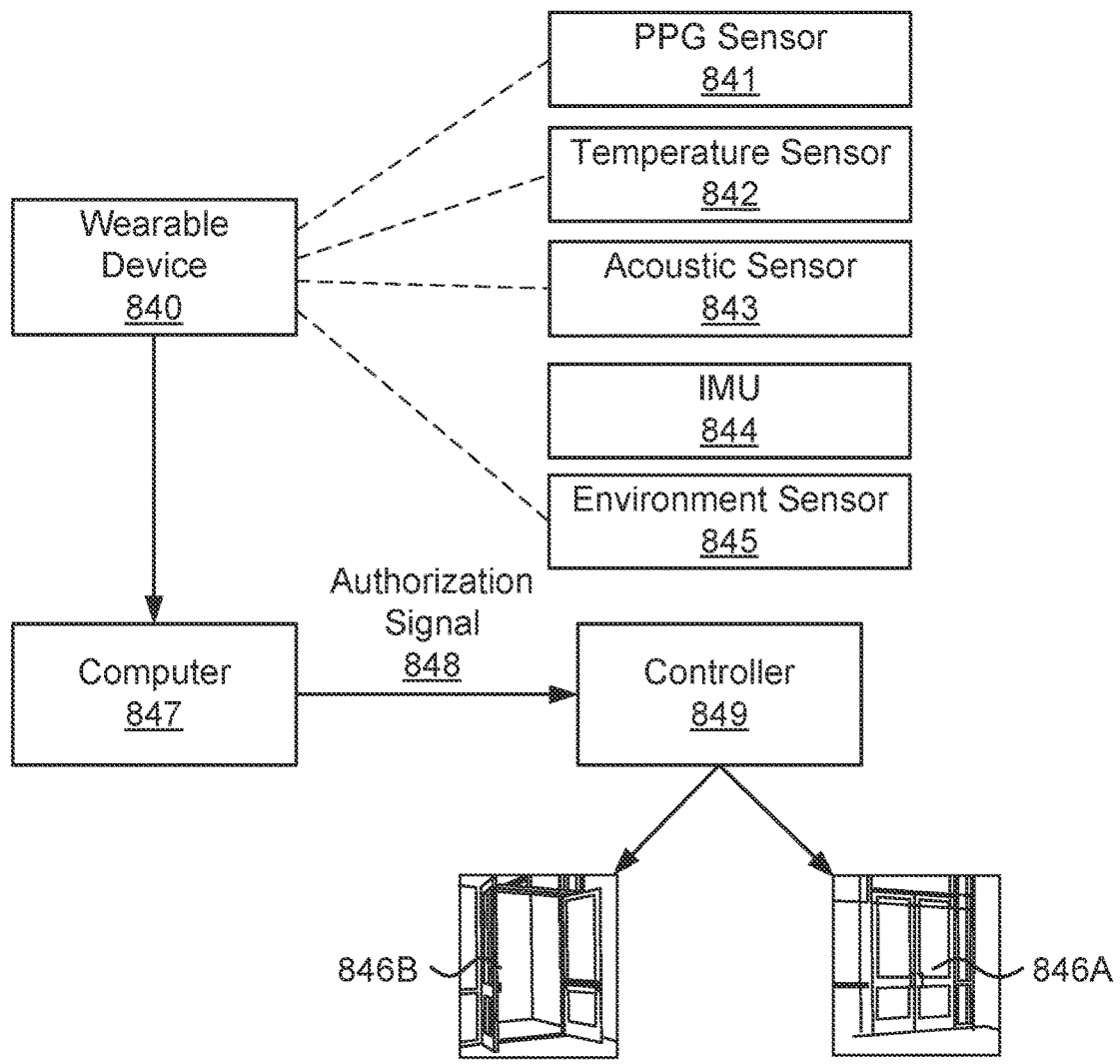
FIG. 1 is a schematic illustration embodiments of a system configured to grant passage through a doorway based on a user's health state.

Herein the terms "photoplethysmogram signal", "photoplethysmographic signal", "photoplethysmography signal", and other similar variations are interchangeable and refer to the same type of signal. A photoplethysmogram signal may be referred to as a "PPG signal", or an "iPPG signal" when specifically referring to a PPG signal obtained from a camera. The terms "photoplethysmography device", "photoplethysmographic device", "photoplethysmogram device", and other similar variations are also interehangeable and refer to the same type of device that measures a signal from which it is possible to extract the photoplethysmogram signal. The photoplethysmography device may be referred to as "PPG device".

Sentences in the form of "a sensor configured to measure a signal indicative of a photoplethysmogram signal" refer to at least one of: (i) a contact PPG device, such as a pulse oximeter that illuminates the skin and measures changes in light absorption, where the changes in light absorption are indicative of the PPG signal, and (ii) a non-contact camera that captures images of the skin, where a computer extracts the PPG signal from the images using an imaging photoplethysmography (iPPG) technique. Other names known in the art for iPPG include: remote photoplethysmography (rPPG), remote photoplethysmographic imaging, remote imaging photoplethysmography, remote-PPG, and multi-site photoplethysmography (MPPG).

A PPG signal is often obtained by using a pulse oximeter, which illuminates the skin and measures changes in light absorption. Another possibility for obtaining the PPG signal is using an imaging photoplethysmography (iPPG) device. As opposed to contact PPG devices, iPPG does not require contact with the skin and is obtained by a non-contact sensor, such as a video camera.

A time series of values measured by a PPG device, which is indicative of blood flow changes due to pulse waves, is typically referred to as a waveform (or PPG waveform to indicate it is obtained with a PPG device). It is well known that PPG waveforms show significant gender-related differences, age-related differences, and health-related differences. As a result, the PPG waveforms of different people often display different characteristics (e.g., slightly different shapes and/or amplitudes). In addition, the PPG waveform depends on the site at which it is measured, skin temperature, skin tone, and other parameters.

The analysis of PPG signals usually includes the following steps: filtration of a PPG signal (such as applying bandpass filtering and/or heuristic filtering), extraction of feature values from fiducial points in the PPG signal (and in some cases may also include extraction of feature values from non-fiducial points in the PPG signal), and analysis of the feature values.

One type of features that is often used when performing calculations involving PPG signals involves fiducial points related to the waveforms of the PPG signal and/or to functions thereof (such as various derivatives of the PPG signal). There are many known techniques to identify the fiducial points in the PPG signal, and to extract the feature values. The following are some non-limiting examples of how to identify fiducial points.

Figure 15:
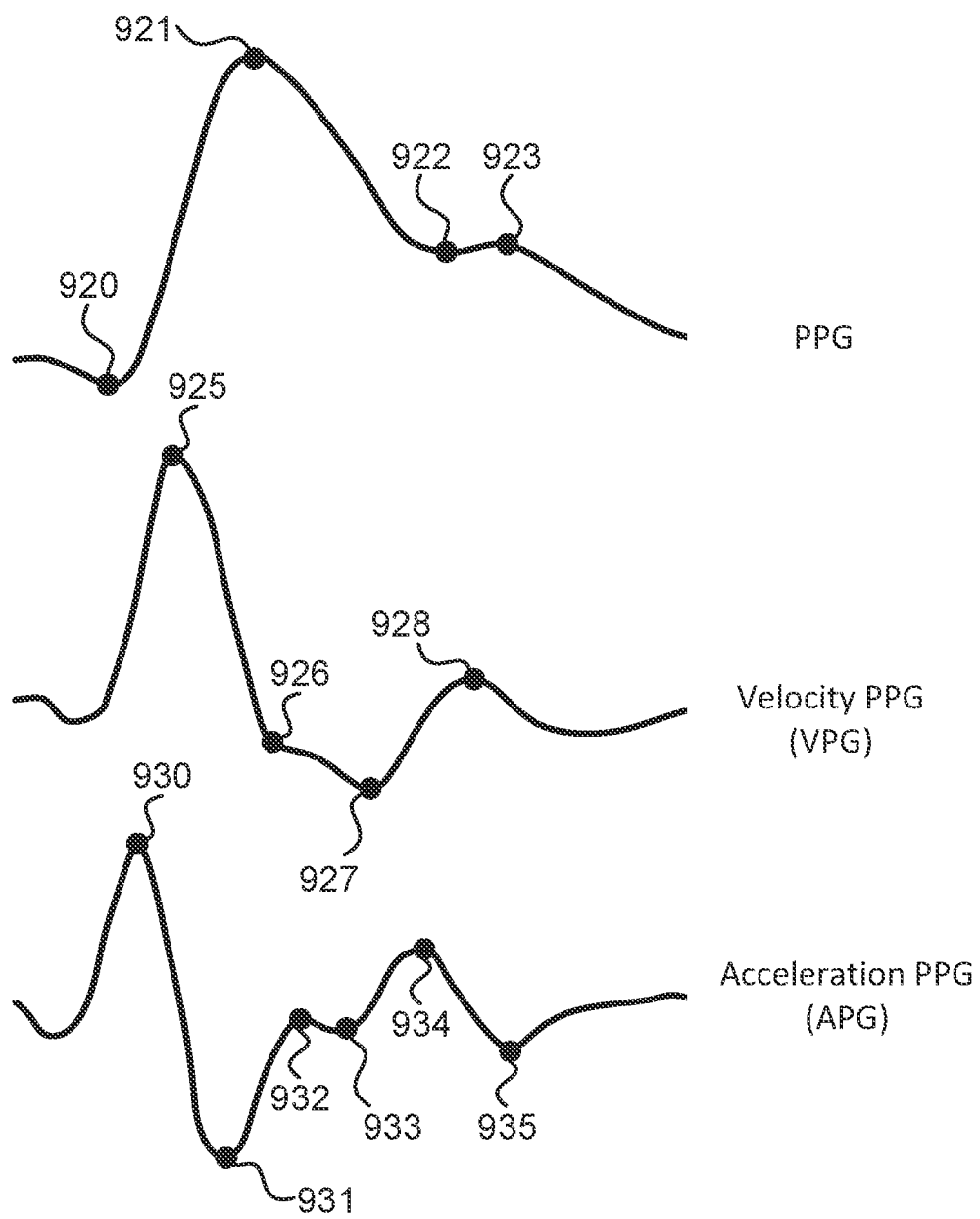
FIG. 15 is a schematic illustration of some of the various fiducial points for PPG signals often used in the art.

FIG. 15 is a schematic illustration of some of the various fiducial points often used in the art (and described below). These examples of fiducial points include fiducial points of the PPG signal, fiducial points in the first derivative of the PPG signal (velocity photoplethysmogram, VPG), and fiducial points in the second derivative of the PPG signal (acceleration photoplethysmogram, APG).

Fiducial points in the PPG signal may include: the systolic notch 920, which is the minimum at the PPG signal onset; the systolic peak 921, which is the maximum of the PPG signal; the dicrotic notch 922, which coincident with e 934 (see below at the second derivative of the PPG signal); and the diastolic peak 923, which is the first local maximum of the PPG signal after the dicrotic notch and before 0.8 of the duration of the cardiac cycle, or if there is no such local maximum, then the first local maximum of the second derivative after e and before 0.8 of the duration of the cardiac cycle.

Fiducial points in the first derivative of the PPG signal (velocity photoplethysmogram, VPG) may include: the maximum slope peak in systolic of VPG 925; the local minima slope in systolic of VPG 926; the global minima slope in systolic of VPG 927; and the maximum slope peak in diastolic of VPG 928.

Fiducial points in the second derivative of the PPG signal (acceleration photoplethysmogram, APG) may include: a 930, which is the maximum of APG prior to the maximum of VPG; b 931, which is the first local minimum of APG following a; c 932, which is the greatest maximum of APG between b and e, or if no maxima then the first of (i) the first maximum of VPG after e, and (ii) the first minimum of APG after e; d 933, which is the lowest minimum of APG after c and before e, or if no minima then coincident with c; e 934, which is the second maximum of APG after maximum of VPG and before 0.6 of the duration of the cardiac cycle, unless the c wave is an inflection point, in which case take the first maximum; and f 935, which is the first local minimum of APG after e and before 0.8 of the duration of the cardiac cycle.

Fiducial points in the third derivative of the PPG signal (PPG''') may include: the first local maximum of PPG''' after b; and the last local minimum of PPG''' before d, unless c=d, in which case take the first local minimum of PPG''' after d, and if there is a local maximum of the PPG signal between this point and the dicrotic notch then use it instead.

Feature values of the PPG signal may also be extracted from relationships in the PPG signal and/or its derivatives. The following are some non-limiting examples such possible feature values: pulse width, peak to peak time, ratio of areas before and after dicrotic notch in a complete cycle, baseline wander (BW), which is the mean of the amplitudes of a beat's peak and trough; amplitude modulation (AM), which is the difference between the amplitudes of each beat's peak and trough; and frequency modulation (FM), which is the time interval between consecutive peaks.

Examples of additional features that can be extracted from the PPG signal, together with schematic illustrations of the feature locations on the PPG signal, can be found in the following three publications: (i) Peltokangas, Mikko, et al. "Parameters extracted from arterial pulse waves as markers of atherosclerotic changes: performance and repeatability." IEEE journal of biomedical and health informatics 22.3 (2017): 750-757; (ii) Ahn, Jae Mok. "New aging index using signal features of both photoplethysmograms and acceleration plethysmograms." Healthcare informatics research 23.1 (2017): 53-59; (iii) Charlton, Peter H., et al. "Assessing mental stress from the photoplethysmogram: a numerical study." Physiological measurement 39.5 (2018): 054001, and (iv) Peralta, Elena, et al. "Optimal fiducial points for pulse rate variability analysis from forehead and finger photoplethysmographic signals." Physiological measurement 40.2 (2019): 025007.

Although the above mentioned references describe manual feature selection, the features may be selected using any appropriate feature engineering technique, including using automated feature engineering tools that help data scientists to reduce data exploration time, and enable non-experts, who may not be familiar with data science and/or PPG characteristics, to quickly extract value from their data with little effort.

Unless there is a specific reference to a specific derivative of the PPG signal, phrases of the form of "based on the PPG signal" refer to the PPG signal and any derivative thereof, including the first derivative of the PPG signal, the second derivative of the PPG signal, and the third derivative of the PPG signal. For example, a sentence in the form of "a computer configured to detect a physiological signal based on the PPG signal" is to be interpreted as "a computer configured to detect a physiological signal based on at least one of: the PPG signal, a first derivative of the PPG signal, a second derivative of the PPG signal, a the third derivative of the PPG signal, and/or any other derivative of the PPG signal".

Algorithms for filtration of the PPG signal, extraction of feature values from fiducial points in the PPG signal, and analysis of the feature values extracted from the PPG signal are well known in the art, and can be found for example in the following references: (i) Allen, John. "Photoplethysmography and its application in clinical physiological measurement." Physiological measurement 28.3 (2007): R1, and also in the thousands of references citing this reference; (ii) Elgendi, Mohamed. "On the analysis of fingertip photoplethysmogram signals." Current cardiology reviews 8.1 (2012): 14-25, and also in the hundreds of references citing this reference; (iii) Holton, Benjamin D., et al. "Signal recovery in imaging photoplethysmography." Physiological measurement 34.11 (2013); 1499, and also in the dozens of references citing this reference, (iv) Sun, Yu, and Nitish Thakor. "Photoplethysmography revisited: from contact to noncontact, from point to imaging." IEEE Transactions on Biomedical Engineering 63.3 (2015): 463-477, and also in the dozens of references citing this reference, (v) Kumar, Mayank, Ashok Veeraraghavan, and Ashutosh Sabharwal. "DistancePPG: Robust non-contact vital signs monitoring using a camera." Biomedical optics express 6.5 (2015): 1565-1588, and also in the dozens of references citing this reference, (vi) Wang, Wenjin, et al. "Algorithmic principles of remote PPG." IEEE Transactions on Biomedical Engineering 64.7 (2016): 1479-1491, and also in the dozens of references citing this reference, and (vii) Rouast, Philipp V., et al. "Remote heart rate measurement using low-cost RGB face video: a technical literature review." Frontiers of Computer Science 12.5 (2018): 858-872, and also in the dozens of references citing this reference.

Various embodiments described herein involve calculations based on machine learning approaches. Herein, the terms "machine learning approach" and/or "machine learning-based approaches" refer to learning from examples using one or more approaches. Examples of machine learning approaches include: decision tree learning, association rule learning, regression models, nearest neighbors classifiers, artificial neural networks, deep learning, inductive logic programming, support vector machines, clustering, Bayesian networks, reinforcement learning, representation learning, similarity and metric learning, sparse dictionary learning, genetic algorithms, rule-based machine learning, and/or learning classifier systems.

Herein, a "machine learning-based model" is a model trained using one or more machine learning approaches. For brevity's sake, at times, a "machine learning-based model" may simply be called a "model". Referring to a model as being "machine learning-based" is intended to indicate that the model is trained using one or more machine learning approaches (otherwise, "model" may also refer to a model generated by methods other than machine learning).

Herein, "feature values" (also known as feature vector, feature data, and numerical features) may be considered input to a computer that utilizes a model to perform the calculation of a value, such as a value indicative of one or more vital signs of a user. It is to be noted that the terms "feature" and "feature value" may be used interchangeably when the context of their use is clear. However, a "feature" typically refers to a certain type of value, and represents a property, while "feature value" is the value of the property with a certain instance (i.e., the value of the feature in a certain sample).

It is to be noted that when it is stated that feature values are generated based on data comprising multiple sources, it means that for each source, there is at least one feature value that is generated based on that source (and possibly other data). For example, stating that feature values are generated from an image capturing first and second regions ($IM_{ROI1}$ and $IM_{ROI2}$, respectively) means that the feature values include at least a first feature value generated based on $IM_{ROI1}$ and a second feature value generated based on $IM_{ROI2}$.

In addition to feature values generated based on measurements taken by sensors mentioned in a specific embodiment, at least some feature values utilized by a computer of the specific embodiment may be generated based on additional sources of data that were not specifically mentioned in the specific embodiment. Some examples of such additional sources of data include: (i) contextual information such as the time of day (e.g., to account for effects of the circadian rhythm), day of month (e.g., to account for effects of the lunar rhythm), day in the year (e.g., to account for seasonal effects), and/or stage in a menstrual cycle; (ii) information about the user being measured such as sex, age, weight, height, body build, genetics, medical records, and/or intake of substances; (iii) measurements of the environment, such as temperature, humidity level, noise level, elevation, air quality, a wind speed, precipitation, and infrared radiation; and/or (iv) values of physiological signals of the user obtained by sensors that are not mentioned in the specific embodiment, such as an electrocardiogram (ECG) sensor, an electroencephalography (EEG) sensor, a galvanic skin response (GSR) sensor, a movement sensor, an acoustic sensor, and/or a temperature sensor.

A machine learning-based model of a specific embodiment may be trained, in some embodiments, based on data collected in day-to-day, real world scenarios. As such, the data may be collected at different times of the day, while users perform various activities, and in various environmental conditions. Utilizing such diverse training data may enable a trained model to be more resilient to the various effects that different conditions can have on the measurements, and consequently, be able to achieve better detection of a required parameter in real world day-to-day scenarios.

The machine learning-based model may be personalized for a specific user. For example, after receiving a verified diagnosis of an extent of a physiological condition (such as blood pressure level, extent of a cardiovascular disease, extent of a pulmonary disease, extent of a migraine attack, etc.), the computed can use the verified diagnosis as labels and generate from a physiological measurement (such as the PPG signal, the temperature signal, the movement signal, and/or the audio signal) feature values to train a personalized machine learning-based model for the user. Then the computer can utilize the personalized machine learning-based model for future calculations of the extent of the physiological condition based on feature values.

Sentences in the form of "inward-facing head-mounted camera" refer to a camera configured to be worn on a user's head and to remain pointed at its ROI, which is on the user's face, also when the user's head makes angular and lateral movements (such as movements with an angular velocity above 0.1 md/sec, above 0.5 rad/sec, and/or above 1 rad/sec). A head-mounted camera (which may be inward-facing and/or outward-facing) may be physically coupled to a frame worn on the user's head, may be physically coupled to eyeglasses using a clip-on mechanism (configured to be attached to and detached from the eyeglasses), may be physically coupled to a hat or a helmet, or may be mounted to the user's head using any other known device that keeps the camera in a fixed position relative to the user's head also when the head moves. Sentences in the form of "sensor physically coupled to the frame" mean that the sensor moves with the frame, such as when the sensor is fixed to (or integrated into) the frame, and/or when the sensor is fixed to (or integrated into) an element that is physically coupled to the frame, and/or when the sensor is connected to the frame with a clip-on mechanism.

Sentences in the form of "a frame configured to be worn on a user's head" or "a frame worn on a user's head" refer to a mechanical structure that loads more than 50% of its weight on the user's head. For example, an eyeglasses frame may include two temples connected to two rims connected by a bridge, the frame in Oculus Rift™ includes the foam placed on the user's face and the straps; and the frame in Google Glass™ is similar to an eyeglasses frame. Additionally or alternatively, the frame may connect to, be affixed within, and/or be integrated with, a helmet (e.g., a safety helmet, a motorcycle helmet, a combat helmet, a sports helmet, a bicycle helmet, etc.), goggles, and/or a brainwave-measuring headset.

Sentences in the form of "a frame configured to be worn on a user's head in a consistent manner" refer to a frame that is located in the same position relative to the head when worn repeatedly, and thus sensors attached to that frame are most likely to be positioned each time at the same location relative to the head. For example, eyeglasses frames, goggles, and helmets are all included under the definition of a frame that is worn in a consistent manner. However, a flexible headband, or adhesive sensors that are placed manually one by one, are not worn in a consistent manner, because these sensors are most likely to be positioned each time in a different location relative to the head.

The term "smartglasses" refers to any type of a device that reminds eyeglasses, and includes a frame configured to be worn on a user's head in a consistent manner, and includes electronics to operate one or more sensors. The frame may be an integral part of the smartglasses, and/or an element that is connected to the smartglasses. Examples of smartglasses include: any type of eyeglasses with electronics (whether prescription or plano), sunglasses with electronics, safety goggles with electronics, sports goggle with electronics, augmented reality devices, virtual reality devices, and mixed reality devices. In addition, the term "eyeglasses frame" refers to one or more of the following devices, whether with or without electronics: smartglasses, prescription eyeglasses, plano eyeglasses, prescription sunglasses, plano sunglasses, safety goggles, sports goggle, an augmented reality device, virtual reality devices, and a mixed reality device.

The term "smart-helmet" refers to a helmet that includes a frame configured to be worn on a user's head in a consistent manner, and includes electronics to operate one or more sensors. The frame may be an integral part of the smart-helmet, and/or an element that is connected to the smart-helmet. Examples of smart-helmets include: a safety helmet with electronics, a motorcycle helmet with electronics, a combat helmet with electronics, a sports helmet with electronics, and a bicycle helmet with electronics.

Examples of electronics that may be included in smartglasses and/or a smart-helmet include one or more of the following electronic components: a computer, a microcontroller, a processor, a memory, and a communication interface. The electronics of the smartglasses and/or smart-helmets may be integrated in various ways. For example, the electronics may be integrated into the package of one of the sensors, such as a camera housing that is physically coupled to a helmet, where the housing includes the imaging sensor and its processor, memory, power supply and wireless communication unit. In another example, the electronics may be integrated into the frame, such as a microcontroller, power supply and wireless communication unit that are integrated into an eyeglasses frame, and configured to operate a PPG device and a microphone that are physically coupled to the frame.

The term "Visible-light camera" refers to a non-contact device designed to detect at least some of the visible spectrum, such as a video camera with optical lenses and CMOS or CCD sensor. The term "thermal camera" refers to a non-contact device that measures electromagnetic radiation having wavelengths longer than 2500 nanometer (nm) and does not touch its region of interest (ROI). A thermal camera may include one sensing element (pixel), or multiple sensing elements that are also referred to herein as "sensing pixels", "pixels", and/or focal-plane array (FPA). A thermal camera may be based on an uncooled thermal sensor, such as a thermopile sensor, a microbolometer sensor (where microbolometer refers to any type of a bolometer sensor and its equivalents), a pyroelectric sensor, or a ferroelectric sensor.

A reference to a "camera" herein may relate to various types of devices. In one example, a camera may be a visible-light camera. In another example, a camera may capture light in the ultra-violet range. In another example, a camera may capture near infrared radiation (e.g., wavelengths between 750 and 2000 nm). And in still another example, a camera may be a thermal camera.

When a camera is inwand-facing and head-mounted, challenges faced by systems known in the art that are used to acquire images, which include non-head-mounted cameras, may be simplified and even eliminated with some of the embodiments described herein. Some of these challenges may involve dealing with complications caused by movements of the user, image registration, region of interest (ROI) alignment, tracking based on hot spots or markers, and motion compensation.

The term "temperature sensor" refers to a device that measures temperature and/or temperature change. The temperature sensor may be a contact thermometer (such as a thermistor, a thermocouple), and/or a non-contact thermal cameras (such as a thermopile sensor, a microbolometer sensor, a pyroelectric sensor, or a ferroelectric sensor). Some examples of temperature sensors useful to measure skin temperature include: thermistors, thermocouples, thermoelectric effect, thermopiles, microbolometers, and pyroelectric sensors. Some examples of temperature sensors useful to measure environment temperature include: thermistors, resistance temperature detectors, thermocouples, thermopiles, and semiconductor-based sensors.

The term "movement sensor" refers to a sensor comprising one or more of the following components: a 3-axis gyroscope, a 3-axis accelerometer, and a 3-axis magnetometer. The movement sensor may also include a sensor that measures barometric pressure.

The term "acoustic sensor" refers to a device that converts sound waves into an electrical signal. An acoustic sensor can be a microphone, such as a dynamic microphone that works via electromagnetic induction, a piezoelectric microphone that uses the phenomenon of piezoelectricity, a fiber-optic microphone that converts acoustic waves into electrical signals by sensing changes in light intensity, a Micro-Electrical-Mechanical System (MEMS) microphone (such as silicon MEMS and piezoelectric MEMS), and/or other sensors that measure sound waves, such as described in the following examples: (i) Han, Jac Hyun, et al. "Basilar membrane-inspired self-powered acoustic sensor enabled by highly sensitive multi tunable frequency band." Nano Energy 53 (2018): 198-205, describes a self-powered flexible piezoelectric acoustic sensor having high sensitivity, (ii) Rao, Jihong, et al. "Recent Progress in Self-Powered Skin Sensors." Sensors 19.12 (2019): 2763, describes various self-powered acoustic skin sensors, such as an integrated triboelectric nanogenerator (TENG) with a polymer tube that can pick up and recover human throat voice even in an extremely noisy or windy environment, and (iii) Scanlon, Michael V. Acoustic sensor for voice with embedded physiology. Army Research Lab Adelphi MD, 1999, describes a gel-coupled acoustic sensor able to collect information related to the function of the heart, lungs, and changes in voice patterns.

Herein, the term "blood pressure" is indicative of one or more of the following: the systolic blood pressure of the user, the diastolic blood pressure of the user, and the mean arterial pressure (MAP) of the user. It is specifically noted that the term "blood pressure" is not limited to the systolic and diastolic blood pressure pair.

The terms "substance intake" or "intake of substances" refer to any type of food, beverage, medications, drugs, smoking/inhaling, and any combination thereof.

Some embodiments of systems, methods, and/or computer products for managing access by controlling passage through a doorway are described below. An aspect of these embodiments is utilization of wearable devices, worn by users, in order to determine whether their physiological signals indicates they are healthy, and thus should be allowed through the doorway. Physiological signals may also be used to determine that a person wearing the wearable device, and seeking to pass through the doorway, is the same person determined to be in a healthy state.

FIG. 1 is a schematic illustration embodiments of a system configured to grant passage through a doorway based on a user's health state. In one embodiment, the system includes at least a wearable device 840 and a computer 847. The computer 847 utilizes measurements of the user, taken with the wearable device 840, both on that day, and on earlier days, to determine if the user's health state permits passage through the doorway, and also to determine whether the user wearing the wearable device 840 is the person who wore the wearable device 840 when the earlier measurements were taken. Some embodiments of the system may optionally include additional elements such as a controller 849, which is configured to command an automatic door to open, close, lock and/or unlock, based on signals sent from the computer 847.

The wearable device 840 may include various types of sensors that may be used to measure the user wearing the wearable device and/or the environment that is user is in. In some embodiments, the wearable device includes a photoplethysmogram (PPG) sensor 841 that measures a signal indicative of a photoplethysmogram (PPG) signal of the user wearing the wearable device 840, and a temperature sensor 842 that measures a temperature of the user. Optionally, the PPG sensor 841 and/or the temperature sensor 842 may be head-mounted sensors, such as sensors coupled to, and/or embedded in, frames of smartglasses, such as the smartglasses illustrated in FIG. 2, which is discussed below.

Optionally, the wearable device 840 may include additional sensors, such as an acoustic sensor 843, a inertial measurement unit (IMU) 844, and/or an environment sensor 845. These sensors may provide signals that can be utilized by the computer 847 to determine the user's health state, as discussed further below.

In some embodiments, the PPG sensor 841 may be a contact PPG device. Some examples of configurations for the PPG sensor 841, which may be used in different embodiments, include: a contact PPG device embedded in the nosepiece of smartglasses in order to take measurements indicative of blood flow at and/or near the nose, a contact PPG device embedded inside an earbud in order to take measurements indicative of blood flow in the ear, a contact PPG device embedded in a smart band or smartwatch to take measurements indicative of blood flow in the wrist, or a contact PPG device embedded in a patch that may be attached to a portion of the body in order to take measurements of blood flow at the attached region.

The contact PPG device may include one or more light sources configured to illuminate a region on the user's body with which the contact PPG device comes in contact. For example, the one or more light sources may include light emitting diodes (LEDs) that illuminate the region. Optionally, the one or more LEDs include at least two LEDs, where each illuminates the region with light at a different wavelength. In one example, the at least two LEDs include a first LED that illuminates the region with green light and a second LED that illuminates the region with infrared light. The contact PPG device may also include one or more photodetectors configured to detect extents of reflections from the region. In another example, the contact PPG device includes four light sources, which may be monochromatic (such as 625 nm, 740 nm, 850 nm, and 940 nm), and a CMOS or CCD image sensor (without a near-infrared filter, at least until 945 nm).

In other embodiments, the PPG sensor 841 may be a non-contact device. For example, the PPG sensor 841 may be a video camera configured to capture images of a region that includes skin on the user's head (e.g., images that include a region of the forehead, a cheek, and/or a temple). From these images, PPG signals may be extracted utilizing various techniques known in the art at described herein. In one example, the video camera is an inward-facing head-mounted video camera, such as an inward-facing camera coupled to a frame of smartglasses. Additional details about utilizing inward-facing cameras to obtain PPG signals, including possible locations of the cameras, properties of the cameras (e.g., weight, imaging resolution, use of radiation filters for certain spectrum interval, and/or utilization of emitters), as well as various approaches that may be used to process images are provided in in more detail in US Patent Application 2020/0397306, "Detecting fever and intoxication from images and temperatures", which is incorporated herein by reference.

Different types of temperature sensors may be used in embodiments described herein. In some examples, the temperature sensor 842 may be a contact temperature sensor, such as a sensor embedded in a nose piece of smartglasses, embedded in an earbud, or embedded in a patch attached to a region of the user's body. In other examples, the temperature sensor 842 may be a non-contact sensor, such as a thermal camera that takes measurements of a certain region on the user's face. In one example, the thermal camera may be configured to take a measurement of the temperature at a temple of the user. In another example, the thermal camera may be configured to take a measurement of the temperature at a periorbital region of the user. In yet another example, the thermal camera may be configured to take a measurement of the temperature at user's forehead.

The temperature of the user measured by the temperature sensor 842 may refer to different types of values. In one example, "the temperature of the user" is a temperature of the skin of the user at the area measured by the temperature sensor 842. In another example, "the temperature of the user" refers to a value of the user's core body temperature, which is estimated based on a measurement of the temperature sensor 842.

In some embodiments, estimating values based on measurements of the temperature sensor 842, such as estimating the core body temperature may involve utilization of measurements from additional sensors. For example, core body temperature may be estimated utilizing images of the user's face captured with a video camera and/or temperatures of the environment (e.g., obtained by the environment sensor 845). Utilizing these multiple sources of data is discussed in more detail in US Patent Application 2020/0397306, "Detecting fever and intoxication from images and temperatures", which is incorporated herein by reference. Additionally, in some embodiments, the wearable device 840 may include multiple temperature sensors, which may measure temperature at various locations on the user's face. For example, the multiple temperature sensors may be head-mounted sensors, such as temperature sensors embedded in frames of smartglasses, which take measurements of multiple regions on the user's head. Calculation of temperature values by aggregating measurements from multiple regions is discussed in more detail in US Patent Application 2021/0007607, "Monitoring blood sugar level with a comfortable head-mounted device", which is incorporated herein by reference.

The wearable device 840 may optionally include one or more acoustic sensors, such as the acoustic sensor 843, which are configured to take audio recordings of the user. In one example, the one or more acoustic sensors are mounted to a frame worn on the user's head, such as a frame of smartglasses, at fixed positions relative to the head of the user. The audio recordings of the user may include recordings of sounds produced by the user, such as sounds of respiration, coughing, speech, and the like. Indications of the user's respiration and/or extent of coughing may be signals utilized to calculate a health score of a user, as discussed below.

In one embodiment, the wearable device 840 includes the IMU 844. Optionally, the IMU 844 may be head-mounted, such as an IMU embedded in frames of smartglasses. Optionally, the IMU 844 measures a signal indicative of one or more of the following: movements of the user's body (e.g., due to walking, climbing stairs, etc.), movements of the head of user, an orientation of the head of the user with respect to the earth's gravity (i.e., an angle between the head's orientation and the direction in which gravity acts). It is to be noted that various patterns of movements of the user's head may be detected using approaches known in that art to detect activities (e.g., walking or running), as well as whether the user is coughing, talking, or breathing.

In another embodiment, the wearable device 840 includes the environment sensor 845. Optionally, the environment sensor 845 measures the temperature of the environment. Examples of possible embodiments for a sensor that measures the temperature of the environment include: (i) a non-contact temperature sensor, such as a thermopile or a microbolometer sensor, and (ii) a contact temperature sensor, such as a thermistor or a thermocouple. Additionally or alternatively, the environment sensor 845 may be a humidity sensor (hygrometer).

It is to be noted that references to the wearable device 840 being worn by a user may be interpreted as one or more wearable devices worn by said user. When the wearable device 840 refers to more than one wearable device, the aforementioned sensors need not be comprised in a single device. For example, the reference to the wearable device 840 may, in some examples, refer to a first device, e.g., a smartwatch with a contact PPG sensor, and a second device, e.g., a smart shirt with embedded temperature sensors. In other examples, such as the smartglasses illustrated in FIG. 2, various sensors are coupled to a single wearable device.

Figure 2:
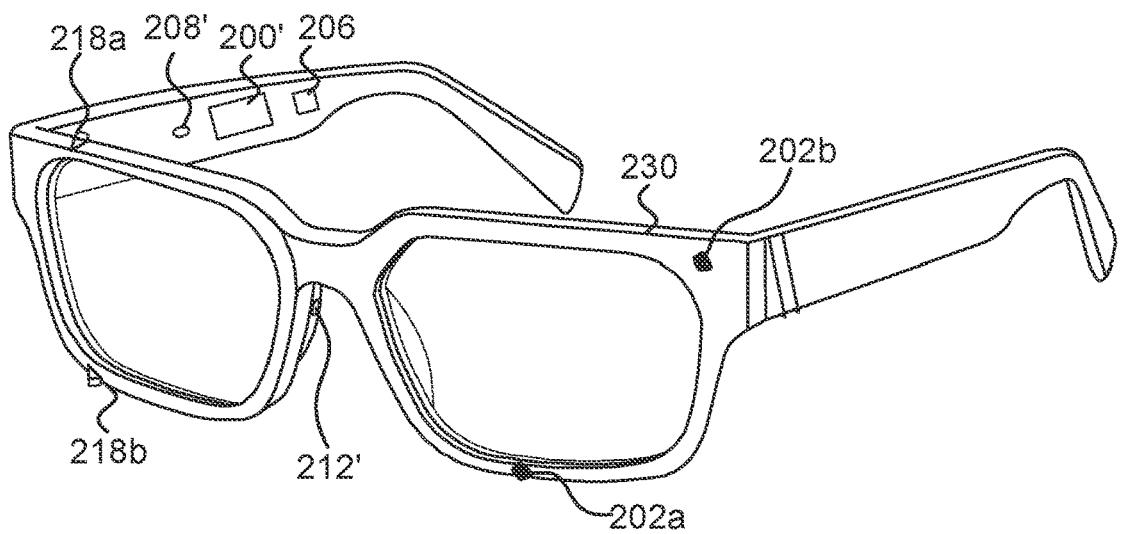
FIG. 2 illustrates an example of smartglasses that may be considered an embodiment of a wearable device that is utilized in some embodiments described herein.

FIG. 2 illustrates an example of smartglasses that may be considered an embodiment of the wearable device 840 that is utilized in some embodiments described herein. FIG. 2 illustrates just one possible embodiment of a combination of some of the components described in FIG. 1. The smartglasses include at least a frame 230, which is configured to be worn on a user's head, and several sensors configured to measure the user and/or the environment. Acoustic sensors 202a and 202b, which may be used to take audio recordings of the user, are mounted at fixed positions on the frame 230 (below and above the left lens, respectively). Contact PPG device 212' is located in the nose piece, and may be utilized to generate a PPG signal of the user, from which the heart rate of the user may be derived, as well as other blood flow-related parameters. Inward-facing cameras 218a and 218b are attached to the frame 230 at locations that are above and below the right lens, respectively. The inward-facing camera 218a is pointed upwards and configured to capture images of a region above the user's eyes (e.g., a portion of the forehead). The inward-facing camera 218b is pointed downwards and configured to capture images of a region below the user's eyes (e.g., a portion of a cheek). A non-contact thermal sensor 208' is coupled to a temple of the smartglasses, which is part of the frame 230, and is configured to measure temperature at a region on the user's face. Additional thermal sensors may be coupled to the frame 230 and be used to measure temperatures at different regions. Environment temperature sensor 210, which may also be a non-contact thermal sensor, is coupled to the frame 230 such that it is pointed away from the user's face in order to measure the temperature of the environment. Movement sensor 206 is also coupled to the frame 230 such that it measures the motion of the user's head. The computer 200' is coupled to the frame 230 and may perform at least some, and in some embodiments, all, of the operations attributed to some of the computers in this disclosure, such as the computer 847.

The computer 847 analyzes measurements taken by the wearable device 840 of the user wearing the wearable device 840, and optionally of the environment the user is in at the time. Optionally, this analysis may involve calculations with measurements taken at different times: (i) "current measurements", which are taken with the wearable device 840 during a period that starts a certain time before the analysis is performed (e.g., a few hours before that time) and/or leading up to when the analysis is performed, and (ii) "baseline measurements" taken with the wearable device 840 on one or more earlier days. Optionally, the current measurements are taken over a duration of at least five minutes. Optionally, the baseline measurements include more than an hour of measurements, taken over a period of several days.

In different embodiments, a reference to "the computer 847", or other computers described in this disclosure, may refer to different components and/or a combination of components. In some embodiments, the computer 847 may include a processor located on the wearable device 840. In some embodiments, at least some of the calculations attributed to the computer 847, and possibly all of those calculations, may be performed on a remote processor that is not on the wearable device 840, such as a processor on the user's smartphone and/or a cloud-based server. Thus, references to calculations being performed by the "computer 847" can also be interpreted as calculations being performed utilizing one or more computers, with some of these one or more computers being in the wearable device 840. Examples of computers that may be utilized to perform the calculations of one or more computers, which may be collectively referred to as "the computer 847", are computer 400 or computer 410, illustrated in FIG. 70A and FIG. 70B, respectively.

In one embodiment, analysis of the current measurements and the baseline measurements, which are taken by the wearable device 840, involves the computer 847 performing the following: calculating a health score based on a difference between the baseline measurements and the current measurements, and calculating an extent of similarity between characteristics of the PPG signal in the current measurements and characteristics of the PPG signal in the baseline measurements. These two values may then be used to determine whether the health of the user of whom the current measurements and baseline measurements were taken, permits passage through the doorway. Herein, characteristics of the PPG signal may be any information that is derived from multiple PPG waveforms in the PPG signal of the user (e.g., relationship between fiducial points), a pulse wave template, and/or other forms of templates of PPG signals known in the art.

The current measurements of a user are measurements that reflect the present state of the user, such as the state of the user during the hours leading up to an intended time of passage through the doorway and/or at that time. As such, the current measurements include measurements of the user taken with the wearable device 840 on that same day, and possibly up to the intended time of passage through the doorway. In one example, the current measurements include measurements taken with the wearable device 840 during a period spanning one hour before the intended time of passage through the doorway and/or the time the health score and the extent of similarity are calculated. In another example, the current measurements include measurements taken with the wearable device 840 sometime during a period spanning between 3 hours before the time the health score and the extent of similarity are calculated and the time these values are calculated.

The baseline measurements include measurements that reflect a typical state of the user on earlier days (i.e., the user's baseline state). As such, the baseline measurements include measurements of the user taken with the wearable device 840 on one or more days before the intended time of passage through the doorway. In one example, the baseline measurements include measurements taken at least a day before the current measurements were taken. In another example, the baseline measurements include measurements that were taken several days, weeks, and even months before the current measurements were taken.

In some embodiments, comparing the current measurements and the baseline measurements serves two purposes. First, differences between the current measurements and the baseline measurements are used to detect deviation from a baseline state that may be indicative of a change in the health state of the user (this is reflected in the calculated health score). Second, similarities between these sets of measurements, and in particular in characteristics of PPG signals in both sets of measurements, may be used to establish, with a certain degree of certainty, that the baseline measurements and the current measurements are of the same person. This form of biometric identification can help reduce the likelihood of mistakes and/or deceptive behavior that involves measuring a first user and then providing the wearable device 840 to a second user, who poses as the first user, in order to trick the system.

In one embodiment, following calculation of the aforementioned health score and the similarity between characteristics of the PPG signal in the current measurements and the characteristics of the PPG signal in the baseline measurements, these values are evaluated in order to determine whether the user should be allowed to pass through the doorway. Optionally, responsive to the health score reaching a first threshold and the extent of the similarity reaching a second threshold, the computer 847 transmits an authorization signal 848 that permits the passage of the user through the doorway. Optionally, the authorization signal 848 indicates that a health state of the user permits passage through the doorway.

It is to be noted that herein reference to a value "reaching a threshold" means the value is at least the threshold's value (i.e., a value that reaches a threshold is equal to the threshold or greater than the threshold).

"Health scores" of users may have different types of values, in different embodiments. However, generally speaking, a value of a health score of a user is indicative of the extent to which a user is healthy and/or non-contagious. Optionally, a health score may refer to an extent to which a user displays symptoms and/or is considered contagious with respect to a certain disease (e.g., the flu, COVID-19, or some other communicable disease). Alternatively, a health score may refer to an extent to which a user is considered healthy according to general wellness considerations that involve one or more of the user's vital signs (e.g., whether the core body temperature is elevated, blood oxygen saturation is in a normal range, etc.) In one example, health scores are binary values (e.g., sick/healthy, or contagious/non-contagious). In another example, a health score of a user may be a numerical value indicative of an extent to which a user is healthy and/or non-contagious (e.g., values on a scale of 1 to 10, where 1 is very sick and 10 is very healthy). In still another example, a health score of a user may a value indicative of a probability a user is healthy and/or non-contagious.

In some embodiments, having a health score that reaches the first threshold may mean that the user is not considered to be in a state that endangers others. For example, if the health score reaches the first threshold, the user may be considered non-contagious. Additionally or alternatively, having a health score that reaches the first threshold may mean that the user is considered healthy. Additional details regarding how the computer 847 may calculate health scores in different embodiments is provided further below.

Setting a value of the first threshold may be done in various ways. In one example, the threshold is set empirically based on health scores calculated for multiple people. The health status at the time measurements of these people were taken and/or their health status on the following day or two may also be known and monitored. The value of the first threshold is then selected to ensure that health scores of a desired proportion of the people who are known to be healthy and/or non-contagious is above the first threshold. Additionally or alternatively, the value of the first threshold may be selected to ensure that health scores of a desired proportion of the people who are known to be sick and/or contagious is below the first threshold.

The extent of similarity between characteristics of the PPG signal in the current measurements and characteristics of the PPG signal in the baseline measurements is indicative, in some embodiments, of a probability that the baseline measurements and the current measurements are measurements of the same person. In some embodiments, the extent of similarity is a value that describes a distance of the current measurements from a template derived from the baseline measurements. In other embodiments, the extent of similarity is a value calculated utilizing a machine learning-based model provided with feature values generated from the current measurements and the baseline measurements, and is indicative of a probability that the current measurements and the baseline measurements are of the same person. Additional details regarding how the computer 847 may calculate the extent of similarity in different embodiments is provided further below.

Having the extent of similarity between characteristics of the PPG signal in the current measurements and characteristics of the PPG signal in the baseline measurements reach the second threshold is indicative, in some embodiments, that a probability the current measurements and baseline measurements are of the same person are at least a certain predetermined probability. For example, the predetermined probability may be greater than 50%, greater than 75%, greater than 90%, greater than 95%, or greater than 99%.

Setting a value of the second threshold may be done in various ways. In one example, the second threshold may be arbitrarily set to a predetermined value (e.g., a certain level of similarity). In other examples, the second threshold may be arbitrarily set according to performance (e.g., values in a confusion matrix). In one example, this may be done by collecting current measurements and baseline measurements of multiple people, and then the extents of similarity are calculated for "matches" (current measurements and baseline measurements of the same person), and "mismatches" (current measurements of one person and baseline measurements of a different person). The value of the second threshold may then selected to ensure that a desired proportion of extents of similarities calculated in cases of matches is above the second threshold. Additionally or alternatively, the value of the second threshold may be selected to ensure that a desired proportion of extents of similarities calculated in cases of mismatches is below the second threshold.

In some embodiments, the baseline measurements used to calculate the health score of the user may be selected from a larger pool of measurements of the user, in such a way so that user was in a condition (while the selected baseline measurements were taken) that is similar to the condition the user is in when the current measurements are taken. Being in "a similar condition" may mean different things in different embodiments.

In one example, the computer 847 selects the baseline measurements such that a difference between the temperature in the environment, measured while the baseline measurements were taken with environment sensor 845, and a temperature in the environment, measured while the current measurements were taken, is below a predetermined threshold. Optionally, the predetermined threshold is below 7° C.

In another example, the computer 847 calculates, based on measurements of the IMU 844 that are part of the current measurements, a current level of physical activity that belongs to a set comprising: being stationary, and walking. The computer 847 selects the baseline measurements that were taken while the user's movements were indicative of a similar level of physical activity.

Transmitting the authorization signal 848 is intended to enable the user wearing the wearable device 840 to pass through the doorway. This may be done in different ways. In one embodiment, transmitting the authorization signal 848 involves sending a message to an access control system that adds an identifier of the user wearing the wearable device 840, and/or an identifier of the wearable device, to a list of users and/or wearable devices that are allowed passage through the doorway. In another embodiment, transmitting the authorization signal 848 causes the doorway to change its state in order to enable the user to enter (some examples of such embodiments involve the controller 849, discussed in more detail below). Optionally, this change in state is temporary and done in response to detecting the presence of the user and/or the wearable device 840 in the vicinity of the doorway.

Certain embodiments described herein limit the type of information that is transmitted in the authorization signal 848, enabling to preserve privacy along with providing an approach to curb the spread of disease. In some embodiments, transmission of the authorization signal 848 does not involve providing an indication of the identity of the user and/or does not involve authentication of said identity. For example, transmission of the authorization signal 848 may not involve sending the user's name, identification number, social security number, credit card number, or any other data that can be used to uniquely identify who the user is. In some embodiments, transmission of the authorization signal 848 does not involve providing an indication of the identity of the wearable device 840, such as a MAC address or a SIM card serial number (ICCID). Thus, in some embodiments, transmission of the authorization signal 848, even on multiple occasions, does not have to involve transmitting information that directly contributes to identification of the user and/or of the wearable device 840 (which can be used to identify a user who purchased the device and/or uses it on a regular basis).

Transmission of the authorization signal 848 may be done in different ways and/or when different conditions are met, in different embodiments. In some embodiments, the authorization signal 848 is transmitted once, which is sufficient to effect changes in the doorway that enable the user wearing the wearable device 840 to pass through the doorway. In other embodiments, the authorization signal 848 is transmitted when the wearable device 840 detects its location is in the vicinity of the doorway (e.g., based on GPS location, triangulation from Wi-Fi or cellular transmissions, and other similar detection methods). In still other embodiments, the authorization signal 848 may be sent in response of receiving a communication, e.g., from the controller 849, indicating a request for the transmission of the authorization signal 848.

Transmission of the authorization signal 848 may cease in response to detecting certain conditions, such as detecting that the wearable device 840 is not in the vicinity of the doorway, that the wearable device 840 has passed through the doorway, and/or that the wearable device 840 might have been removed from the user wearing it.

Encryption and security are important factors of some of the embodiments described herein. This involves protection from eavesdropping and abuse by external parties, for example, parties intending to steal information about the user wearing the wearable device 840 and/or copy an authorization signal and transmit it on another occasion. Encryption and security are also helpful in protecting from abuse by wearers of the wearable device 840. e.g., in order to falsify the health state and/or identity of the wearer of the wearable device 840. There are many approaches, algorithms, and types of hardware known in the art that may be used to secure the wearable device 840, the computer 847, and the integrity of communications between these components (which include the authorization signal 848 and optionally other communications too). The following are some limited examples of approaches that may be used. Various security measures known in the art, which may be utilized in some embodiments (including additional approaches not mentioned below) are described in references mentioned below.

In some embodiments, sensors on the wearable device 840, such as the PPG sensor 841, the temperature sensor 842, and/or other sensors may incorporate a hardware-based layer of security. For example, the data they send to other components of the wearable device 840 and/or the computer 847 involve a method of data masking, such as encryption using a chaotic stream cipher. An example of an implementation of such an approach for sensor-level encryption of temperature measurements is provided in Hedayatipour, et al. "A temperature sensing system with encrypted readout using analog circuits." 2019 *IEEE* 62nd *International Midwest Symposium on Circuits and Systems* (*MWSCAS*). IEEE, 2019.

In some embodiments, when transmitting the authorization signal 848, the computer 847 utilizes one or more cryptographic approaches to encrypt the authorization signal 848 and/or authenticate the wearable device 840. In one example, the computer 847 may utilize a static token, which may be inaccessible to other hardware component unless the conditions for transmitting the authorization signal 848 are met. In another example, synchronous dynamic tokens may be used, e.g., involving a timer to rotate through various combinations produced by a cryptographic algorithm. In this example, both a component receiving the authorization signal 848 and the computer 847 possess synchronized clocks. In another example, asynchronous tokens may be generated by the computer 847 and used for the authorization signal 848 without the need for a synchronized clock, e.g., using an implementation of a one-time pad or a cryptographic algorithm. In yet another example, the authorization signal 848 may be transmitted via a challenge and response scheme. In this example, public key cryptography can be used to prove possession of a private key without revealing that key. An authentication server may encrypt a challenge (typically a random number, or at least data with some random parts) with a public key; the computer 847 proves it possesses a copy of the matching private key by providing the decrypted challenge.

In some embodiments, the computer 847 may utilize A Trusted Platform Module (TPM) to implement one or more of the various security measures described herein. For example, the TPM may include a unique RSA key burned into it, which is used for asymmetric encryption. Additionally, the TPM may be used to generate, store, and protect other keys used in the encryption and decryption process.

More details about measures known in the art that may be implemented in embodiments described herein, via hardware, software, and/or firmware, in order protect the fidelity of the authorization signal 848 and/or secure communications between sensors and the computer 847 and/or the computer 847 and other parties are described in the reference El-Hajj, et al. "A survey of internet of things (IoT) authentication schemes", *Sensors* 19.5 (2019); 1141, and Alaba, et al. "Internet of Things security: A survey." *Journal of Network and Computer Applications* 88 (2017): 10-28.

The controller 489 is configured to command an automatic door to open and/or unlock, permitting the passage through the doorway, responsive to receiving the authorization signal 848. The automatic door includes a barrier that restricts the passage through the doorway when the automatic door is in a closed and/or locked position. FIG. 1 illustrates two positions for an automatic door, being closed (846A) and being open (846B), for example, following transmission of the authorization signal 848.

In some embodiments, the controller 849 commands the automatic door to close and/or remain shut, thereby restricting the passage through the doorway, after detecting that the user has passed through the doorway and/or not receiving an additional transmission of the authorization signal 848 within a predetermined time. For example, each transmission of the authorization signal 848 opens the automatic door for a few seconds, and then the controller 849 commands it to shut (unless another authorization signal is transmitted). In some embodiments, the controller 849 may receive a signal indicating that the user has passed through the doorway (e.g., from the wearable device 840 or some other device), which triggers it to command the automatic door to shut and/or remain shut.

In addition to transmitting the authorization signal 848 that leads to opening of the automatic door, in some embodiments the computer 480 may also transmit a second signal responsive to the health score not reaching the first threshold and/or the extent of the similarity not reaching the second threshold. Optionally, upon receiving the second signal, the controller 849 commands the automatic door to close and/or remain shut, thereby restricting the passage through the doorway.

There are various types of automatic doors that may be controlled by embodiments of systems described herein. Some examples of types of automatic doors are illustrated in FIG. 3.

In one embodiment, the automatic door is an entrance door to a room and/or building, and commanding the automatic door to open unlocks the door and/or moves the door to an open position, enabling the user to enter the interior of the room and/or building. For example, FIG. 3 illustrates two types of entrance doors to building that may controlled using embodiments of system described herein. Sliding door 850A may be opened and/or closed based on commands of the controller 849. Turnstile door 850B may commanded by the controller 849 to turn and/or enable the door to revolve when pushed. Similarly the controller 849 may command the turnstile door 850B to stop turning and/or resist effort to force it to revolve (e.g., the door may move to a locked position that can resist force applied in an effort to make the turnstile door 850B revolve).

In another embodiment, the automatic door belongs to a vehicle 850C, and commanding the automatic door to open unlocks the door and/or moves the door to an open position, enabling the user to enter the cabin of the vehicle.

In yet another embodiment, the automatic door is a gate 850D that includes a turnstile, and commanding the automatic door to open enables the turnstile to revolve and/or revolving the turnstile, enabling the user to pass through the gate.

The health score of the user (who is wearing the wearable device 840) may be calculated in different ways by the computer 847. In some embodiments, this calculation involves utilizing differences between the baseline measurements and the current measurements of the user to determine whether there is a deviation from an expected baseline of the user and/or whether the deviation is indicative that the user may be ill and/or contagious and thus, in order to curb the spread of disease, e.g., COVID-19 or the flu, the user should not be permitted to pass through the doorway and put other people at risk.

In some embodiments, calculation of the health score by the computer 847 involves calculating, based on the baseline measurements, an expected value of a physiological signal of the user. For example, the value of the physiological signal may be skin temperature, estimated core body temperature, blood oxygen saturation, heart rate, heart rate variability, extent of coughing, or blood pressure. Additionally, calculation of the health score by the computer 847 may involve calculating, based on the current measurements, a current value of the physiological signal (for which the expected value is calculated). Given these two values, the computer 847 can then set the value of the of the health score based on a difference between the expected value and the current value of the physiological signal.

In one embodiment, the physiological signal is body temperature, and calculating of the health score utilizes a function that returns a value that is below the first threshold when a current body temperature is greater than an expected body temperature by at least a certain margin. Optionally, the certain margin is at least 0.4° C. Thus, for example, if the user is 0.5° C., warmer than expected, the health score that is calculated in this embodiment is such that it falls below the first threshold.

In another embodiment, the physiological signal is blood oxygen saturation ($SpO_2$), and calculating of the health score utilizes a function that returns a value that is below the first threshold when a current $SpO_2$ is lower than an expected $SpO_2$ by at least a certain margin. Optionally, the certain margin is at least 0.03. Thus, for example, if the user's $SpO_2$ is lower by 0.04 than expected, the health score that is calculated in this embodiment is such that it falls below the first threshold. Additionally or alternatively, the health score may depend on a qualitative change in values of $SpO_2$. For example, if it is determined that a user's baseline state is to have an $SpO_2$ level that is always above a certain threshold (e.g., 0.92) and based on the current measurements, the $SpO_2$ falls below the certain threshold, that can lead to assignment of a health score that is below the first threshold.

It is to be noted that calculation of the health score may depend on differences between expected values and current values of more than one physiological signal. Thus, in examples below the calculation of the health score may be based differences between expected and current values of multiple physiological signals. For example, the health score may be a value that depends on a first difference between expected and current values of the user's temperature and a second difference between expected and current values of the user's blood oxygen saturation levels.

Calculation of the health score may be done in different ways, in different embodiments. In some embodiments, current values of one or more physiological signals and baseline values of the one or more of the physiological signals, and/or difference between these current and baseline values, are provided to a predetermined function that calculates the health score. Optionally, the predetermined function may be represented as a lookup table that provides values of health scores determined manually, e.g., by medical experts based on their experience. Optionally, parameters of the predetermined function may be determined by regression that uses outcome variables that are health scores that were manually determined based on medical records of users.

Calculating the baseline values and/or the expected values of physiological signals may involve utilization of machine learning-based approaches. In some embodiments, calculating a current value of the physiological signal may involve generating feature values based on the current measurements, and utilizing a model to calculate the current value of the physiological signal based on the feature values. Similarly, calculating a baseline value of the physiological signal may involve generating additional feature values based on the baseline measurements, and utilizing the model to calculate the baseline value of the physiological signal based on the additional feature values. Optionally, the model is generated from training data that includes: previous measurements of the user taken with the wearable device 840, and values of the physiological signal (considered "labels" or "outcome values") obtained utilizing a sensor that is not part of the wearable device 840. Additionally or alternatively, the model may be generated from training data that includes: previous measurements of other users taken with units of the same type as the wearable device 840, and values of the physiological signal (considered "labels" or "outcome values") obtained utilizing a sensor that is not part of the units of the same type as the wearable device 840.

In some embodiments, at least some feature values utilized to calculate values of one or more physiological signals (e.g., heart rate, heart rate variability, blood pressure, or respiration) are derived from a PPG signal measured utilizing the PPG sensor 841. To this end, various approaches may be employed, which are known in the art, in order to identify landmarks in a cardiac waveform (e.g., systolic peaks, diastolic peaks) may be employed, and/or extract various types of known values that may be derived from the cardiac waveform, as described in the following examples.

In one embodiment, at least some of the feature values generated based on the PPG signal may be indicative of waveform properties that include: systolic-upstroke time, diastolic time, and the time delay between the systolic and diastolic peaks, as described in Samria, Rohan, et al. "Noninvasive cuffless estimation of blood pressure using Photoplethysmography without electrocardiograph measurement." 2014 IEEE REGION 10 SYMPOSIUM. IEEE, 2014.

In another embodiment, at least some of the feature values generated based on the PPG signal may be derived from another analysis approach of PPG waveforms, as described in US Patent Application US20180206733, entitled "Device, method and system for monitoring and management of changes in hemodynamic parameters". This approach assumes the cardiac waveform has the following structure: a minimum/starting point (A), which increases to a systolic peak (B), which decreases to a dicrotic notch (C), which increases to a dicrotic wave (D), which decreases to the starting point of the next pulse wave (E). Various features that may be calculated, as suggested in the aforementioned publication, include: value of A, value of B, value of C, value of D, value of E, systol area that is the area under ABCE, diastol area that is the area under CDE, and the ratio between BC and DC.

In still another embodiment, various approaches described in Elgendi, $M_{move}$ (2012), "On the analysis of fingertip photoplethysmogram signals". Current cardiology reviews, 8(1), 14-25, may be used in order to generate at least some of the feature values based on the PPG signal.

Additional discussion regarding feature values related to PPG signals that may be extracted from images (e.g., when the PPG sensor 841 is a video camera) and their utilization for machine learning-related calculations, similar to the described above, are provided in U.S. Pat. No. 10,791,938, titled "Smartglasses for detecting congestive heart failure", which is incorporated herein by reference.

In some embodiments, at least some feature values utilized to calculate the values of one or more physiological signals are generated from measurements of the temperature of the user, taken with the temperature sensor 842. Additionally or alternatively, one or more of the feature values may be generated from measurements of the temperature of the environment in which the user was in at the time, as measured for example, by the environment sensor 845. In one embodiment, the feature values include a temperature value itself (e.g., a value measured by the temperature sensor 842 and/or a value measured by the environment sensor 845). Additionally or alternatively, the feature values may include a difference between the temperature and a previously taken temperature (e.g., a temperature taken 10 minutes before or one hour before). Additionally or alternatively, the feature values may include a difference between the temperature and a baseline temperature, which is determined based on the baseline measurement. In one example, the feature values include a value indicative of the difference between a temperature of the user, and the average temperature of the user, as measured by the temperature sensor 842 on multiple previous days. In another example, the feature values include a value indicative of the difference between temperature of the environment, and the average temperature measured in the environment on multiple previous days.

In some embodiments, in which the wearable device 840 includes a movement sensor (e.g., the IMU 844), one or more of the feature values may be generated by the computer 847 from a signal indicative of movements of the user. Optionally, these one or more feature values are indicative of extents of one or more of the following movements: movements of the user's body (e.g., due to walking, climbing stairs, etc.), movements of the head of user, an orientation of the head of the user with respect to the earth's gravity (i.e., an angle between the head's orientation and the direction in which gravity acts).

In some embodiments, in which the wearable device 840 includes one or acoustic sensors, such as the acoustic sensor 843, the computer 847 may generate at least some feature values utilized to calculate the values of one or more physiological signals, based on audio recordings of the user. Optionally, these generated feature values may be "raw" or minimally processed values, such as various acoustic features derived from the audio recordings, as described in are provided in U.S. Pat. No. 10,791,938, titled "Smartglasses for detecting congestive heart failure", which is incorporated herein by reference. Optionally, at least some of the feature values may include higher level, respiration parameters calculated from the audio recordings such as: breathing rate, respiration volume, an indication whether the user is breathing mainly through the mouth or through the nose, exhale (inhale) duration, post-exhale (post-inhale) breathing pause, a dominant nostril, a shape of the exhale stream, smoothness of the exhale stream, and/or temperature of the exhale stream. Various algorithmic approaches may be utilized to extract parameters related to respiration from an acoustic signal. Some examples of possible approaches are provided in (i) Pramono, Renard Xaviero Adhi, Stuart Bowyer, and Esther Rodriguez-Villegas. "Automatic adventitious respiratory sound analysis: A systematic review." PloS one 12.5 (2017): e0177926, and (ii) US patent Application No. 2019/0029563, titled "Methods and apparatus for detecting breathing patterns". Optionally, at least some of the feature values generated based on the audio recordings may be indicative of the extent of behavior such as coughing and wheezing, as described in more detail in U.S. Pat. No. 10,813,559, titled "Detecting respiratory tract infection based on changes in coughing sounds", which is incorporated herein by reference.

In one non-limiting example, feature values generated by the computer 847 in order to calculate values of one or more physiological signals include: intensities of fiducial points (systolic peaks and systolic notches) identified in PPG signals extracted from measurements taken by the PPG sensor 841. Additionally the feature values generated by the computer 847 in order to calculate values of one or more physiological signals include: temperatures of the user measured by the temperature sensor 842 and temperatures of the environment measured by the environment sensor 845. In another non-limiting example, feature values generated by the computer 847 in order to calculate values of one or more physiological signals include values obtained by binning according to filterbank energy coefficients, using MFCC transform on results of FFT of audio recordings recorded by the acoustic sensor 843.

Calculation of the health score by the computer 847 may involve, in some embodiments, utilization of various machine learning methods. In some embodiments, the computer 847 generates feature values based on data comprising the current measurements and the baseline measurements, which are taken by the wearable device 840, as described above. The computer 847 can then utilize a model (also referred herein as the "health score model") to calculate, based on the feature values, the health score. Optionally, the health score model may be generated based on data of multiple users, which is collected under different conditions. In one example, the health score model is generated based on training data comprising a first set of training measurements of a plurality of users taken with wearable devices such as the wearable device 840 while the plurality of users were healthy and a second set of training measurements of the plurality of users, taken with the wearable devices, while the plurality of users were not healthy.

The data collected from the multiple users, which is used to generate the health score model, may include measurements taken at different times, while the multiple users were in various conditions of health. Optionally, for each certain user, from among the multiple users, the training data included certain first and second measurements taken with a wearable device like the wearable device 840, while the certain user had certain first and second known extents of health and/or risks of being contagious, respectively. Thus, the training data reflects measurements in which there is a known change in the state of the health, for the multiple users. Optionally, data of the multiple users is used to create samples, where each sample includes feature values generated based on measurements of a certain user and a label which is indicative of the health score that is to be assigned to the user at the time. For example, labels may be set by a physician who checked the certain user, self-reported by the certain user, and/or derived from medical records of the certain user. Optionally, the samples are generated based on measurements collected in diverse conditions (on different times of day, different locations, different environmental conditions, etc.)

Various computational approaches may be utilized to train the health score model based on the samples described above. In one example, training the model may also involve selecting the first threshold based on the samples. Optionally, a machine learning-based training algorithm known in the art may be utilized to train the model based on the samples. Optionally, the health score model includes parameters of at least one of the following types of models: a regression model, a neural network, a nearest neighbor model, a support vector machine, a support vector machine for regression, a naïve Bayes model, a Bayes network, and a decision tree.

The computer 847 may generate various types of features based on the data it receives from the wearable device 840, such as the current measurements and baseline measurements. Additionally, some of the feature values may be generated based on the additional sources of data, such as additional sensors on the wearable device 840 or sensors that are not on the wearable device 840.

In some embodiments, feature values utilized to calculate the health score include one or more of the following values: a value of a physiological signal of the user calculated based on the current measurements, a value of the physiological signal of the user calculated based on the baseline measurements, and a value indicative of a difference between the value of the physiological signal of the user calculated based on the current measurements and the value of the physiological signal of the user calculated based on the baseline measurements. Optionally, the physiological signal may be a value from among: skin temperature, estimated core body temperature, blood oxygen saturation, heart rate, heart rate variability, respiration rate, extent of coughing, or blood pressure. Optionally, the computer 847 may utilize machine learning-based approaches, as described above, to calculate the values of the physiological signal from the current and/or baseline measurements. In some embodiments, at least some of the feature values utilized to calculate the health score may maybe one or more of the various types of features values described herein (further above) as being utilized to calculate values of physiological signals from measurements taken by the wearable device 840.

Utilizing the various feature values described above can enable representation of changes to the physiological state of the user between a baseline state and the user's current state, which can assist in determining whether the user is healthy and/or non-contagious at the present time In one non-limiting example, feature values generated by the computer 847 based on the current measurements and the baseline measurements in order to calculate the health score of the user include: a baseline temperature of the user, a current temperature of the user, a baseline blood oxygen saturation level, and a current blood oxygen saturation level. Optionally, these values may be calculated using machine-learning based approaches, as already described further above.

In another non-limiting example, feature values generated by the computer 847 based on the current measurements and the baseline measurements in order to calculate the health score of the user include: a baseline extent of coughing and a current extent of coughing. Optionally, these values may be calculated based on recordings of the user with the acoustic sensor 843 and/or measurements of movements of the user, as measured with the IMU 844.

In another non-limiting example, feature values generated by the computer 847 in order to calculate the health score of the user include temperatures in the environment at different times, as measured with the environment sensor 845.

Utilization of PPG signals for biometric authentication is known in the art. In some embodiments, the computer 847 may employ one or more of the techniques described below in order to calculate the extent of the similarity between the characteristics of the PPG signal in the current measurements and the characteristics of the PPG signal in the baseline measurements.

When the similarity between the characteristics of the PPG signal in the current measurements and the characteristics of the PPG signal in the baseline measurements reaches the second threshold, this means that with a least with a certain probability, the current measurements and the baseline measurement are of the same person. This can be considered some form of authentication of the user. This form of authentication does not require providing information identifying who the person is. "Authentication", as the term is typically used in the art in the context of PPG-based biometric authentication, involves comparison with templates of PPG signals in a database. For example, when current measurements are compared to a template in a database that includes multiple users along with their identifiers, this can be considered a form of authentication (since the system then knows which of the users was matched).

Some embodiments described herein do not involve utilization of information that identifies the user being authenticated, and the process of comparing their PPG signals to previous measurements of PPG signals may not be referred to with the specific term "authentication". Nonetheless, various teachings in the art for authenticating users based on PPG signals can be used in embodiments described herein by a simple adaptation. For example, instead of comparing a PPG signal in the current measurements to PPG signals and/or templates stored in a database, the PPG signal in the current measurements can be compared to a previously measured PPG signal from the baseline measurements (which may be stored locally, e.g., on the wearable device 840 and/or in a user's own account). This process may not necessarily involve disclosure of the identity of the user, but nonetheless can utilize the same computational techniques known in the art for authenticating users based on PPG signals.

In one embodiment, the computer 847 may utilize one or more procedures of that are part of an implementation of the teachings provided in Yadav, et al., "Evaluation of PPG biometrics for authentication in different states." 2018 *International Conference on Biometrics (ICB)*. IEEE, 2018, which is incorporated herein by reference. Yadav et al, describe computational procedures in which PPG signals can be used for user authentication by employing a combination of Continuous Wavelet Transform (CWT) and Direct Linear Discriminant Analysis (DLDA), which is demonstrated to have robustness under different conditions involving different emotions (e.g., stress), physical exercise and time-lapse. Optionally, the computer 847 may utilize one or more of the pre-processing techniques described therein (filtering, peak detection, false peak removal, and segmentation). Optionally, the computer 847 may generate a baseline template from the PPG signal in the baseline measurements and a current template from the PPG signal in the current measurements utilizing the template generation approach described therein (CWT-based feature extraction and LDA-based dimensionality reduction). Optionally, calculating the extent of similarity between the characteristics of the PPG signal in the baseline measurements and the characteristics of the PPG signal in the current measurements may then be done by calculating the Pearson distance between vectors generated from the current and baseline templates, as described therein.

In another embodiment, the computer 847 may utilize one or more procedures of that are part of an implementation of the teachings provided in Sancho, et al., "Biometric authentication using the PPG: A long-term feasibility study." *Sensors* 18.5 (2018): 1525, which is incorporated herein by reference. Sancho et al, perform a comparative study of various computational approaches that may be used for PPG-based biometric authentication. Optionally, the computer 847 may utilize one or more of the pre-processing techniques described therein (filtering, PPG cycle detection, cycle normalization and alignment). Optionally, the computer 847 may generate a baseline template from the PPG signal in the baseline measurements and a current template from the PPG signal in the current measurements utilizing one of the template generation approaches described therein that are based on various feature extraction procedures (Cycles Average, KLT Average, Multi-Cycles, KLT Multi-Cycles). Optionally, calculating the extent of similarity between the characteristics of the PPG signal in the baseline measurements and the characteristics of the PPG signal in the current measurements may then be done utilizing one or more of the matching techniques described therein (e.g., Manhattan distance or Euclidian distance between the templates).

In some embodiments, user authentication based on the current and baseline measurements (or determining that these measurements are of the same person) may done using additional signals measured by sensors on the wearable device 840. In one example, voice analysis of recordings taken by the acoustic sensor 843 may be analyzed to determine that similar acoustic spectral properties appear in both sets of measurements. In another example, gait characteristics of movements measured by the IMU 844 may be compared to determine whether the person wearing the wearable device 840 while the baseline measurements and the current measurements were measured are similar.

In some embodiments, it may be desirable to ensure that following collection of the current measurements and/or transmission of the authorization signal 848, the person wearing the wearable device 840 does not remove it (e.g., in order to let someone else wear it an gain passage through the doorway). This is especially important in embodiments in which the authorization signal 848 does not include information that identifies the person wearing the wearable device 848. In these embodiments, the authorization signal 848 in essence attests that the person wearing the device is healthy and thus should be allowed through the doorway, thus it is important that that assumption still be true during passage through the doorway, otherwise the integrity of the doorway, and its ability to curb the spread of disease may be compromised.

Therefore, in some embodiments, the computer 847 determines, based on measurements taken with the wearable device 840, whether the wearable device was removed from the user's body while the current measurements were taken or after the current measurements were taken, and responsive to making a determination that he wearable device 840 has been removed, the computer 847 refrains from transmitting the authorization signal 848 and/or transmits an additional signal that makes other components (e.g., the controller 489) ignore the authorization signal 848, if it has already been sent.

In one embodiment, the computer 847 identifies when the wearable device 840 has been removed from the user wearing it based on detecting an interference in the amplitude of the PPG signal and/or phase shift of detected reflected light measured by the PPG sensor 841 that exceeds a certain threshold. Large interferences in measured PPG signals often occur when a PPG sensor's contact with the body is weakened or broken (such as when the wearable device 840 is removed). These interferences occur because ambient light and interferences of ambient light are much stronger than the signal detected when the PPG sensor is attached to the body (for contact PPG sensors). Video camera-based PPG sensors (e.g., used for iPPG) will also experience dramatic signal changes when the device is removed because, for a certain period, the images captured by video camera will have completely different color schemes. Thus, virtually any removal of the PPG sensor 841 from the body causes a large interference in the measured PPG signal which is typically not observed when the device housing the PPG sensor is firmly in place.

In another embodiment, the computer 847 identifies when the wearable device 840 is removed from the user wearing it based on detecting a rapid change in temperatures measured by the temperature sensor 842. Physiological body temperature (e.g., core body temperature and skin temperature) typically change at a slow pace, and do not have sudden changes of values such as decreases of several degrees within a few seconds. However, if the wearable device 840 is removed from the body, the temperature sensor 842 is likely to measure the environment and/or other regions of the body, at least for a short period (e.g., until the wearable device 840 is worn again by a person). Nonetheless, such a removal typically generates a spike in temperature that exceeds a predetermined threshold characteristic of temperature changes observed when the wearable device 840 is firmly in place.

Removal of the wearable device 840, whether done intentionally or accidentally, makes the current measurements non-trustworthy, since it is possible that some other person has put on the wearable device 840, in order to take advantage of the health score that has already been calculated with it. In order to be able to transmit the authorization signal 848 again, the computer 847 needs to re-establish that the same person who previously wore the wearable device 840 is wearing it again. Thus, in some embodiments, the computer 847 performs the following steps responsive to making the determination that the wearable device 840 has been removed. The computer 847 receives additional measurements of the user, taken by the wearable device 840 at most three hours after the current measurements were taken. The computer 847 then calculates an additional similarity between characteristics of the PPG signal in the current measurements and characteristics of the PPG signal in the additional measurements. If the additional similarity reaches the second threshold (and the previously calculated health score reaches the first threshold), the computer 847 transmits the authorization signal 848. Optionally, the additional similarity reaching the second threshold is indicative of a probability that the current measurements and the additional measurements are of the same person is above a predetermined threshold. It is to be noted that such a reauthorization may be done, in some embodiments, in a short period and not require extensive collection of additional measurements. In one example, the additional measurements are collected for less than one minute. In another example, the additional measurements are collected for less than 15 seconds.

In some embodiments, the computer 847 may report to the user the calculated health score. Since this is sensitive information, it may be prudent to determine that the person receiving this information is indeed the user. To this ends, the computer 847 may receive additional measurements of the user, taken with the wearable device 840, and then calculate an additional extent of similarity between characteristics of the PPG signal in the additional measurements and characteristics of the PPG signal in the baseline measurements. The computer 847 also calculates an additional health score based on a difference between the baseline measurements and the additional measurements. If the extent of similarity reaches the second threshold, the computer 847 may report the additional health score to the user and/or provide the user with an indication of whether the health state of the user permits passage through the doorway.

Curbing the spread of airborne communicable diseases, such as COVID-19 or the flu, is often done with extreme measures, such as restrictions on peoples' movements, closing places of business, and blanket orders for quarantines. The reason such extreme measures are often used is that it is difficult to determine, on a population-wide scale, who are the symptomatic people who pose a risk of spreading the communicable disease (and limit restrictions to those people). Thus, for practical reasons, often whole populations are treated as if they all pose a risk, and are subject to many restrictions, even though the majority of these people are not symptomatic and cannot spread the disease.

This, there is a need for a way to ease restrictions imposed on travel and commerce that will enable healthy and non-symptomatic people the opportunity to congregate or commute in a safe manner that greatly reduces the risk of contracting an airborne communicable disease.

One aspect of this disclosure involves utilization of wearable devices to facilitate the making of reservations for places in spaces shared with other people. (e.g., a reservation at a restaurant, reserving a seat in public transportation, etc.). Since the space is shared by others, it can be very beneficial to make sure that all the people in the shared space are healthy and/or non-contagious in order to curb the spread of disease. In some embodiments described herein, the wearable devices are utilized to determine whether the person making a reservation is likely to be healthy and/or non-contagious, and also whether the person showing up to make use of the reservation is the same person who originally made the reservation.

One aspect of this disclosure includes a method for managing reservations with wearable-based health state verifications. In one embodiment, the method includes the following steps: receiving a request to make a reservation that involves occupying a place in a space shared with other people; receiving a first indication generated based on first measurements taken during a first period by a wearable device, where the first measurements comprise values of physiological signals of the wearer of the wearable device during the first period, and the first indication indicates said wearer is healthy; providing an identifier of the reservation that reserves the place at a certain time for the wearer of the wearable device during the first period; receiving a second indication generated based on second measurements taken by the wearable device during a second period that is after the first period, wherein at least some of the second measurements were taken less than three hours before the certain time, the second measurements comprise values of physiological signals of the wearer of the wearable device during the second period, and the second indication indicates: (i) the wearer of the wearable device during the second period is the same person who wore the wearable device during the first period, and (ii) that same person is still healthy; and approving access to the space to the wearer of the wearable device.

In one example, the space is an interior of a cabin of a vehicle that accommodates a driver and/or a plurality of passengers.

In another example, the space is an interior of a building housing an eating establishment and/or entertainment complex, and the space accommodates multiple patrons. Optionally, the reservation is indicative of a certain seat reserved for the wearer of the wearable device.

In yet another example, the space is an interior of one of the following: a cabin of a public transport vehicle, a passenger train car, a cabin of an aircraft, and a ferry. Optionally, the reservation is indicative of a certain seat reserved for the wearer of the wearable device.

In one embodiment, the wearable device includes a first sensor configured to measure a signal indicative of a photoplethysmogram signal (PPG signal) of a user, and a second sensor configured to measure a temperature of the user.

In one embodiment, the method optionally includes a step of providing an interface through which the request to make the reservation is entered in response to receiving the first indication.

In one embodiment, the method optionally includes a step of canceling the reservation and/or revoking an approval of access to the space given to the wearer of the wearable device during the first period, responsive to receiving a third indication that said wearer is no longer healthy.

In one embodiment, the method optionally includes a step of canceling the reservation and/or revoking an approval of access to the space given to the wearer of the wearable device during the first period responsive to receiving a third indication indicating the wearable device has been removed from said wearer.

In one embodiment, the method optionally includes a step of providing a description of a protocol for behavior that is to be adhered to in order to preserve the reservation. Optionally, the description describes at least one of restrictions involving locations in which to remain, locations to avoid, instructions pertaining to removal of the wearable device, and instructions pertaining to extent of measurements that need to be provided with the wearable device. Optionally, the method includes a step of canceling the reservation and/or revoking an approval of access to the space given to the wearer of the wearable device during the first period responsive to receiving a fourth indication indicating that the wearer of the wearable device did not adhere to the protocol.

In one embodiment, the method optionally includes a step of commanding an automatic door that facilitates passage into the space to open and/or remain open, responsive to receiving a fifth indication indicating that the wearable device is in a vicinity of the automatic door and that the wearer of the wearable device at that time is the same person as the wearer of the wearable device during the first period.

In one embodiment, the method optionally includes a step of commanding an automatic door that facilitates passage into the space to close and/or remain shut, thus restricting passage into the space, responsive to receiving a sixth indication indicating that the wearable device is in a vicinity of the automatic door and that the wearer of the wearable device at that time is not the same person as the wearer of the wearable device during the first period.

In one embodiment, the first indication does not include information identifying the wearer of the wearable device during the first period and/or the second indication and the reservation do not include information identifying the wearer of the wearable device during the first period.

Another aspect of this disclosure is a system configured to manage access using reservations and wearable-based health state verifications. In one embodiment, the system includes a wearable device and a computer. The wearable device includes: a first sensor configured to measure a signal indicative of a photoplethysmogram signal (PPG signal) of a wearer of the wearable device, and a second sensor configured to measure a temperature of said wearer. The computer receives a request to make a reservation that involves occupying a place in a space shared with other people, and receives a first indication generated based on first measurements taken during a first period by the wearable device. Optionally, the first indication indicates a wearer of the wearable device is healthy. The computer provides an identifier of the reservation that reserves the place at a certain time for the wearer of the wearable device during the first period. The computer, at a later time, receives a second indication generated based on second measurements taken by the wearable device during a second period that is after the first period. Optionally, at least some of the second measurements were taken less than three hours before the certain time, and the second indication indicates: (i) the wearer of the wearable device during the second period is the same person who wore the wearable device during the first period, (ii) that said same person is still healthy, and (iii) that said same person is in the vicinity of an automatic door that facilitates passage into the space. The computer then commands the automatic door to open and/or remain open.

In one embodiment, the computer commands the automatic door to close and/or remain shut, thus restricting passage into the space, responsive to receiving a third indication, sent after the second indication, indicating that the wearer of the wearable device at that time is not the same person as the wearer of the wearable device during the first period.

In one example, the automatic door belongs to a vehicle, and commanding the automatic door to open unlocks the door and/or moves the door to an open position, enabling the user to enter the cabin of the vehicle.

In another example, the automatic door is an entrance door to a room and/or building, and commanding the automatic door to open unlocks the door and/or moves the door to an open position, enabling the user to enter the interior of the room and/or building.

In yet another example, the automatic door is a gate comprising a turnstile or a revolving door, and commanding the automatic door to open enables the turnstile or the revolving door to revolve and/or revolving the turnstile or the revolving door, enabling the user to pass through the gate.

Yet another aspect of this disclosure is a non-transitory computer readable medium storing one or more computer programs configured to cause a processor based system to execute steps of the aforementioned method.

Wearable-based health state verification, which can be provided by systems such as embodiments illustrated in FIG. 1, can pave the way to novel applications that involve incorporating measures intended to curb the spread of disease into well-established practices. One such scenario involves making reservations that reserve a place for a user in a space that is shared with other users (e.g., a reservation at a restaurant, reserving a seat in public transportation, etc.). Since the space is shared by others, it can be very beneficial to make sure that all the people in the shared space are healthy and/or non-contagious in order to curb the spread of disease. The following embodiments demonstrate how wearable devices can be used to provide health-state verifications in order to make reservations in a safer more efficient way. In some embodiments, the fact the wearable devices can both determine a user's health state and ensure that the user whose health state is verified is the one wearing the wearable device, can be leveraged in order to manage reservations in a manner that does not compromise user privacy.

Figure 5:
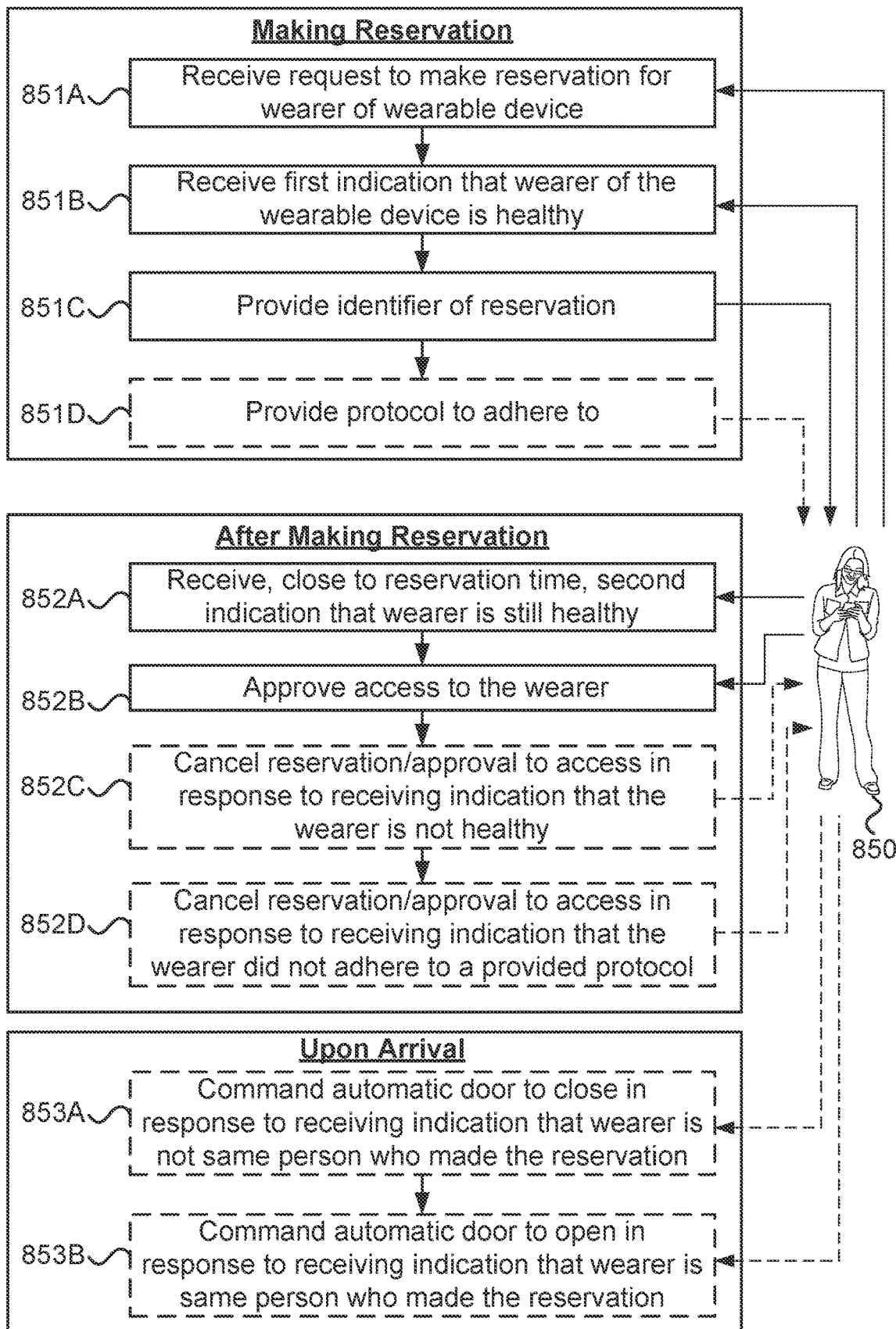
FIG. 5 illustrates steps that may be part of embodiments of a method for managing reservations with wearable-based health state verifications.

FIG. 5 illustrates steps that may be part of embodiments of a method for managing reservations with wearable-based health state verifications. The method may be implemented using embodiments of systems illustrated in FIG. 4, which is discussed further below. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform steps from among the steps illustrated in FIG. 5 and/or additional steps mentioned below. Conceptually, the steps of the method may be divided into certain steps that are performed while making a reservation, and additional steps that are performed after the reservation is made and/or upon arrival of a user to the venue for which the reservation was made.

Embodiments of the method illustrated in FIG. 5 include several steps involved in making a reservation:

In Step 851A, receiving (e.g., by a computer 854, which is discussed below), a request to make a reservation that involves occupying a place in a space shared with other people. Optionally, the request is made by the wearer of a wearable device that is used to take measurements of a user (e.g., user 850, illustrated in FIG. 4).

In Step 851B, receiving a first indication generated based on first measurements taken during a first period by the wearable device. The first measurements include values of physiological signals of the wearer of the wearable device during the first period, and the first indication indicates said wearer is healthy. Optionally, the first indication does not include information identifying the wearer of the wearable device. Optionally, the first measurements are taken over a duration of at least five minutes. Optionally, the first measurements are taken at least an hour before a time for which the reservation is made. Optionally, the first measurements are taken while the user 850 is not in the vicinity of the space that is to be shared with other people.

In one embodiment, the method includes an optional step of providing an interface through which the request to make the reservation is entered in response to receiving the first indication. This way, reservations are only placed by people who are healthy, which can save time and/or avoid disappointment due to filling out details of a reservation only to shortly thereafter learn that the reservation cannot be made due to there not being a required indication of the state of health.

And In Step 851C, the method includes a step of providing an identifier of the reservation, which reserves the place at a certain time for the wearer of the wearable device during the first period. Optionally, neither the reservation nor the identifier of the reservation include information that identifies the person for whom the reservation is made (i.e., the person wearing the wearable device). For example, the identifier may include a certain code that is not easy to guess or forge, and thus only the maker of the reservation is like to be able to produce the code if requested.

In some embodiments, the first measurements include a signal indicative of a PPG signal of the wearer of the wearable device and a temperature of the wearer of the wearable device. Optionally, the wearable device used to provide the first measurements received in Step 851B is the wearable device 840 that includes PPG sensor 841 and temperature sensor 842, which provide the aforementioned PPG signal and temperature of the wearer of the wearable device.

In some embodiments, the first indication is generated by a certain computer, such as the computer 847, by calculating a value indicative of the health state of the wearer of the wearable device that is based on the first measurements. Optionally, the certain computer may utilize one or more of the approaches described above, with respect to the calculation of the health score of a user by the computer 847. In one example, the value indicative of the health state of the wearer of the wearable device is calculated by a function that evaluates the first measurements and compares them to certain thresholds. For example, if the temperature is below 37.5° C., and the blood oxygen saturation is above 0.92, that person is considered healthy. In another example, the certain computer may utilize one or more the machine learning approaches described with respect to calculation of the health score by the computer 847, such as generating feature values based on the first measurements and utilizing a model to calculate, based on the feature values, a value that indicates whether the wearer of the wearable device is healthy and/or non-contagious (which is used to decide whether to send the first indication).

In other embodiments, the first indication is the authorization signal 848 and/or the first indication is sent based on the same criteria that would lead to sending the authorization signal 848, by the computer 847. Optionally, the first indication is sent by the computer 847 following calculation of a health score for the wearer of the wearable device, which reaches the first threshold and calculation of similarity of PPG signals that reaches the second threshold. In this case, the first measurements may be considered the "current measurements" mentioned with respect to embodiments illustrated in FIG. 1. To calculate the health score and the similarity of PPG signals, the first measurements are compared to baseline measurements, taken at earlier times by the wearable device, as described above in the discussion regarding embodiments illustrated in FIG. 1.

Various types of reservations may be made with the method illustrated in FIG. 5. In one example, the reservation may involve reserving a vehicle, whose cabin space is shared with a driver and/or other vehicles. Optionally, the certain time of the reservation corresponds to an expected arrival time of the vehicle. In another example, the reservation involves reserving a place at the certain time in a building housing an eating establishment and/or entertainment complex, which may be shared by multiple patrons. Optionally, the reservation is indicative of a certain seat reserved for the wearer of the wearable device. In yet another example, the reservation is for a seat in one or more of the following: a public transport vehicle, a passenger train car, an aircraft, and a ferry. Optionally, the reservation is indicative of a certain seat reserved for the wearer of the wearable device.

Embodiments of the method illustrated in FIG. 5 include additional steps that may take place some time after the reservation is made:

In Step 582A, receiving a second indication generated based on second measurements taken by the wearable device during a second period that is after the first period. Optionally, the second measurements include values of physiological signals of the wearer of the wearable device during the second period. Optionally, the second indication indicates: (i) the wearer of the wearable device during the second period is the same person who wore the wearable device during the first period, and (ii) that same person is still healthy. Optionally, the second indication does not include information the identifies the wearer of the wearable device during the first and/or second periods.

And in Step 852B, approving access to the space to the wearer of the wearable device.

Approving the access may be done in various ways. In one example, after receiving the second indication the wearable device may be sent an access code enabling entrance to the space. In another example, after receiving the second indication, the wearable device may transmit information identifying the wearer of the wearable device, which may be utilized to grant the wearer to access to the space. In this example, identifying information of the wearer of the wearable device is only provided if the wearer is healthy and about to make use of the reservation. No identifying information is provided if the wearer of the wearable device does not want to keep the reservation, or if it turns out that the wearer is not healthy.

The second period takes place near the time of the reservation. Thus, the second measurements can reflect the health status of the wearer of the wearable device at the certain time for which the reservation is made. In one example, the second period ends less than three hours before the certain time (to which the reservation corresponds). In another example, the second period ends less than five minutes before the certain time. In yet another example, the second period overlaps with an arrival time of the wearer of the wearable device at a venue of the reservations (i.e., in vicinity of the shared space that is to be shared with other people).

The second indication is similar in its nature to the first indication, and thus, can involve using similar computational approaches used to generate the first indication that is received in Step 851B. For example, determining that the wearer of the wearable device is still healthy can be done by calculating a second value indicative of the health state of the wearer of the wearable device that is based on the second measurements. In the case that the computational approach involves calculation of a health score based on differences between current measurements and baseline measurements, the second measurements may be used as the "current measurements" for the purpose of calculation of the health score.

The second indication also indicates that the wearer of the wearable device during the second period is the same person who wore the wearable device during the first period. Optionally, this fact is determined by calculating an extent of similarity between characteristics of the PPG signal in the second measurements and characteristics of the PPG signal in the first measurements. Optionally, this extent of similarity is compared with the second threshold, and if it reaches it, a determination is made that the first measurements and second measurements are of the same person.

Embodiments of the method illustrated in FIG. 5 may optionally include additional steps that may take place upon arrival to a venue of the reservation (i.e., arrival in the vicinity of the space that is to be shared with others). Optionally, these steps involve operating an automatic door the facilitates access to the space.

In one embodiment, the method optionally includes step 853A, which involves commanding an automatic door that facilitates passage into the space to open and/or remain open, responsive to receiving an indication that the wearable device is in a vicinity of the automatic door and that the wearer of the wearable device at that time is the same person as the wearer of the wearable device during the first period. Optionally, the indication is generated by receiving transmissions from the wearable device that can be detected only when the wearable device is near (e.g., up to 10 meters) from the automatic door. Additionally or alternatively, multiple receivers near the automatic door may be utilized to triangulate transmission of the wearable device and determine its location. Optionally, determining that the wearer of the wearable device at that time is the same person as the wearer of the wearable device during the first period may done by calculating an extent of similarity of characteristics of PPG signal in measurements taken when the wearer is near the automatic door with characteristics of PPG signals in the first measurements, and observing that the extent of similarity reaches the second threshold.

In another embodiment, the method optionally includes step 853B, which involves commanding an automatic door that facilitates passage into the space to close and/or remain shut, thus restricting passage into the space, responsive to receiving an indication indicating that the wearable device is in a vicinity of the automatic door and that the wearer of the wearable device at that time is not the same person as the wearer of the wearable device during the first period. Optionally, determining that the wearer of the wearable device at that time is not the same person as the wearer of the wearable device during the first period may done by calculating an extent of similarity of characteristics of PPG signals in measurements taken when the wearer is near the automatic door with characteristics of PPG signals in the first measurements, and observing that the extent of similarity does not reach the second threshold.

In some embodiments, the method may optionally include Step 851D that involves providing a description of a protocol for behavior that is to be adhered to (by the wearer of the wearable device and/or the wearable device itself) in order to preserve the reservation. Optionally, the description describes at least one of the following: restrictions involving locations in which to remain, locations to avoid, instructions pertaining to removal of the wearable device (e.g., prohibiting the removal of the wearable device), and instructions pertaining to extent of measurements that need to be provided with the wearable device (e.g., frequency and/or duration of measurements that should be taken using the wearable device). Optionally, the method may include a step that involves canceling the reservation and/or revoking an approval of access to the space given to the wearer of the wearable device during the first period, responsive to receiving an indication indicating that the wearer of the wearable device did not adhere to the protocol. For example, if it is detected from transmissions of the wearable device that the wearer went into a forbidden area and/or that at least a certain extent of measurements were not taken, then the reservation may be canceled.

In some embodiments, the integrity of managing reservations by verifying health states, as described above, relies on the fact that reservations should be kept for users who are healthy and for whom this state is verifiable. If a user is not healthy and/or if this fact cannot be verified, the user's reservation should be canceled. Thus, in some embodiments, the method me optionally include Step 852C, which involves canceling the reservation and/or revoking an approval of access to the space given to the wearer of the wearable device during the first period, responsive to receiving an indication that said wearer is no longer healthy. Optionally, this indication may be sent automatically by the computer 847 as part of a protocol according to which the wearable device and/or the computer 847 are to adhere.

In some embodiments, the integrity of managing reservations by verifying health states, as described above, relies on the fact that reservations should only be honored for users who made them. For example, it is undesirable for it to be possible for one person, who is healthy, to make a reservation and then give the wearable device used to make the reservation to another person, whose health state has not been verified, in order for that person to gain access to shared space. Thus, in some embodiments, the method optionally includes Step 852D, which involves canceling the reservation and/or revoking an approval of access to the space given to the wearer of the wearable device during the first period responsive to receiving an indication indicating the wearable device has been removed from said wearer. Optionally, this indication may be sent automatically by the computer 847.

FIG. 4 illustrates components of an embodiment of a system configured to manage access using reservations and wearable-based health state verifications. The system include the wearable device 840, which includes at least: a first sensor (the PPG sensor 841) that measures a signal indicative of a photoplethysmogram signal (PPG signal) of a wearer of the wearable device 840, and a second sensor (temperature sensor 842) that measures a temperature of said wearer. The system also includes a computer 854, and optionally, an automatic door 855.

The computer 854 manages the process of making and managing reservations, and in this process communicates with the wearable device 840 and/or a computer that sends indications on behalf of the wearable device 840 (and/or on behalf of the wearer of the wearable device 840), such as the computer 847.

In one embodiment, the computer 854 receives a request to make a reservation that involves occupying a place in a space shared with other people. For example, the request may be transmitted from a device used by a user wearing the wearable device 840, a computer that is in communication with the wearable device 840, such as the computer 847 (which may optionally be part of the wearable device 840), or some other computer. Additionally, the computer 854 receives a first indication generated based on first measurements taken during a first period by the wearable device 840. In one example, the first period ends at most three hours before the first indication is generated. Optionally, the first indication is generated by the computer 847 and it indicates that the wearer of the wearable device 840 is healthy. In response to receiving the first indication, the computer 854 provides an identifier of the reservation, which reserves the place at a certain time for the wearer of the wearable device 840 during the first period.

At a later time, which is closes to the certain time of the reservation, the computer 854 receives a second indication generated based on second measurements taken by the wearable device 840 during a second period that is after the first period. Optionally, at least some of the second measurements are taken less than three hours before the certain time, and the second indication indicates: (i) the wearer of the wearable device during the second period is the same person who wore the wearable device during the first period, (ii) that said same person is still healthy, and (iii) that said same person is in the vicinity of an automatic door 855 that facilitates passage into the space. Optionally, the second indication is generated by the computer 847.

In some embodiments, after receiving the second indication, the computer 854 commands the automatic door 855 to open and/or remain open. Optionally, this command is issued following a detection of transmissions of the wearable device 840 indicating that the wearable device is near the automatic door 855.

In other embodiments, the computer 854 commands the automatic door 855 to close and/or remain shut, thus restricting passage into the space, responsive to receiving a third indication, sent after the second indication, indicating that the wearer of the wearable device at that time is not the same person as the wearer of the wearable device during the first period. For example, the computer 847 may send the third indication if an extent of similarity between characteristics of PPG signals in additional measurements taken while the wearable device 840 was near the automatic door 855 and characteristics of PPG signals in the first or second measurements fall below the second threshold.

Social distancing has emerged as one of the keystone measures put in place to curb the spread of airborne infectious diseases. However, strict social distancing is often difficult to maintain in real life, since people still need to work, commute, and maintain some level of social contact in their daily and professional lives. While people can try and be careful and maintain a certain physical distance from people around them, there are situations in which such contact can accidently occur despite people's vigilance and best intentions. One scenario in which, accidental and unwanted contact can occur with people involves passage through doorways (e.g., building entrances, office doors, etc.) When one approaches a closed door, it is usually not clear if there is someone on the other side and/or whether that person is healthy and/or non-contagious. Thus, in order to avoid such unwanted contacts, especially with people whose health state is unverified, there is a need for a novel type of doorways that can assist in maintaining safe social distancing practices.

Figure 6:
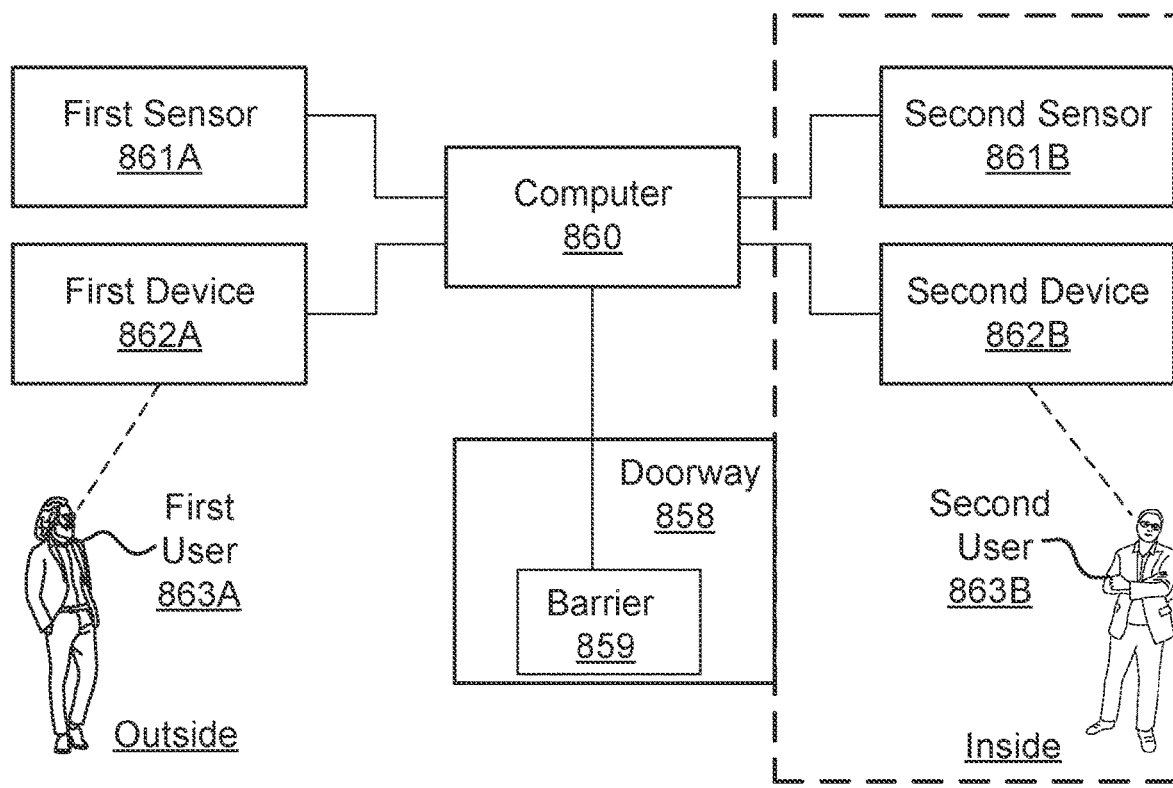
FIG. 6 is a schematic illustration of a doorway system.

FIG. 6 illustrates a doorway system that includes a doorway 858 that facilitates passage from an inside to an outside, and/or from the outside to the inside. The doorway 858 includes a barrier 859, disposed in the doorway 858, that moves between an opened position and a closed position based on commands sent by a computer 860. When in the closed position, the barrier 859 restricts passage through the doorway 858, and when in the opened position, the barrier 859 does not restrict the passage through the doorway.

The doorway system includes one or more sensors that measure: a first signal indicative of whether there is a first user 863A on the outside of the doorway, and a second signal indicative of whether there is a second user 863B on the inside of the doorway. In one example, the doorway system includes at least one of: a first sensor 861A that is capable of detecting whether the first user 863A is outside and a second sensor 861B that is capable of detecting whether the second user 863B is on the inside.

The computer 860 operates the doorway 858 in a manner that helps restrict contact between people that may be dangerous and contribute to the spread of disease. Optionally, this is done by restricting entrance of people who are not healthy through the doorway 858 in to the inside.

Figure 70A:
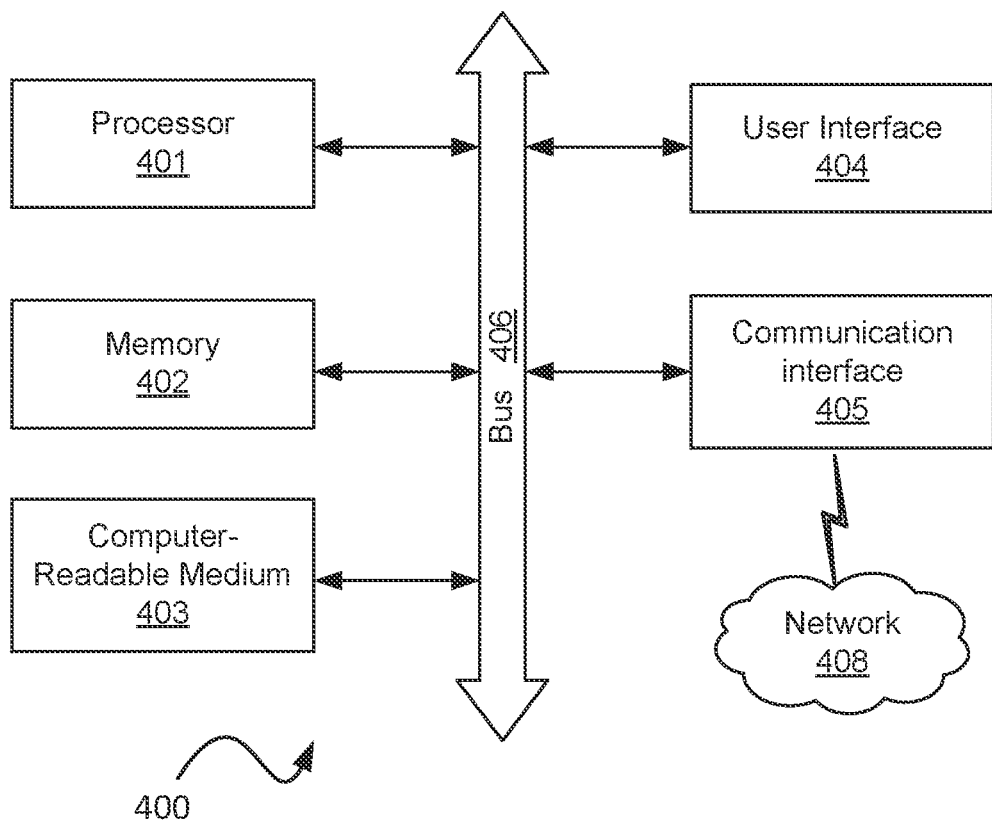
FIG. 70A and FIG. 70B are schematic illustrations of possible embodiments for computers.
Figure 70B:
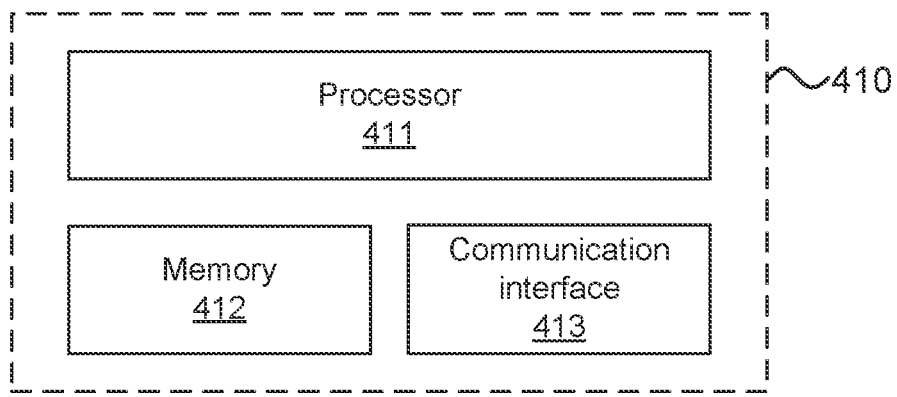

Examples of computers that may be utilized to perform the calculations of one or more computers that may be collectively referred to as "the computer 860" are computer 400 or computer 410, illustrated in FIG. 70A and FIG. 70B, respectively.

The computer 860 operates the doorway 858 in a manner that restricts passage through the doorway 858 when the first user 863A is on the outside, the second user 863B is on the inside, and at least one of them is not verified as being healthy and/or non-contagious. In some embodiments, this characteristic of the doorway 858 is implemented by the computer 860 as follows:

The computer 860 determines whether there are users on either side of the doorway 858. This involves detecting based on the first signal whether the first user 863A is on the outside, and detecting based on the second signal whether the second user 863B is on the inside.

If the first user 863A is on the outside, the first user 863A may be admitted if a first indication is received, indicating that the first user 863A is healthy and/or non-contagious. Optionally, the first indication is received from a first device 862A carried and/or worn by the first user 863A. Optionally, the first indication does not include information identifying the first user 863A.

In some embodiments, receiving the first indication is sufficient for the computer 860 to command barrier 859 to move to an open position and/or remain in the opened position (since there is no risk that the first user 863A will put people inside at risk). However, in other embodiments, the computer 860 may restrict the entrance of the first user 863A if that will put the first user 863A at risk because someone else, whose health state is not verified as being healthy and/or non-contagious is on the inside.

In some embodiments, if the computer 860A detects the first user 863A is on the outside and the first indication indicates the first user 863A is healthy, but the computer 860 detects the second user 863B is on the inside, the computer 860 will not allow the first user 863A without verifying the health state of the second user 863B. Thus, in such a situation, the computer 860 commands the barrier 859 to move to an opened position and/or remain in the opened position, responsive to receiving, from a second device 862B carried and/or worn by the second user 863B, a second indication indicating the second user 863B is healthy.

In some embodiments, the first device 862A carried and/or worn by the first user 863A receives measurements of physiological signals of the first user 863A. Optionally, the physiological signals include a PPG signal and a temperature signal (i.e., one or more measurements of the temperature of the first user 863A). Optionally, the physiological signals are sent by the wearable device 840.

In one embodiment, the first indication is sent by the computer 847. Optionally, the first device 862A carried and/or worn by the first user 863A is the wearable device 840.

Similarly, in some embodiments, the second device 862B carried and/or worn by the second user 863B receives measurements of physiological signals of the second user 863B. Optionally, the physiological signals include a PPG signal and a temperature signal (i.e., one or more measurements of the temperature of the second user 863B). Optionally, the physiological signals are sent by the wearable device 840.

In one embodiment, the second indication is sent by the computer 847. Optionally, the second device 862B carried and/or worn by the second user 863B is the wearable device 840. Optionally, the second indication does not include information identifying the second user 863B.

In some embodiments, the computer 860 commands the barrier 859 to move to the closed position and/or remain in the closed position, under certain conditions. One condition that may cause the computer 860 to do so is if it detects, based on the first signal that the first user 863A is on the outside, it detects, based on the second signal that the second user 863B is not on the inside, and does not receive the first indication indicating the first user 863A is healthy. Another condition under which the computer 860 may command the barrier 859 to move to the closed position and/or remain in the closed position is if the computer 860 detects, based on the first signal that the first user 863A is on the outside, it detects, based on the second signal that the second user 863B is on the inside, and does not receive at least one of the first indication indicating the first user 863A is healthy and the second indication indicating the second user 863B is healthy, respectively.

Various examples of doorways that may be controlled by the system illustrated in FIG. 6 are illustrated in FIG. 3.

In one example, the barrier 859 is a door that belongs to a vehicle 850C, and commanding the barrier to move to the opened position and/or remain in the opened position comprises commanding the door to unlock and/or move to a position that enables the first user 863A to enter a passenger cabin of the vehicle 850C.

In another example, the barrier 859 is an entrance door to a room and/or building (e.g., door 850A), and commanding the barrier to move to the opened position and/or remain in the opened position comprises commanding the entrance door to unlock and/or move to a position that enables the first user 863A to enter the interior of the room and/or building.

In yet another example, the barrier 859 is a turnstile or a revolving door belonging to a gate (e.g., door 850B or gate 850D), and commanding the barrier to move to the opened position and/or remain in the opened position comprises enabling the turnstile or the revolving door to revolve and/or moving the turnstile or the revolving door, which enables the first user 863A to pass through the gate.

A presence of multiple users are on the inside and/or on the outside may require the computer 860 to adjust the operation of the doorway 858 in order to help reduce unwanted contacts with users whose health state is not verified as being healthy and/or non-contagious.

In one embodiment, the computer 860 commands the barrier 859 to move to the closed position and/or remain in the closed position, responsive to detecting, based on the first signal, that a plurality of users are on the outside, and not receiving, for each user from among the plurality of the users, an indication indicating said user is healthy, which is sent by a device carried and/or worn by said user.

In another embodiment, when the first user 863A is detected on the outside, the computer 860 may command the barrier 859 to move to the closed position and/or remain in the closed position, responsive to: detecting, based on the second signal, that a plurality of users are on the inside, and not receiving, for each user from among the plurality of the users, an indication indicating that said user is healthy, which is sent by a device carried and/or worn by said user.

The first and/or second indications mentioned above may be transmitted at the request of the computer 860. In one embodiment, the computer 860 transmits a request for the first indication indicating the first user is healthy, responsive to detecting that the first user 863A is on the outside, and/or transmits a request for the second indication indicating the second user 863B is healthy, responsive to detecting that the second user 863B is on the inside.

In some embodiments, the first and second signals may be signals generated by devices worn and/or carried by the first user 863A and the second user 863B, respectively. In these embodiments, the one or more sensors may include a receiver that detects the first and second signals and/or a plurality of receivers that triangulate locations of the devices that sent these signals. In other embodiments, the first and second signals may be signals from which the computer 860 detects the presence of the first user 863A and the second user 863B, respectively.

In one example, the one or more sensors include a camera aimed to the outside, the first signal includes images of the outside, and detecting the first user 863A is outside involves identifying presence of a person in the images.

In another example, the one or more sensors include a thermal sensor aimed to the outside, the first signal includes thermal measurements of the outside, and detecting the first user 863A is outside involves identifying a thermal signature corresponding to a person in the thermal measurements.

In yet another example, the one or more sensors include a pressure sensor disposed in a surface on the outside, the first signal includes values indicative of pressure applied to the pressure sensor, and detecting the first user 863A is outside involves identifying the values reflect application of a pressure corresponding to a weight of a person.

Figure 8:
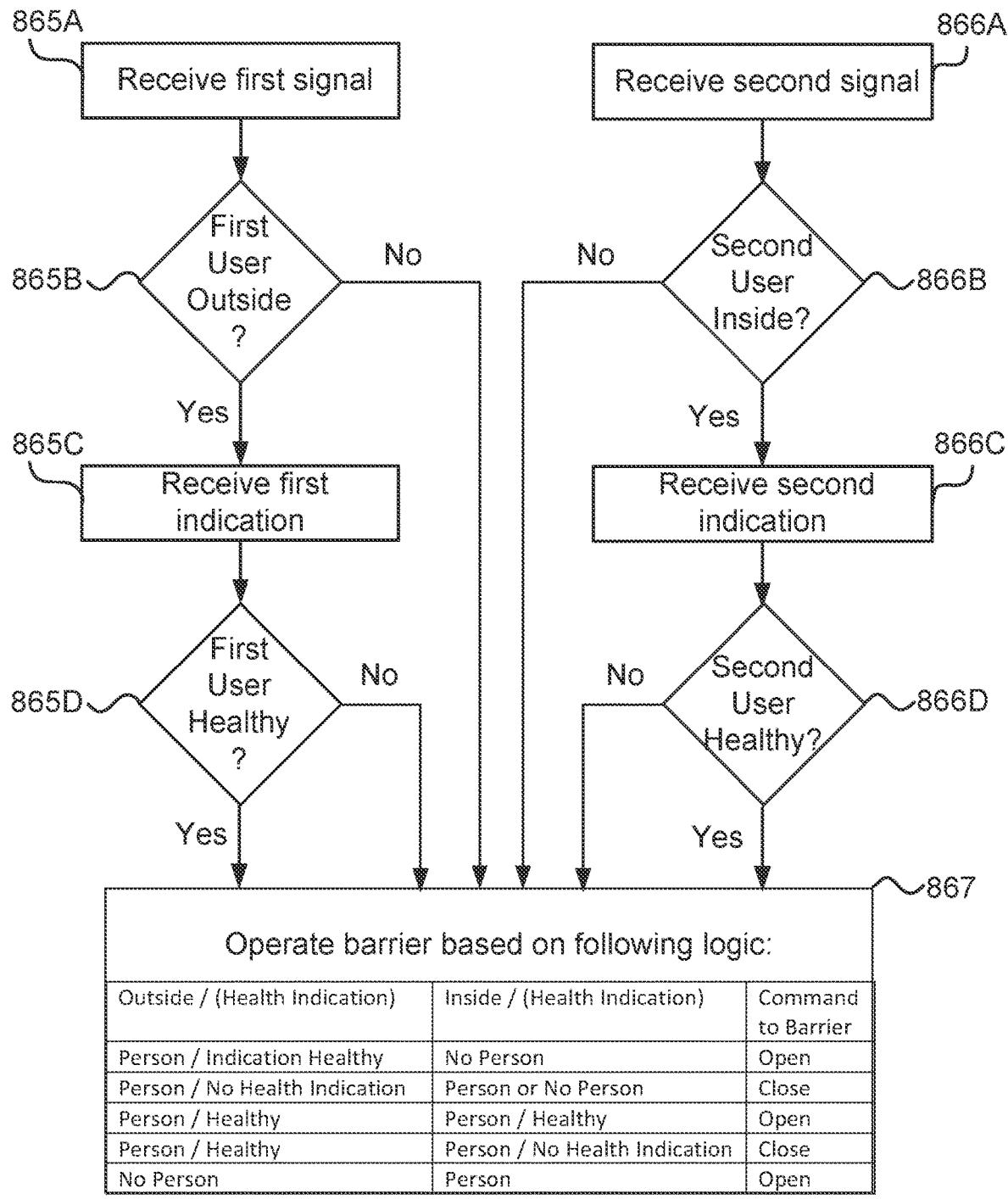
FIG. 8 illustrates a flowchart according to which a computer may operate a barrier disposed in a doorway.

FIG. 8 illustrates a flowchart according to which the computer 860 may command the barrier 859 to open and/or close. Steps 865A and 866A involve receiving the first and second signals, respectively. Steps 865B and 866B involve determining whether the first user 863A is outside and the second user 863B is inside, respectively. Steps 865C and 866C involve receiving the first and second indications, respectively. Steps 865D and 866D involve determining whether the first user 863A is healthy and whether the second user 863B is healthy, respectively. Information determined based on some, or all of the aforementioned steps is provided to the computer 860, which in step 867 operates the barrier according to the logic described in the table included in that the illustration of that step.

The steps illustrated in FIG. 8 may be used to implement a method for controlling the doorway 858. This method may be implemented using an embodiment of a system illustrated in FIG. 6, which is discussed above. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform steps mentioned below.

In one embodiment, the method for controlling the doorway 858 includes the following steps:

In Step 865A, receiving a first signal indicative of whether there is a first user on an outside of the doorway 858.

In Step 865B, detecting based on the first signal that the first user is on the outside.

In Step 865C, receiving, from a first device carried and/or worn by the first user, a first indication indicating the first user is healthy.

In Step 866A, receiving a second signal indicative of whether there is a second user on the inside of the doorway.

In Step 866B, detecting based on the second signal whether the second user is on the inside.

And in Step 867, operating the barrier 859 according to the logic in the table in FIG. 8, which involves commanding the barrier 859 to move to the opened position and/or remain in the opened position, responsive to: (i) detecting that the second user is not on the inside (in Step 866B), or (ii) detecting that the second user is on the inside (in Step 866B) and receiving, from a second device carried and/or worn by the second user, a second indication (in Step 866C), which in Step 866D is determined to indicate the second user is healthy.

In one embodiment, the method for controlling the doorway 858 may optionally include a step of commanding the barrier to move to the closed position and/or remain in the closed position, responsive to: (i) detecting based on the first signal that the first user is on the outside (in Step 865B), detecting based on the second signal that the second user is not on the inside (in Step 866B), and not receiving the first indication indicating the first user is healthy, or (ii) detecting based on the first signal that the first user is on the outside (in Step 865B), detecting based on the second signal that the second user is not on the inside (in Step 866B), and not receiving at least one of the first indication indicating the first user is healthy and the second indication indicating the second user is healthy.

In one embodiment, the method for controlling the doorway 858 may optionally include the following steps: commanding the barrier to move to the closed position and/or remain in the closed position, responsive to detecting, based on the first signal, that a plurality of users are on the outside, and not receiving, for each user from among the plurality of the users, an indication indicating said user is healthy, which is sent by a device carried and/or worn by said user.

In one embodiment, the method for controlling the doorway 858 may optionally include the following steps: commanding the barrier to move to the closed position and/or remain in the closed position, responsive to: detecting, based on the second signal, that a plurality of users are on the inside, and not receiving, for each user from among the plurality of the users, an indication indicating that said user is healthy, which is sent by a device carried and/or worn by said user.

In one embodiment, the method for controlling the doorway 858 may optionally include the following step: transmitting a request for the first indication indicating the first user is healthy, responsive to detecting that the first user is on the outside.

Combating the spread of communicable diseases is often done with extreme measures, such as restrictions on peoples' movements and blanket orders for quarantines. The reason such extreme measures are often used is that it is difficult to determine, on a population-wide scale, who are the symptomatic people who pose a risk of spreading the communicable disease (and limit restrictions to those people). Thus, for practical reasons, often whole populations are treated as if they all pose a risk, and are subject to many restrictions, even though the majority of these people are not symptomatic and cannot spread the disease.

Due to the great toll of such measures, which often lead to wide-scale disruption to the economy, they are not sustainable on the long run. However, lifting these restriction prematurely can also have devastating consequences, since it can rekindle the spread of diseases that were on the decline.

The main problem lies in the ability to identify who are the people who pose risk to others (e.g., due to them being symptomatic individuals). While wearable devices with sensors capable of measuring physiological signals of their wearers have been suggested as possible tools that can be used to combat the spread of communicable diseases, so far they have mostly not been adopted in practical applications that go beyond reporting to users their physiological state. Thus, there is a need for ways to utilize wearable devices to loosen blanket restrictions imposed in order to curb the spread of communicable diseases. This can enable more people to go to their work place, school, etc., but needs to be done in a safe manner that does not pose a significant risk of increasing the spread of disease.

Managing physical access to locations (e.g., work places, public spaces) can be especially challenging when precautions need to be taken in order to curb the spread of diseases such as the flu or COVID-19. Some embodiments described herein use authenticated wearable-based health state verifications in order to authorize access to such locations, which can help curb the spread of these diseases.

Figure 7:
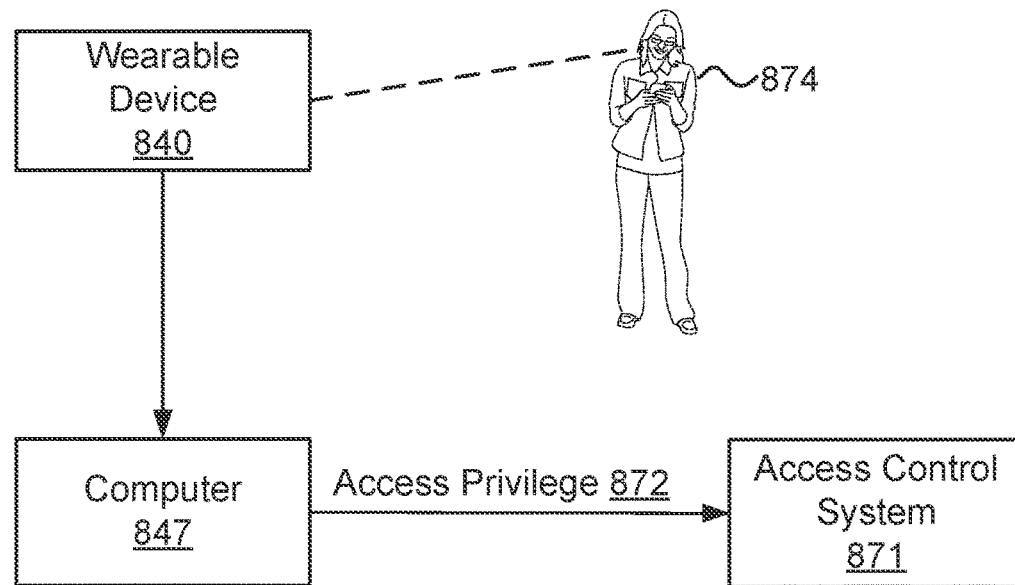
FIG. 7 is a schematic illustration of components of a system configured to authorize physical access to a location based on an authenticated health score.

FIG. 7 is a schematic illustration of components of a system configured to authorize physical access to a location, such as a work place, a public building, etc., based on an authenticated health score. In one embodiment, the system includes at least the wearable device 840 and the computer 847. In this embodiment, the computer 847 utilizes measurements of a user 874 taken with the wearable device 840, that day and on earlier days, to determine both if the user's health state permits access to the location, and also to authenticate the user 874. The system may optionally include additional elements such as an access control system 871, which is configured to allow or deny access to the location based on indications received from the computer 847. Embodiments of the system illustrated in FIG. 7 share many of the components and characteristics of embodiments of the system illustrated in FIG. 1, which is discussed in detail above, possibly with one or more differences. One of the differences involves the computer 847 calculating an authentication score in order to provide or revoke an access privilege 872. This process involves conveying information about the identity of the user being authenticated, which is not aspect that is necessarily present in embodiments of the system illustrated in FIG. 1. Some of the embodiments of the system illustrated in FIG. 1 do not involve providing information that may identify the user wearing the wearable device 840.

In one embodiment, the computer 847 analyzes measurements taken by the wearable device 840 of the user 874 and optionally, of the environment the user 874 is in at the time. This analysis involves calculations involving measurements taken at different times: (i) "current measurements" which are taken with the wearable device 840 during a period that starts a certain time before the analysis is performed (e.g., a few hours before) and/or leading up to when the analysis is performed, and (ii) "baseline measurements" taken with the wearable device 840 on or more earlier days. Optionally, the current measurements are taken over a duration of at least five minutes. Optionally, the baseline measurements include more than an hour of measurements taken over a period of several days.

In some embodiments, the computer 847 calculates a health score for the user 874 based on a difference between the baseline measurements and the current measurements, as explained in detail above (see description of embodiments according to FIG. 1). Additionally, the computer 847 calculates an authentication score based on a similarity between characteristics of a PPG signal in the current measurements and characteristics of a PPG signal in the baseline measurements. Optionally, the authentication score is proportional to the extent of similarity between characteristics of a PPG signal in the current measurements and characteristics of a PPG signal in the baseline measurements. Calculation of the extent of said similarity is explained in detail above (see description of embodiments according to FIG. 1). In some embodiments, the authentication score equals the extent of the similarity between characteristics of a PPG signal in the current measurements and characteristics of a PPG signal in the baseline measurements.

In one embodiment, responsive to the health score reaching a first threshold and the authentication score reaching a second threshold, the computer 847 grants the user 874 the access privilege 872, which enables the user 874 to access the location. Optionally, granting the access privilege 872 involves transmitting an indication to the access control system 871, which may be a system that controls entryways into the location. Optionally, this transmitted indication includes information identifying the user 874 (e.g., a name, an employee number, a national identification number, or some other identifier) and/or information indicating the health state of the user 874. In one example, granting access to the location involves adding an identifier of the user 874 to a list of people permitted to enter the location. In another example, revoking access to the location involves removing an identifier of the user 874 from the list of people permitted to enter the location.

An access privilege previously granted to the user 874 may be revoked under certain conditions, such as it not being clear if it is still safe to let the user 874 enter the location. In one embodiment, the computer 847 revokes the access privilege 872, responsive to the health score not reaching the first threshold and/or the authentication score not reaching the second threshold.

In some embodiments, knowledge about the health state of people who typically access the location can be used to set the first threshold. For example, if many of those people became ill, this may mean that there is an outbreak of an illness associated somehow with the location. In such a case, it may be desirable to increase the first threshold in order to reduce the chance of people who may be beginning to become ill, which may be only slightly symptomatic, of gaining access to the location. In one example, the computer 847 increases the first threshold responsive to receiving a certain indication indicative of number of people, who are ill and who accessed the location in a preceding period of time, reaches a third threshold. Optionally, increasing the first threshold reduces tendency to deny and/or revoke privileges to access the location.

The calculated health score may be utilized to generate a certificate indicative of the health state of the user 874. In one embodiment, the computer 847 may provide an indication the user 874 is healthy, responsive to the health score reaching the first threshold and the authentication score reaching the second threshold. In another embodiment, the computer 847 may provide an indication that the user 874 is ill (a "sick note"), responsive to the health score not reaching the first threshold and the authentication score reaching the second threshold. Optionally, these indications regarding the health state of the user 874 may include information identifying the user 874.

When the health state of the user 874 changes, this can lead to changing the indication about the state of the user 874. For example, when the health of the user 874 improves, a sick note provided to the user 874 may be canceled based on measurements taken with the wearable device 840. In one embodiment, the computer 847 receives additional measurements of the user 874 taken with the wearable device 840 at least four hours after the current measurements were taken. The computer 847 calculates an additional health score based on a difference between the baseline measurements and the additional measurements. The computer 847 also calculates an additional user authentication score based on a similarity between characteristics of the PPG signal in the additional measurements and the characteristics of the PPG signal in the baseline measurements. The computer 847 then provides an indication that the user 874 is no longer ill responsive to the additional health score reaching the first threshold and the additional user authentication score reaching the second threshold.

When the health state of multiple users is tracked using the system illustrated in FIG. 7, this can provide insights into the dynamics of illness, which can be used to predict how long the user 874 may be ill. In one embodiment, the computer 847 generates feature values based on the current measurements and the baseline measurements (e.g., feature values described herein as being generated from that data), and utilizes a model to calculate, based on the feature values, a value indicative of a duration of illness of the user 874. Optionally, the model is generated based on data comprising a first set of training measurements of a plurality of users taken while the plurality of users were not ill, a second set of training measurements of the plurality of users taken during illnesses of the plurality of users, and indications of durations of the illnesses. Optionally, the training measurements were taken using wearable devices, such as the wearable device 840.

Figure 9:
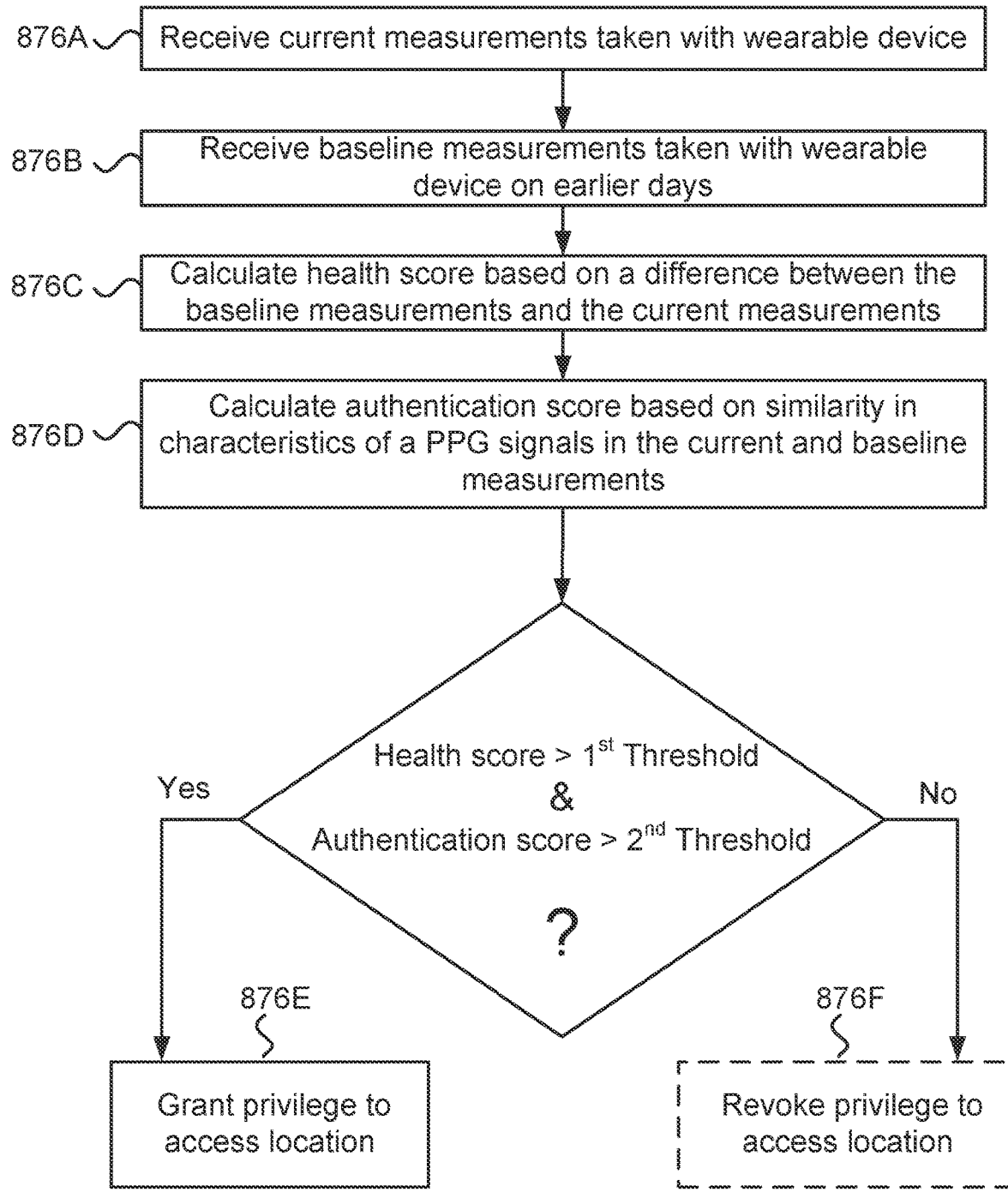
FIG. 9 illustrates steps that may be part of embodiments of a method for managing authorization of access to a location based on authenticated health scores.

FIG. 9 illustrates steps that may be part of embodiments of a method for managing authorization of access to a location based on authenticated health scores. The method may be implemented using embodiments of systems illustrated in FIG. 7, which is discussed above. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform steps from among the steps illustrated in FIG. 9 and/or additional steps mentioned below.

In one embodiment, the method for managing authorization of access to a location based on authenticated health scores includes at least the following steps:

In Step 876A, receiving current measurements of a user taken with a wearable device that includes: a first sensor configured to measure a signal indicative of a photoplethysmogram signal (PPG signal) of a user, and a second sensor configured to measure a temperature of the user. For example, the current measurements may be taken with the wearable device 840.

In Step 876B, receiving baseline measurements of the user taken with the wearable device during one or more earlier days.

In Step 876C, calculating a health score based on a difference between the baseline measurements and the current measurements.

In Step 876D, calculating an authentication score based on a similarity between characteristics of a PPG signal in the current measurements and characteristics of a PPG signal in the baseline measurements.

And in Step 876, responsive to determining the health score reaches a first threshold and the authentication score reaches a second threshold, granting the user a privilege to access the location.

In one embodiment, the method may optionally include Step 876F, which involves revoking the privilege of the user to access the location, responsive to the health score not reaching the first threshold and/or the authentication score not reaching the second threshold.

In one embodiment, the method may optionally include a step involving increasing the first threshold responsive to receiving a certain indication indicative of number of people, who are ill and who accessed the location in a preceding period of time, reaches a third threshold. Optionally, increasing the first threshold reduces tendency to revoke privileges to access the location.

Due to the many interactions that can occur in places of gatherings, such as workplaces, schools, theaters, etc., these locations can be considered dangerous to enter during times of epidemics. It is difficult to keep track of the health state of all the people who entered a location, and thus ascertain if visits to the location pose any risk of contracting a disease. Without knowing the risk from visiting a potentially dangerous location (due to the many people present there), it may be necessary to employ drastic measures to isolate visitors to the location from other people in order to reduce the risk of disease transmission. Thus, there is a need of a way to ascertain the risk of contracting a disease posed by a visit to a location, in order to be able to choose appropriate and proportionate measures to take following the visit.

Some embodiments disclosed herein utilize wearable devices that measure physiological signals of their wearer in order to determine whether people who were at a location were healthy, and thus be able to certify the location as contagion-safe. Being in a contagion-safe location poses little risk of contracting a communicable disease. Therefore, visitors to such a location may not need to take additional measures, such as isolation from other people, which are often required when coming from locations in which there are many people whose health state is unknown.

Figure 10:
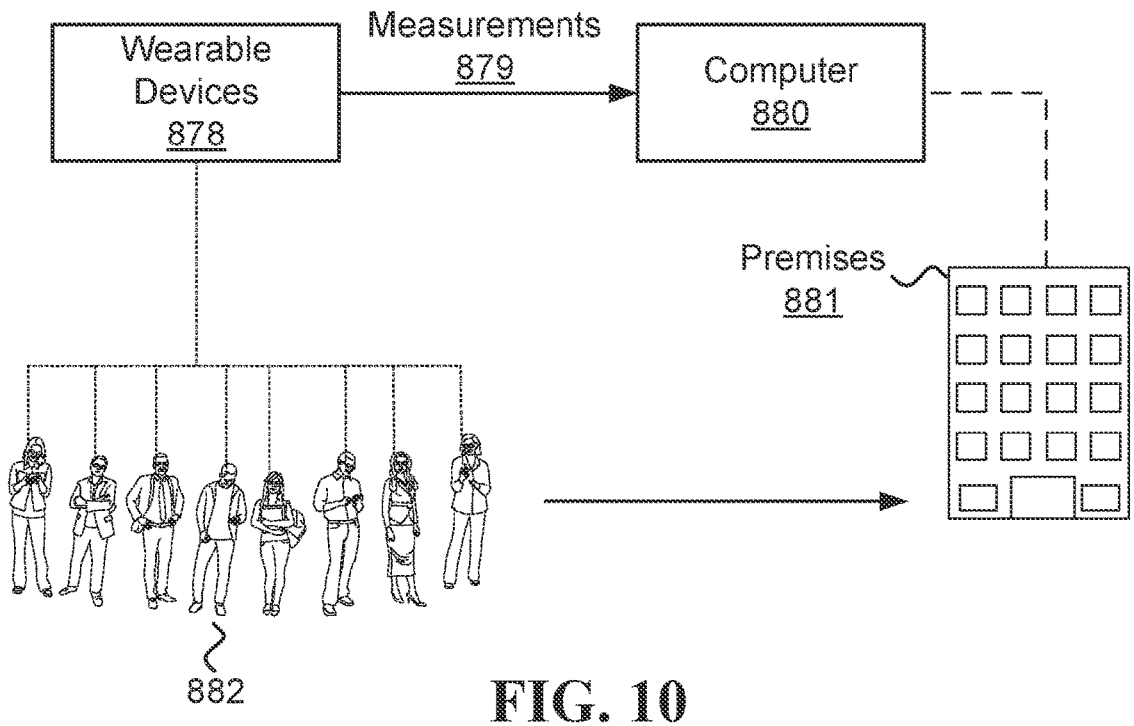
FIG. 10 is a schematic illustration of an embodiment of a system configured to certify a premises as contagion-safe.

FIG. 10 is a schematic illustration of an embodiment of a system configured to certify a premises 881 as contagion-safe. For example, the premises 881 may be a place of work, a school, or a nursing home facility. In some embodiments, the system includes wearable devices 878 that take measurements 879 of users 882 who are wearing the wearable devices 878. Optionally, the measurements 879 include photoplethysmogram signals of the users 882 and temperature signals of the users 882. Optionally, each of the wearable devices 878 is an embodiment of the wearable device 840, described in detail further above. Optionally, at least some of the wearable devices 878 are smartglasses, such as the smartglasses illustrated in FIG. 2.

Embodiments of the system illustrated in FIG. 10 also include a computer 880 which performs several steps in order to determine whether to certify the premises 881 as contagion-safe. In one embodiment, the computer 880 calculates health scores of the users 882 based on measurements 879 of the users 882 taken while the users were not on the premises 881. The computer 880 identifies which of the users 882 are non-symptomatic users based on their health scores reaching a threshold (such as the first threshold mentioned in the context of embodiments illustrated in FIG. 1). The computer 880 also authenticates the identities of the non-symptomatic users based on at least some of the measurements 879 (i.e., at least some of the measurements 879 that are of the non-symptomatic users). Optionally, the predetermined period is set according to characteristics of an epidemic for which the system protects. For example, the predetermined period may be set to a value between one day and ten days, depending on the time it typically takes for symptoms of the epidemic to manifest with infected individuals.

In some embodiments, calculation of the health scores of the users 882 based on the measurements 879 by the computer 880, may be done in the same manner described in embodiments disclosed herein involving the computer 847 calculating health scores based on current and baseline measurements (in which case the measurements 879 include measurements taken over multiple days).

In some embodiments, calculation of the health scores of the users 882 based on the measurements 879 by the computer 880, may be done in the same manner described in embodiments disclosed herein involving the computer 847 calculating health scores by utilizing one or more the machine learning approaches described with respect to calculation of health scores by the computer 847, such as generating feature values based on measurements of a user, from among the measurements 879, and utilizing a model to calculate, based on the feature values, a value that indicates whether that user is healthy and/or non-contagious.

In some embodiments, authenticating the identities of the non-symptomatic users based on at least some of the measurements 879 may be done by the computer 880 in the same manner described in embodiments disclosed herein involving the computer 847. For example, the computer 880 may calculate the extent of similarity of PPG signals of a certain user in measurements from among the measurements 879 with a template generated based on previously measured PPG signals of that certain user. Optionally, if the extent of similarity exceeds a threshold, the certain user may be considered authenticated. Additionally or alternatively, in some embodiments, authenticating the certain user may utilize additional signals from among measurements 879 mentioned herein as useful for authentication, such as acoustic signals and/or movement signals.

Based on the authenticated identities of the non-symptomatic users from among the users 882, the computer 880 determines whether to certify the premises 881 as contagion-safe.

In some embodiments, certifying the premises 881 as contagion-safe means providing an indication to one or more of the users 882, other people, and/or other computer systems, that the premises 881 is contagion-safe. An indication of a certification of the premises 881 as contagion-safe can be used for various applications, such as deciding on quarantine or stay-at-home orders for people who visited the premises 881, assessment of risk these people are ill, and/or assessment of a risk of exposure to people form among the users 882. Optionally, the indication is indicative of the fact that only the non-symptomatic users, whose authentication was successful, entered the premises 881 during the predetermined period. Alternatively, the indication is indicative of the fact that the non-symptomatic users whose authentication was successful comprise at least a certain predetermined proportion of all of the users 882 who visited the premises 881.

In some embodiments, de-certifying the premises 881 as contagion-safe means sending an a second indication canceling the indication sent when certifying the premises 881 as contagion-safe and/or sending an indication to one or more of the users 882, other people, and/or other computer systems, indicating that the premises is not contagion-safe.

In some embodiments, the computer 880 certifies the premises 881 as contagion-safe responsive to determining that, from among the users 882, only non-symptomatic users, whose authentication was successful, entered the premises 881 during a predetermined period.

In other embodiments, the computer 880 certifies the premises 881 as contagion-safe responsive to determining that that the non-symptomatic users whose authentication was successful comprise at least a certain predetermined proportion of all of the users 882 who visited the premises 881. The predetermined proportion may be selected by the operator at the premises 881. For example, the operator may decide that the threshold is 90% of non-symptomatic users in the premises 881, whose authentication was successful, in order to certify the premises 881 as contagion-safe. And if the percent of the non-symptomatic authenticated users falls below 90% then the certification of the premises as contagion-safe is revoked. Additionally or alternatively, the operator may decide that the threshold is density below 0.3 per square meter of non-symptomatic users, density below 0.06 per square meter of users for which symptom status is unknown, and density below 0.03 per square meter of symptomatic users.

In some embodiments, the computer 880 may present e.g., via a user interface, an indication proportional to at least one of percent and/or density of the following: the non-symptomatic users in the premises 881, symptomatic users in the premises 881, and users for which symptom status is unknown. Optionally, the presented indications support decision of other users whether to visit the premises 881 at that time.

In one embodiment, the computer 880 may receive a location of a certain user at the premises 881, and recommend the certain user use certain personal protection equipment based on the indication proportional to the at least one of the present and/or the density. This recommendation can help the certain user to decide whether personal protection equipment is required, and to what extent. For example, whether using face mask should be enough, and whether gloves ar also needed.

It is to be noted that in different embodiments, a reference to "the computer 880" may refer to different components and/or a combination of components. In some embodiments, the computer 880 may be a server or a collection of servers (e.g., on a computing cloud). In some embodiments, at least some of the functionality attributed to the computer 880, such as calculating the health scores of the users 882 and/or authenticating the non-symptomatic users, may be performed by computers associated with those users, such as cloud-based servers hosting accounts of those users and/or processors on devices of those users (e.g., smartphones) or wearable devices of those users. Thus, references to calculations being performed by the "computer 880", and the like, should be interpreted as calculations being performed utilizing one or more computers, as described in the examples above. Examples of computers that may be utilized to perform the calculations of one or more computers that may be collectively referred to as "the computer 880" are computer 400 or computer 410, illustrated in FIG. 70A and FIG. 70B, respectively.

In some embodiments, the computer 880 may notify certain users, e.g., via user interfaces of devices the carry (e.g., screens of smartphones) or user interfaces of the wearable devices 878, whether they are permitted on the premises 881. In one example, a user interface may be used to notify a non-symptomatic user that said non-symptomatic user is allowed on the premises 881. In another example, the computer 880 may identify some of the users 882 as symptomatic users based on their measurements taken while not on the premises 881. For example, their health scores may be below a threshold. In this example, a user interface may be utilized to notify a symptomatic user, prior that user's arriving to the premises 881, that that user is not allowed on the premises 881.

In some embodiments, the computer 880 receives identities of at least some of the users 882 who arrived at the premises 881 and determines based on the identities, whether a user, who is not among the non-symptomatic users, entered the premises 881. The identities may be received via various systems. In one example, the identities are received from a security system that utilizes video cameras and image recognition to determine who entered the premises 881. In another example, the identities are received from a security system that logs entry to the premises 881 via a key card mechanism. In still another example, the identities may be received via identification of transmissions of the wearable devices 878 and/or other mobile devices carried by the users 882 (e.g., smartphones).

In some embodiments, the computer 880 identifies some of the users 882 as symptomatic users based on their health scores being below the threshold, and decertifies the premises 881 as contagion-safe responsive to detecting that a symptomatic user entered the premises 881 after the predetermined period. Optionally, the computer 880 receives an indication of a time at which the symptomatic user left the premises 881, and re-certifies the premises 881 as contagion-safe after a predetermined duration from that time. Optionally, obtaining the time the symptomatic user left the premises 881 may be done using one of more of the techniques mentioned above (e.g., image processing, access control system or time card system, etc.).

In one embodiment, the computer 880 may identify that a person not wearing one of the wearable devices 878 (a non-cleared person) entered the premises 881 after the predetermined period, and decertify the premises 881 as contagion-safe responsive to detecting that the non-cleared person entered the premises 881.

In one embodiment, the computer 880 may identify, after the predetermined period, that a user on the premises 881 became ill, and decertify the premises 881 as contagion-safe.

In some embodiments, the health scores are calculated with respect to a certain disease, and certification of the premises 881 as contagion-safe is indicative that only non-symptomatic users with respect to the certain disease, whose authentication was successful, entered the premises 881 during the predetermined period. Optionally, the computer 880 may confirm, based on external medical records, immunity of one or more people who had the certain disease and refrain from decertifying the premises 881 due to their entry to the premises 881 during the predetermined period.

Figure 12:
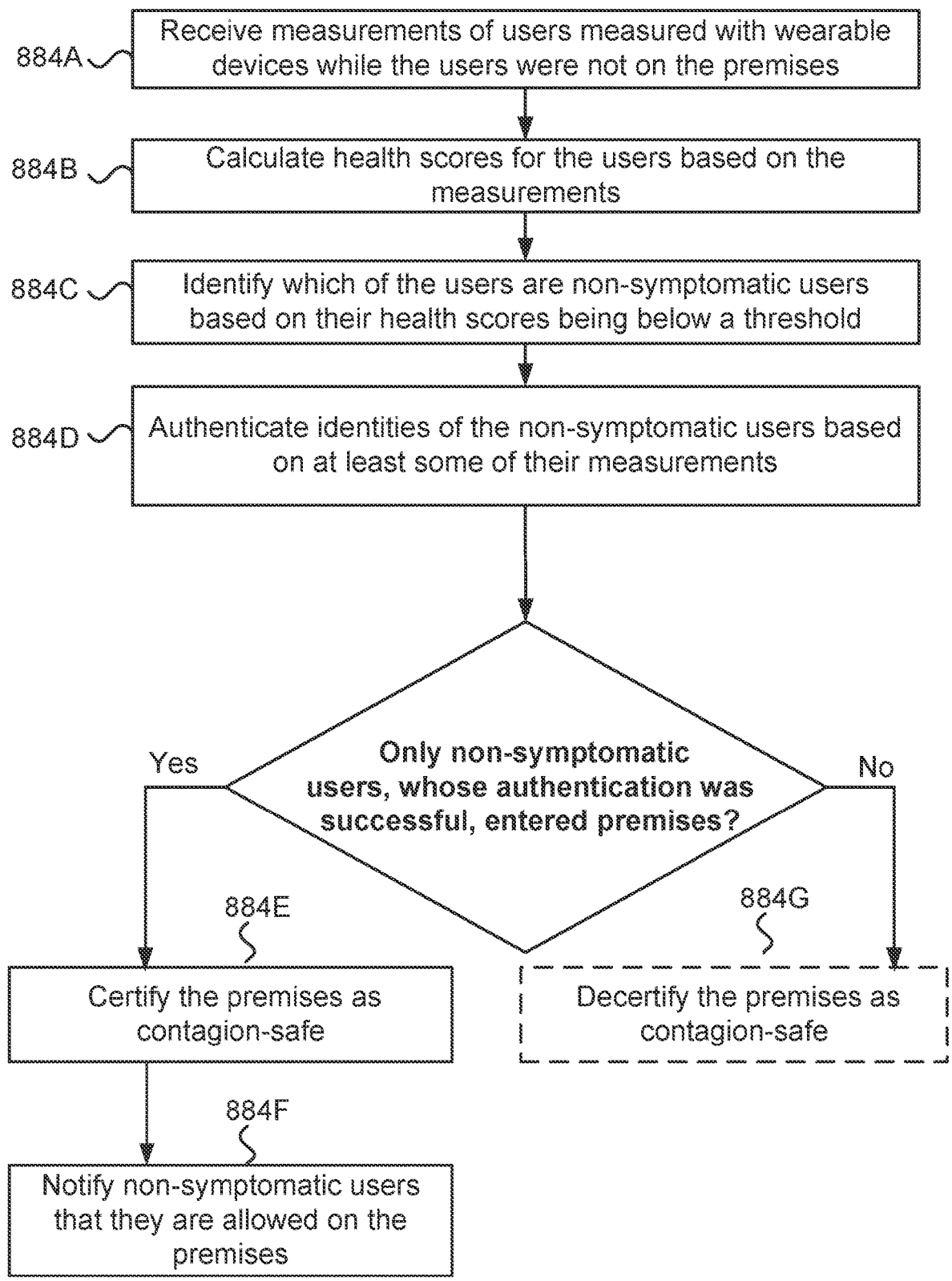
FIG. 12 illustrates steps that may be part of embodiments of a method for certifying a premises as contagion-safe.

FIG. 12 illustrates steps that may be part of embodiments of a method for certifying a premises as contagion-safe. The method may be implemented using embodiments of systems illustrated in FIG. 10, which is discussed above. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform steps from among the steps illustrated in FIG. 12 and/or additional steps mentioned below.

In one embodiment, the method for certifying a premises as contagion-safe includes at least the following steps:

In Step 884A, receiving measurements of users measured with wearable devices (e.g., units of the wearable device 840), while the users were not on the premises. Optionally, the measurements include photoplethysmogram signals of users and temperature signals of the users.

In Step 884B, calculating health scores of the users based on the measurements.

In Step 884C, identifying which of the users are non-symptomatic users based on their health scores being reaching a threshold.

In Step 884D, authenticating identities of the non-symptomatic users based on at least some of their measurements.

And in Step 884E certifying the premises as contagion-safe responsive to determining that, from among the users, only non-symptomatic users, whose authentication was successful, entered the premises during a predetermined period.

In one embodiment, the method may optionally include Step 884F involving notifying the non-symptomatic users that they are allowed on the premises. Additionally or alternatively, the method may include optional steps involving: identifying some of the users as symptomatic users based on their measurements measured while not on the premises, and notifying the symptomatic users, prior to their arriving to the premises, that they are not allowed on the premises.

In one embodiment, the method may optionally include Step 884G involving: identifying some of the users as symptomatic users based on their health scores being below the threshold, and decertifying the premises as contagion-safe responsive to detecting that a symptomatic user entered the premises after the predetermined period. Optionally, the method may also include steps involving: receiving an indication of a time when the symptomatic user left the premises, and re-certifying the premises as contagion-safe after a predetermined duration from that time.

In one embodiment, the method may optionally include a step involving: identifying, after the predetermined period, that a user on the premises became ill, and decertifying the premises as contagion-safe.

Due to the many interactions that can occur in places of gathering, such as workplaces, schools, theaters, etc., these locations can be considered dangerous to enter during times of epidemics. It is difficult to keep track of the health state of all the people who entered a location, and thus ascertain if visits to the location posed a substantial risk. One way in which the risk of visiting such a location can be reduced is by ensuring that only healthy people, who are likely to be non-symptomatic and/or non-contagious, may be present at the location. Thus, there needs to be an easy way to make such determinations on a wide scale.

Some embodiments disclosed herein utilize wearable devices that measure physiological signals of users in order to determine whether the users are healthy, and thus should be allowed to enter a location that is assumed to be contagion-sage. In one example, this can be useful for certifying a nursing home is contagion-safe, and then screening new residents prior to their admission in order to keep the nursing home free of disease. In another example, this approach can be used to pre-screen passengers intending to take a flight, in order to keep off the aircraft any passengers who may be symptomatic and spread a disease onboard.

Figure 11:
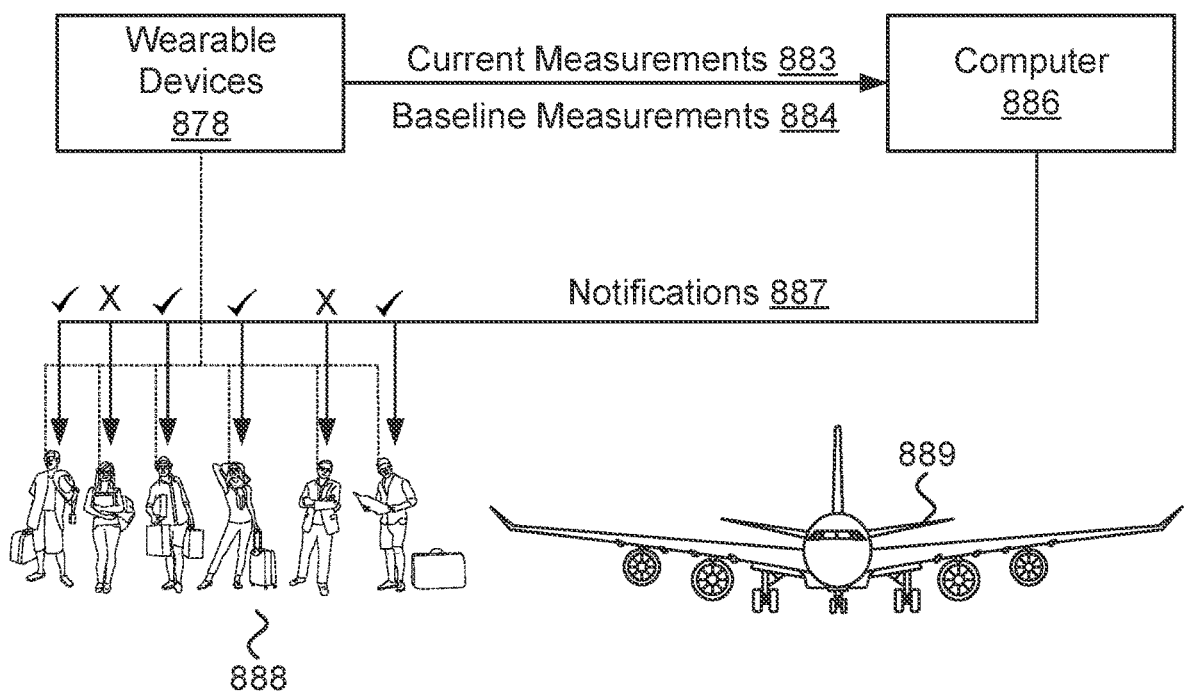
FIG. 11 is a schematic illustration of an embodiment of a system for managing access to a contagion-safe premises.

FIG. 11 a schematic illustration of an embodiment of a system for managing access to a contagion-safe premises. In some embodiments, the system includes wearable devices 878 that take measurements of users 888 who are wearing the wearable devices 878. Additionally, the system includes a computer 886, which performs several steps in order to manage access to the contagion-safe premises.

In some embodiments, the wearable devices 878 take measurements of the users 888 that include photoplethysmogram signals of the users 888 and temperature signals of the users 888. Optionally, each of the wearable devices 878 is an embodiment of the wearable device 840, described in detail further above. Optionally, at least some of the wearable devices 878 are smartglasses, such as the smartglasses illustrated in FIG. 2.

In some embodiments, the measurements of the users 888 taken with the wearable devices 878 include current measurements 883 of the users 888 and baseline measurements 884 of the users 888.

The current measurements 883 include for each user from among the users 888, measurements of the user, taken with a wearable device from among the wearable devices 878, up to 4 hours before an intended arrival time of the user to a premises 889. Optionally, current measurements 883 include measurements that are intended to reflect the state of the user during the hours leading up to an intended time of arriving at the premises 889.

The baseline measurements 884 include for each user from among the users 888, measurements of the user, taken with a wearable device from among the wearable devices 878 at least 10 hours before the intended arrival time of the user (i.e., the baseline measurements are taken 10 hours before the intended arrival or even earlier than 10 hours before the intended arrival). These measurements are intended to reflect a typical state of the user at an earlier time (e.g., the user's baseline state).

The computer 886 calculates health scores of the users 888 based on differences between the current measurements 883 and the baseline measurements 884. Optionally, the health score of each certain user from among the users 888 is calculated based on current measurements of the certain user, from among the current measurements 883, and baseline measurements of the certain user, from among the baseline measurements 884. Calculation of the health score for the certain user may be done in the same manner described herein in which the computer 847 calculates the health score based on differences between the current measurements and baseline measurements in embodiments illustrated in FIG. 1. Optionally, the calculation of the health score of the certain user is performed by a processor on a device of the certain user.

The computer 886 utilizes the health scores of the users 888 in order to identify a subset of the users 888 as non-symptomatic users. Optionally, this identification is done by comparing the health scores of the users 888 to a threshold, and selecting the users whose health score reaches the threshold (e.g., this threshold may be the first threshold mentioned in the context of embodiments illustrated in FIG. 1).

The computer 886 also authenticates identities of the non-symptomatic users based on at least some of their current measurements (i.e., measurements from among the current measurements 883 that are taken from them). Optionally, such an authentication is performed by the computer 886 in the same manner described in embodiments disclosed herein involving the computer 847. For example, the computer 886 may calculate the extent of similarity of PPG signals of a certain user in current measurements from among the current measurements 883 with a template generated based on previously measured PPG signals of that certain user (which may be in a database). Optionally, if the extent of similarity exceeds a threshold, the certain user may be considered authenticated. Additionally or alternatively, in some embodiments, authenticating the certain user may utilize additional signals from among current measurements 883 mentioned herein as useful for authentication, such as acoustic signals and/or movement signals.

The computer 886 may then utilize authentications of non-symptomatic users in order to manage access to the premises 889.

In one embodiment, the computer 886 notifies the non-symptomatic users, prior to their respective intended arrival times, that they are allowed on the premises 889.

In one embodiment, the computer 886 send notifications 887 to the users 888, indicating to each user whether the user will be allowed on the premises 889.

In one embodiment, the computer 886 receives additional measurements of a certain user among the non-symptomatic users, taken with a wearable device from among the wearable devices 878 after the current measurements of the certain user were taken, calculates an additional health score of the certain user based on differences between the additional measurements of the certain user and baseline measurements of the certain user, detects that the additional health score does not reach the threshold, and notifies the certain user that he/she not allowed on the premises 889.

In one embodiment, the computer 886 identifies a second subset of the users 888 as symptomatic users based on their health scores not reaching the threshold, and notifies the symptomatic users, prior to their respective arrival times, that they are not allowed on the premises 889.

In one embodiment, the computer 886 certifies the premises 889 as contagion-safe responsive to receiving an indication that none of the symptomatic users entered the premises 889 during a predetermined period. In one example, the indication that none of the symptomatic users entered the premises is received from a physical access security system that identifies the person at the gate/door/premises, such as: proximity card access system, smart card access system, swipe card access system, multi-technology access system, keypad access system, biometric access system, mobile access system, and/or video intercom access system.

In one embodiment, the premises 889 is an airplane, the intended arrival time is a boarding time to the airplane. Optionally, the computer 886 directs the non-symptomatic users and people who were not identified as non-symptomatic users to different airplanes. Alternatively, the computer 886 places the users 888 in the airplane according to cohorts, such that >75% of the passengers who sit in proximity of up to two rows from people who were not identified as non-symptomatic users are also people who were not identified as non-symptomatic users, and >75% of the passengers who sit in proximity of up to two rows from the non-symptomatic users are non-symptomatic users.

In another embodiment, the premises 889 is a train passenger car, and the computer 886 directs the non-symptomatic users and people who were not identified as non-symptomatic users to different cars.

Figure 13:
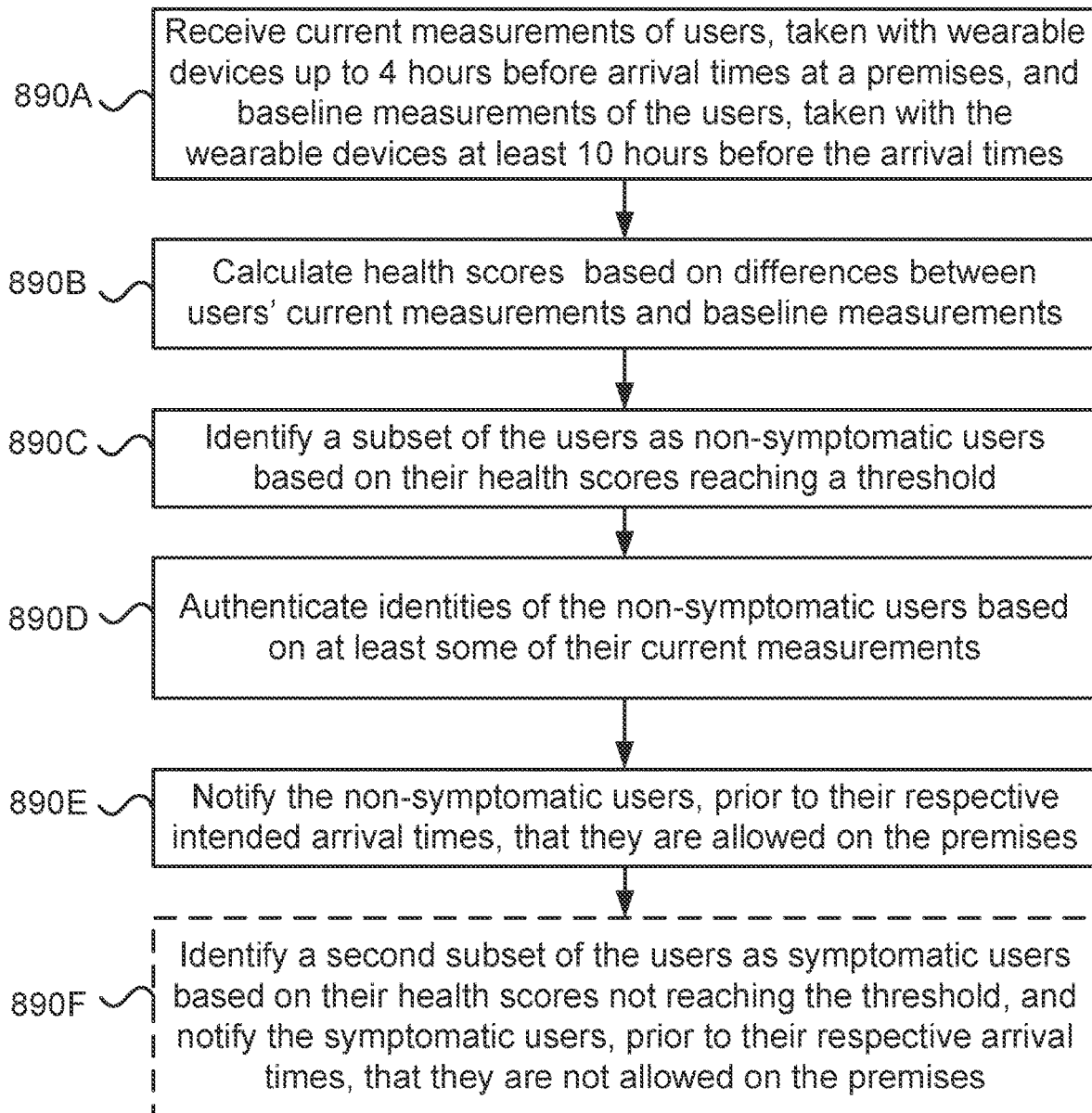
FIG. 13 illustrates steps that may be part of embodiments of a method for managing access to a contagion-safe premises.

FIG. 13B illustrates steps that may be part of embodiments of a method for managing access to a contagion-safe premises. The method may be implemented using embodiments of systems illustrated in FIG. 11, which is discussed above. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform steps from among the steps illustrated in FIG. 13B and/or additional steps mentioned below.

In one embodiment, the method for managing access to a contagion-safe premises includes at least the following steps:

In Step 890A, receiving measurements of users, measured with wearable devices, comprising photoplethysmogram signals and temperature signals. Optionally, the measurements include, for each users from among the users, current measurements and baseline measurements. Optionally, the current measurements of the user are measured with a wearable device up to 4 hours before an intended arrival time of the user to a premises, and baseline measurements of the user are measured with the wearable device at least 10 hours before the intended arrival time of the user.

In Step 890B, calculating, for each user from among the users, a health score of the user based on a difference between current measurements of the user and baseline measurements of the user.

In Step 890C, identifying a subset of the users as non-symptomatic users based on their health scores reaching a threshold.

In Step 890D, authenticating identities of the non-symptomatic users based on at least some of their current physiological signals.

And in Step 890E, notifying the non-symptomatic users, prior to their respective intended arrival times, that they arm allowed on the premises.

In one embodiment, the method optionally includes Step 890F that involves: identifying a second subset of the users as symptomatic users based on their health scores not reaching the threshold, and notifying the symptomatic users, prior to their respective arrival times, that they are not allowed on the premises.

In one embodiment, the method optionally includes a step of certifying the premises as contagion-safe responsive to receiving an indication that none of the symptomatic users entered the premises during a predetermined period.

In another embodiment, the method optionally includes the following steps: receiving additional measurements of a certain user among the non-symptomatic users, taken after the current measurements of the certain user were taken, calculating an additional health score of the certain user based on differences between the additional measurements of the certain user and baseline measurements of the certain user, detecting that the additional health score does not reach the threshold, and notifying the certain user that he/she not allowed on the premises.

Figure 14A:
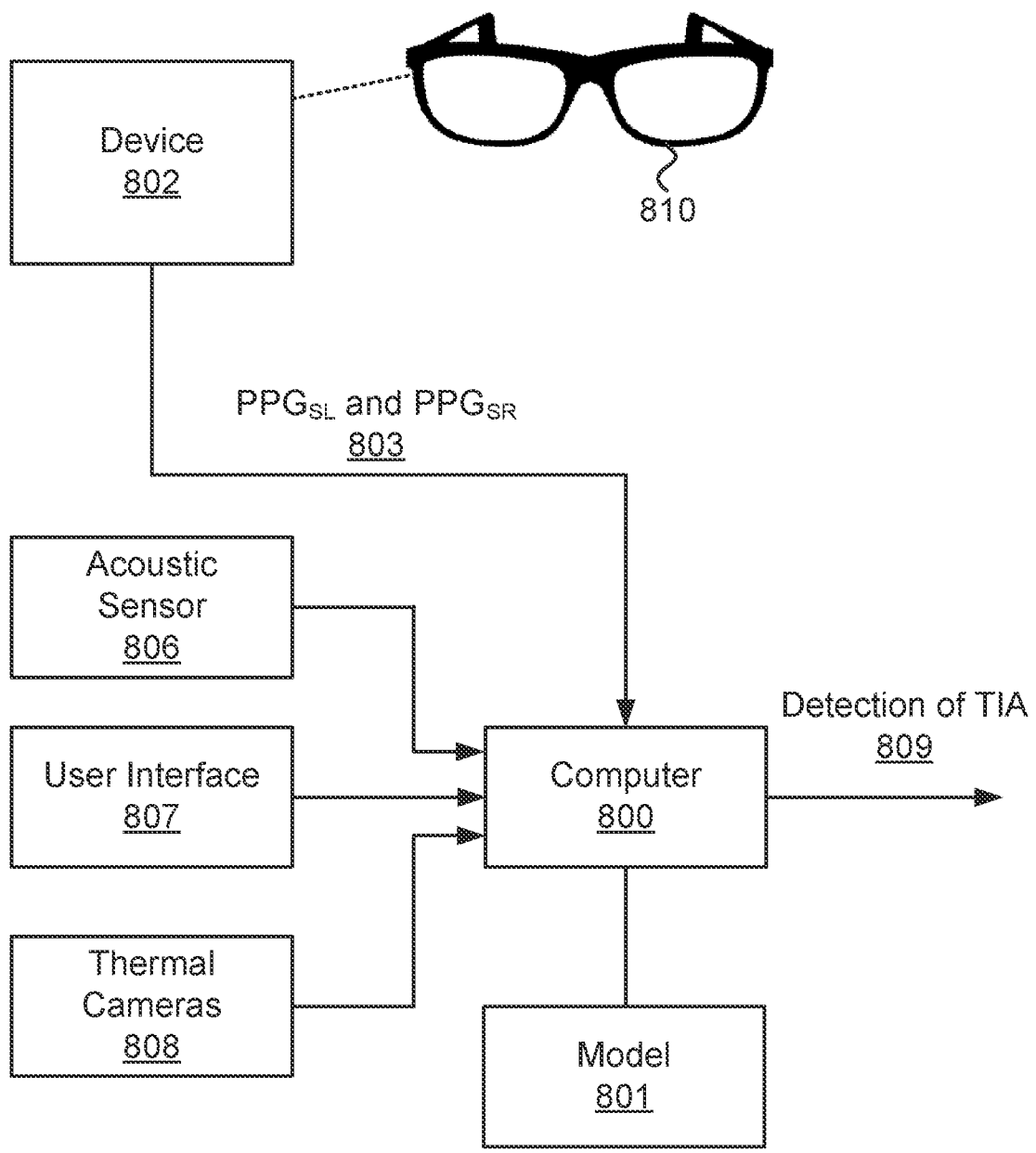
FIG. 14A illustrates an embodiment of a system configured to detect an occurrence of a transient ischemic attack (TIA)

FIG. 14A illustrates an embodiment of a system configured to detect an occurrence of a transient ischemic attack (TIA). In one embodiment, a device 802 that may include one or more different components (as described below) as well as a computer 800. In some embodiments, the system may optionally include additional elements such as a frame 810, an acoustic sensor 806, a user interface 807, and/or thermal cameras 808.

The device 802 is configured to measure first and second signals indicative of photoplethysmogram signals at first and second regions on the left and right sides of a user's head ($PPG_{SL}$ and $PPG_{SR}$, respectively, and jointly denoted in the figure with reference numeral 803). There are various types of devices which the device 802 may be or include.

In one embodiment, the device 802 is a video camera that is not head-mounted, such as a camera of a mobile phone, a camera of a laptop, and/or a webcam. Optionally, images captures by the video camera include regions on both sided of the user's head, and $PPG_{SL}$ and $PPG_{SR}$ 803 are generated based on different respective regions in these images.

In other embodiments, the device 802 includes left-side and right-side head-mounted devices. The left-side head-mounted device is configured to measure $PPG_{SL}$, and the right-side head-mounted device is configured to measure $PPG_{SR}$. Optionally, each of the left-side and right-side head-mounted devices is configured to be mounted less than 10 cm away from the user's head. Optionally, each of the left-side and right-side head-mounted devices is configured to be mounted less than 1 cm away from the user's head.

Different types of devices may be used as the left-side head-mounted device and the right-side head-mounted device. Some examples of types of devices that may be used include contact photoplethysmography devices (contact PPG devices) and inward-facing cameras (which are typically not in physical contact with the head). Herein, a "contact photoplethysmography device" is a photoplethysmography device that comes in contact with the user's skin, and typically occludes the area being measured. An example of a contact PPG device is the well-known pulse oximeter.

In some embodiments, the left-side head-mounted device and the right-side head-mounted device are the same type of device (e.g., both are contact PPG devices or both are inward-facing cameras). In other embodiments, the left-side head-mounted device and the right-side head-mounted device may be different types of devices. For example, the left-side head-mounted device may be a contact PPG device, while the right-side head-mounted device may be an inward-facing camera (or vice versa).

Figure 14B:
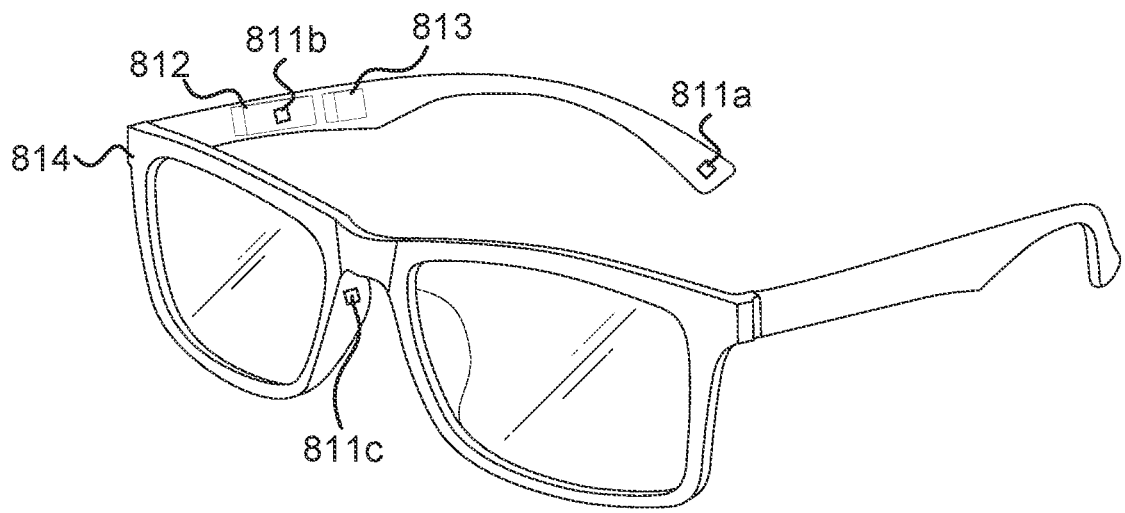
FIG. 14B illustrates smartglasses that include contact PPG devices.
Figure 14C:
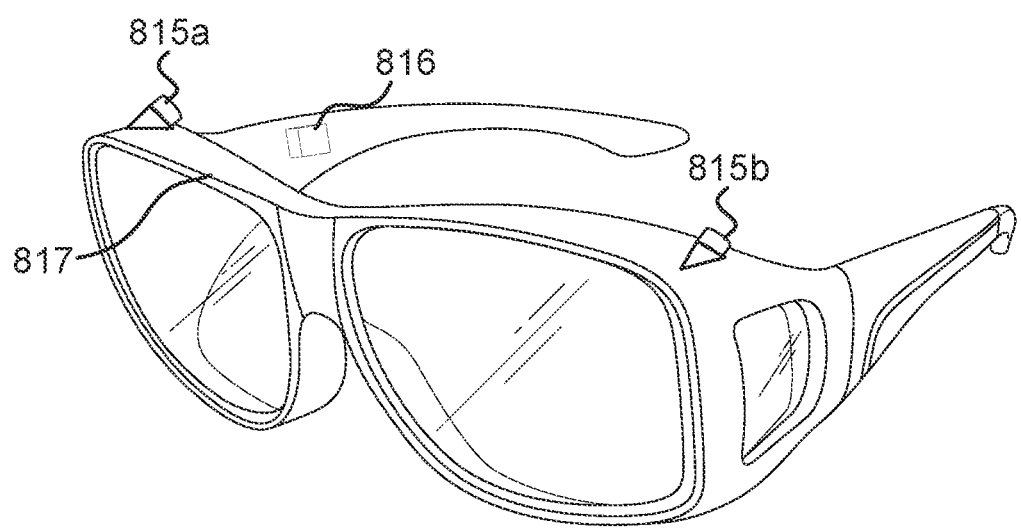
FIG. 14C illustrates smartglasses that include first and second inward-facing cameras.

In some embodiments, various devices, such as the device 802 and/or the computer 800 may be physically coupled to the frame 810, which may belong to smartglasses or to a smart-helmet, which is designed to measure the user in day-to-day activities, over a duration of weeks, months, and/or years. FIG. 14B and FIG. 14C illustrate smartglasses that may be utilized to realize the invention described herein.

In some embodiments, at least one of the left-side and right-side head-mounted devices includes a contact PPG device. Optionally, the at least one of the left-side and right-side head-mounted devices include a contact PPG device that is physically coupled to an eyeglasses or smartglasses frame and is in contact with one of the following regions: the nose, a temple, and a regions in the vicinity of an ear (e.g., within a distance of less than 5 cm from the center of the concha).

FIG. 14B illustrates smartglasses that include contact PPG devices that may be used to obtain PPG signals, such as $PPG_{SL}$ and $PPG_{SR}$ 803 described above. The contact PPG devices are coupled to a frame 814. The contact PPG devices may be coupled at various locations on the frame 814 and thus may come in contact with various regions on the user's head. For example, contact PPG device 811a is located on the right temple tip, which brings it to contact with a region behind the user's ear (when the user wears the smartglasses). Contact PPG device 811b is located on the right temple of the frame 814, which puts it in contact with a region on the user's right temple (when wearing the smartglasses). It is to be noted that in some embodiments, in order to bring the contact PPG device close such that it touches the skin, various apparatuses may be utilized, such as spacers (e.g., made from rubber or plastic), and/or adjustable inserts that can help bridge a possible gap between a frame's temple and the user's face. Such an apparatus is spacer 812 which brings contact PPG device 811b in contact with the user's temple when the user wears the smartglasses.

Another possible location for a contact PPG device is the nose bridge, as contact PPG device 811c is illustrated in the figure. It is to be noted the contact PPG device 811c may be embedded in the nose bridge (or one of its components), and/or physically coupled to a part of the nose bridge. The figure also illustrates computer 813, which may be utilized in some embodiments, to perform processing of PPG signals and/or for detection of an occurrence of a stroke, as described further below.

It is to be noted that FIG. 14B illustrates but a few of the possible locations for contact PPG devices on a frame. Additionally, some embodiments may include additional contact PPG devices on each side of the frames. Furthermore, it is to be noted that while contact PPG devices on the left side were not illustrated in the figure, additional PPG devices may be located in similar locations to the ones of PPG devices 811a to 811c are located, but on the left side of the frame.

In some embodiments, the left-side and/or right-side head-mounted devices include left and/or right inward-facing cameras, respectively, which are configured to be mounted more than 5 mm away from the user's head. Optionally, $PPG_{SL}$ and $PPG_{SR}$ 803 are recognizable from color changes in regions in images taken by the left and right inward-facing cameras, respectively.

In one embodiment, each of the left and right inward-facing cameras utilizes a sensor having more than 30 pixels, and each of the images taken by the left and right inward-facing cameras covers a skin area greater than 6 cm^2, which is illuminated by ambient light. In another embodiment, each of the left and right inward-facing cameras utilizes a sensor having more than 20 pixels, and each of the images taken by the left and right inward-facing cameras covers a skin area greater than 2 cm^2, which is illuminated by ambient light. In still another embodiment, each of the first and second inward-facing cameras utilizes a sensor comprising at least 3×3 pixels configured to detect electromagnetic radiation having wavelengths in at least a portion of the range of 200 nm to 1200 nm. Optionally, the aforementioned skin areas are located on the user's left and right cheeks. Additionally of alternatively, the skin areas may be located on the left and right sides of the user's forehead.

In one embodiment, the system includes first and second active light sources configured to illuminate portions of the right side of the face and portions of the left side of the face, respectively. In one example, the first and second active light sources are head-mounted light sources configured to illuminate their respective portions of the face with electromagnetic radiation having wavelengths in at least a portion of the range of 750 nm to 1200 nm.

FIG. 14C illustrates smartglasses that include first and second inward-facing cameras, such as the ones described above. The figure illustrates a frame 817 to which a first inward-facing camera 815a is coupled above the lens that is in front of the right eye, and a second inward-facing camera 815b that is coupled to the frame 817 above the lens that is in front of the left eye. The figure also illustrates a computer 816 that is coupled to the frame 817, and may be utilized to process images obtained by the first inward-facing camera 815a and/or the second inward-facing camera 815b, and/or perform the detection of the occurrence of the TIA based on $PPG_{SL}$ and $PPG_{SR}$ 803, which are recognizable in images captured by those cameras.

Herein, sentences of the form "a PPG signal is recognizable in images" or "a PPG signal is recognizable from color changes in a region in images" refer to effects of blood volume changes due to pulse waves that may be extracted from a series of images of the region. These changes may be identified and/or utilized by a computer (e.g., in order to generate a signal indicative of the blood volume at the region), but need not necessarily be recognizable to the naked eye (e.g., because of their subtlety, the short duration in which they occur, or involvement of light outside of the visible spectrum). For example, blood flow may cause facial skin color changes (FSCC) that corresponds to different concentrations of oxidized hemoglobin due to varying volume of blood at a certain region due to different stages of a cardiac pulse, and/or the different magnitudes of cardiac output.

In some embodiments, the system configured to detect occurrence of a TIA may further include first and second outward-facing head-mounted cameras for taking images of the environment to the right and to the left of the user's head, respectively. Images taken by these cameras, which are indicative of illumination towards the face, may be utilized to improve the accuracy of detecting the occurrence of the TIA.

In one example, the first and second outward-facing head-mounted cameras may be thermal cameras that take thermal measurements of the environment. Heat from the environment may affect the surface blood flow, and thus reduce the accuracy of detecting the occurrence of the TIA. By taking the thermal measurements of the environment into account, the computer is able to detect, and maybe even compensate, for temperature interferences from the environment. Examples of outward-facing head-mounted thermal cameras include thermopile-based and/or microbolometer-based cameras having one or more pixels.

In another example, the first and second outward-facing head-mounted cameras may be visible-light cameras (such as CMOS cameras), and/or light intensity sensors (such as photodiodes, photoresistors, and/or phototransistor). Illumination from the environment may affect the surface blood flow (especially when heating the skin), and/or interfere with the photoplethysmogram signals to be measured, and thus reduce the accuracy of detecting the TIA. By taking the illumination from the environment into account, the computer is able to detect, and maybe even compensate, for the interferences from the environment.

The computer 800 is configured, in one embodiment, to detect the occurrence of a TIA based on $PPG_{SL}$ and $PPG_{SR}$ 803. Optionally, "detection of the occurrence of the TIA" refers to detecting whether the user experienced a TIA during a time that falls within the first, second, and third periods. Optionally, the computer 800 forwards an indication of a detection of the TIA 809 to a device of the user and/or to another computer system. Optionally, a detection of a TIA occurs when $PPG_{SL}$ and $PPG_{SR}$ 803 exhibit a certain pattern of a changing extent of asymmetry between $PPG_{SL}$ and $PPG_{SR}$. Optionally, the pattern includes the following: (i) an asymmetry between $PPG_{SL}$ and $PPG_{SR}$, which is below a threshold, during a first period spanning more than a day; (ii) an asymmetry between $PPG_{SL}$ and $PPG_{SR}$, which exceeds the threshold, during a second period following the first period and spanning between 5 and 180 minutes; and (iii) an asymmetry between $PPG_{SL}$ and $PPG_{SR}$, which falls below the threshold, during a third period following the second period. In this embodiment, the meaning that the second period following the first period, and that the third period following the second period, is that the second period starts shortly after the first period, and the third period starts shortly after the second period. The duration of "shortly after" depends on the use case, and can be less than 60 minutes after, less than 10 minutes after, or less than a minute after.

Examples of computers that may be utilized to perform calculations involved in the detection of the occurrence of the TIA are computers modeled according to computer 400 or computer 410 illustrated in FIG. 70A and FIG. 70B, respectively. Additional examples are the computers 813 and 816 illustrated in FIG. 14B and FIG. 14C, respectively. It is to be noted that the use of the singular term "computer" is intended to imply one or more computers, which jointly perform the functions attributed to "the computer" herein. In particular, in some embodiments, some functions attributed to the computer, such as preprocessing $PPG_{SR}$ and $PPG_{SL}$, may be performed by a processor on a wearable device (e.g., smartglasses) and/or a computing device of the user (e.g., smartphone), while other functions, such as the analysis of sensor data and determining whether the user experienced a TIA, may be performed on a remote processor, such as a cloud-based server. In other embodiments, essentially all functions attributed to the computer herein may be performed by a processor on a wearable device (e.g., smartglasses to which the head-mounted devices are coupled) and/or some other device carried by the user, such as a smartwatch or smartphone.

The computer 800 detects the occurrence of the TIA based on $PPG_{SL}$ and $PPG_{SR}$ 803 that exhibit the aforementioned pattern over the first, second and third periods. This detection may be done in different ways, in different embodiments.

In one embodiment, the computer 800 directly detects the pattern, by explicitly determining that the three components of the pattern occurred. That is, that an asymmetry between $PPG_{SL}$ and $PPG_{SR}$, was below the threshold, during a first period spanning more than a day. Additionally, the computer 800 detects that the asymmetry between $PPG_{SL}$ and $PPG_{SR}$ exceeded the threshold during a second period following the first period, which spanned between 5 and 180 minutes. And finally, the computer 800 detects that the asymmetry between $PPG_{SL}$ and $PPG_{SR}$, fell below the threshold, during a third period following the second period. Optionally, the computer 800 may rely on additional considerations to detect the occurrence of the TIA, which are related to physiological signals calculated based on $PPG_{SL}$ and $PPG_{SR}$, as discussed below.

In another embodiment, the computer 800 may utilize a machine learning-based approach, which involves generating feature values based on $PPG_{SL}$ and $PPG_{SR}$, which were taken over at least the first, second, and third periods. These feature values may be indicative of various properties and relationships between $PPG_{SL}$ and $PPG_{SR}$ over different periods of time, which include at least the aforementioned first, second, and third periods. The feature values may optionally include at least some values indicative of the extent of asymmetry between $PPG_{SL}$ and $PPG_{SR}$ during different periods of time. Optionally, the computer 800 utilizes a model 801 to calculate a value indicative of whether the user had a TIA. Additional discussion regarding this machine learning-based approach is provided below.

Since PPG signals are indicative of the extent of blood flow, a change in asymmetry between $PPG_{SL}$ and $PPG_{SR}$ can be indicative of changes to the blood flow on one of the sides of the head. Asymmetric changes (e.g., an increase or decrease to the blood flow on one of the sided of the head) are typically different from symmetric changes that can be caused by factors such as physical activity (which typically affects the blood flow on both sides in the same way). An asymmetric change to the blood flow can mean that one side has been affected by an event, such as a stroke or TIA, which does not influence the other side. In one example, the asymmetric change to blood flow involves a change in blood flow velocity on left side of the head that is at least 10% greater or 10% lower than a change in blood flow velocity on one right side of the head. In another example, the asymmetric change to blood flow involves a change in the volume of blood the flows during a certain period in the left side of the head that is at least 10% greater or 10% lower than the volume of blood that flows during the certain period in the right side of the head. In yet another example, the asymmetric change to blood flow involves a change in the direction of the blood flow on one side of the head (e.g., as a result of a stroke), which is not necessarily observed at the symmetric location on the other side of the head.

The asymmetrical changes in the blood flow according to which the computer 800 detects the occurrence of the TIA are recognizable in $PPG_{SL}$ and $PPG_{SL}$. Referring to an asymmetrical change to blood flow as being "recognizable in $PPG_{SL}$ and $PPG_{SR}$" means that values extracted from $PPG_{SL}$ and $PPG_{SR}$ provide an indication that an asymmetric change to the blood flow has occurred. That is, a difference that has emerged in the $PPG_{SL}$ and $PPG_{SR}$ may reflect a change in blood flow velocity on one side of the head, a change in blood flow volume, and/or a change in blood flow direction, as described in the examples above. It is to be noted, that the change in blood flow does not need to be directly quantified from the values $PPG_{SL}$ and $PPG_{SR}$ in order for it to be "recognizable in $PPG_{SL}$ and $PPG_{SR}$". Rather, in some embodiments, feature values generated based on $PPG_{SL}$ and $PPG_{SR}$ may be used by a machine learning-based model to detect the occurrence of the TIA.

In some embodiments, the device 802 is used to acquire multiple PPG signals, which may optionally include additional PPG signals in addition to $PPG_{SL}$ and $PPG_{SR}$ (e.g., utilizing more than two contact PPG devices or by analyzing more than two regions in images acquired by video cameras). Having multiple PPG signals, measured at different sides of the head, can assist in detecting an asymmetric change to blood flow in different ways. In one example, an asymmetric change in blood flow may be characterized in an increase in volume at a certain region and/or side of the head, compared to other regions and/or the other side of the head. In this example, the amplitude of the PPG signal at the certain region may show a greater increase compared to increases observed with PPG signals at other regions and/or on the other side of the head. In another example, an asymmetric change in blood flow may be characterized by a decrease in blood velocity at a certain region and/or side of the head, compared to other regions and/or the other side of the head. In this example, a pulse arrival time (PAT) at the certain region may exhibit a larger delay compared to the delay of PATs at other regions and/or at the other side of the head. In still another example, an asymmetric change in blood flow may be characterized by a change in a direction of blood flow at a certain region, compared to other regions and/or the symmetric region on the other side of the head. In this example, an order at which pulse waves arrive at different regions (as evident by PPG signals at the different regions) may be indicative of the direction of blood flow. Thus, a change in the arrival order of pulse waves on one side of the head, which does not occur at regions on the other side of the head, may indicate an asymmetrical change of a direction of blood flow.

In some embodiments, the computer 800 detects the occurrence of the TIA by utilizing previously taken PPG signals of the user (i.e., previously taken $PPG_{SL}$ and $PPG_{SR}$). This enables an extent of asymmetrical change to be observed, since it provides a baseline according to which it is possible to compare current $PPG_{SL}$ and $PPG_{SR}$ such that it may be determined that a change to blood flow on one side of the head is not the same as a change on the other side of the head. In some embodiments, previously taken $PPG_{SL}$ and $PPG_{SR}$ are utilized to calculate a baseline blood flow, such as values representing the extent of blood flow at the different sides of the head, and/or at different regions. Optionally, calculating the baseline blood flow may be done based on previously taken $PPG_{SL}$ and $PPG_{SR}$ that were measured at least an hour before the beginning of the first period. Optionally, the previously taken $PPG_{SL}$ and $PPG_{SR}$ include PPG signals measured at least a day before the first period. Optionally, the previously taken $PPG_{SL}$ and $PPG_{SR}$ include PPG signals measured more than a week before the first period.

A baseline for the blood flow may be calculated in various ways. In a first example, the baseline is a function of the average measurements of the user (which include previously taken $PPG_{SL}$ and $PPG_{SR}$), which were taken before the first period. In a second example, the baseline may be a function of the situation the user is in, such that previous measurements taken during similar situations are weighted higher than previous measurements taken during less similar situations. A PPG signal may show different characteristics in different situations because of the different mental and/or physiological states of the user in the different situations. As a result, a situation-dependent baseline can improve the accuracy of detecting the occurrence of the TIA. In a third example, the baseline may be a function of an intake of some substances (such as food, beverage, medications, and/or drugs), such that previous measurements taken after consuming similar substances are weighted higher than previous measurements taken after not consuming the similar substances and/or after consuming less similar substances. A PPG signal may show different characteristics after the user consumes different substances because of the different mental and/or physiological states the user may enter after consuming the substances, especially when the substances include things such as medications, drugs, alcohol, and/or certain types of food. As a result, a substance-dependent baseline can improve the accuracy of detecting the occurrence of the TIA.

In addition to $PPG_{SL}$ and $PPG_{SR}$ having the aforementioned pattern involving changes to asymmetry, in some embodiments, the computer 800 may base the detection of the occurrence of the TIA on certain parameters calculated based on $PPG_{SL}$ and $PPG_{SR}$. Optionally, the computer 800 may calculate, based on $PPG_{SL}$ and $PPG_{SR}$, one or more of the following values: heart rate (HR), heart rate variability (HRV), and blood pressure (BP).

In one embodiment, the computer 800 may detect the occurrence of the TIA based on one or more of the following changes between the first period and the second period: an increase in the HR, a decrease in the HRV, and an increase in the BP. Additionally or alternatively, the computer 800 may detect the occurrence of the TIA also based on one or more of the following changes occurring between the second period and the third period: a decrease in the HR, an increase in the HRV, and a decrease in the BP. Calculation of HR, HRV, and BP may be done using various techniques known in the art. For example, calculation of HR can be done by detecting the time that elapses between systolic peaks, and HRV may be determined based on the variance of those times. In another example, BP may be calculated based on various techniques described in U.S. Pat. No. 10,349,887 titled "Blood pressure measuring smartglasses", issued on Jul. 16, 2019, and U.S. Pat. No. 10,376,163 titled "Blood pressure from inward-facing head-mounted cameras", which was issued on Aug. 13, 2019.

In one embodiment, the computer 800 may calculate, based on $PPG_{SL}$ and $PPG_{SR}$, values indicative of blood pressure variability (BPV), based on the variance observed between the values of BP during a period of time. Optionally, the computer 800 may detect the occurrence of the TIA also based on: (i) an increase in the BPV between the first period and the second period, and (ii) a decrease in the BPV between the second period and the third period.

Obtaining $PPG_{SL}$ and $PPG_{SR}$ from measurements taken by contact PPG devices and/or cameras may involve, in some embodiments, performing various preprocessing operations in order to assist in calculations and/or in extraction of the PPG signals. Optionally, the measurements may undergo various preprocessing steps prior to being used by the computer 800 to detect the occurrence of the TIA. Some non-limiting examples of the preprocessing include: normalization of pixel intensities (e.g., to obtain a zero-mean unit variance time series signal), and conditioning a time series signal by constructing a square wave, a sine wave, or a user defined shape, such as that obtained from an ECG signal or a PPG signal as described in U.S. Pat. No. 8,617,081.

In some embodiments, one or more cameras are utilized to obtain $PPG_{SL}$ and $PPG_{SR}$, images taken by the one ore more cameras may undergo various preprocessing to improve the signal, such as color space transformation (e.g., transforming RGB images into a monochromatic color or images in a different color space), blind source separation using algorithms such as independent component analysis (ICA) or principal component analysis (PCA), and various filtering techniques, such as detrending, bandpass filtering, and/or continuous wavelet transform (CWT). Various preprocessing techniques known in the art that may assist in extracting an PPG signals from images are discussed in Zaunseder et al. (2018), "Cardiovascular assessment by imaging photoplethysmography—a review". Biomedical Engineering 63(5), 617-634. An example of preprocessing that may be used in some embodiments is given in U.S. Pat. No. 9,020,185, titled "Systems and methods for non-contact heart rate sensing", which describes how a times-series signals obtained from video of a user can be filtered and processed to separate an underlying pulsing signal by, for example, using an ICA algorithm.

In some embodiments, detection of the occurrence of the TIA may involve calculation of pulse arrival times (PATs) at the first and second regions on the left and right sides of a user's head. Optionally, a PAT calculated from an PPG signal represents a time at which the value representing blood volume (in the waveform represented in the PPG) begins to rise (signaling the arrival of the pulse). Alternatively, the PAT may be calculated as a different time, with respect to the pulse waveform, such as the time at which a value representing blood volume reaches a maximum or a certain threshold, or the PAT may be the average of the time the blood volume is above a certain threshold. Another approach that may be utilized to calculate a PAT from an iPPG signal is described in Sola et al. "Parametric estimation of pulse arrival time: a robust approach to pulse wave velocity", Physiological measurement 30.7 (2009): 603, which describe a family of PAT estimators based on the parametric modeling of the anacrotic phase of a pressure pulse.

In addition to $PPG_{SL}$ and $PPG_{SR}$ obtained by the device 802, in some embodiments, the computer 800 may utilize measurements obtained by other sensors and/or devices in order to detect whether there was an occurrence of a TIA.

In some cases, TIA may cause difficulties in swallowing resulting from neurologic deficit affecting the pharyngeal muscles. This will cause characteristic coughing and/or throat clearing sounds, and possibly new sounds associated with swallowing activity. In one embodiment, the acoustic sensor 806 is used to measure sounds indicative of coughing of the user (referred to herein as "coughing sounds"). In this embodiment, the computer 700 may to detect the occurrence of the TIA also based on a change to the coughing sounds involving one or more of the following: (i) a decrease below a first threshold in power of coughing sounds during the second period relative to power of coughing sounds during the first period, and (ii) a decrease below a second threshold in power spectral density of the coughing sounds during the second period relative to power spectral density of the coughing sounds during the first period. Detection of coughing sounds from audio, and/or the detection of the extent of coughing sounds, may rely on various techniques known in the art for audio analysis. Optionally, the extent of coughing is proportional to the duration during which coughing sounds were detected and/or the volume at which the coughing sounds were detected.

In another embodiment, the computer 800 may utilize measurements taken using the acoustic sensor 806 to determine an extent to which the user's speech is slurred. Optionally, the computer 800 may detect the occurrence of the TIA also based on a difference between the following two extents reaching a threshold: (i) a first extent to which the user's speech was slurred during the first period, and (ii) a second extent to which the user's speech was slurred during the second period. Detection of slurred speech may be done using audio analysis techniques known in the art. Slurred speech is one of the signs of a stroke, so temporary increases in slurred speech may be a sign of a TIA.

In another embodiment, the user interface 807 (e.g., a speaker or screen on a wearable device) may be utilized to ask the user questions. The computer 800 may utilize measurements taken using the acoustic sensor 806, and detect the occurrence of the TIA also based on an increase in the difference between the following two delays reaching a threshold: (i) a first delay it took the user to answer a question during the first period, and (ii) a second delay it took the user to answer a question during the second period. The delay it takes the user to answer a question may be manifested in various ways. In a first example, the time (in seconds) it takes the user to answer the question may increase while having the TIA. In a second example, difficulties in finding the right words may increase, which may increase the length of pauses between words while having the TIA, and thus increase the time it takes the user to answer the question.

In another embodiment, the computer 800 may utilize measurements taken using the acoustic sensor 806 to detect changes to parameters that characterize the user's speech: a decrease in the fundamental frequency, a decrease in speech volume, a decrease in speech fluency, an increase in average time per syllable, an increase in average voicing time per syllable, an increase in average non-voiced time per syllable, an increase in hesitation during speech, and an increase in initial response time to questions. Optionally, the computer 800 may utilize indications of changes to parameters that characterize the user's speech to detect the occurrence of the TIA, which is known to often have an effect on speech patterns.

In some embodiments, the thermal cameras 808, which may include left-side and right-side head-mounted thermal cameras, are used to take first and second measurements indicative of temperatures in regions to right and to the left of the vertical symmetry axis ($T_R$ and $T_L$, respectively) that divides a user's face. Optionally, the computer 800 may detect the occurrence of the TIA also based on an increase in a difference between $T_R$ and $T_L$ during the second period relative to a difference between $T_R$ and $T_L$ during the first period. It is to be noted that differences between $T_R$ and $T_L$ are sign sensitive. For example, the change between $T_R=34°$ C., and $T_L=33.8°$ C., to $T_R=33.7°$ C. and $T_L=33.8°$ C., is a change of 0.3° C.

The computer 800 may utilize indications of other medical phenomena which may be determined based on $PPG_{SL}$ and $PPG_{SR}$ to assist in the detection of the occurrence of the TIA.

In one embodiment, the computer 800 calculates, based on $PPG_{SL}$ and $PPG_{SR}$, values indicative of severity of arrhythmia experienced by the user during the first, second, and third periods. Optionally, the computer 800 detects the occurrence of the TIA also based on: (i) an increase in the severity of arrhythmia during the second period relative to the first period, and (ii) a decrease in the severity of arrhythmia during the third period relative to the second period.

In one embodiment, the computer 800 suggests to the user to take images of at least one of the retinas during the second period. The computer 800 may then compare the images of the retinas with previously taken images of the user's retinas, and utilize the comparison to detect the occurrence of the TIA.

Detection of the occurrence of the TIA may involve the computer 800 utilizing an approach that may be characterized as involving machine learning. In some embodiments, such a detection approach may involve the computer 800 generating feature values based on data that includes $PPG_{SL}$ and $PPG_{SR}$ and optionally other data, and then utilizing a previously trained model 801 to calculate one or more values indicative of whether there was an occurrence of a TIA. It is to be noted that when the computer 800 calculates a value that is indicative whether there was an occurrence of a TIA, at least some of the feature values may reflect the fact that an asymmetrical change to blood flow had occurred, which follows the pattern mentioned above. Optionally, the additional data used to generate at least some of the feature values includes previous measurements of $PPG_{SL}$ and $PPG_{SR}$ of the user, and/or measurements from additional sensors and/or data sources as discussed below.

Feature values generated based on PPG signals may include various types of values, which may be indicative of dynamics of the blood flow at the respective regions to which the PPG signals correspond. Optionally, these feature values may relate to properties of a pulse waveform (e.g., fiducial points), which may be a specific pulse waveform (which corresponds to a certain beat of the heart), or a window of pulse waveforms (e.g., an average property of pulse waveforms in a certain window of time).

Some examples of feature values that may be generated based on a pulse waveform include: the area under the pulse waveform, the amplitude of the pulse waveform, a derivative and/or second derivative of the pulse waveform, a pulse waveform shape, pulse waveform energy, and pulse transit time (to the respective ROI). Optionally, some feature values may be derived from fiducial points identified in the PPG signals; these may include values such as magnitudes of the PPG signal at certain fiducial points, offsets between different fiducial points at the like, and/or other differences between fiducial points. Some examples of fiducial point-based feature values may include one or more of the following: a magnitude of a systolic peak, a magnitude of a diastolic peak, duration of the systolic phase, and duration of the diastolic phase. Additional examples of feature values may include properties of the cardiac activity, such as the heart rate and heart rate variability (as determined from the PPG signal). Additionally, some feature values may include values of other physiological signals that may be calculated based on PPG signals, such as blood pressure and cardiac output.

It is to be noted that the aforementioned feature values may be calculated in various ways. In one example, some feature values are calculated for each PPG signal individually. In another example, some feature values are calculated after normalizing a PPG signal with respect to previous measurements from the corresponding PPG device used to measure the PPG signal. In other examples, at least some of the feature values may be calculated based on an aggregation of multiple PPG signals (e.g., different pixels/regions in images captured by an iPPG device), or by aggregating values from multiple contact PPG devices.

In some embodiments, at least some of the feature values may represent comparative values, which provide an indication of the difference in blood flow, and/or in some other property that may be derived from a PPG signal, between various regions on the head and/or between various times. Thus, some feature values may reflect dynamics of asymmetry overtime between $PPG_{SL}$ and $PPG_{SR}$.

In some embodiments, at least some of the feature values may be "raw" or minimally processed measurements of the at least one right-side head-mounted device and/or at least one left-side head-mounted device. In one example, at least some of the feature values may be values obtained from contact PPG devices. In another example, at least some of the feature values may be pixel values obtained by inward-facing head-mounted cameras. Optionally, the pixel values may be provided as input to functions in order to generate at feature values that are low-level image-based features. Some examples of low-level features, which may be derived from images, include feature generated using Gabor filters, local binary patterns (LBP) and their derivatives, algorithms such as SIFT and/or SURF (and their derivatives), image keypoints, histograms of oriented gradients (HOG) descriptors, and products of statistical procedures such independent component analysis (ICA), principal component analysis (PCA), or linear discriminant analysis (LDA). Optionally, one or more of the feature values may be derived from multiple images taken at different times, such as volume local binary patterns (VLBP), cuboids, and/or optical strain-based features. In one example, one or more of the feature values may represent a difference between values of pixels at one time t and values of other pixels at a different region at some other time t+x (which, for example, can help detect different arrival times of a pulse wave).

In some embodiments, at least some feature values may be generated based on other data sources (in addition to $PPG_{SL}$ and $PPG_{SR}$). In some examples, at least some feature values may be generated based on additional PPG signals acquired using additional PPG devices (in addition to the device 802). In other examples, at least some feature values may be generated based on measurements of other sensors, such as movement sensors (which may be head-mounted, wrist-worn, or carried by the user some other way), head-mounted thermal cameras (e.g., the thermal cameras 808), or other sensors used to measure the user (e.g., the acoustic sensor 806). In other examples, at least son feature values may be indicative of environmental conditions, such as the temperature, humidity, and/or extent of illumination (e.g., as obtained utilizing an outward-facing head-mounted camera). Additionally, some feature values may be indicative of physical characteristics of the user, such as age, sex, weight, Body Mass Index (BMI), skin tone, and other characteristics and/or situations the user may be in (e.g., level of tiredness, consumptions of various substances, etc.)

Stress is a factor that can influence the diameter of the arteries, and thus influence calculated values that relate to the PPG signals and/or blood flow. In one embodiment, the computer receives a value indicative of a stress level of the user, and generates at least one of the feature values based on the received value. Optionally, the value indicative of the stress level is obtained using a thermal camera. In one example, the system may include an inward-facing head-mounted thermal camera that takes measurements of a penorbital region of the user, where the measurements of a periorbital region of the user are indicative of the stress level of the user. In another example, the system includes an inward-facing head-mounted thermal camera that takes measurements of a region on the forehead of the user, where the measurements of the region on the forehead of the user are indicative of the stress level of the user. In still another example, the system includes an inward-facing head-mounted thermal camera that takes measurements of a region on the nose of the user, where the measurements of the region on the nose of the user are indicative of the stress level of the user.

Hydration is a factor that affects blood viscosity, which can affect the speed at which the blood flows in the body. In one embodiment, the computer 800 receives a value indicative of a hydration level of the user, and generates at least one of the feature values based on the received value. Optionally, the system includes an additional camera that detects intensity of radiation that is reflected from a region of exposed skin of the user, where the radiation is in spectral wavelengths chosen to be preferentially absorbed by tissue water. In one example, said wavelengths are chosen from three primary bands of wavelengths of approximately 1100-1350 nm, approximately 1500-1800 nm, and approximately 2000-2300 nm. Optionally, measurements of the additional camera are utilized by the computer as values indicative of the hydration level of the user.

The following are examples of embodiments that utilize additional inputs to generate feature values used to detect the occurrence of the TIA. In one embodiment, the computer 800 receives a value indicative of a temperature of the user's body, and generates at least one of the feature values based on the received value. In another embodiment, the computer 800 receives a value indicative of a movement of the user's body, and generates at least one of the feature values based on the received value. For example, the computer may receive the input form a head-mounted Inertial Measurement Unit (IMU) that includes a combination of accelerometers, gyroscopes, and optionally magnetometers, and/or an IMU in a mobile device carried by the user. In yet another embodiment, the computer 800 receives a value indicative of an orientation of the user's head, and generates at least one of the feature values based on the received value. For example, the computer 800 may receive the values indicative of the head's orientation from an outward-facing head-mounted camera, and/or from a nearby non-wearable video camera. In still another embodiment, the computer 800 receives a value indicative of consumption of a substance by the user, and generates at least one of the feature values based on the received value. Optionally, the substance comprises a vasodilator and/or a vasoconstrictor.

The model 801 utilized to detect the occurrence of the TIA may be generated, in some embodiments, based on data obtained from one or more users, corresponding to times in which the one or more users did not suffer from a stroke or a TIA, and additional data obtained while the users had a stroke or TIA and/or following that time. Thus, this training data may reflect PPG signals and/or blood flow both at normal times, and changes to PPG signals and/or blood flow that may ensue due to the TIA.

The aforementioned training data may be used to generate samples, each sample including feature values generated based on PPG signals of a certain user and optionally additional data (as described above), and a label. The PPG signals include measurements of the certain user (e.g., taken with the device 802) at a certain time, and optionally previous measurements of the user taken before the certain time. The label is a value related to the TIA (e.g., an indication of whether the user had a TIA and/or its severity).

In some embodiments, the model 801 used by the computer 800 to detect the occurrence of a TIA may be generated, at least in part, based on data obtained from a diverse set of users (e.g., users of different ages, weights, sexes, preexisting medical conditions, etc.). Optionally, the data used to train the model which is used to detect occurrence of a TIA with a certain user includes data of other users with similar characteristics to the certain user (e.g., similar weight, age, sex, height, and/or preexisting condition).

In order to achieve a robust model, which may be useful for detecting an occurrence of a TIA in a diverse set of conditions, in some embodiments, the samples used for the training of the model 801 may include samples based on data collected when users were in different conditions. Optionally, the samples are generated based on data collected on different days, while indoors and outdoors, and while different environmental conditions persisted. In one example, the model is trained on samples generated from a first set of training data taken during daytime, and is also trained on other samples generated from a second set of training data taken during nighttime. In a second example, the model is trained on samples generated from a first set of training data taken while users were exercising and moving, and is also trained on other samples generated from a second set of data taken while users were sitting and not exercising.

Utilizing the model 801 to detect the occurrence of the TIA may involve the computer 800 performing various operations, depending on the type of model. The following are some examples of various possibilities for the model 801 and the type of calculations that may be accordingly performed by the computer 800, in some embodiments, in order to calculate a value indicative of whether the TIA occurred: (a) the model 801 comprises parameters of a decision tree. Optionally, the computer 800 simulates a traversal along a path in the decision tree, determining which branches to take based on the feature values. A value indicative of whether a TIA occurred may be obtained at the leaf node and/or based on calculations involving values on nodes and/or edges along the path; (b) the model 801 comprises parameters of a regression model (e.g., regression coefficients in a linear regression model or a logistic regression model). Optionally, the computer 800 multiplies the feature values (which may be considered a regressor) with the parameters of the regression model in order to obtain the value indicative of whether the TIA occurred; and/or (c) the model 801 comprises parameters of a neural network. For example, the parameters may include values defining at least the following: (i) an interconnection pattern between different layers of neurons, (ii) weights of the interconnections, and (iii) activation functions that convert each neuron's weighted input to its output activation. Optionally, the computer 800 provides the feature values as inputs to the neural network, computes the values of the various activation functions and propagates values between layers, and obtains an output from the network, which is the value indicative of whether there was an occurrence of a TIA.

In some embodiments, a machine learning approach that may be applied to calculating a value indicative of whether the user had the TIA may be characterized as "deep learning". In one embodiment, the model 801 may include parameters describing multiple hidden layers of a neural network. Optionally, the model 801 may include a convolution neural network (CNN). In one example, the CNN may be utilized to identify certain patterns in video images, such as the patterns of corresponding to blood volume effects and ballistocardiographic effects of the cardiac pulse. Due to the fact that calculating a value indicative of whether there was an occurrence of a TIA may be based on multiple, possibly successive, images that display a certain pattern of change over time (i.e., across multiple frames), these calculations may involve retaining state information that is based on previous images. Optionally, the model 801 may include parameters that describe an architecture that supports such a capability. In one example, the model may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

The following method for detecting an occurrence of a transient ischemic attack (TIA) may be used by systems modeled according to FIG. 14A, FIG. 14B or FIG. 14C. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, receiving first and second signals indicative of photoplethysmogram signals at first and second regions on the left and right sides of a user's head ($PPG_{SL}$ and $PPG_{SR}$, respectively). Optionally, $PPG_{SL}$ and $PPG_{SR}$ are measured using the device 802, as discussed above.

And in Step 2, detecting the occurrence of the TIA based on $PPG_{SL}$ and $PPG_{SR}$, which exhibit a pattern comprising: (i) asymmetry between $PPG_{SL}$ and $PPG_{SR}$, which is below a threshold, during a first period spanning more than a day; (ii) asymmetry between $PPG_{SL}$ and $PPG_{SR}$, which exceeds the threshold, during a second period following the first period and spanning between 5 and 180 minutes; and (iii) asymmetry between $PPG_{SL}$ and $PPG_{SR}$, which falls below the threshold, during a third period following the second period.

In one embodiment, the method optionally includes a step of generating, based on $PPG_{SL}$ and $PPG_{SR}$, feature values indicative of heart rate (HR), heart rate variability (HRV), and blood pressure (BP). Optionally, detecting the occurrence of the TIA also involves utilizing a machine learning-based model trained to detect the following changes between the first period and the second period: an increase in the HR, a decrease in the HRV, and an increase in the BP. Optionally, the method also includes a step of utilizing the machine learning-based model for detecting the occurrence of the TIA also based on detecting the following changes between the second period and the third period: a decrease in the HR, an increase in the HRV, and a decrease in the BP.

In one embodiment, the method optionally includes a step of taking measurements of the user's speech (e.g., with the acoustic sensor 806), and asking the user questions (e.g., via the user interface 807). Optionally, detecting of the occurrence of the TIA is also based on an increase in the difference between the following two delays reaching a threshold: (i) a first delay it took the user to answer a question during the first period, and (ii) a second delay it took the user to answer a question during the second period.

In another embodiment, the method optionally includes a step of taking measurements of the user's speech (e.g., with the acoustic sensor 806), and detecting the occurrence of the TIA is also based on one or more of the following parameters of the user's speech: a decrease in the fundamental frequency, a decrease in speech volume, a decrease in speech fluency, an increase in average time per syllable, an increase in average voicing time per syllable, an increase in average non-voiced time per syllable, an increased in repeated or prolonged word searching sounds, and an increase in initial response time to questions.

In one embodiment the method optionally includes a step of generating, based on $PPG_{SL}$ and $PPG_{SR}$, feature values indicative of severity of arrhythmia experienced by the user during the first, second, and third periods. Optionally, the detecting of the occurrence of the TIA involves utilizing a machine learning-based model trained for diagnosing the TIA based on detecting an increase in the severity of arrhythmia during the second period relative to the first period, and detecting a decrease in the severity of arrhythmia during the third period relative to the second period.

A "thermal camera" refers herein to a non-contact device that measures electromagnetic radiation having wavelengths longer than 2500 nanometer (nm) and does not touch its region of interest (ROI). A thermal camera may include one sensing element (pixel), or multiple sensing elements that are also referred to herein as "sensing pixels", "pixels", and/or focal-plane array (FPA). A thermal camera may be based on an uncooled thermal sensor, such as a thermopile sensor, a microbolometer sensor (where microbolometer refers to any type of a bolometer sensor and its equivalents), a pyroelectric sensor, or a ferroelectric sensor.

Sentences in the form of "thermal measurements of an ROI" (usually denoted $TH_{ROI}$ or some variant thereof) refer to at least one of: (i) temperature measurements of the ROI ($T_{ROI}$), such as when using thermopile or microbolometer sensors, and (ii) temperature change measurements of the ROI ($\Delta T_{ROI}$), such as when using a pyroelectric sensor or when deriving the temperature changes from temperature measurements taken at different times by a thermopile sensor or a microbolometer sensor.

In some embodiments, a device, such as a thermal camera, may be positioned such that it occludes an ROI on the user's face, while in other embodiments, the device may be positioned such that it does not occlude the ROI. Sentences in the form of "the system/camera does not occlude the ROI" indicate that the ROI can be observed by a third person located in front of the user and looking at the ROI, such as illustrated by all the ROIs in FIG. 22, FIG. 26 and FIG. 34. Sentences in the form of "the system/camera occludes the ROI" indicate that some of the ROIs cannot be observed directly by that third person, such as ROIs 19 and 37 that are occluded by the lenses in FIG. 16A, and ROIs 97 and 102 that are occluded by cameras 91 and 96, respectively, in FIG. 24.

Although many of the disclosed embodiments can use occluding thermal cameras successfully, in certain scenarios, such as when using an HMS on a daily basis and/or in a normal day-to-day setting, using thermal cameras that do not occlude their ROIs on the face may provide one or more advantages to the user, to the HMS, and/or to the thermal cameras, which may relate to one or more of the following: esthetics, better ventilation of the face, reduced weight, simplicity to wear, and reduced likelihood to being tarnished.

A "Visible-light camera" refers to a non-contact device designed to detect at least some of the visible spectrum, such as a camera with optical lenses and CMOS or CCD sensor. The term "inward-facing head-mounted camera" refers to a camera configured to be worn on a user's head and to remain pointed at its ROI, which is on the user's face, also when the user's head makes angular and lateral movements (such as movements with an angular velocity above 0.1 rad/sec, above 0.5 rad/sec, and/or above 1 rad/sec). A head-mounted camera (which may be inward-facing and/or outward-facing) may be physically coupled to a frame worn on the user's head, may be attached to eyeglass using a clip-on mechanism (configured to be attached to and detached from the eyeglasses), or may be mounted to the user's head using any other known device that keeps the camera in a fixed position relative to the user's head also when the head moves. Sentences in the form of "camera physically coupled to the frame" mean that the camera moves with the frame, such as when the camera is fixed to (or integrated into) the frame, or when the camera is fixed to (or integrated into) an element that is physically coupled to the frame. The abbreviation "CAM" denotes "inward-facing head-mounted thermal camera", the abbreviation "CAM$_{out}$" denotes "outward-facing head-mounted thermal camera", the abbreviation "VCAM" denotes "inward-facing head-mounted visible-light camera", and the abbreviation "VCAM$_{out}$" denotes "outward-facing head-mounted visible-light camera".

Sentences in the form of "a frame configured to be worn on a user's head" or "a frame worn on a user's head" refer to a mechanical structure that loads more than 50% of its weight on the user's head. For example, an eyeglasses frame may include two temples connected to two rims connected by a bridge; the frame in Oculus Rift™ includes the foam placed on the user's face and the straps; and the frames in Google Glass™ and Spectacles by Snap Inc. are similar to eyeglasses frames. Additionally or alternatively, the frame may connect to, be affixed within, and/or be integrated with, a helmet (e.g., sports, motorcycle, bicycle, and/or combat helmets) and/or a brainwave-measuring headset.

When a thermal camera is inward-facing and head-mounted, challenges faced by systems known in the art that are used to acquire thermal measurements, which include non-head-mounted thermal cameras, may be simplified and even eliminated with some of the embodiments described herein. Some of these challenges may involve dealing with complications caused by movements of the user, image registration, ROI alignment, tracking based on hot spots or markers, and motion compensation in the IR domain.

In various embodiments, cameras are located close to a user's face, such as at most 2 cm, 5 cm, 10 cm, 15 cm, or 20 cm from the face (herein "cm" denotes to centimeters). The distance from the face/head in sentences such as "a camera located less than 15 cm from the face/head" refers to the shortest possible distance between the camera and the face/head. The head-mounted cameras used in various embodiments may be lightweight, such that each camera weighs below 10 g, 5 g, 1 g, and/or 0.5 g (herein "g" denotes to grams).

Figure 16A:
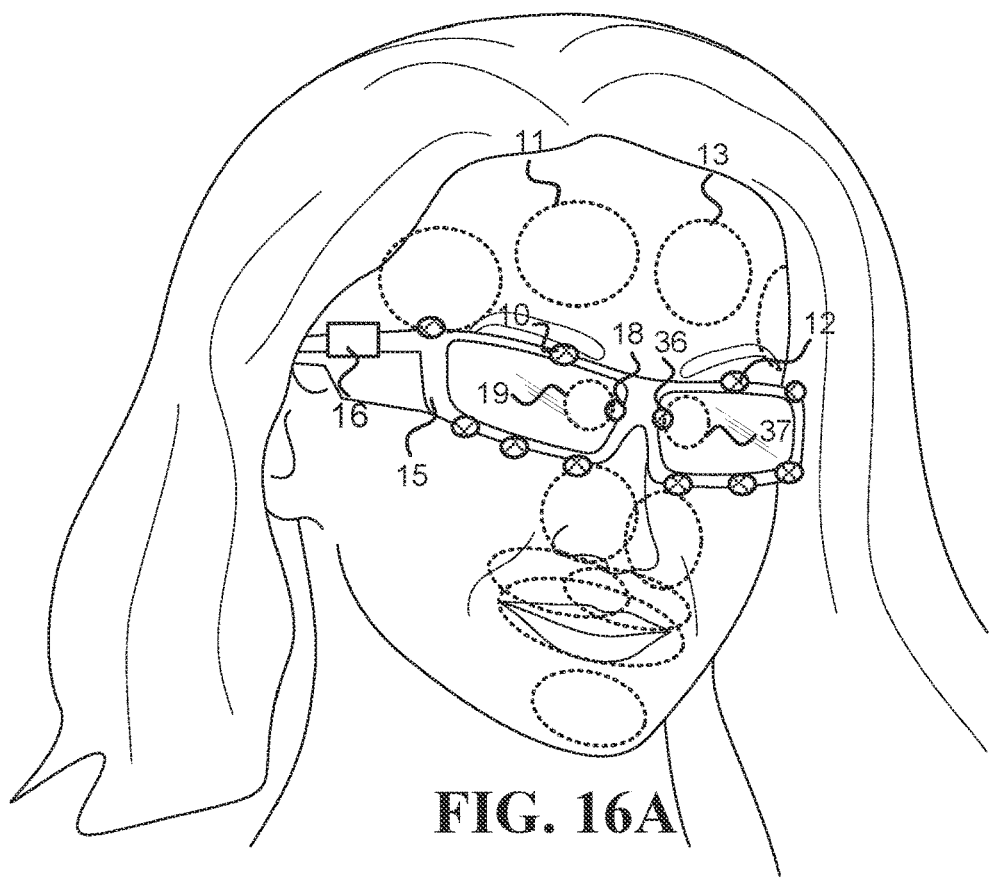
FIG. 16A and FIG. 16B illustrate various inward-facing head-mounted cameras coupled to an eyeglasses frame.
Figure 16B:
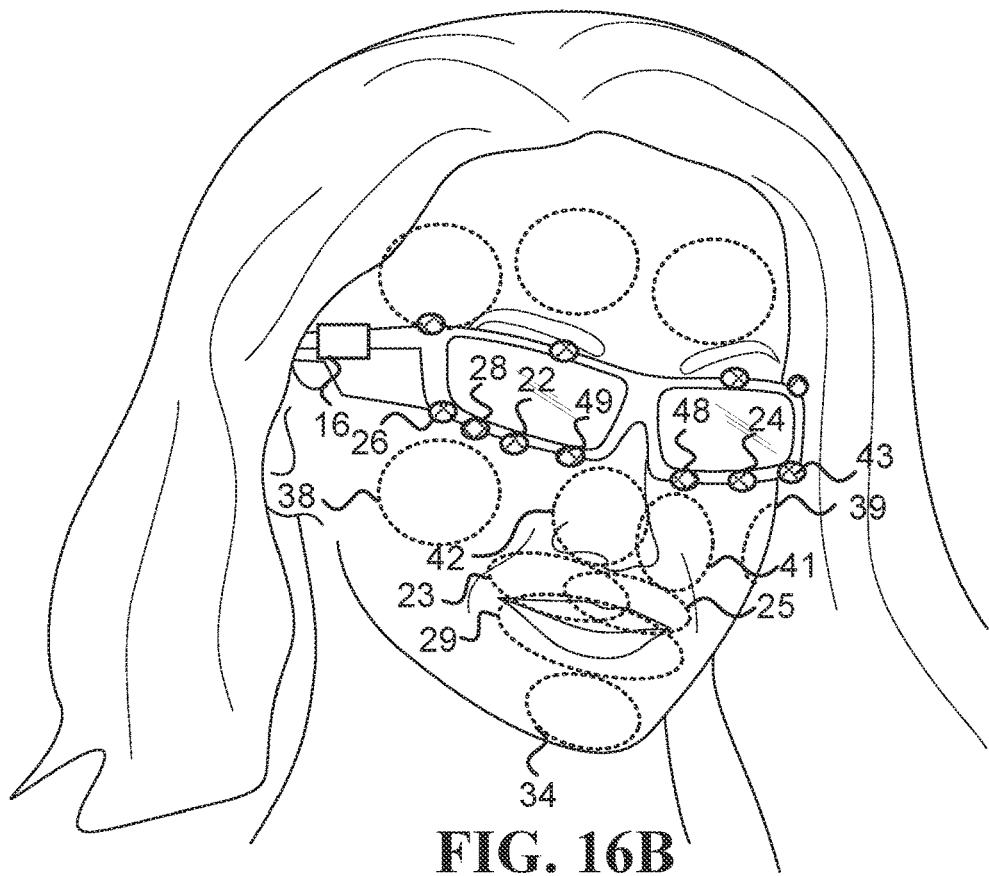

The following figures show various examples of HMSs equipped with head-mounted cameras. FIG. 16A illustrates various inward-facing head-mounted cameras coupled to an eyeglasses frame 15. Cameras 10 and 12 measure regions 11 and 13 on the forehead, respectively. Cameras 18 and 36 measure regions on the periorbital areas 19 and 37, respectively. The HMS further includes an optional computer 16, which may include a processor, memory, a battery and/or a communication module. FIG. 16B illustrates a similar HMS in which inward-facing head-mounted cameras 48 and 49 measure regions 41 and 41, respectively. Cameras 22 and 24 measure regions 23 and 25, respectively. Camera 28 measures region 29. And cameras 26 and 43 measure regions 38 and 39, respectively.

FIG. 17 illustrates inward-facing head-mounted cameras coupled to an augmented reality device such as Microsoft HoloLens™. FIG. 18 illustrates head-mounted cameras coupled to a virtual reality device such as Facebook's Oculus Rif™. FIG. 19 is a side view illustration of head-mounted cameras coupled to an augmented reality device such as Google Glass™. FIG. 20 is another side view illustration of head-mounted cameras coupled to a sunglasses frame.

Figure 21:
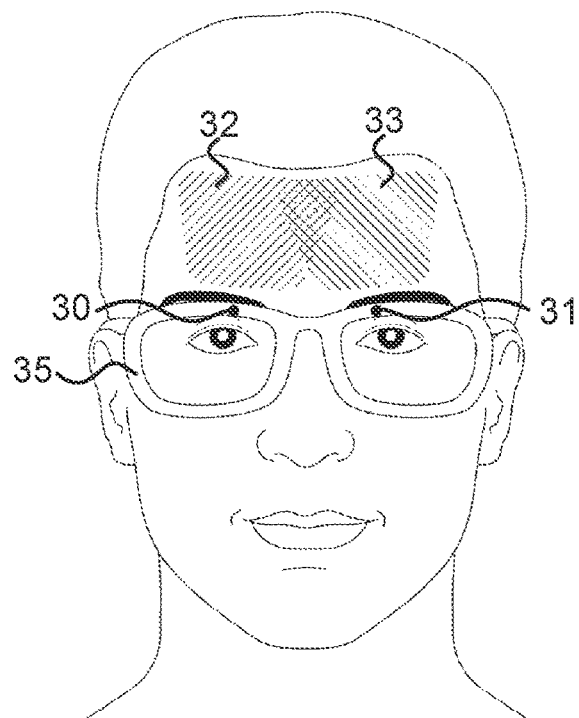
FIG. 21, FIG. 22, FIG. 23 and FIG. 24 illustrate head-mounted systems (HMSs) configured to measure various ROIs relevant to some of the embodiments describes herein.
Figure 22:
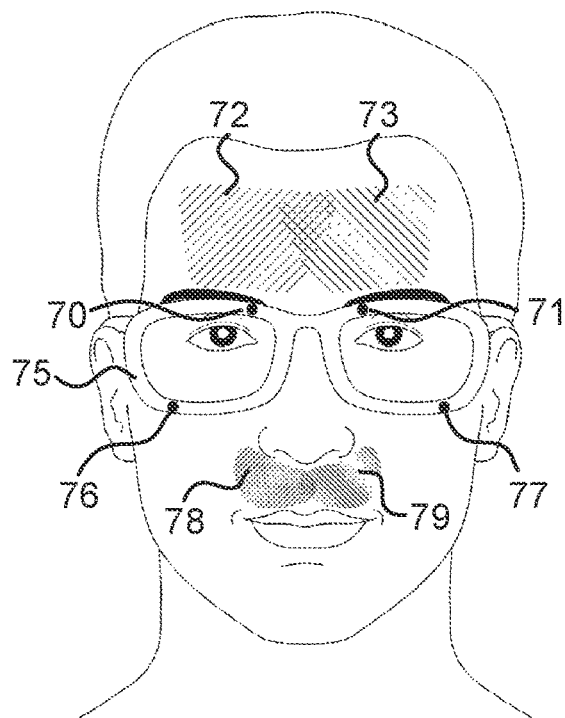
Figure 23:
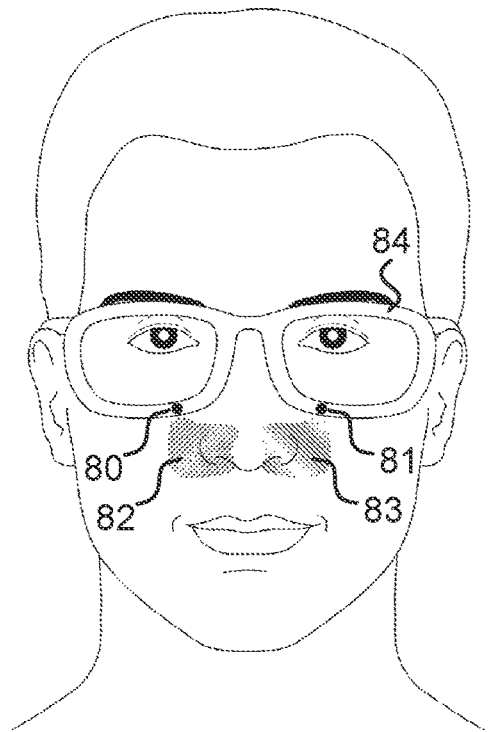
Figure 24:
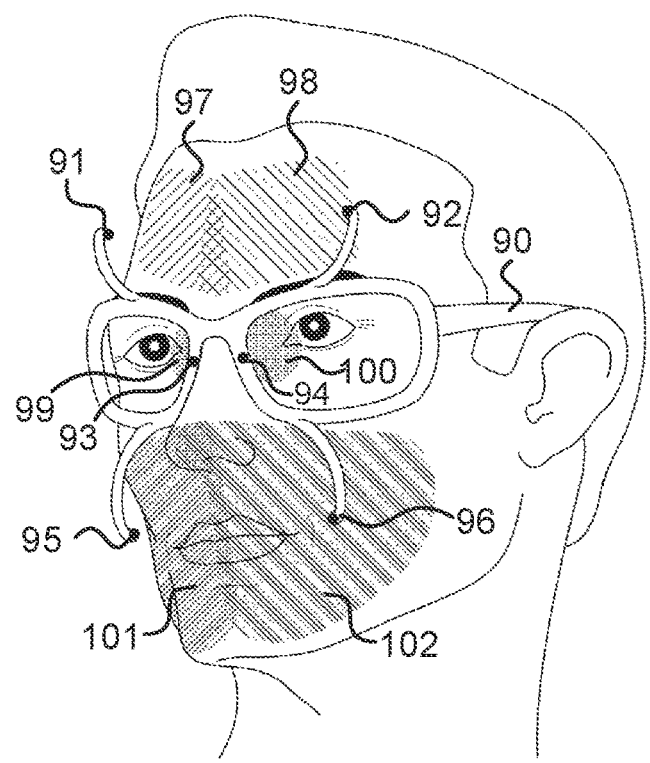

FIG. 21 to FIG. 24 illustrate HMSs configured to measure various ROIs relevant to some of the embodiments describes herein. FIG. 21 illustrates a frame 35 that mounts inward-facing head-mounted cameras 30 and 31 that measure regions 32 and 33 on the forehead, respectively. FIG. 22 illustrates a frame 75 that mounts inward-facing head-mounted cameras 70 and 71 that measure regions 72 and 73 on the forehead, respectively, and inward-facing head-mounted cameras 76 and 77 that measure regions 78 and 79 on the upper lip, respectively. FIG. 23 illustrates a frame 84 that mounts inward-facing head-mounted cameras 80 and 81 that measure regions 82 and 83 on the sides of the nose, respectively. And FIG. 24 illustrates a frame 90 that includes (i) inward-facing head-mounted cameras 91 and 92 that are mounted to protruding arms and measure regions 97 and 98 on the forehead, respectively, (ii) inward-facing head-mounted cameras 95 and 96, which are also mounted to protruding arms, which measure regions 101 and 102 on the lower part of the face, respectively, and (iii) head-mounted cameras 93 and 94 that measure regions on the periorbital areas 99 and 100, respectively.

Figure 25:
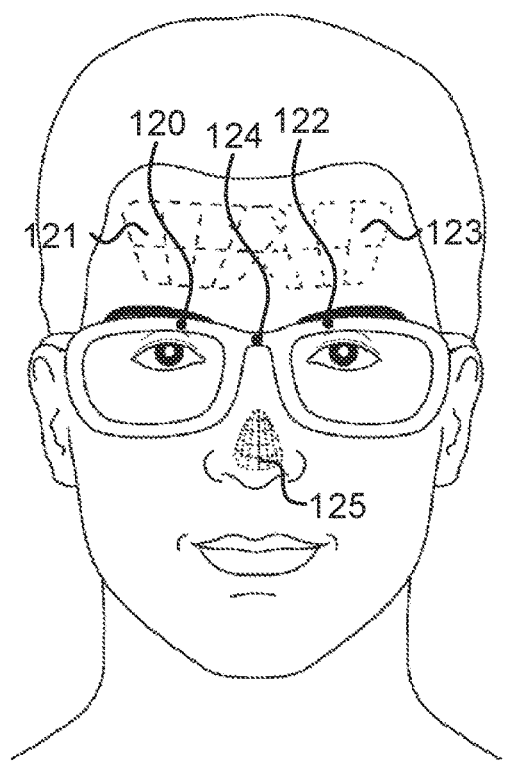
FIG. 25, FIG. 26, FIG. 27 and FIG. 28 illustrate various embodiments of systems that include inward-facing head-mounted cameras having multi-pixel sensors (FPA sensors)
Figure 26:
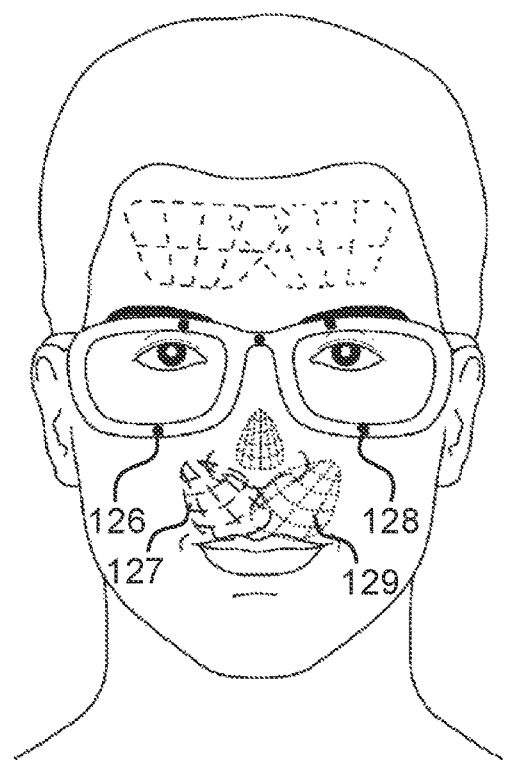
Figure 27:
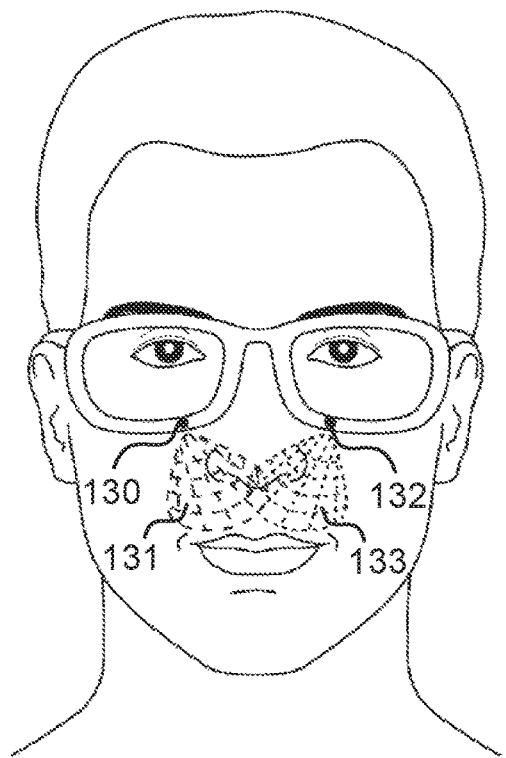
Figure 28:
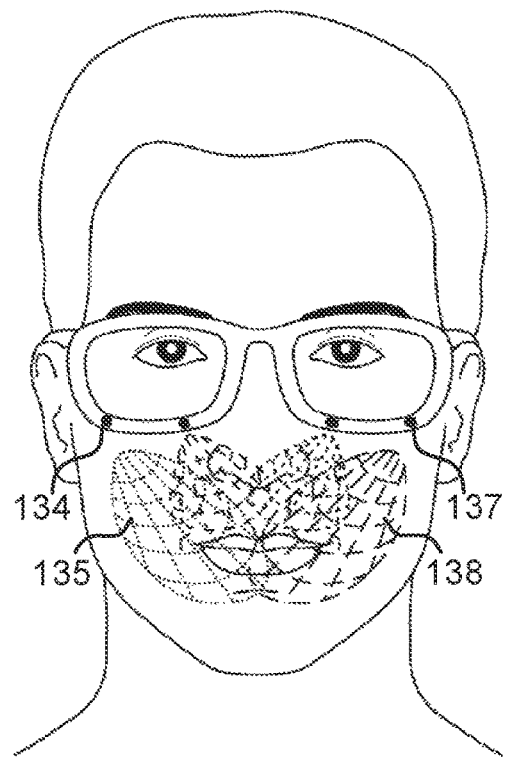

FIG. 25 to FIG. 28 illustrate various inward-facing head-mounted cameras having multi-pixel sensors (FPA sensors), configured to measure various ROIs relevant to some of the embodiments describes herein. FIG. 25 illustrates head-mounted cameras 120 and 122 that measure regions 121 and 123 on the forehead, respectively, and mounts head-mounted camera 124 that measure region 125 on the nose. FIG. 26 illustrates head-mounted cameras 126 and 128 that measure regions 127 and 129 on the upper lip, respectively, in addition to the head-mounted cameras already described in FIG. 25. FIG. 27 illustrates head-mounted cameras 130 and 132 that measure larger regions 131 and 133 on the upper lip and the sides of the nose, respectively. And FIG. 28 illustrates head-mounted cameras 134 and 137 that measure regions 135 and 138 on the right and left cheeks and right and left sides of the mouth, respectively, in addition to the head-mounted cameras already described in FIG. 27.

In some embodiments, the head-mounted cameras may be physically coupled to the frame using a clip-on device configured to be attached/detached from a pair of eyeglasses in order to secure/release the device to/from the eyeglasses, multiple times. The clip-on device holds at least an inward-facing camera, a processor, a battery, and a wireless communication module. Most of the clip-on device may be located in front of the frame (as illustrated in FIG. 29B, FIG. 30B, and FIG. 33), or alternatively, most of the clip-on device may be located behind the frame, as illustrated in FIG. 31B and FIG. 32B.

Figure 29A:
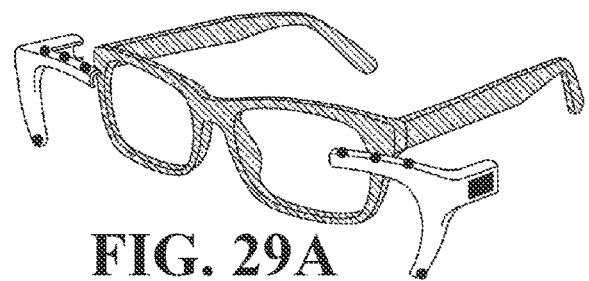
FIG. 29A, FIG. 29B, and FIG. 29C illustrate embodiments of two right and left clip-on devices that are configured to attached/detached from an eyeglasses frame.
Figure 29B:
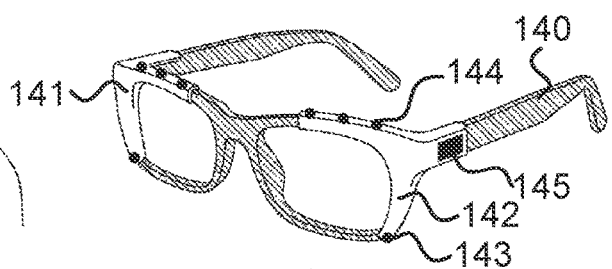
Figure 29C:
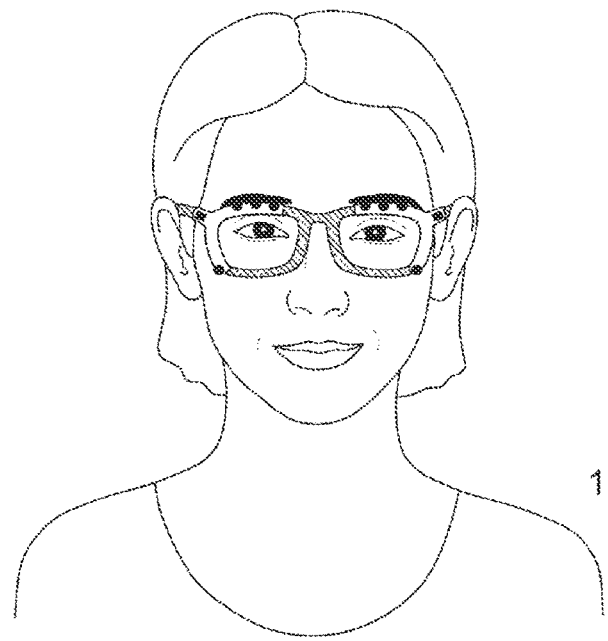

FIG. 29A, FIG. 29B, and FIG. 29C illustrate two right and left clip-on devices 141 and 142, respectively, configured to attached/detached from an eyeglasses frame 140. The clip-on device 142 includes an inward-facing head-mounted camera 143 pointed at a region on the lower part of the face (such as the upper lip, mouth, nose, and/or cheek), an inward-facing head-mounted camera 144 pointed at the forehead, and other electronics 145 (such as a processor, a battery, and/or a wireless communication module). The clip-on devices 141 and 142 may include additional cameras illustrated in the drawings as black circles.

Figure 30A:
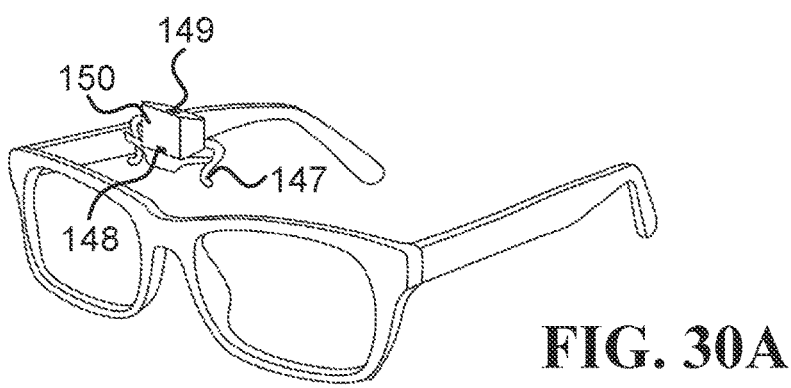
FIG. 30A and FIG. 30B illustrate an embodiment of a clip-on device that includes inward-facing head-mounted cameras pointed at the lower part of the face and the forehead.
Figure 30B:
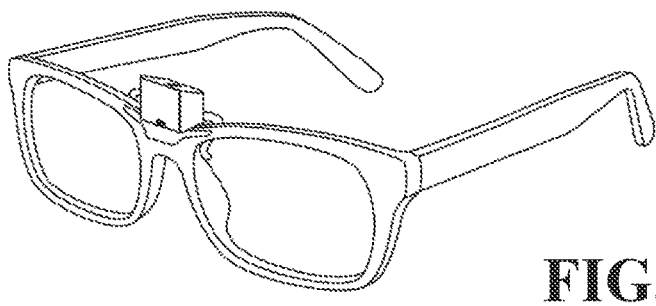

FIG. 30A and FIG. 30B illustrate a clip-on device 147 that includes an inward-facing head-mounted camera 148 pointed at a region on the lower part of the face (such as the nose), and an inward-facing head-mounted camera 149 pointed at the forehead. The other electronics (such as a processor, a battery, and/or a wireless communication module) is located inside the box 150, which also holds the cameras 148 and 149.

Figure 31A:
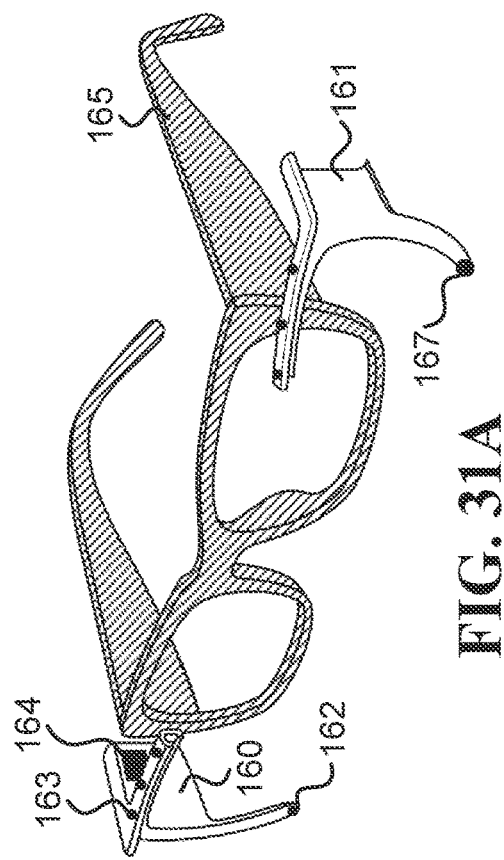
FIG. 31A and FIG. 31B illustrate embodiments of right and left clip-on devices that are configured to be attached behind an eyeglasses frame.
Figure 31B:
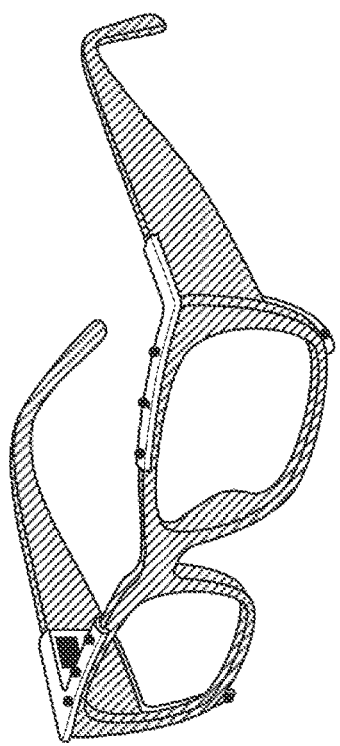

FIG. 31A and FIG. 31B illustrate two right and left clip-on devices 160 and 161, respectively, configured to be attached behind an eyeglasses frame 165. The clip-on device 160 includes an inward-facing head-mounted camera 162 pointed at a region on the lower part of the face (such as the upper lip, mouth, nose, and/or cheek), an inward-facing head-mounted camera 163 pointed at the forehead, and other electronics 164 (such as a processor, a battery, and/or a wireless communication module). The clip-on devices 160 and 161 may include additional cameras illustrated in the drawings as black circles.

Figure 32A:
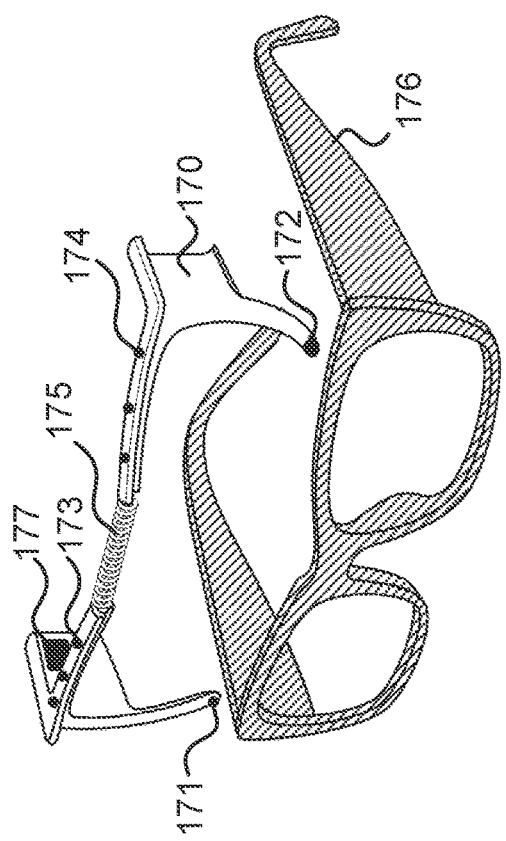
FIG. 32A and FIG. 32B illustrate an embodiment of a single-unit clip-on device that is configured to be attached behind an eyeglasses frame.
Figure 32B:
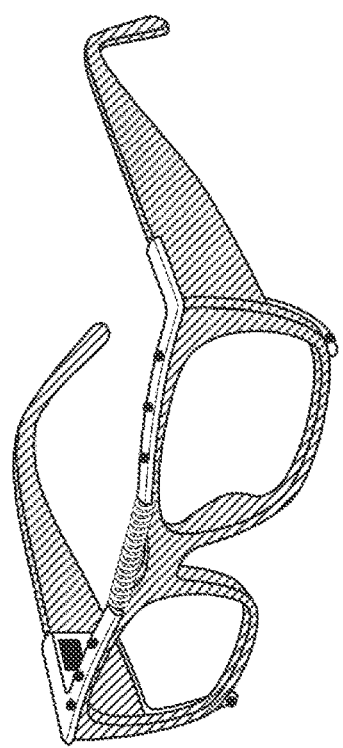
Figure 33:
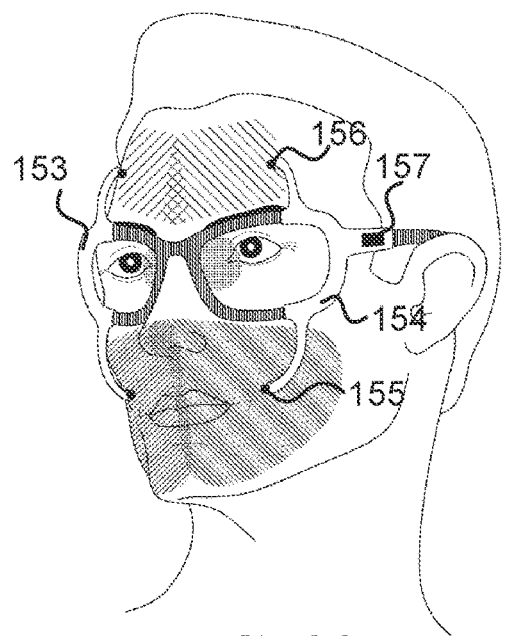
FIG. 33 illustrates embodiments of right and left clip-on devices, which are configured to be attached/detached from an eyeglasses frame, and have protruding arms to hold inward-facing head-mounted cameras.

FIG. 32A and FIG. 32B illustrate a single-unit clip-on device 170, configured to be attached behind an eyeglasses frame 176. The single-unit clip-on device 170 includes inward-facing head-mounted cameras 171 and 172 pointed at regions on the lower part of the face (such as the upper lip, mouth, nose, and/or cheek), inward-facing head-mounted cameras 173 and 174 pointed at the forehead, a spring 175 configured to apply force that holds the clip-on device 170 to the frame 176, and other electronics 177 (such as a processor, a battery, and/or a wireless communication module). The clip-on device 170 may include additional cameras illustrated in the drawings as black circles.

FIG. 33 illustrates two right and left clip-on devices 153 and 154, respectively, configured to attached/detached from an eyeglasses frame, and having protruding arms to hold the inward-facing head-mounted cameras. Head-mounted camera 155 measures a region on the lower part of the face, head-mounted camera 156 measures regions on the forehead, and the left clip-on device 154 further includes other electronics 157 (such as a processor, a battery, and/or a wireless communication module). The clip-on devices 153 and 154 may include additional cameras illustrated in the drawings as black circles.

It is noted that the elliptic and other shapes of the ROIs in some of the drawings ar just for illustration purposes, and the actual shapes of the ROIs are usually not as illustrated. It is possible to calculate the accurate shape of an ROI using various methods, such as a computerized simulation using a 3D model of the face and a model of a head-mounted system (HMS) to which a thermal camera is physically coupled, or by placing a LED instead of the sensor (while maintaining the same field of view) and observing the illumination pattern on the face. Furthermore, illustrations and discussions of a camera represent one or more cameras, where each camera may have the same FOV and/or different FOVs. Unless indicated to the contrary, the cameras may include one or more sensing elements (pixels), even when multiple sensing elements do not explicitly appear in the figures; when a camera includes multiple sensing elements then the illustrated ROI usually refers to the total ROI captured by the camera, which is made of multiple regions that are respectively captured by the different sensing elements. The positions of the cameras in the figures are just for illustration, and the cameras may be placed at other positions on the HMS.

Sentences in the form of an "ROI on an area", such as ROI on the forehead or an ROI on the nose, refer to at least a portion of the area. Depending on the context, and especially when using a CAM having just one pixel or a small number of pixels, the ROI may cover another area (in addition to the area). For example, a sentence in the form of "an ROI on the nose" may refer to either: 100% of the ROI is on the nose, or some of the ROI is on the nose and some of the ROI is on the upper lip.

Various embodiments described herein involve detections of physiological responses based on user measurements. Some examples of physiological responses include stress, an allergic reaction, an asthma attack, a stroke, dehydration, intoxication, or a headache (which includes a migraine). Other examples of physiological responses include manifestations of fear, startle, sexual arousal, anxiety, joy, pain or guilt. Still other examples of physiological responses include physiological signals such as a heart rate or a value of a respiratory parameter of the user. Optionally, detecting a physiological response may involve one or more of the following: determining whether the user has/had the physiological response, identifying an imminent attack associated with the physiological response, and/or calculating the extent of the physiological response.

In some embodiments, detection of the physiological response is done by processing thermal measurements that fall within a certain window of time that characterizes the physiological response. For example, depending on the physiological response, the window may be five seconds long, thirty seconds long, two minutes long, five minutes long, fifteen minutes long, or one hour long. Detecting the physiological response may involve analysis of thermal measurements taken during multiple of the above-described windows, such as measurements taken during different days. In some embodiments, a computer may receive a stream of thermal measurements, taken while the user wears an HMS with coupled thermal cameras during the day, and periodically evaluate measurements that fall within a sliding window of a certain size.

In some embodiments, models are generated based on measurements taken over long periods. Sentences of the form of "measurements taken during different days" or "measurements taken over more than a week" are not limited to continuous measurements spanning the different days or over the week, respectively. For example, "measurements taken over more than a week" may be taken by eyeglasses equipped with thermal cameras, which are worn for more than a week, 8 hours a day. In this example, the user is not required to wear the eyeglasses while sleeping in order to take measurements over more than a week. Similarly, sentences of the form of "measurements taken over more than 5 days, at least 2 hours a day" refer to a set comprising at least 10 measurements taken over 5 different days, where at least two measurements are taken each day at times separated by at least two hours.

Utilizing measurements taken of a long period (e.g., measurements taken on "different days") may have an advantage, in some embodiments, of contributing to the generalizability of a trained model. Measurements taken over the long period likely include measurements taken in different environments and/or measurements taken while the measured user was in various physiological and/or mental states (e.g., before/after meals and/or while the measured user was sleepy/energetic/happy/depressed, etc.). Training a model on such data can improve the performance of systems that utilize the model in the diverse settings often encountered in real-world use (as opposed to controlled laboratory-like settings). Additionally, taking the measurements over the long period may have the advantage of enabling collection of a large amount of training data that is required for some machine learning approaches (e.g., "deep learning").

Detecting the physiological response may involve performing various types of calculations by a computer. Optionally, detecting the physiological response may involve performing one or more of the following operations: comparing thermal measurements to a threshold (when the threshold is reached that may be indicative of an occurrence of the physiological response), comparing thermal measurements to a reference time series, and/or by performing calculations that involve a model trained using machine learning methods. Optionally, the thermal measurements upon which the one or more operations are performed are taken during a window of time of a certain length, which may optionally depend on the type of physiological response being detected. In one example, the window may be shorter than one or more of the following durations: five seconds, fifteen seconds, one minute, five minutes, thirty minute, one hour, four hours, one day, or one week. In another example, the window may be longer than one or more of the aforementioned durations. Thus, when measurements arm taken over a long period, such as measurements taken over a period of more than a week, detection of the physiological response at a certain time may be done based on a subset of the measurements that falls within a certain window near the certain time; the detection at the certain time does not necessarily involve utilizing all values collected throughout the long period.

In some embodiments, detecting the physiological response of a user may involve utilizing baseline thermal measurement values, most of which were taken when the user was not experiencing the physiological response. Optionally, detecting the physiological response may rely on observing a change to typical temperatures at one or more ROIs (the baseline), where different users might have different typical temperatures at the ROIs (i.e., different baselines). Optionally, detecting the physiological response may rely on observing a change to a baseline level, which is determined based on previous measurements taken during the preceding minutes and/or hours.

In some embodiments, detecting a physiological response involves determining the extent of the physiological response, which may be expressed in various ways that are indicative of the extent of the physiological response, such as: (i) a binary value indicative of whether the user experienced, and/or is experiencing, the physiological response, (ii) a numerical value indicative of the magnitude of the physiological response, (iii) a categorical value indicative of the severity/extent of the physiological response, (iv) an expected change in thermal measurements of an ROI (denoted $TH_{ROI}$ or some variation thereof), and/or (v) rate of change in $TH_{ROI}$. Optionally, when the physiological response corresponds to a physiological signal (e.g., a heart rate, a breathing rate, and an extent of frontal lobe brain activity), the extent of the physiological response may be interpreted as the value of the physiological signal.

One approach for detecting a physiological response, which may be utilized in some embodiments, involves comparing thermal measurements of one or more ROIs to a threshold. In these embodiments, the computer may detect the physiological response by comparing the thermal measurements, and/or values derived therefrom (e.g., a statistic of the measurements and/or a function of the measurements), to the threshold to determine whether it is reached. Optionally, the threshold may include a threshold in the time domain, a threshold in the frequency domain, an upper threshold, and/or a lower threshold. When a threshold involves a certain change to temperature, the certain change may be positive (increase in temperature) or negative (decrease in temperature). Different physiological responses described herein may involve different types of thresholds, which may be an upper threshold (where reaching the threshold means≥the threshold) or a lower threshold (where reaching the threshold means≤the threshold); for example, each physiological response may involve at least a certain degree of heating, or at least a certain degree cooling, at a certain ROI on the face.

Another approach for detecting a physiological response, which may be utilized in some embodiments, may be applicable when the thermal measurements of a user are treated as time series data. For example, the thermal measurements may include data indicative of temperatures at one or more ROIs at different points of time during a certain period. In some embodiments, the computer may compare thermal measurements (represented as a time series) to one or more reference time series that correspond to periods of time in which the physiological response occurred. Additionally or alternatively, the computer may compare the thermal measurements to other reference time series corresponding to times in which the physiological response did not occur. Optionally, if the similarity between the thermal measurements and a reference time series corresponding to a physiological response reaches a threshold, this is indicative of the fact that the thermal measurements correspond to a period of time during which the user had the physiological response. Optionally, if the similarity between the thermal measurements and a reference time series that does not correspond to a physiological response reaches another threshold, this is indicative of the fact that the thermal measurements correspond to a period of time in which the user did not have the physiological response. Time series analysis may involve various forms of processing involving segmenting data, aligning data, clustering, time warping, and various functions for determining similarity between sequences of time series data. Some of the techniques that may be utilized in various embodiments are described in Ding, Hui, et al. "Querying and mining of time series data: experimental comparison of representations and distance measures." Proceedings of the VLDB Endowment 1.2 (2008): 1542-1552, and in Wang, Xiaoyue, et al. "Experimental comparison of representation methods and distance measures for time series data." Data Mining and Knowledge Discovery 26.2 (2013): 275-309.

Herein, "machine learning" methods refers to learning from examples using one or more approaches. Optionally, the approaches may be considered supervised, semi-supervised, and/or unsupervised methods. Examples of machine learning approaches include: decision tree learning, association rule learning, regression models, nearest neighbors classifiers, artificial neural networks, deep learning, inductive logic programming, support vector machines, clustering, Bayesian networks, reinforcement learning, representation learning, similarity and metric learning, sparse dictionary learning, genetic algorithms, rule-based machine learning, and/or learning classifier systems.

Herein, a "machine learning-based model" is a model trained using machine learning methods. For brevity's sake, at times, a "machine learning-based model" may simply be called a "model". Referring to a model as being "machine learning-based" is intended to indicate that the model is trained using machine learning methods (otherwise, "model" may also refer to a model generated by methods other than machine learning).

In some embodiments, which involve utilizing a machine learning-based model, a computer is configured to detect the physiological response by generating feature values based on the thermal measurements (and possibly other values), and/or based on values derived therefrom (e.g., statistics of the measurements). The computer then utilizes the machine learning-based model to calculate, based on the feature values, a value that is indicative of whether, and/or to what extent, the user is experiencing (and/or is about to experience) the physiological response. Optionally, calculating said value is considered "detecting the physiological response". Optionally, the value calculated by the computer is indicative of the probability that the user has/had the physiological response.

Herein, feature values may be considered input to a computer that utilizes a model to perform the calculation of a value, such as the value indicative of the extent of the physiological response mentioned above. It is to be noted that the terms "feature" and "feature value" may be used interchangeably when the context of their use is clear. However, a "feature" typically refers to a certain type of value, and represents a property, while "feature value" is the value of the property with a certain instance (sample). For example, a feature may be temperature at a certain ROI, while the feature value corresponding to that feature may be 36.9° C., in one instance and 37.3° C., in another instance.

In some embodiments, a machine learning-based model used to detect a physiological response is trained based on data that includes samples. Each sample includes feature values and a label. The feature values may include various types of values. At least some of the feature values of a sample are generated based on measurements of a user taken during a certain period of time (e.g., thermal measurements taken during the certain period of time). Optionally, some of the feature values may be based on various other sources of information described herein. The label is indicative of a physiological response of the user corresponding to the certain period of time. Optionally, the label may be indicative of whether the physiological response occurred during the certain period and/or the extent of the physiological response during the certain period. Additionally or alternatively, the label may be indicative of how long the physiological response lasted. Labels of samples may be generated using various approaches, such as self-report by users, annotation by experts that analyze the training data, automatic annotation by a computer that analyzes the training data and/or analyzes additional data related to the training data, and/or utilizing additional sensors that provide data useful for generating the labels. It is to be noted that herein when it is stated that a model is trained based on certain measurements (e.g., "a model trained based on $TH_{ROI}$ taken on different days"), it means that the model was trained on samples comprising feature values generated based on the certain measurements and labels corresponding to the certain measurements. Optionally, a label corresponding to a measurement is indicative of the physiological response at the time the measurement was taken.

Various types of feature values may be generated based on thermal measurements. In one example, some feature values are indicative of temperatures at certain ROIs. In another example, other feature values may represent a temperature change at certain ROIs. The temperature changes may be with respect to a certain time and/or with respect to a different ROI. In order to better detect physiological responses that take some time to manifest, in some embodiments, some feature values may describe temperatures (or temperature changes) at a certain ROI at different points of time. Optionally, these feature values may include various functions and/or statistics of the thermal measurements such as minimum/maximum measurement values and/or average values during certain windows of time.

It is to be noted that when it is stated that feature values are generated based on data comprising multiple sources, it means that for each source, there is at least one feature value that is generated based on that source (and possibly other data). For example, stating that feature values are generated from thermal measurements of first and second ROIs ($TH_{ROI1}$ and $TH_{ROI2}$, respectively) means that the feature values may include a first feature value generated based on $TH_{ROI1}$ and a second feature value generated based on $TH_{ROI2}$. Optionally, a sample is considered generated based on measurements of a user (e.g., measurements comprising $TH_{ROI1}$ and $TH_{ROI2}$) when it includes feature values generated based on the measurements of the user.

In addition to feature values that are generated based on thermal measurements, in some embodiments, at least some feature values utilized by a computer (e.g., to detect a physiological response or train a mode) may be generated based on additional sources of data that may affect temperatures measured at various facial ROIs. Some examples of the additional sources include: (i) measurements of the environment such as temperature, humidity level, noise level, elevation, air quality, a wind speed, precipitation, and infrared radiation; (ii) contextual information such as the time of day (e.g., to account for effects of the circadian rhythm), day of month (e.g., to account for effects of the lunar rhythm), day in the year (e.g., to account for seasonal effects), and/or stage in a menstrual cycle; (iii) information about the user being measured such as sex, age, weight, height, and/or body build. Alternatively or additionally, at least some feature values may be generated based on physiological signals of the user obtained by sensors that are not thermal cameras, such as a visible-light camera, a photoplethysmogram (PPG) sensor, an electrocardiogram (ECG) sensor, an electroencephalography (EEG) sensor, a galvanic skin response (GSR) sensor, or a thermistor.

The machine learning-based model used to detect a physiological response may be trained, in some embodiments, based on data collected in day-to-day, real world scenarios. As such, the data may be collected at different times of the day, while users perform various activities, and in various environmental conditions. Utilizing such diverse training data may enable a trained model to be more resilient to the various effects different conditions can have on the values of thermal measurements, and consequently, be able to achieve better detection of the physiological response in real world day-to-day scenarios.

Since real world day-to-day conditions are not the same all the time, sometimes detection of the physiological response may be hampered by what is referred to herein as "confounding factors". A confounding factor can be a cause of warming and/or cooling of certain regions of the face, which is unrelated to a physiological response being detected, and as such, may reduce the accuracy of the detection of the physiological response. Some examples of confounding factors include: (i) environmental phenomena such as direct sunlight, air conditioning, and/or wind; (ii) things that are on the user's face, which are not typically there and/or do not characterize the faces of most users (e.g., cosmetics, ointments, sweat, hair, facial hair, skin blemishes, acne, inflammation, piercings, body paint, and food leftovers); (iii) physical activity that may affect the user's heart rate, blood circulation, and/or blood distribution (e.g., walking, running, jumping, and/or bending over); (iv) consumption of substances to which the body has a physiological response that may involve changes to temperatures at various facial ROIs, such as various medications, alcohol, caffeine, tobacco, and/or certain types of food; and/or (v) disruptive facial movements (e.g., frowning, talking, eating, drinking, sneezing, and coughing).

Occurrences of confounding factors may not always be easily identified in thermal measurements. Thus, in some embodiments, systems may incorporate measures designed to accommodate for the confounding factors. In some embodiments, these measures may involve generating feature values that are based on additional sensors, other than the thermal cameras. In some embodiments, these measures may involve refraining from detecting the physiological response, which should be interpreted as refraining from providing an indication that the user has the physiological response. For example, if an occurrence of a certain confounding factor is identified, such as strong directional sunlight that heats one side of the face, the system may refrain from detecting that the user had a stroke. In this example, the user may not be alerted even though a temperature difference between symmetric ROIs on both sides of the face reaches a threshold that, under other circumstances, would warrant alerting the user.

Training data used to train a model for detecting a physiological response may include, in some embodiments, a diverse set of samples corresponding to various conditions, some of which involve occurrence of confounding factors (when there is no physiological response and/or when there is a physiological response). Having samples in which a confounding factor occurs (e.g., the user is in direct sunlight or touches the face) can lead to a model that is less susceptible to wrongfully detect the physiological response (which may be considered an occurrence of a false positive) in real world situations.

When a model is trained with training data comprising samples generated from measurements of multiple users, the model may be considered a general model. When a model is trained with training data comprising at least a certain proportion of samples generated from measurements of a certain user, and/or when the samples generated from the measurements of the certain user are associated with at least a certain proportion of weight in the training data, the model may be considered a personalized model for the certain user. Optionally, the personalized model for the certain user provides better results for the certain user, compared to a general model that was not personalized for the certain user. Optionally, personalized model may be trained based on measurements of the certain user, which were taken while the certain user was in different situations; for example, train the model based on measurements taken while the certain user had a headache/epilepsy/stress/anger attack, and while the certain user did not have said attack. Additionally or alternatively, the personalized model may be trained based on measurements of the certain user, which were taken over a duration long enough to span different situations; examples of such long enough durations may include: a week, a month, six months, a year, and three years.

Training a model that is personalized for a certain user may require collecting a sufficient number of training samples that are generated based on measurements of the certain user. Thus, initially detecting the physiological response with the certain user may be done utilizing a general model, which may be replaced by a personalized model for the certain user, as a sufficiently large number of samples are generated based on measurements of the certain user. Another approach involves gradually modifying a general model based on samples of the certain user in order to obtain the personalized model.

After a model is trained, the model may be provided for use by a system that detects the physiological response. Providing the model may involve performing different operations. In one embodiment, providing the model to the system involves forwarding the model to the system via a computer network and/or a shared computer storage medium (e.g., writing the model to a memory that may be accessed by the system that detects the physiological response). In another embodiment, providing the model to the system involves storing the model in a location from which the system can retrieve the model, such as a database and/or cloud-based storage from which the system may retrieve the model. In still another embodiment, providing the model involves notifying the system regarding the existence of the model and/or regarding an update to the model. Optionally, this notification includes information needed in order for the system to obtain the model.

A model for detecting a physiological response may include different types of parameters. Following are some examples of various possibilities for the model and the type of calculations that may be accordingly performed by a computer in order to detect the physiological response: (a) the model comprises parameters of a decision tree. Optionally, the computer simulates a traversal along a path in the decision tree, determining which branches to take based on the feature values. A value indicative of the physiological response may be obtained at the leaf node and/or based on calculations involving values on nodes and/or edges along the path; (b) the model comprises parameters of a regression model (e.g., regression coefficients in a linear regression model or a logistic regression model). Optionally, the computer multiplies the feature values (which may be considered a regressor) with the parameters of the regression model in order to obtain the value indicative of the physiological response; and/or (c) the model comprises parameters of a neural network. For example, the parameters may include values defining at least the following: (i) an interconnection pattern between different layers of neurons, (ii) weights of the interconnections, and (iii) activation functions that convert each neuron's weighted input to its output activation. Optionally, the computer provides the feature values as inputs to the neural network, computes the values of the various activation functions and propagates values between layers, and obtains an output from the network, which is the value indicative of the physiological response.

A user interface (UI) may be utilized, in some embodiments, to notify the user and/or some other entity, such as a caregiver, about the physiological response and/or present an alert responsive to an indication that the extent of the physiological response reaches a threshold. The UI may include a screen to display the notification and/or alert, a speaker to play an audio notification, a tactile UI, and/or a vibrating UI. In some embodiments, "alerting" about a physiological response of a user refers to informing about one or more of the following: the occurrence of a physiological response that the user does not usually have (e.g., a stroke, intoxication, and/or dehydration), an imminent physiological response (e.g., an allergic reaction, an epilepsy attack, and/or a migraine), and an extent of the physiological response reaching a threshold (e.g., stress and/or anger reaching a predetermined level).

Figure 34:
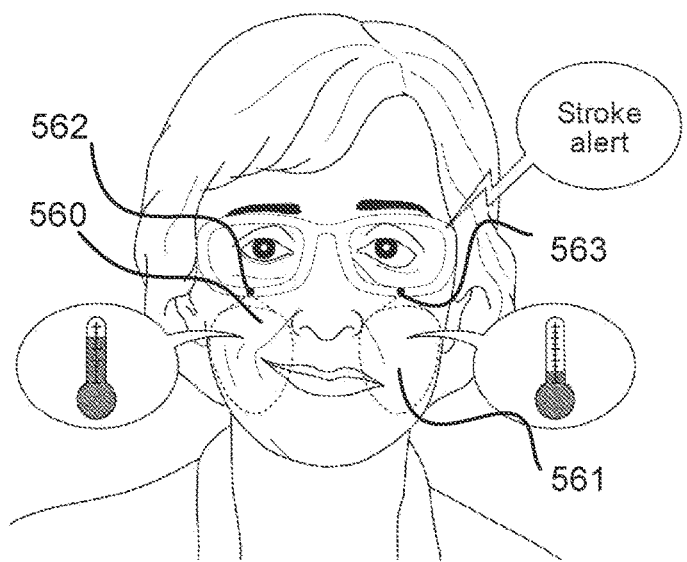
FIG. 34 illustrates a scenario in which an alert regarding a possible stroke is issued.

FIG. 34 illustrates a scenario in which an alert regarding a possible stroke is issued. The figure illustrates a user wearing a frame with at least two CAMs (562 and 563) for measuring ROIs on the right and left cheeks (ROIs 560 and 561, respectively). The measurements indicate that the left side of the face is colder than the right side of the face. Based on these measurements, and possibly additional data, the system detects the stroke and issues an alert. Optionally, the user's facial expression is slightly distorted and asymmetric, and a VCAM provides additional data in the form of images that may help detecting the stroke.

The CAMs can take respiratory-related thermal measurements when their ROIs are on the user's upper lip, the user's mouth, the space where the exhale stream form the user's nose flows, and/or the space where the exhale stream from the user's mouth flows. In some embodiments, one or more of the following respiratory parameters may be calculated based on the respiratory-related thermal measurements taken during a certain period of time:

"Breathing rate" represents the number of breaths per minute the user took during the certain period. The breathing rate may also be formulated as the average time between successive inhales and/or the average between successive exhales.

"Respiration volume" represents the volume of air breathed over a certain duration (usually per minute), the volume of air breathed during a certain breath, tidal volume, and/or the ratio between two or more breaths. For example, the respiration volume may indicate that a first breath was deeper than a second breath, or that breaths during a first minute were shallower than breaths during a second minute.

"Mouth breathing vs nasal breathing" indicates whether during the certain period the user breathed mainly through the mouth (a state characterized as "mouth breathing") or mainly through the nose (a state characterized as "nose breathing" or "nasal breathing"). Optionally, this parameter may represent the ratio between nasal and mouth breathing, such as a proportion of the certain period during which the breathing was more mouth breathing, and/or the relative volume of air exhaled through the nose vs the mouth. In one example, breathing mainly through the mouth refers to inhaling more than 50% of the air through the mouth (and less than 50% of the air through the nose).

"Exhale duration/Inhale duration" represents the exhale (s) duration during the certain period, the inhale(s) duration during the certain period, and/or a ratio of the two aforementioned durations. Optionally, this respiratory parameter may represent one or more of the following: (i) the average duration of the exhales and/or inhales, (ii) a maximum and/or minimum duration of the exhales and/or inhales during the certain period, and (iii) a proportion of times in which the duration of exhaling and/or inhaling reached a certain threshold.

"Post-exhale breathing pause" represents the time that elapses between when the user finishes exhaling and starts inhaling again. "Post-inhale breathing pause" represents the time that elapses between when the user finishes inhaling and when the user starts exhaling after that. The post exhale/inhale breathing pauses may be formulated utilizing various statistics, such as an average post exhale/inhale breathing pause during a certain period, a maximum or minimum duration of post exhale/inhale breathing pause during the certain period, and/or a proportion of times in which the duration of post exhale/inhale breathing pause reached a certain threshold.

"Dominant nostril" is the nostril through which most of the air is exhaled (when exhaling through the nose). Normally the dominant nostril changes during the day, and the exhale is considered balanced when the amount of air exhaled through each nostril is similar. Optionally, the breathing may be considered balanced when the difference between the volumes of air exhaled through the right and left nostrils is below a predetermined threshold, such as 20% or 10%. Additionally or alternatively, the breathing may be considered balanced during a certain duration around the middle of the switching from right to left or left to right nostril dominance. For example, the certain duration of balanced breathing may be about 4 minutes at the middle of the switching between dominant nostrils.

"Temperature of the exhale stream" may be measured based on thermal measurements of the stream that flows from one or both nostrils, and/or the heat pattern generated on the upper lip by the exhale stream from the nose. In one example, it is not necessary to measure the exact temperature of the exhale stream as long as the system is able to differentiate between different temperatures of the exhale stream based on the differences between series of thermal measurements taken at different times. Optionally, the series of thermal measurements that are compared are temperature measurements received from the same pixel(s) of a head-mounted thermal camera.

"Shape of the exhale stream" (also referred to as "SHAPE") represents the three-dimensional (3D) shape of the exhale stream from at least one of the nostrils. The SHAPE changes during the day and may reflect the mental, physiological, and/or energetic state of a user. Usually the temperature of the exhale stream is different from the temperature of the air in the environment this enables a thermal camera, which captures a portion of the volume through which the exhale stream flows, to take a measurement indicative of the SHAPE, and/or to differentiate between different shapes of the exhale stream (SHAPEs). Additionally, the temperature of the exhale stream is usually different from the temperature of the upper lip, and thus exhale streams having different shapes may generate different thermal patterns on the upper lip. Measuring these different thermal patterns on the upper lip may enable a computer to differentiate between different SHAPEs. In one embodiment, differences between values measured by adjacent thermal pixels of CAM, which measure the exhale stream and/or the upper lip over different time intervals, may correspond to different SHAPEs. In one example, it is not necessary to measure the exact SHAPE as long as it is possible to differentiate between different SHAPEs based on the differences between the values of the adjacent thermal pixels. In another embodiment, differences between average values, measured by the same thermal pixel over different time intervals, may correspond to different SHAPEs. In still another embodiment, the air that is within certain boundaries of a 3D shape that protrudes from the user's nose, which is warmer than the environment air, as measured by CAM, is considered to belong to the exhale stream.

In one embodiment, the SHAPE may be represented by one or more thermal images taken by one or more CAMs. In this embodiment, the shape may correspond to a certain pattern in the one or more images and/or a time series describing a changing pattern in multiple images. In another embodiment, the SHAPE may be represented by at least one of the following parameters: the angle from which the exhale stream blows from a nostril, the width of the exhale stream, the length of the exhale stream, and other parameters that are indicative of the 3D SHAPE. Optionally, the SHAPE may be defined by the shape of a geometric body that confines it, such as a cone or a cylinder, protruding from the user's nose. For example, the SHAPE may be represented by parameters such as the cone's height, the radius of the cone's base, and/or the angle between the cone's altitude axis and the nostril.

"Smoothness of the exhale stream" represents a level of smoothness of the exhale stream from the nose and/or the mouth. In one embodiment, the smoothness of the exhale stream is a value that can be determined based on observing the smoothness of a graph of the respiratory-related thermal measurements. Optionally, it is unnecessary for the system to measure the exact smoothness of the exhale stream as long as it is able to differentiate between smoothness levels of respiratory-related thermal measurements taken at different times. Optionally, the compared thermal measurements taken at different times may be measured by the same pixels and/or by different pixels. As a rule of thumb, the smoother the exhale stream, the lower the stress and the better the physical condition. For example, the exhale stream of a healthy young person is often smoother than the exhale stream of an elderly person, who may even experience short pauses in the act of exhaling.

There are well known mathematical methods to calculate the smoothness of a graph, such as Fourier transform analysis, polynomial fit, differentiability classes, multivariate differentiability classes, parametric continuity, and/or geometric continuity. In one example, the smoothness of $TH_{ROI}$ indicative of the exhale stream is calculated based on a Fourier transform of a series of $TH_{ROI}$. In the case of Fourier transform, the smaller the power of the high-frequencies portion, the smoother the exhale is, and vice versa. Optionally, one or more predetermined thresholds differentiate between the high-frequency and low-frequency portions in the frequency domain. In another example, the smoothness of $TH_{ROI}$ indicative of the exhale stream is calculated using a polynomial fit (with a bounded degree) of a series of $TH_{ROI}$. Optionally, the degree of the polynomial used for the fit is proportional (e.g., linear) to the number of exhales in the time series. In the case of polynomial fit, the smoothness may be a measure of the goodness of fit between the series of $TH_{ROI}$ and the polynomial. For example, the lower the squared error, the smoother the graph is considered. In still another embodiment, the smoothness of $TH_{ROI}$ indicative of the exhale stream may be calculated using a machine learning-based model trained with training data comprising reference time series of $TH_{ROI}$ for which the extent of smoothness is known.

In an alternative embodiment, a microphone is used to measure the exhale sounds. The smoothness of the exhale stream may be a value that is proportional to the smoothness of the audio measurement time series taken by the microphone (e.g., as determined based on the power of the high-frequency portion obtained in a Fourier transform of the time series of the audio).

There are various approaches that may be employed in order to calculate values of one or more of the respiratory parameters mentioned above based on respiratory-related thermal measurements. Optionally, calculating the values of one or more of the respiratory parameters may be based on additional inputs, such as statistics about the user (e.g., age, gender, weight, height, and the like), indications about the user's activity level (e.g., input from a pedometer), and/or physiological signals of the user (e.g., heart rate and respiratory rate). Roughly speaking, some approaches may be considered analytical approaches, while other approaches may involve utilization of a machine learning-based model.

In some embodiments, one or more of the respiratory parameters mentioned above may be calculated based on the respiratory-related thermal measurements by observing differences in thermal measurements. In one embodiment, certain pixels that have alternating temperature changes may be identified as corresponding to exhale streams. In this embodiment, the breathing rate may be a calculated frequency of the alternating temperature changes at the certain pixels. In another embodiment, the relative difference in magnitude of temperature changes at different ROIs, such as the alternating temperature changes that correspond to breathing activity, may be used to characterize different types of breathing. For example, if temperature changes at ROI near the nostrils reach a first threshold, while temperature changes at an ROI related to the mouth do not reach a second threshold, then the breathing may be considered nasal breathing; while if the opposite occurs, the breathing may be considered mouth breathing. In another example, if temperature changes at an ROI near the left nostril and/or on the left side of the upper lip are higher than temperature changes at an ROI near the right nostril and/or on the right side of the upper lip, then the left nostril may be considered the dominant nostril at the time the measurements were taken. In still another example, the value of a respiratory parameter may be calculated as a function of one or more input values from among the respiratory-related thermal measurements.

In other embodiments, one or more of the respiratory parameters may be calculated by generating feature values based on the respiratory-related thermal measurements and utilizing a model to calculate, based on the feature values, the value of a certain respiratory parameter from among the parameters mentioned above. The model for the certain respiratory parameter is trained based on samples. Each sample comprises the feature values based on respiratory-related thermal measurements, taken during a certain period of time, and a label indicative of the value of the certain respiratory parameter during the certain period of time. For example, the feature values generated for a sample may include the values of pixels measured by the one or more cameras, statistics of the values of the pixels, and/or functions of differences of values of pixels at different times. Additionally or alternatively, some of the feature values may include various low-level image analysis features, such as feature derived using Gabor filters, local binary patterns and their derivatives, features derived using algorithms such as SIFT, SURF, and/or ORB, image keypoints, HOG descriptors and features derived using PCA or LDA. The labels of the samples may be obtained through various ways. Some examples of approaches for generating the labels include manual reporting (e.g., a user notes the type of his/her breathing), manual analysis of thermal images (e.g., an expert determines a shape of an exhale stream), and/or utilizing sensors (e.g., a chest strap that measures the breathing rate and volume).

Training the model for the certain respiratory parameter based on the samples may involve utilizing one or more machine learning-based training algorithms, such as a training algorithm for a decision tree, a regression model, or a neural network. Once the model is trained, it may be utilized to calculate the value of the certain respiratory parameter based on feature values generated based on respiratory-related thermal measurements taken during a certain period, for which the label (i.e., the value of the certain respiratory parameter) may not be known.

In one embodiment, a system configured to calculate a respiratory parameter includes an inward-facing head-mounted thermal camera (CAM) and a computer. CAM is worn on a user's head and takes thermal measurements of a region below the nostrils ($TH_{ROI}$), where $TH_{ROI}$ are indicative of the exhale stream. The "region below the nostrils", which is indicative of the exhale stream, refers to one or more regions on the upper lip, the mouth, and/or air volume (s) through which the exhale streams from the nose and/or mouth flow. The flowing of the typically warm air of the exhale stream can change the temperature at the one or more regions, and thus thermal measurements of these one or more regions can provide information about properties of the exhale stream. The computer (i) generates feature values based on $TH_{ROI}$, and (ii) utilizes a model to calculate the respiratory parameter based on the feature values. The respiratory parameter may be indicative of the user's breathing rate, and the model may be trained based on previous $TH_{ROI}$ of the user taken during different days. FIG. 49B illustrates one embodiment of a system for calculating a respiratory parameter. The system includes a computer 445 and CAM that is coupled to the eyeglasses frame worn by the user 420 and provides $TH_{ROI}$ 443.

The computer 445 generates feature values based on $TH_{ROI}$ 443, and possibly other sources of data. Then the computer utilizes a model 442 to calculate, based on the feature values, a value 447 of the respiratory parameter. The value 447 may be indicative of at least one of the following: breathing rate, respiration volume, whether the user is breathing mainly through the mouth or through the nose, exhale (inhale) duration, post-exhale (post-inhale) breathing pause, a dominant nostril, a shape of the exhale stream, smoothness of the exhale stream, and/or temperature of the exhale stream. Optionally, the respiratory parameters calculated by the computer 445 may be indicative of the respiration volume. Optionally, the value 447 is stored (e.g., for life-logging purposes) and/or forwarded to a software agent operating on behalf of the user (e.g., in order for the software agent to make a decision regarding the user).

The feature values generated by the computer 445 may include any of the feature values described in this disclosure that are utilized to detect a physiological response. Optionally, the thermal measurements may undergo various forms of filtering and/or normalization. For example, the feature values generated based on $TH_{ROI}$ may include: time series data comprising values measured by CAM, average values of certain pixels of CAM, and/or values measured at certain times by the certain pixels. Additionally, the feature values may include values generated based on additional measurements of the user taken by one or more additional sensors (e.g., measurements of heart rate, heart rate variability, brainwave activity, galvanic skin response, muscle activity, and/or an extent of movement). Additionally or alternatively, at least some of the feature values may include measurements of the environment in which the user is in, and/or confounding factors that may interfere with the detection.

A user interface (UI) 448 may be utilized to present the value 447 of the respiratory parameter and/or present an alert (e.g., to the user 420 and/or to a caregiver). In one example, UT 448 may be used to alert responsive to an indication that the value 447 reaches a threshold (e.g., when the breathing rate exceeds a certain value and/or after the user 420 spent a certain duration mouth breathing instead of nasal breathing). In another example, UT 448 may be used to alert responsive to detecting that the probability of a respiratory-related attack reaches a threshold.

In one embodiment, the value 447 may be indicative of the smoothness of the exhale stream. Optionally, the value 447 may be presented to the user 420 to increase the user's awareness to the smoothness of his/her exhale stream. Optionally, responsive to detecting that the smoothness is below a predetermined threshold, the computer 445 may issue an alert for the user 420 (e.g., via the UI 448) in order to increase the user's awareness to the user's breathing.

The model 442 is trained on data that includes previous $TH_{ROI}$ of the user 420 and possibly other users. Optionally, the previous measurements were taken on different days and/or over a period longer than a week. Training the model 442 typically involves generating samples based on the previous $TH_{ROI}$ and corresponding labels indicative of values of the respiratory parameter. The labels may come from different sources. In one embodiment, one or more of the labels may be generated using a sensor that is not a thermal camera, which may or may not be physically coupled to a frame worn by the user. The sensor's measurements may be analyzed by a human expert and/or a software program in order to generate the labels. In one example, the sensor is part of a smart shirt and/or chest strap that measures various respiratory (and other) parameters, such as Hexoskin™ smart shirt. In another embodiment, one or more of the labels may come from an external source such as an entity that observes the user, which may be a human observer or a software program. In yet another embodiment, one or more of the labels may be provided by the user, for example by indicating whether he/she is breathing through the mouth or nose and/or which nostril is dominant.

The samples used to train the model 442 usually include samples corresponding to different values of the respiratory parameter. In some embodiments, the samples used to train the model 442 include samples generated based on $TH_{ROI}$ taken at different times of the day, while being at different locations, and/or while conducting different activities. In one example, the samples are generated based on $TH_{ROI}$ taken in the morning and $TH_{ROI}$ taken in the evening. In another example, the samples are generated based on $TH_{ROI}$ of a user taken while being indoors, and $TH_{ROI}$ of the user taken while being outdoors. In yet another example, the samples are generated based on $TH_{ROI}$ taken while a user was sitting down, and $TH_{ROI}$ taken while the user was walking, running, and/or engaging in physical exercise (e.g., dancing, biking, etc.).

Additionally or alternatively, the samples used to train the model 442 may be generated based on $TH_{ROI}$ taken while various environmental conditions persisted. For example, the samples include first and second samples generated based on $TH_{ROI}$ taken while the environment had first and second temperatures, with the first temperature being at least 10° C., warmer than the second temperature. In another example, the samples include samples generated based on measurements taken while there were different extents of direct sunlight and/or different extents of wind blowing.

Various computational approaches may be utilized to train the model 442 based on the samples described above. In one example, training the model 442 may involve selecting a threshold based on the samples. Optionally, if a certain feature value reaches the threshold then a certain respiratory condition is detected (e.g., unsmooth breathing). Optionally, the model 442 includes a value describing the threshold. In another example, a machine learning-based training algorithm may be utilized to train the model 442 based on the samples. Optionally, the model 442 includes parameters of at least one of the following types of models: a regression model, a neural network, a nearest neighbor model, a support vector machine, a support vector machine for regression, a naïve Bayes model, a Bayes network, and a decision tree.

In some embodiments, a deep learning algorithm may be used to train the model 442. In one example, the model 442 may include parameters describing multiple hidden layers of a neural network. In one embodiment, when $TH_{ROI}$ include measurements of multiple pixels, the model 442 may include a convolution neural network (CNN). In one example, the CNN may be utilized to identify certain patterns in the thermal images, such as patterns of temperatures in the region of the exhale stream that may be indicative of a respiratory parameter, which involve aspects such as the location, direction, size, and/or shape of an exhale stream from the nose and/or mouth. In another example, calculating a value of a respiratory parameter, such as the breathing rate, may be done based on multiple, possibly successive, thermal measurements. Optionally, calculating values of the respiratory parameter based on thermal measurements may involve retaining state information that is based on previous measurements. Optionally, the model 442 may include parameters that describe an architecture that supports such a capability. In one example, the model 442 may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using bidirectional recurrent neural network architecture (BRNN).

The computer 445 may detect a respiratory-related attack (such as an asthma attack, an epileptic attack, an anxiety attack, a panic attack, and a tantrum) based on feature values generated based on $TH_{ROI}$ 443. The computer 445 may further receive additional inputs (such as indications of consuming a substance, a situation of the user, and/or thermal measurements of the forehead), and detect the respiratory-related attack based on the additional inputs. For example, the computer 445 may generate one or more of the feature values used to calculate the value 447 based on the additional inputs.

In a first embodiment, the computer 445 utilizes an indication of consumption of a substance to detect a respiratory-related attack. Optionally, the model 442 is trained based on: a first set of $TH_{ROI}$ (taken while the user experienced a respiratory-related attack after consuming the substance, and a second set of $TH_{ROI}$ taken while the user did not experience a respiratory-related attack after consuming the substance. The duration to which "after consuming" refers depends on the substance and may last from minutes to hours. Optionally, the consuming of the substance involves consuming a certain drug and/or consuming a certain food item, and the indication is indicative of the time and/or the amount consumed.

In a second embodiment, the computer 445 utilizes an indication of a situation of the user to detect a respiratory-related attack. Optionally, the model 442 is trained based on: a first set of $TH_{ROI}$ taken while the user was in the situation and experienced a respiratory-related attack, and a second set of $TH_{ROI}$ taken while the user was in the situation and did not experience a respiratory-related attack. Optionally, the situation involves (i) interacting with a certain person, (ii) a type of activity the user is conducting, selected from at least two different types of activities associated with different levels of stress, and/or (iii) a type of activity the user is about to conduct (e.g., within thirty minutes), selected from at least two different types of activities associated with different levels of stress.

In a third embodiment, the system includes another CAM that takes thermal measurements of a region on the forehead ($TH_F$) of the user, and the computer 445 detects a respiratory related attack based on $TH_{ROI}$ and $TH_F$. For example $TH_{ROI}$ and $TH_F$ may be utilized to generate one or more of the feature values used to calculate the value indicative of the probability that the user is experiencing, or is about to experience, the respiratory-related attack. Optionally, the model 442 was trained based on a first set of $TH_{ROI}$ and $TH_F$ taken while the user experienced a respiratory-related attack, and a second set of $TH_{ROI}$ and $TH_F$ taken while the user did not experience a respiratory-related attack.

The system may optionally include a sensor 435 that takes measurements $m_{move}$ 450 that are indicative of movements of the user 420; the system further detects the physiological response based on $m_{move}$ 450. The sensor 435 may include one or more of the following sensors: a gyroscope and/or an accelerometer, an outward-facing visible-light camera (that feeds an image processing algorithm to detect movement from a series of images), a miniature radar (such as low-power radar operating in the range between 30 GHz and 3,000 GHz), a miniature active electro-optics distance measurement device (such as a miniature Lidar), and/or a triangulation wireless device (such as a GPS receiver). Optionally, the sensor 435 is physically coupled to the frame or belongs to a device carried by the user (e.g., a smartphone or a smartwatch).

In a first embodiment, the computer 445 may detect the respiratory-related attack if the value 447 of the respiratory parameter reaches a first threshold, while $m_{move}$ 450 do not reach a second threshold. In one example, reaching the first threshold indicates a high breathing rate, which may be considered too high for the user. Additionally, in this example, reaching the second threshold may mean that the user is conducting arduous physical activity. Thus, if the user is breathing too fast and this is not because of physical activity, then the computer 445 detects this as an occurrence of a respiratory-related attack (e.g., an asthma attack or a panic attack).

In a second embodiment, the computer 445 may generate feature values based on mm, 450 in addition to $TH_{ROI}$ 443, and utilize an extended model to calculate, based on these feature values, a value indicative of the probability that the user is experiencing, or is about to experience, the respiratory related attack. In one example, the feature values used along with the extended model (which may be the model 442 or another model) include one or more of the following: (i) values comprised in $TH_{ROI}$ 443, (ii) values of a respiratory parameter of the user 420, which are generated based on $TH_{ROI}$ 443 (*iii*) values generated based on additional measurements of the user 420 (e.g., measurements of heart rate, heart rate variability, brainwave activity, galvanic skin response, muscle activity, and an extent of movement), (iv) measurements of the environment in which the user 420 was in while $TH_{ROI}$ 443 were taken, (v) indications of various occurrences which may be considered confounding factors (e.g., touching the face, thermal radiation directed at the face, or airflow directed at the face), and/or (vi) values indicative of movements of the user (which are based on $m_{move}$ 450).

The extended model is trained on samples generated from prior $m_{move}$ and $TH_{ROI}$, and corresponding labels indicating times of having the respiratory-related attack. The labels may come from various sources, such as measurements of the user (e.g., to detect respiratory distress), observations by a human and/or software, and/or the indications may be self-reported by the user. The samples used to train the extended model may be generated based on measurements taken over different days, and encompass measurements taken when the user was in different situations.

Usually the exhaled air warms up the skin below the nostrils, and during inhale the skin below the nostrils cools. This enables the system to identify the exhale based on measuring an increase in the temperature of the skin below the nostrils an inhale, and identify the inhale based on measuring a decrease in the temperature of the skin below the nostrils.

Synchronizing a physical effort with the breathing is highly recommended by therapists and sport instructors. For example, some elderly and/or unfit people can find it difficult to stand up and/or make other physical efforts because many of them do not exhale while making the effort, and/or do not synchronize the physical effort with their breathing. These people can benefit from a system that reminds them to exhale while making the effort, and/or helps them synchronize the physical effort with their breathing. As another example, in many kinds of physical activities it is highly recommended to exhale while making a physical effort and/or exhale during certain movements (such as exhale while bending down in Uttanasana).

In one embodiment, the computer 445 determines based on $m_{move}$ 450 and $TH_{ROI}$ 443 whether the user exhaled while making a physical effort above a predetermined threshold. Optionally, the computer receives a first indication that the user is making or is about to make the physical effort, commands a user interface (UI) to suggest the user to exhale while making the physical effort, and commands the UI to play a positive feedback in response to determining that the user managed to exhale while making the physical effort. Additionally, the computer may further command the UI to play an explanation why the user should try next time to exhale while making the physical effort in response to determining that the user did not exhale while making the physical effort.

FIG. 39A to FIG. 40C illustrate how the system described above may help train an elderly user to exhale during effort. In FIG. 39A the system identifies that the user inhaled rather than exhaled while getting up from a sitting position in a chair, the system alerts the user about this finding and suggests that next time the user should exhale while getting up. In FIG. 39B, the system identifies that the user exhaled at the correct time and commends the user on doing so. Examples of physical efforts include standing up, sitting down, manipulating with the hands an item that requires applying a significant force, defecating, dressing, leaning over, and/or lifting an item.

In FIG. 40A the system identifies that the user inhaled rather than exhaled while bending down to the dishwasher, and presents a thumbs-down signal (e.g., on the user's smartphone). In FIG. 40B the system identifies that the user exhaled while bending down to the dishwasher, and presents a thumbs-up signal. In FIG. 40C illustrates a smartphone app for counting the thumbs-up and thumbs-down signals identified during a day. The app may show various statistics, such as thumbs-up/thumbs-down during the past week, from start training with the app, according to locations the user is, while being with certain people, and/or organized according to types of exercises (such as a first counter for yoga, a second counter for housework, and a third counter for breathing during work time).

Figure 41A:
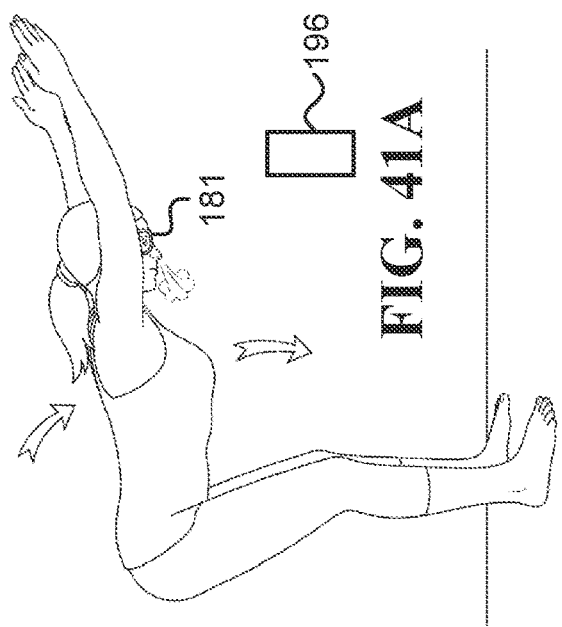
FIG. 41A and FIG. 41B illustrate a fitness app running on smartphone, which instructs the user to exhale while bending down, and to inhale while straightening up.
Figure 41B:
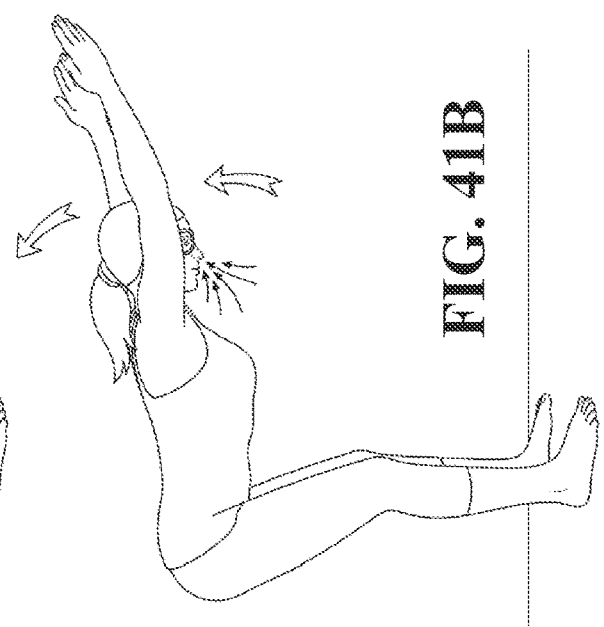

In one embodiment, the computer 445: (i) receives from a fitness app (also known as a personal trainer app) an indication that the user should exhale while making a movement, (ii) determines, based on $m_{move}$ when the user is making the movement, and (iii) determines, based on $TH_{ROI}$, whether the user exhaled while making the movement. Optionally, the computer commands the UI to (i) play a positive feedback in response to determining that the user managed to exhale while making the physical effort, and/or (ii) play an alert and/or an explanation why the user should try next time to exhale while making the physical effort in response to determining that the user did not exhale while making the physical effort. FIG. 41A illustrates a fitness app running on smartphone 196, which instructs the user to exhale while bending down. CAM coupled to eyeglasses frame 181 measures the user breathing and is utilized by the fitness app that helps the user to exhale correctly. FIG. 41B illustrates instructing the user to inhale while straightening up.

Figure 42:
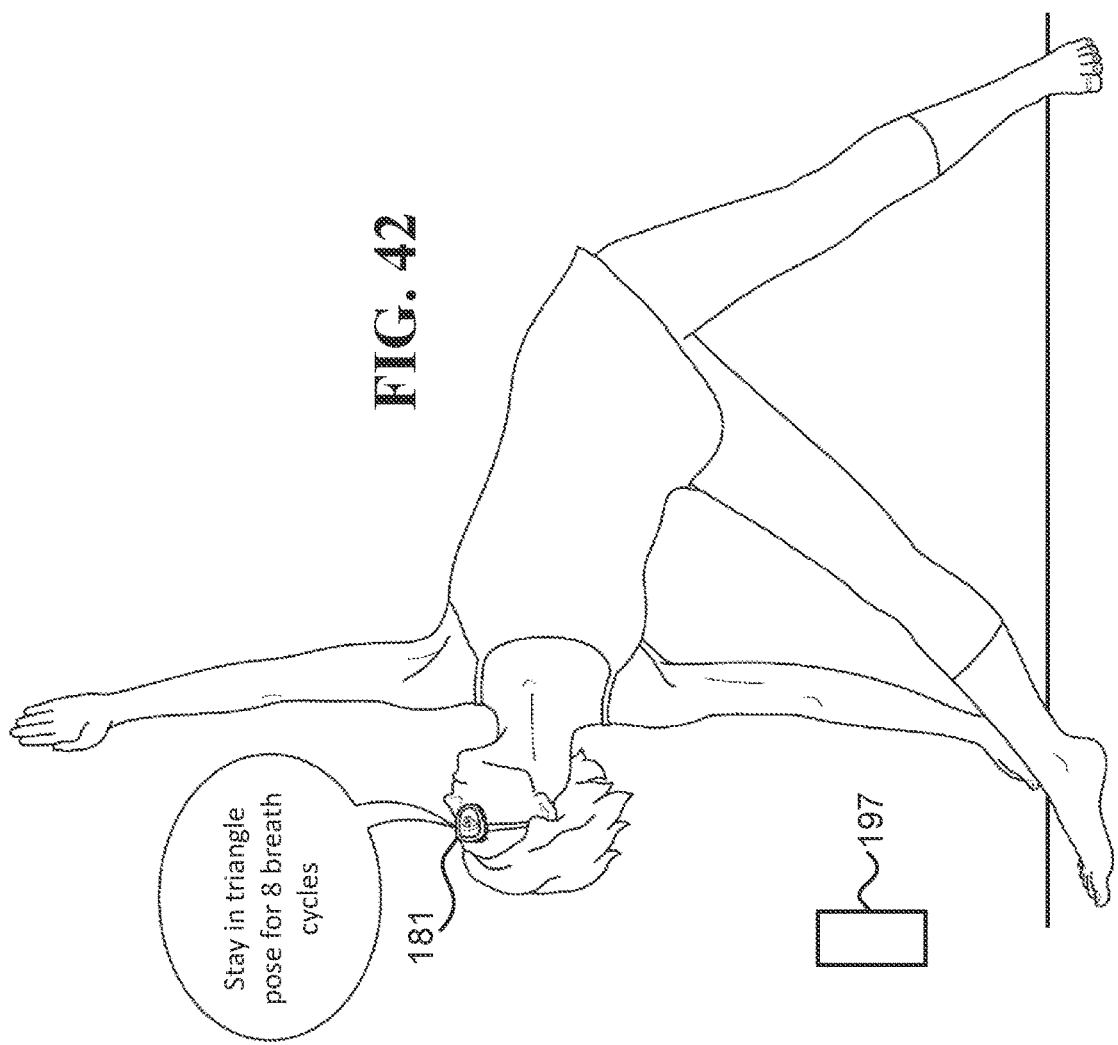
FIG. 42 illustrates a fitness app running on smartphone, which instructs the user to stay in a triangle pose for 8 breath cycles.

In another embodiment, the computer 445: (i) receives from a fitness app a certain number of breath cycles during which the user should perform a physical exercise, such as keeping a static yoga pose for a certain number of breath cycles, or riding a spin bike at a certain speed for a certain number of breath cycles, (ii) determines, based on $m_{move}$, when the user performs the physical exercise, and (iii) counts, based on $TH_{ROI}$, the number of breath cycles the user had while performing the physical exercise. Optionally, the computer commands the UI to play an instruction switch to another physical exercise responsive to detecting that the user performed the physical exercise for the certain number of breath cycles. Additionally or alternatively, the computer commands the UI to play a feedback that refers to the number of counted breath cycles responsive to detecting that the user performed the physical exercise for a number of breath cycles that is lower than the certain number of breath cycles. FIG. 42 illustrates a fitness app running on smartphone 197, which instructs the user to stay in a triangle pose for 8 breath cycles. CAM coupled to eyeglasses frame 181 measures the breathing and is utilized by the fitness app that calculates the breath cycles and counts the time to stay in the triangle pose according to the measured breath cycles.

The duration of exhaling and inhaling (denoted herein $t_{exhale}$ and $t_{inhale}$ respectively) can have various physiological effects. For example, for some users, breathing with prolonged inhales (relative to the exhales) can increase the possibility of suffering an asthma attack. In particular, keeping the duration of exhaling longer than the duration of inhaling (i.e., $t_{exhale}/t_{inhale} \geq 1$, and preferably $t_{exhale}/t_{inhale} \geq 1$) may provide many benefits, such as having a calming effect and relieving asthma symptoms. In one embodiment, a computer is further configured to calculate, based on $TH_{ROI}$, the ratio between exhale and inhale durations ($t_{exhale}/t_{inhale}$).

Many people are not aware of their breathing most of the time. These people can benefit from a system that is able to calculate $t_{exhale}/t_{inhale}$ and provide them with feedback when it is beneficial to increase the ratio. In one embodiment, a computer suggests the user, via the UI, to increase $t_{exhale}/t_{inhale}$ when it falls below a threshold. Optionally, the computer updates occasionally the calculation of $t_{exhale}/t_{inhale}$, and suggests to progressively increase $t_{exhale}/t_{inhale}$ at least until reaching a ratio of 1.5. Optionally, the computer stops suggesting to the user to increase $t_{exhale}/t_{inhale}$ responsive to identifying that $t_{exhale}/t_{inhale} \geq 2$. In another embodiment, the computer is configured to: (i) receive a first indication that the user's stress level reaches a first threshold, (ii) identify, based on $TH_{ROI}$, that the ratio between exhaling and inhaling durations ($t_{exhale}/t_{inhale}$) is below a second threshold that is below 1.5, and (iii) command the UI to suggest to the user to prolong the exhale until $t_{exhale}/t_{inhale}$ reaches a third threshold that is at least 1.5.

Figure 45:
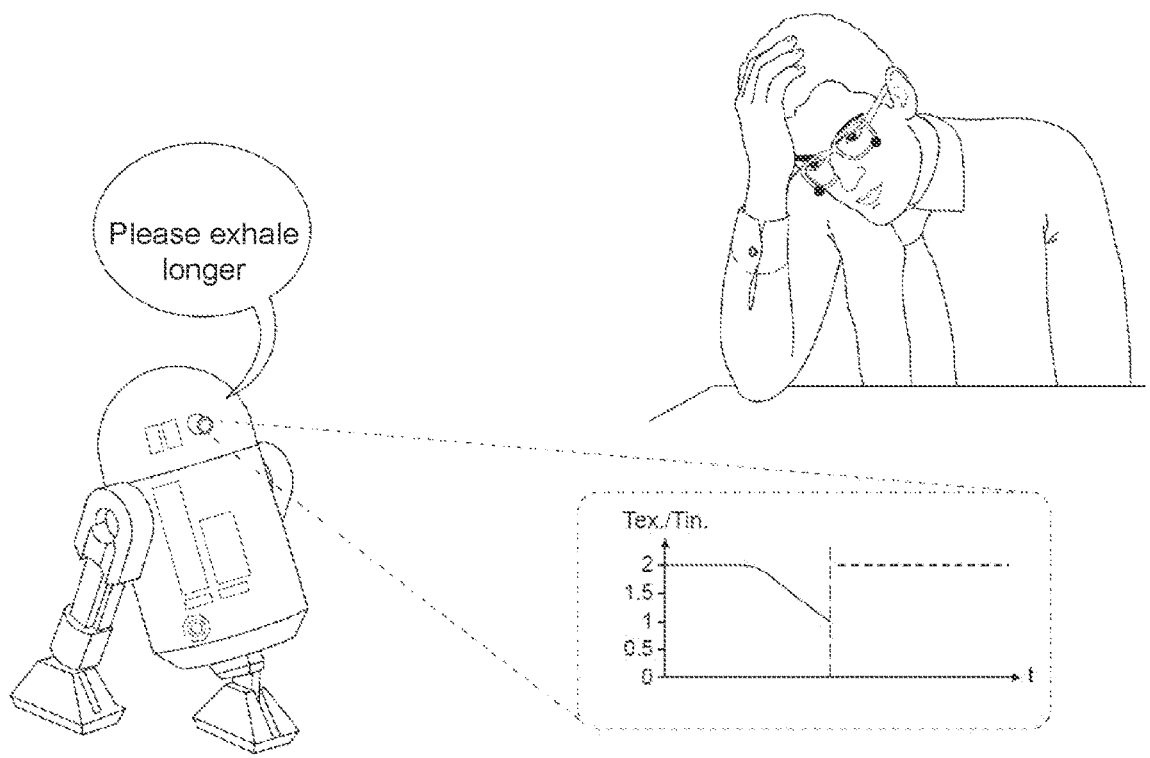
FIG. 45 illustrates a virtual robot that the user sees via augmented reality (AR), which urges the user to increase the ratio between the duration of the user's exhales and inhales.

FIG. 37 illustrates a situation in which an alert is issued to a user when it is detected that the ratio $t_{exhale}/t_{inhale}$ is too low. Another scenario in which such an alert may be issued to a user is illustrated in FIG. 45, which shows a virtual robot that the user sees via augmented reality (AR). The robot urges the user to increase the ratio between the duration of the user's exhales and inhales in order to alleviate the stress that builds up. Monitoring of respiratory parameters, and in particular, the ratio $t_{exhale}/t_{inhale}$ can help a user address a variety of respiratory-related symptoms, as described in the following examples.

Figure 46:
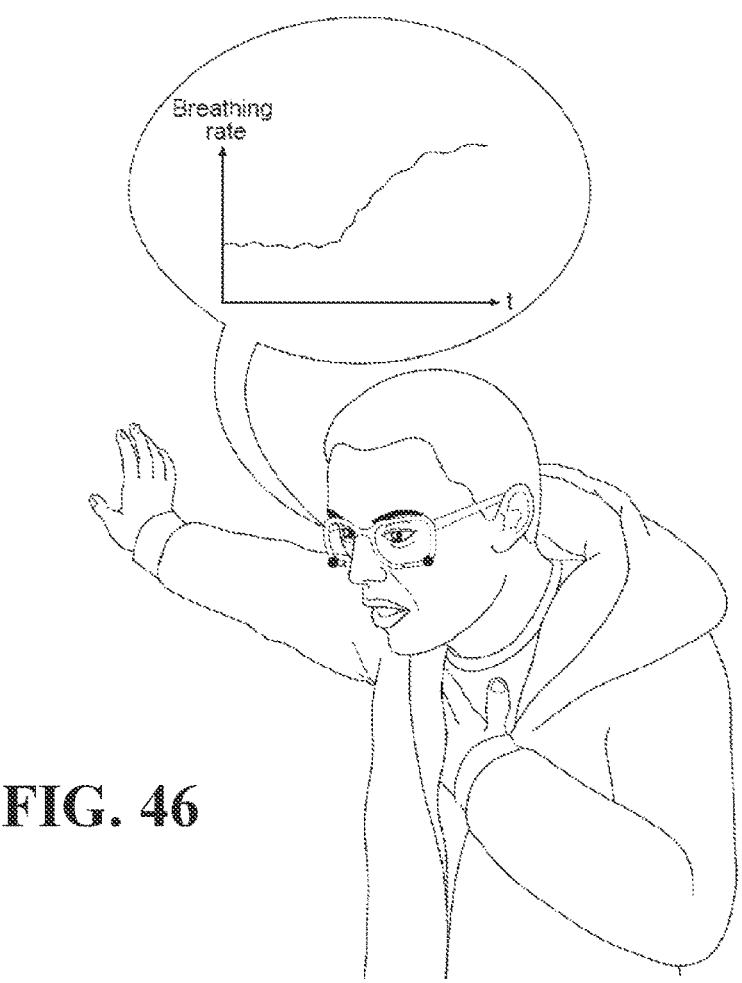
FIG. 46 illustrates an asthmatic patient who receives an alert that his breathing rate increased to an extent that often precedes an asthma attack.

Asthma attacks are related to a person's breathing. Identifying certain changes in respiratory parameters, such as breathing rate above a predetermined threshold, can help a computer to detect an asthma attack based on the thermal measurements. Optionally, the computer utilizes a model, which was trained on previous measurements of the user taken while the user had an asthma attack, to detect the asthma attack based on the thermal measurements. FIG. 46 illustrates an asthmatic patient who receives an alert (e.g., via an augmented reality display) that his breathing rate increased to an extent that often precedes an asthma attack. In addition to the breathing rate, the computer may base its determination that an asthma attack is imminent on additional factors, such as sounds and/or movement analysis as described below.

In a first embodiment, the computer may receive recordings of the user obtained with a microphone. Such recordings may include sounds that can indicate that an asthma attack is imminent; these sounds may include: asthmatic breathing sounds, asthma wheezing, and/or coughing. Optionally, the computer analyzes the recordings to identify occurrences of one or more of the above sounds. Optionally, taking into account the recordings of the user can affect how the computer issues alerts regarding an imminent asthma attack. For example, a first alert provided to the user in response to identifying the increase in the user's breathing rate above the predetermined threshold without identifying at least one of the body sounds may be less intense than a second alert provided to the user in response to identifying both the increase in the user's breathing rate above the predetermined threshold and at least one of the body sounds. Optionally, in the example above, the first alert may not be issued to the user at all.

In a second embodiment, the computer may receive measurements obtained from a movement sensor worn by the user and configured to measure user movements. Some movements that may be measured and may be related to an asthma attack include: spasms, shivering, and/or sagittal plane movements indicative of one or more of asthma wheezing, coughing, and/or chest tightness. Optionally, the computer analyzes the measurements of the movement sensor to identify occurrences of one or more of the above movements. Optionally, considering the measured movements can affect how the computer issues alerts regarding an imminent asthma attack. For example, a first alert provided to the user in response to identifying an increase in the user's breathing rate above a predetermined threshold, without measuring a movement related to an asthma attack is less intense than a second alert provided to the user in response to identifying the increase in the user's breathing rate above the predetermined threshold while measuring a movement related to an asthma attack.

In some embodiments, a first alert may be considered less intense than a second alert if it is less likely to draw the user's attention. For example, the first alert may not involve a sound effect or involve a low-volume effect, while the second alert may involve a sound effect (which may be louder than the first's). In another example, the first alert may involve a weaker visual cue than the second alert (or no visual cue at all). Examples of visual cues include flashing lights on a device or images brought to the foreground on a display. In still another example, the first alert is not provided to the user and therefore does not draw the user's attention (while the second alert is provided to the user).

In one embodiment, responsive to a determination that an asthma attack is imminent, the UI suggests the user to take a precaution, such as increasing $t_{exhale}/t_{inhale}$, preforming various breathing exercises (e.g., exercises that involve holding the breath), and/or taking medication (e.g., medication administered using an inhaler), in order to decrease or prevent the severity of the imminent asthma attack. Optionally, detecting the signs of an imminent asthma attack includes identifying an increase in the breathing rate above a predetermined threshold.

Stress is also related to a person's breathing. In one embodiment, a computer receives a first indication that the user's stress level reaches a threshold and receives a second indication (i) that the ratio between exhaling and inhaling durations is below 1.5 ($t_{exhale}/t_{inhale}<1.5$), and/or (ii) that the user's breathing rate reached a predetermined threshold. Then the computer may command a UI to suggest the user to increase $t_{exhale}/t_{inhale}$ to at least 1.5. Optionally, the computer receives the first indication from a wearable device, calculates $t_{exhale}/t_{inhale}$ based on $TH_{ROI}$ (which is indicative of the exhale stream), and commands the UI to provide the user with an auditory and/or visual feedback indicative of the change in $t_{exhale}/t_{inhale}$ in response to the suggestion to increase the ratio. Optionally, the computer may command the UI to update the user about changes in the stress level in response to increasing $t_{exhale}/t_{inhale}$, and may provide positive reinforcement to help the user to maintain the required ratio at least until a certain improvement in the stress level is achieved.

FIG. 38 illustrates one embodiment of a system configured to collect thermal measurements related to respiration, in which four inward-facing head-mounted thermal cameras (CAMs) are coupled to the bottom of an eyeglasses frame 181. CAMs 182 and 185 are used to take thermal measurements of regions on the right and left sides of the upper lip (186 and 187, respectively), and CAMs 183 and 184 are used to take thermal measurements of a region on the user's mouth 188 and/or a volume protruding out of the user's mouth. At least some of the ROIs may overlap, which is illustrated as vertical lines in the overlapping areas. Optionally, one or more of the CAMs includes a microbolometer focal-plane array (FPA) sensor or a thermopile FPA sensor.

In one embodiment, a computer detects whether the user is breathing mainly through the mouth or through the nose based on measurements taken by CAMs 182, 183, 184 and 185. Optionally, the system helps the user to prefer breathing through the nose instead of breathing through the mouth by notifying the user when he/she is breathing through the mouth, and/or by notifying the user that the ratio between mouth breathing and nose breathing reaches a predetermined threshold. In one embodiment, the computer detects whether the user is breathing mainly through the right nostril or through the left nostril based on measurements taken by CAMs 182 and 185.

The system may further include an inward-facing head-mounted visible-light camera 189 to take images (IM) of a region on the nose and/or mouth, which are used to calculate a respiratory parameter (e.g., detect whether the user is breathing mainly through the mouth or through the nose, detect the inhale duration, and/or detect the post-inhale pause duration). In one embodiment, one or more feature values may be generated based on IM. The feature values may be generated using various image processing techniques and represent various low-level image properties. Some examples of such features may include features generated using Gabor filters, local binary patterns and their derivatives, features generated using algorithms such as SIFT, SURF, and/or ORB, and features generated using PCA or LDA. The one or more feature values may be utilized in the calculation of the respiratory parameter in addition to feature values generated based on the thermal measurements.

Figure 43:
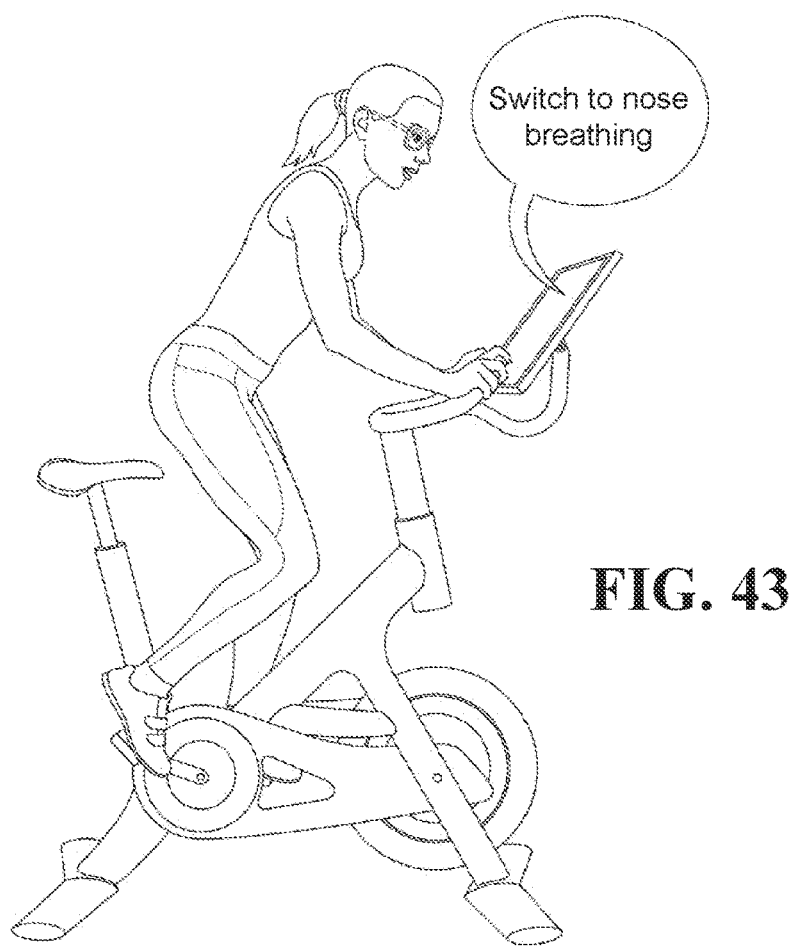
FIG. 43 illustrates notifying a user about mouth breathing and suggesting to breathe through the nose.
Figure 44:
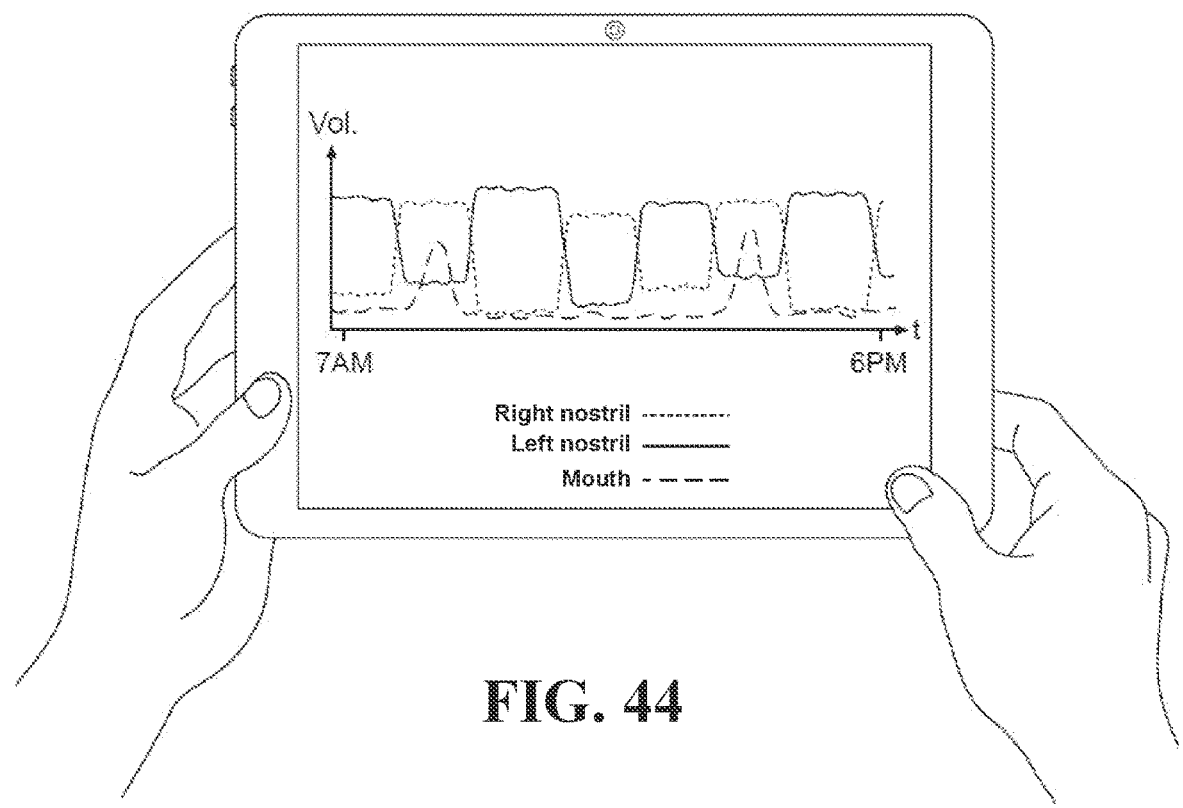
FIG. 44 illustrates an exemplary UI that shows statistics about the dominant nostril and mouth breathing during the day.

In one embodiment, the inward-facing head-mounted visible-light camera 189 takes images of a region on the user's mouth, and IM are indicative of whether the mouth is open or closed. A computer utilizes a model to detect, based on IM and $TH_{ROI}$ (such as the thermal measurements taken by at least one of CAMs 182-185), whether the user is breathing mainly through the mouth or through the nose. Optionally, the model was trained based on: a first set of $TH_{ROI}$ taken while IM was indicative that the mouth is open, and a second set of $TH_{ROI}$ taken while IM was indicative that the mouth is closed. Optionally, the system may help the user to prefer breathing through the nose instead of breathing through the mouth by notifying the user when he/she is breathing through the mouth, and/or by notifying the user that the ratio between mouth breathing and nose breathing reaches a predetermined threshold. FIG. 43 illustrates notifying the user that she breathes mainly through the mouth and should switch to breathing through the nose, while having a physical exercise such as spinning. FIG. 44 illustrates an exemplary UI that shows statistics about the dominant nostril and mouth breathing during the day.

In one embodiment, the inward-facing head-mounted visible-light camera 189 takes images of a region on the nose, and the computer identifies an inhale (and/or differentiates between an inhale and a breathing pause that follows the inhale) based on image processing of IM to detect movements of the nose, especially at the edges of the nostrils, which are indicative of inhaling.

FIG. 36 illustrates another embodiment of a system configured to collect thermal measurements related to respiration, in which four CAMs are coupled to a football helmet. CAMs 190 and 191 are used to take thermal measurements of regions on the right and left sides of the upper lip (appear as shaded regions on the users face), and CAMs 192 and 193 are used to take thermal measurements of a region on the user's mouth and/or a volume protruding out of the user's mouth. The illustrated CAMs are located outside of the exhale streams of the mouth and nostrils in order to maintain good measurement accuracy also when using thermal sensors such as thermopiles.

In some embodiments, the system further includes at least one in-the-ear earbud comprising a microphone to measure sounds inside the ear canal. A computer may identify an inhale based on analysis of the recordings from the earbud. Optionally, the inhale sounds measured by the earbud are stronger when the dominant nostril is the nostril closer to the ear in which the earbud is plugged in, compared to the inhale sounds measured by the earbud when the other nostril is the dominant nostril. Optionally, the computer detects whether the user is breathing mainly through the mouth or through the nose based on the thermal measurements and the sounds measured by the earbud. And then the system can help the user to prefer nasal breathing over mouth breathing by alerting the user when he/she breathes mainly through the mouth.

In some embodiments, the dominant nostril at a given time is the nostril through which most of the air is exhaled (with a closed mouth). Optionally, the dominant nostril is the nostril through which at least 70% of the air is exhaled. The different types of nostril dominance are illustrated in FIG. 47A to FIG. 47C. FIG. 47A is a schematic illustration of a left dominant nostril (note the significantly larger exhale stream from the left nostril). FIG. 47B is a schematic illustration of a right dominant nostril. And FIG. 47C is a schematic illustration of a balanced nasal breathing.

FIG. 48 is a schematic illustration of one embodiment of a system configured to identify the dominant nostril. The system includes at least one CAM 750, a computer 752, and an optional UI 754. CAM 750 may be similar to the CAMs in FIG. 38. CAM 750 takes thermal measurements of first and second ROIs below the right and left nostrils ($TH_{ROI1}$ and $TH_{ROI2}$, respectively) of the user. Optionally, each CAM does not occlude any of the user's mouth and nostrils. Optionally, each CAM is located less than 15 cm from the user's face and above the user's upper lip. Optionally, each CAM weighs below 10 g or below 2 g, and utilizes microbolometer or thermopile sensors. Optionally, each CAM includes multiple sensing elements that are configured to take $TH_{ROI1}$ and/or $TH_{ROI2}$. In one example, each CAM includes at least 6 sensing elements, and each of $TH_{ROI1}$ and $TH_{ROI2}$ is based on measurements of at least 3 sensing elements. Optionally, the system includes a frame to which CAM is physically coupled.

In one embodiment, the at least one CAM includes at least first and second thermal cameras (CAM1 and CAM2, respectively) that take $TH_{ROI1}$ and $TH_{ROI2}$, respectively, located less than 15 cm from the user's face. CAM1 is physically coupled to the right half of the frame and captures the exhale stream from the right nostril better than it captures the exhale stream from the left nostril, and CAM2 is physically coupled to the left half of the frame and captures the exhale stream from the left nostril better than it captures the exhale stream from the right nostril.

The at least one CAM may be used to capture thermal measurements of various ROIs. In one embodiment, the first region of interest ($ROI_1$) includes a region on the right side of the user's upper lip, and the second region of interest ($ROI_2$) includes a region on the left side of the user's upper lip. In another embodiment, $ROI_1$ includes a portion of the volume of the air below the right nostril where the exhale stream from the right nostril flows and $ROI_2$ includes a portion of the volume of the air below the left nostril where the exhale stream from the left nostril flows. In yet another embodiment, the at least one CAM may take thermal measurements of a region on the mouth and/or a volume protruding out of the mouth ($TH_{ROI3}$) of the user, which is indicative of the exhale stream from the mouth, and the computer identifies the dominant nostril also based on $TH_{ROI3}$. Optionally, the computer may utilize $TH_{ROI3}$ similarly to how it utilizes $TH_{ROI1}$ and $TH_{ROI2}$ to identify the dominant nostril (e.g., the computer may generate feature values based on $TH_{ROI3}$, as discussed below).

The computer identifies the dominant nostril based on $TH_{ROI1}$ and $TH_{ROI2}$ (and possibly other data such as $TH_{ROI3}$), which were taken during a certain duration. Optionally, the certain duration is longer than at least one of the following durations: a duration of one exhale, a duration of one or more breathing cycles, a half a minute, a minute, and five minutes.

In one embodiment, the computer utilizes a model to identify the dominant nostril. Optionally, the model was trained based on previous $TH_{ROI1}$, $TH_{ROI2}$, and indications indicative of which of the nostrils was dominant while the previous $TH_{ROI1}$ and $TH_{ROI2}$ were taken. In one example, the computer generates feature values based on $TH_{ROI1}$ and $TH_{ROI2}$ (and optionally $TH_{ROI3}$), and utilizes the model to calculate, based on the feature values, a value indicative of which of the nostrils is dominant.

In one embodiment, the computer identifies whether the user's breathing may be considered balanced breathing. Optionally, breathing is considered balanced breathing when the streams through the right and the left nostrils are essentially equal, such as when the extent of air exhaled through the left nostril is 40% to 60% of the total of the air exhaled through the nose. Balanced breathing of a normal healthy human usually lasts 14 minutes during the time of switching between the dominant nostrils. Optionally, the computer notifies the user when the user's breathing is balanced. Optionally, the computer suggests to the user, via a UI, to meditate during the balanced breathing.

The total time the different nostrils remain dominant may be indicative of various medical conditions. In one embodiment, when there is a significant imbalance of the daily total time of left nostril dominance compared to total time of right nostril dominance, and especially if this condition continues for two or more days (and is significantly different from the user's average statistics), it may be an indication of an approaching health problem. For example, when the total time of left nostril dominance is greater than the total time of right nostril dominance, the approaching problem may be more mentally related than physically related; and when the total time of right nostril dominance is greater than the total time of left nostril dominance, the approaching problem may be more physically related than mentally related. In another embodiment, a greater extent of left nostril dominance is related to digestion problems, inner gas, diarrhea, and male impotence; and a greater extent of right nostril dominance may be related to high blood pressure, acid reflux, and ulcers.

In one embodiment, the computer monitors nostril dominance over a certain period, and issues an alert when at least one of the following occurs: (i) a ratio between the total times of the right and left nostril dominance during the certain period reaches a threshold (e.g., the threshold may be below 0.3 or above 0.7) (ii) an average time to switch from right to left nostril dominance reaches a threshold (e.g., a threshold longer than 3 hours), and (iii) an average time to switch from left to right nostril dominance reaches a threshold.

The following are some examples of various applications in which the computer may utilize information about the dominant nostril, which is identified based on $TH_{ROI1}$ and $TH_{ROI2}$, in order to assist the user in various ways.

For some people, a certain dominant nostril may be associated with a higher frequency of having certain health problems, such as an asthma attack or a headache. Making a person aware of which nostril is more associated with the health problem can help the user to alleviate the health problem by switching the dominant nostril. Two examples of ways to switch the dominant nostril include: (i) to plug the current dominant nostril and breathe through the other nostril, and (ii) to lay on the side of the current dominant nostril (i.e., lying on the left side to switch from left to right dominant nostril, and vice versa). In one embodiment, the computer detects that the user is having an asthma attack, notifies the user about the current dominant nostril (which is associated with a higher frequency of asthma attacks), and suggests to switch the dominant nostril (to alleviate the asthma attack). In another embodiment, the computer detects the user has a headache, notifies the user about the current dominant nostril (which is associated with a higher frequency of headaches), and suggests to switch the dominant nostril.

Achieving balanced breathing may be a desired goal at some times. Biofeedback training may help extend the duration and/or increase the frequency at which one has balanced breathing. In one embodiment, the computer provides, via the UI, biofeedback for the user to achieve balanced breathing by playing a feedback. The feedback may be generated according to any suitable known method, such as normally playing the feedback when the breathing becomes more balanced, and stopping, rewinding, and/or dithering the feedback when the breathing becomes less balanced. Examples of feedbacks that may be used include playing a movie, running a video game, and/or playing sounds.

In a similar manner, biofeedback training may help the user to achieve a required breathing pattern, such as making a certain nostril dominant, or learning how to change the nostril from which most of the air is exhaled using thought and optionally without touching the nostrils. In one embodiment, the computer provides, via the UI, biofeedback for the user to achieve the required breathing pattern by playing a feedback. The feedback may be generated according to any suitable known method, such as playing a first sound when the use exhales more air from the right nostril than the left nostril, playing a second sound when the use exhales more air from the left nostril than the right nostril, and playing a third sound when the use exhales essentially the same from the right and left nostrils.

In one embodiment, the length of the exhale stream is considered as the distance from the nose at which the exhale stream can still be detected. For each person, there is a threshold that may change during the day and responsive to different situations. When the length of the exhale stream is below the threshold, it may indicate that the person is calm; and when the length of the exhale stream is longer than the threshold, it may indicate excitement. In general, the shorter the length of the exhale stream the less energy is invested in the breathing process and the less stress the person experiences. An exception may be arduous physical activity (which can increase the length of the exhale stream due to larger volumes of air that are breathed). In one embodiment, $TH_{ROI1}$ and $TH_{ROI2}$ are indicative of the length of the exhale stream, and the computer calculates level of excitement of the user based on the length of the exhale stream. Optionally, the longer the length, the higher the excitement/stress, and vice versa. Additionally, the relationship between the length of the exhale stream and the level of excitement may be a function of parameters such as the time in day, the dominant nostril, the user's mental state, the user's physiological state, the environmental air quality, and/or the temperature of the environment. In one example, the at least one CAM uses multiple sensing elements to take thermal measurements of regions located at different lengths below the nostrils. In this example, the larger the number of the sensing elements that detect the exhale stream, the longer the length of the exhale stream. Optionally, the amplitude of the temperature changes measured by the sensing elements is also used to estimate the length, shape, and/or uniformity of the exhale stream.

Ancient yoga texts teach that learning to extend the duration of the time gaps between inhaling and exhaling, and/or between exhaling and inhaling, increases life span. In one embodiment, the computer assists the user to extend the duration of the time gap between inhaling and exhaling by performing at least one of the following: (i) calculating the average time gap between inhaling and exhaling over a predetermined duration, and providing the calculation to the user via a user interface (UI), (ii) calculating the average time gap between inhaling and exhaling over a first predetermined duration, and reminding the user via the UI to practice extending the duration when the average time gap is shorter than a first predetermined threshold, and (iii) calculating the average time gap between inhaling and exhaling over a second predetermined duration, and encouraging the user via the UI when the average time gap reaches a second predetermined threshold. It is to be noted that to stop breathing after exhaling is considered more beneficial but also more dangerous, therefore the system may enable the user to select different required durations for stopping the breathing after inhaling and for stopping breathing after exhaling.

Typically, the dominant nostril switches sides throughout the day, with the duration between each switch varying, depending on the individual and other factors. Disruption of the typical nasal switching cycle may be indicative of physiological imbalance, emotional imbalance, and/or sickness. For example, slower switching of the dominant nostril may be, in some cases, a precursor of some diseases. In one embodiment, the computer learns the typical sequence of switching between dominant nostrils based on previous measurements of the user taken over more than a week, and issues an alert upon detecting an irregularity in the sequence of changes between the dominant nostrils. In one example, the irregularity involves a switching of the dominant nostril within a period of time that is shorter than a certain period typical for the user, such as shorter than forty minutes. In another example, the irregularity involves a lack of switching of the dominant nostril for a period that is greater than a certain period typical for the user, such as longer than three hours. In yet another example, the cycles of the dominant nostril may be described as a time series (e.g., stating for each minute a value indicative of the dominant nostril). In this example, the computer may have a record of previous time series of the user, acquired when the user was healthy, and the computer may compare the time series to one or more of the previous time series in order to determine whether a sufficiently similar match is found. A lack of such a similar match may be indicative of the irregularity.

The following is a discussion of the role of nostril dominance and other breathing aspects in Asian philosophy. According to Asian philosophy, and specifically the Vedas, all objects are made of the Five Great Elements, also known as the Classical elements, which include earth, water, fire, air, and space. The great elements represent types of energy, but they are related to the physical elements they are called after. During left or right nostril dominance, just one element is typically dominant in the body, and this is reflected in the form of the exhale stream (during balanced breath two elements may share dominance). When dominance in breathing is not forced, each of the five great elements in turn may become dominant and then cedes dominance to the next one. The normal order of dominance according to one text is: air, fire, earth, water, and space. The relative ratios of duration of dominance are: earth—5, water—4, fire—3, air—2, space—1. The dominant element affects breathing in two ways: the length of the exhale and the shape of the exhale stream (SHAPE). The average lengths and shapes of the outbreath are as follows according to one yoga textbook: earth—about 24 cm, straight out of the center of the nostril. Water—about 32 cm length, coming from the bottom of the nostril in a slight downward direction. Fire—8 cm, coming from the top of the nostril with an upward slant. Air—about 16 cm, coming from the external side of the nostril (left for the left nostril and right for the right nostril) with a slant outside. Space—very light and short breath from all parts of the nostril.

In one embodiment, the computer identifies, based on $TH_{RO/1}$ and $TH_{RO/2}$, the dominant element out of the five elements. Optionally, the computer monitors if relative durations and order of elements' dominance is regular, i.e. according to the order and duration ratios specified and optionally with approximate length as prescribed, or there is some irregularity. In one embodiment, irregularity may indicate a potential problem with the associated gland: for earth—ovaries or testes/prostate, water—adrenal, fire—intestines, air—none, space—thyroid and para-thyroid. In another embodiment, irregularity may indicate a potential mental and/or physiological problem(s).

If an element's dominance time (as evident from breathing characteristics) is too long, it may be balanced (reduced) by consuming appropriate food and/or drink. For example, air dominance can be reduced by consuming heavy oily food, fire dominance can be reduced by drinking water or by consuming water-absorbing food like buckwheat, and earth dominance can be reduced by eating light food with a lot of fiber.

If a dominant element is too weak (i.e., judging by breathing characteristics compared to the yardstick for that element, or comparing the SHAPE to a baseline SHAPE), it can be strengthened. For example, air dominance can be strengthened by active physical movement fire dominance can be strengthened by breath-of-fire (from kundalini yoga), water dominance can be strengthened by drinking, earth can be strengthened by eating proteins and oily food, and space dominance can be strengthened by visualizing a picture that grows and shrinks in size.

As discussed above, the shape of the exhale stream (SHAPE) from the nostrils changes over time. With the at least one CAM it is possible, in some embodiments, to obtain measurements indicative of at least some of the different typical SHAPEs. A non-limiting reason for the system's ability to measure the different SHAPEs is that the exhale stream has a higher temperature than both the typical temperature of the environment and the typical temperature of the upper lip. As a result the particles of the exhale stream emit at a higher power than both the environment and the upper lip, which enables CAM to measure the SHAPE over time.

As discussed above, different SHAPEs may be characterized by different 3D shape parameters (e.g., the angle from which the exhale stream blows from a nostril, the width of the exhale stream, the length of the exhale stream, and other parameters that are indicative of the 3D SHAPE). Additionally, different SHAPEs may be associated with different states of the user, such as different physiological and/or mental conditions the user may be in. In some embodiments, the computer calculates the SHAPE based on $TH_{RO/1}$ and $TH_{RO/2}$. Optionally, calculating the shape involves calculating values of one or more parameters that characterize the exhale stream's shape (e.g., parameters related to the 3D SHAPE). Optionally, calculating the SHAPE involves generating a reference pattern for the SHAPE. For example, the reference pattern may be a consensus image and/or heat map that is based on $TH_{ROI1}$ and $TH_{ROI2}$ taken over multiple breaths.

In other embodiments, the computer identifies a SHAPE based on $TH_{ROI1}$ and $TH_{ROI2}$. Optionally, the identified SHAPE belongs to a set that includes at least first and second SHAPEs, between which the computer differentiates. Optionally, the first and second SHAPEs are indicative of at least one of the following: two of the five great elements according to the Vedas, two different emotional states of the user, two different moods of the user, two different energetic levels of the user, and a healthy state of the user versus an unhealthy state of the user. In one example, the first SHAPE is indicative of a powerful alert energetic level, while the second SHAPE is indicative of a tired energetic level, and the computer uses this information to improve computerized interactions with the user.

The SHAPE may be related to the dominant nostril at the time. In one embodiment, the first SHAPE occurs more frequently when the right nostril is dominant, and the second SHAPE occurs more frequently when the left nostril is dominant. In another embodiment, both the first and the second SHAPEs occur more frequently when the right nostril is dominant.

In one example, differentiating between the first and second SHAPEs means that there are certain first $TH_{ROI1}$ and $TH_{ROI2}$ that the computer identifies as corresponding to the first SAHPE and not as corresponding to the second SHAPE, and there are certain second $TH_{ROI1}$ and $TH_{ROI2}$ that the computer identifies as corresponding to the second SHAPE and as not corresponding to the first SHAPE. In another example, differentiating between first and second SHAPEs means that there are certain third $TH_{ROI1}$ and $TH_{ROI2}$ that the computer identifies as having a higher affinity to the first SHAPE compared to their affinity to the second SHAPE, and there are certain fourth $TH_{ROI1}$ and $TH_{ROI2}$ that the computer identifies as having a higher affinity to the second SHAPE compared to their affinity to the first SHAPE.

In some embodiments, the SHAPE is identified by the computer based on $TH_{ROI1}$, $TH_{ROI2}$, and optionally other sources of data. Since the SHAPE does not typically change between consecutive breaths, detecting the shape of the exhale may be done based on multiple measurements of multiple exhales. Using such multiple measurements can increase the accuracy of the identification of the shape. In one example, the first and second SHAPEs are identified based on first and second sets of $TH_{ROI1}$ and $TH_{ROI2}$ taken during multiple exhales over first and second non-overlapping respective durations, each longer than a minute.

The computer may utilize different approaches to identify the SHAPE. In one embodiment, the computer may compare $TH_{ROI1}$ and $TH_{ROI2}$ to one or more reference patterns to determine whether $TH_{ROI1}$ and $TH_{ROI2}$ are similar to a reference pattern from among the one or more reference patterns. For example, if the similarity to a reference pattern reaches a threshold, the exhale stream measured with $TH_{ROI1}$ and $TH_{ROI2}$ may be identified as having the shape corresponding to the shape of the reference pattern. Determining whether $TH_{ROI1}$ and $TH_{ROI2}$ are similar to a reference pattern may be done using various image similarity functions, such as determining the distance between each pixel in the reference pattern and its counterpart in $TH_{ROI1}$ and $TH_{ROI2}$. One way this can be done is by converting $TH_{ROI1}$ and $TH_{ROI2}$ into a vector of pixel temperatures, and comparing it to a vector of the reference pattern (using some form of vector similarity metric like a dot product or the L2 norm).

The one or more reference patterns may be generated in different ways. In one embodiment, the one or more reference patterns are generated based on previous $TH_{ROI1}$ and $TH_{ROI2}$ of the user taken on different days. Optionally, the SHAPEs were known while previous $TH_{ROI1}$ and $TH_{ROI2}$ of the user taken. In one example, the SHAPE is associated with a state of the user at the time (e.g., relaxed vs. anxious). In another example, the SHAPE may be determined using an external thermal camera (which is not head-mounted). In yet another example, the SHAPE is determined by manual annotation. In one embodiment, the one or more reference patterns are generated based on previous $TH_{ROI1}$ and $TH_{ROI2}$ of one or more other users.

In some embodiments, the SHAPE may be discovered through clustering. Optionally, the computer may cluster sets of previous $TH_{ROI1}$ and $TH_{ROI2}$ of the user into clusters. Where sets of $TH_{ROI1}$ and $TH_{ROI2}$ in the same cluster are similar to each other and the exhale streams they measured are assumed to have the same shape. Thus, each of the clusters may be associated with a certain SHAPE to which it corresponds. In one example, the clusters include at least first and second clusters that correspond to the aforementioned first and second SHAPEs.

The computer may utilize a machine learning-based model to identify the SHAPE. In one embodiment, the computer generates feature values based on $TH_{ROI1}$ and $TH_{ROI2}$, and utilizes a model to classify $TH_{ROI1}$ and $TH_{ROI2}$ to a class corresponding to the SHAPE. Optionally, the class corresponds to the aforementioned first or second shapes. Optionally, the model is trained based on previous $TH_{ROI1}$ and $TH_{ROI2}$ of the user taken during different days.

In one embodiment, the computer receives an indication of the user's breathing rate, and uses this information along with the SHAPE at that time in order to suggest to the user to perform various activities and/or alert the user. Optionally, the indication of the user's breathing rate is calculated based on $TH_{ROI1}$ and $TH_{ROI2}$. In one example, the SHAPE is correlative with the state of the user, and different states combined with different breathing rates may have different meaning, which cause the computer to suggest different activities. The different activities may vary from different work/learning related activities to different physical activities to different treatments. In one example, the computer suggests to the user, via the UI, to perform a first activity in response to detecting that the breathing rate reached a threshold while identifying the first SHAPE. However, the computer suggest to the user to perform a second activity, which is different from the first activity, in response to detecting that the breathing rate reached the threshold while identifying the second SHAPE. In another example, the computer alerts the user, via the UI, in response to detecting that the breathing rate reached a threshold while identifying the first SHAPE, and the computer does not alert the user in response to detecting that the breathing rate reached the threshold while identifying the second SHAPE. In this example, the SHAPE may be correlated with the state of the user, and different states may be associated with different normal breathing rates. When the difference between the current breathing rate and the normal breathing rate (associated with the current SHAPE) reaches a threshold, the user may be in an abnormal state that warrants an alert.

In another embodiment, the computer configures a software agent that prioritizes activities for the user based on the identified SHAPE, such that a first activity is prioritized over a second activity responsive to identifying the first SHAPE, and the second activity is prioritized over the first activity responsive to identifying the second SHAPE. It is noted that the system may prioritize different activities for different SHAPEs also when the measured breathing rate and respiration volume are the same.

In still another embodiment, the computer learns a flow of typical changes between different SHAPEs based on previous measurements of the user, and issues an alert upon detecting an irregularity related to a flow of changes between the SHAPEs. For example, the irregularity may involve a new SHAPE, more frequent changes between SHAPEs, having certain SHAPEs for more or less time than usual, etc.

In yet another embodiment, the computer receives data about types of foods consumed by the user, stores the data in a memory, and finds correlations between the SHAPEs and the types of foods. These correlations may be used to make suggestions to the user. For example, the computer may suggest the user to eat a first type of food responsive to identifying the first SHAPE, and suggest the user to eat a second type of food responsive to identifying the second SHAPE. According to Ayurveda medicine, it is preferred to eat according to the three doṣhas and the five great elements. In times when the SHAPE is indicative of the dominant element (out of the five great elements), the computer may guide the user which types of food suit the identified dominant element, and/or may help the user to avoid inappropriate types of foods by identifying the types of food the user eats (and/or is about to eat), and alert the user when the identified food is inappropriate to the current dominant element (that was identified based on the SHAPE).

Data obtained from monitoring the dominant nostril can be utilized to make suggestions of activities for the user. FIG. 49A illustrates one embodiment of a system configured to suggest activities according to the dominant nostril. The system includes a sensor 451 for taking measurements 454 indicative of which of the user's nostrils is dominant at the time the measurements 454 were taken. Optionally, the sensor 451 is one or more thermal cameras, such as the thermal cameras illustrated in FIG. 38, however, as discussed below, other types of sensors may be utilized to take the measurements 454. The system also includes a computer 455 and optionally includes a UI 456.

The computer 455 predicts, based on the measurements 454, which of the user's nostrils will be the dominant nostril at a future time. Optionally, responsive to predicting that the right nostril will be dominant at the future time, the computer 455 suggests having at the future time a first activity, which is more suitable for a right dominant nostril than a second activity. Optionally, responsive to predicting that the left nostril will be dominant at the future time, the computer suggests having at the future time the second activity, which is more suitable for a left dominant nostril than the first activity. Optionally, the computer 455 suggests activities utilizing the UI 456. In one example, the first activity requires more verbal-analytical skills and less spatial skills compared to the second activity. In another example, the first activity requires more logic and/or locomotive skills compared to the second activity, and less empathy and/or imagination. In another example, the second activity requires more creativity and less physical effort compared to the first activity.

The suggestions of activities described above may be based on the premise that the dominant nostril is indicative of which of the user's brain hemispheres is more effective at performing activities that are associated with it. It is typically assumed that the left side of the user's brain is expected to be more effective at performing tasks when the right nostril is dominant (compared to when the left nostril is dominant). Conversely, the right side of the user's brain is expected to be more effective at performing tasks when the left nostril is dominant (compared to when the right nostril is dominant). The right hemisphere is usually believed to be better at expressive and creative tasks. Some of the abilities associated with the right hemisphere include recognizing faces, expressing emotions, music, reading emotions, color, images, intuition, and creativity. The left hemisphere is usually believed to be adept to tasks that involve logic, language, and analytical thinking. The left hemisphere is usually described as being better at language, logic, critical thinking, numbers, and reasoning. Thus, certain activities, which require certain skills that are associated with a certain hemisphere, may be more suitable to perform when one nostril is dominant compared to when the other nostril is dominant.

Additionally or alternatively, the suggestions of activities described above may be based on empirical data of the performances of the user and/or performances of other users. By analyzing the user's performances versus the dominant nostril (and optionally other parameters), and/or using big data analysis of the measured performances of many users versus their dominant nostril (and optionally other parameters), it is possible to identify a first set of activities that are statistically significantly more successfully achieved during right dominant nostril, a second set of activities that are statistically significantly more successfully achieved during left dominant nostril, and a third set of activities that are statistically significantly more successfully achieved during a balanced nasal breathing.

To predict the dominant nostril at the future time, the computer 455 relies on the measurements 454, which were taken prior to a current time, at which the prediction is made. Optionally, the future time may be at least five minutes after the current time, at least thirty minutes after the current time, at least one hour after the current time, at least three hours after the current time, or at least six hours after the current time.

In one embodiment, the computer 455 utilizes the measurements 454 to determine when the dominant nostril last switched (before the current time), and uses this information to predict when it will switch next (possibly multiple times). Thus, the computer can extrapolate, based on the measurements 454, a timeline until the future time, indicating which nostril is dominant at different times until (and including) the future time. Optionally, information useful for determining the time line (such as the time each nostril remains dominant) may be based on the measurements 454 and/or previous measurements of the user taken with the sensor 451 during different days.

In another embodiment, the computer 455 predicts the dominant nostril at the future by generating feature values and utilizing a machine learning-based model to estimate the dominant nostril at the future time (e.g., left nostril dominance, right nostril dominance, or balanced breathing). Optionally, the feature values comprise one or more feature values describing aspects of the future time such as the time to which it corresponds (e.g., how much time ahead the future time is), the location the user is expected to be at the future time, and/or an activity the user is expected to partake at the future time. Optionally, the feature values may include one or more features values corresponding to a state of the user at an earlier time that precedes the future time, such as the user's dominant nostril (e.g., as determine based on the measurements 454), manipulation of the dominant nostril performed by the user recently, previous measurements of the user taken after the user manipulated the dominant nostril and/or practiced pranayama and/or listened to brainwave entrainment, an activity the user had during the earlier time, and/or values of physiological signals of the user at the earlier time. In one embodiment, the machine learning-based model is trained based on samples that include measurements 454 taken at certain earlier times and their corresponding dominant nostrils following certain durations after the certain earlier times.

When a first activity is suggested for the future time (over the second activity), it typically means that the first activity is to be preferred over the second activity. Optionally, to suggest having the first activity at the future time means that the computer schedules the first activity at the future time and does not schedule the second activity at the future time. Additionally or alternatively, to suggest having the first activity at the future time means that the computer 455 ranks the first activity at the future time higher than it ranks the second activity at the future time. Optionally, when the first activity is ranked higher than the second activity it means that the first activity is given a stronger recommendation than the second activity. For example, a stronger recommendation may involve the first activity being suggested by displaying it first on a list of suggested activities. In another example, a stronger recommendation may involve suggesting the first activity with a larger image, a more prominent visual effect, and/or a more noticeable auditory signal than the one used to suggest the second activity.

The computer 455 may utilize a determination of which nostril is dominant at the current time and/or a prediction of which nostril will be dominant at the future in order to assist the user in performing activities at suitable times. In a first embodiment, the computer 455 assists the user to spend more time eating certain types of food when the right nostril is dominant. Additionally or alternatively, the computer 455 further assists the user to spend less time eating the certain types of food when the left nostril is dominant. In one example, the computer 455 may assist the user by identifying that the user starts looking for food during left nostril dominance, and reminding the user that eating while the left nostril is dominant is probably due to emotional reasons. In another example, the computer 455 may arrange the user's schedule such that at least 60% of the occurrences of lunch and/or dinner are planned to a time when the right nostril is dominant. Optionally, the computer 455 recommends to the user to have the main meal of the day while the right nostril is dominant. In a second embodiment, the computer 455 assists the user to increase the time spent at the toilet defecating while the right nostril is dominant. Optionally, the computer 455 recommends to the user to spend less time at the toilet defecating while the left nostril is dominant. For example, the computer 455 may recommend to go on a bathroom break when the right nostril is dominant. Optionally, the computer 455 may assist the user to decrease defecating during times of left nostril dominance by reminding the user that it is preferred to defecate during right nostril dominance, especially when suffering from constipation. In a third embodiment, the activity involves creativity, such as creating art, and the computer 455 assists the user to spend more time on the creative activity when the left nostril is dominant.

It is recommended to perform some activities when the breathing through the nose is balanced. In one embodiment, the computer 455 identifies, based on the measurements 454, times in which the breathing through the nose is balanced, and suggests a third activity for those times. Optionally, the third activity is more suitable for balanced breathing compared to the first and second activities. Optionally, the third activity requires higher self-awareness compared to the first and second activities. For example, the third activity may include a spiritual practice (such as meditating or praying), while the first and second activities do not include spiritual practices.

Various hardware configurations may be utilized in different embodiments of the system configured to suggest activities according to the dominant nostril, in order to take the measurements 454 of the user.

In a first embodiment, the system includes a CAM that takes thermal measurements of a region below the user's nostrils (e.g., CAM 183 or CAM 184). In this embodiment, identifying the dominant nostril and/or whether the breathing is balanced may be done by the computer 455 based on signal processing of the thermal measurements taken by CAM.

In a second embodiment, the sensor 451 includes one or more implanted sensors located around the area of the nostrils. In this embodiment, identification of the dominant nostril and/or whether the breathing is balanced may be done based on signal processing of the measurements of the implanted sensors.

In a third embodiment, the sensor 451 includes right and left in-the-ear earbuds comprising microphones, configured to measure sounds inside the right and left ear canals; the computer 455 identifies the dominant nostril based on analysis of the recordings from the earbuds. For example, the computer 455 may identify the dominant nostril based on the assumption that the inhale sounds measured by the in-the-ear earbud in the dominant side are stronger than the inhale sounds measured by the in-the-ear earbud in the non-dominant side.

In a fourth embodiment, the system includes a frame configured to be worn on the user's head, and the sensor 451 comprises a visible-light camera; the visible-light camera is physically coupled to the frame, and takes images of a region on the user's nose. For example, the computer 455 may identify the dominant nostril based on analyzing the images of the nose by identifying movements of the nose, especially at the edges of the nostrils.

In a fifth embodiment, the sensor 451 includes thermistors that are in contact with the nostrils and/or the upper lip in order to take the measurements. Optionally, the dominant nostril may be identified based on signal processing of the thermistors' measurements.

In a sixth embodiment, the sensor 451 includes anemometers located inside the breathing streams of the nostrils in order to take the measurements. Optionally, the dominant nostril is identified based on signal processing of the anemometers' measurements.

In a seventh embodiment, the sensor 451 includes a non-wearable IR camera pointed to the area around the nostrils in order to take the measurements. Optionally, the dominant nostril is identified based on image processing of the measurements of the non-wearable IR camera.

The suggestions provided by the computer 455 may be done as part of various programs that may benefit the user. Optionally, the computer 455 provides functionality of at least one of the following programs: a virtual assistant (i.e., a software agent), a calendar management program, a priority management program, a project management program, a "to do" list program, a work schedule program, and a self-learning program.

Some embodiments of the system may involve notification of the user about which of the nostrils is dominant at a given time (e.g., via UT 456). Optionally, the notification involves providing a user with an indication (e.g., via sound and/or an image) when the dominant nostril changes and/or every certain period of time (e.g., every hour). Additionally or alternatively, notifying the user about which of the nostrils is dominant may involve utilizing different themes for UI 456. In one example, a first theme for UI 456 is utilized when the right nostril is the dominant nostril, and a second theme for UI 456 is utilized when the left nostril is the dominant nostril. Optionally, the first theme is more logical than the second theme (e.g., presenting data and/or suggestions involves providing more facts and/or detailed explanations), and the second theme is more emotional than the first theme (e.g., presenting data and/or suggestions includes more emotional phrases, abstract images, social-related data, and/or less factual information).

In one embodiment, the computer 455 is programmed to converse with the user according to at least first and second modes. The first mode is perceived by the user as more logical than the second mode, and the second mode is perceived by the user as more emotional than the first mode. The computer 455 uses, on average, the first mode more frequently than the second mode when the right nostril is the dominant nostril, and uses, on average, the second mode more frequently than the first mode when the left nostril is the dominant nostril. Examples of logical speech include sentences built around numbers and facts, while emotional speech includes sentences built around emotions and intuition.

The following is a description of steps involved in one embodiment of a method for suggesting activities according to the dominant nostril. The steps described below may be used by systems modeled according to FIG. 49A, and may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform operations of the method.

In one embodiment, the method for alerting about stress includes at least the following steps: In Step 1, taking, utilizing a sensor, measurements of a user, which are indicative of the user's dominant nostril. In Step 2, predicting, based on the measurements, which of the user's nostrils will be the dominant nostril at a future time (that occurs after the measurements in Step 1 were taken). And In Step 3, responsive to predicting that the right nostril will be dominant at the future time, suggesting having at the future time a first activity, which is more suitable for a right dominant nostril than a second activity. Optionally, responsive to predicting that the left nostril will be dominant at the future time, this step involves suggesting having at the future time the second activity, which is more suitable for a left dominant nostril than the first activity. Optionally, the method further includes assisting the user to decrease eating certain types of food during left nostril dominance, and assisting the user to schedule the main meal of the day during right nostril dominance. Optionally, the method further includes learning the typical sequence of switching between dominant nostrils based on previous measurements of the user taken over more than a week, and alerting upon detecting an irregularity in the sequence of changes between the dominant nostrils.

In some embodiments, a system is configured to detect a physiological response based on respiratory parameters. Optionally, the physiological response is stress. Optionally, the respiratory parameters include the breathing rate and breathing rate variability (which is discussed further below).

The breathing rate variability (BRV) is a value that is indicative of the physiological phenomenon of variations between consecutive breathes, observed during a certain period of time (e.g., a minute). In a similar fashion to heart rate variability (HRV), which is the physiological phenomenon of variations between consecutive heartbeats, the extent of BRV can be indicative of various physiological phenomena, such as stress and/or physiological state.

In one embodiment, stress is detected based on thermal measurements of ROIs indicative of respiration performances, such as the mouth area, the upper lip area, and/or an air volume below the nostrils where the exhale from the nose flows. Optionally, $TH_{ROI}$ may be utilized to calculate various respiratory parameters, which include the breathing rate and/or the BRV.

The duration between successive breaths (such as the time between starting successive exhales) and/or breathing irregularity may be calculated using various methods, such as geometric methods, frequency-domain methods, and/or non-linear methods. The computer may calculate the BRV based on $TH_{ROI}$ taken during different periods of time, such as at least one minute long or at least 5 minutes long.

In one embodiment, the breathing rate variability (BRV) and the breathing rate (BR) are utilized by a computer in order to detect when the user is stressed. Optionally, elevated BRV in addition to elevated BR may serve as an indicator of stress. Optionally, elevated BRV, even when the BR is reduced, may serve as an indicator of stress. For example, the computer may calculate $BR_1$ and $BRV_1$ based on $TH_{ROI}$ taken during a first period, calculate $BR_2$ and $BRV_2$ based on $TH_{ROI}$ taken during a second following period, and determine that the user's stress level is higher at the second period relative to the first period because ($BRV_1 < BRV_2$), even though ($BR_1 > BR_2$).

In one embodiment, the computer calculates the stress level based on comparing BR and BRV to various thresholds that correspond to different stress levels. In one example, having a high BRV may lower the threshold on BR that is required in order to detect stress.

In another embodiment, the computer may utilize a machine learning-based model in order to detect the stress level. Optionally, the computer utilizes $TH_{ROI}$ to generate feature values indicative of the BR and/or the BRV, and the model was trained based on samples that each include feature values based on $TH_{ROI}$ and labels indicative of the user's stress level.

Figure 50A:
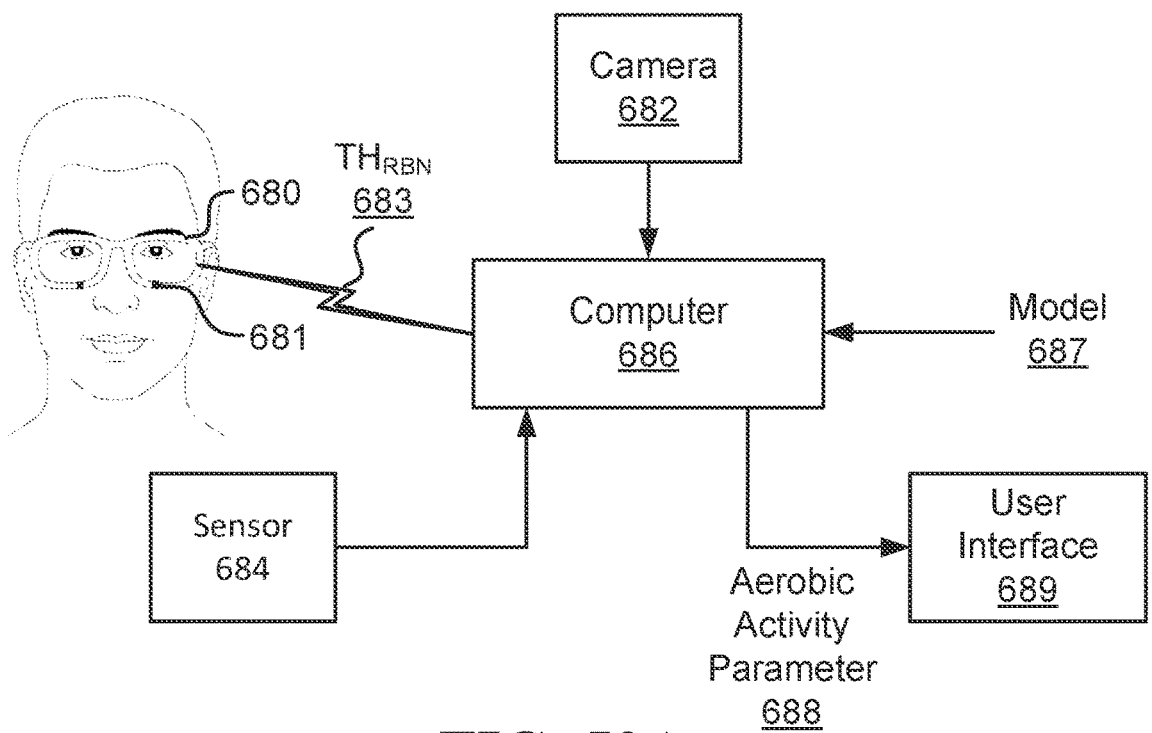
FIG. 50A illustrates an embodiment of a system for estimating an aerobic activity parameter.
Figure 50B:
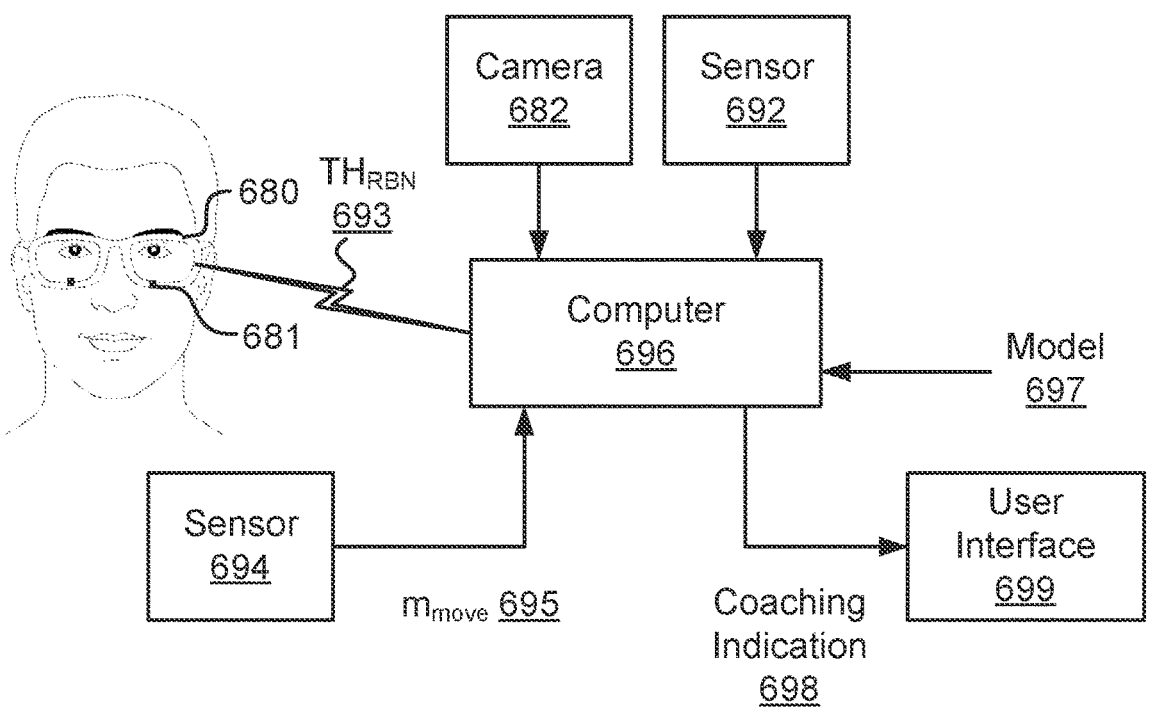
FIG. 50B illustrates an embodiment of an athletic coaching system.

Some embodiments described herein involve utilization of at least one inward-facing head-mounted thermal cameras (such a camera is denoted below CAM) to take thermal measurements of a region below the nostrils (these measurements are denoted below $TH_{RBN}$). $TH_{RBN}$ are indicative of an exhale stream of the user, such as air exhaled from a nostril and/or the mouth of the user. Since exhaled air usually has a different temperature than the environment and/or the human skin, $TH_{RBN}$ can provide indications regarding the user's respiratory activity, such as the breathing rate, whether exhaling is done through the mouth or nose, the respiration volume, and other respiratory parameters described herein. Additionally or alternatively, $TH_{RBN}$ may be used to calculate an aerobic activity parameter (as illustrated in FIG. 50A) and/or a coaching indication (as illustrated in FIG. 50B). The following is a description of embodiments of such systems that utilize $TH_{RBN}$ for such respiratory-related applications. The systems illustrated in FIG. 50A and FIG. 50B include at least one CAM and a computer.

The at least one CAM may include various combinations of one or more CAMs, as described in the various examples given in this disclosure of embodiments that include a single inward-facing head-mounted thermal camera that measures $TH_{RBN}$ (e.g., a single CAM coupled to the bottom of one of the sides of a frame worn by the user) or multiple CAMs (e.g., multiple CAMs coupled to different locations on a frame worn by the user). In one example, the at least one CAM includes CAM 681 illustrated in FIG. 50A. In other examples, the at least one CAM may include one or more of the CAMs described in various figures in this disclosure. For example, FIG. 38 illustrates one embodiment of an HMS that may be used to measure $TH_{RBN}$, in which at least one CAM (four CAMs in this case), is coupled to the bottom of an eyeglasses frame 181. CAMs 182 and 185 are used to take thermal measurements of regions on the right and left sides of the upper lip (186 and 187, respectively), and CAMs 183 and 184 are used to take thermal measurements of a region on the user's mouth 188 and/or a volume protruding out of the user's mouth. At least some of the ROIs may overlap, which is illustrated as vertical lines in the overlapping areas. Optionally, a CAM from among the one or more of the CAMs includes at least one of the following sensors: a thermopile sensor, and a microbolometer sensor. Optionally, a CAM from among the one or more of the CAMs includes a microbolometer focal-plane array (FPA) sensor or a thermopile FPA sensor. Additional examples of systems that include at least one CAM that may be used to take $TH_{RBN}$ are illustrated in FIG. 22 to FIG. 24 as well as FIG. 16B (one or more of the cameras 22, 24, and 28).

In some embodiments, each CAM, from among the at least one CAM, is physically coupled to frame worn on the head of a user (whose measurements are being taken), such as frames of eyeglasses, an augmented reality HMS, a virtual reality HMS, or a mixed reality HMS. In one example, each CAM, from among the at least one CAM, is physically coupled to frame 680. Optionally, each CAM, from among the at least one CAM, is located less than 15 cm from the user's face and weighs less than 10 g. Optionally, the frame holds each CAM, from among the at least one CAM, such that the CAM does not protrude beyond the tip of the user's nose.

In one embodiment, each CAM, from among the at least one CAM, is located above the user's upper lip and less than 15 cm from the user's face, and does not occlude any of the user's mouth and nostrils. Optionally, $TH_{RBN}$ include thermal measurements of at least one of first and second regions below right and left nostrils ($TH_{RBN1}$ and $TH_{RBN2}$, respectively) of the user, which are indicative of exhale streams from the right and left nostrils, respectively. Additionally or alternatively, $TH_{RBN}$ may include thermal measurements of at least one of a region on the mouth and a volume protruding out of the mouth ($TH_{RBN}$) of the user, indicative of exhale stream from the mouth.

The following is a description of one possible utilization of $TH_{RBN}$, which involves calculation of an aerobic activity parameter of a user. FIG. 50A illustrates an embodiment of a system configured to estimate an aerobic activity parameter 688. The system includes at least one CAM (as described above) that is used to measure $TH_{RBN}$ 683 and a computer 686. Some embodiments of the system may optionally include additional elements, such as the frame 680, a head-mounted inward-facing video camera 682, a sensor 684, and a user interface 689.

The computer 686 is configured, in one embodiment, to calculate, based on $TH_{RBN}$ (taken by the at least one CAM), the aerobic activity parameter 688. Optionally, the aerobic activity parameter 688 is indicative of one or more of the following values: oxygen consumption ($VO_2$), maximal oxygen consumption ($VO_2$ max), and energy expenditure (EE). Optionally, the computer 686 may utilize additional inputs to calculate the aerobic activity parameter such as measurements of the heart rate (HR) of the user, values of the activity level of the user, and/or various statistics about the user (e.g., age, weight, height, gender, etc.).

Herein, $VO_2$ refers to a value indicative of the rate of oxygen consumption. This value typically rises as physical activity becomes more strenuous and the body has a larger demand for oxygen for various metabolic processes. In one example, $VO_2$ is a value expressed in units of mL/(kg·min), or some other units proportional to mL/(kg·min). $VO_2$ max refers to a value indicative of the maximal rate of oxygen consumption; typically, the higher $VO_2$ max, the higher the person's cardiorespiratory fitness and endurance capacity during prolonged exercises. EE may refer to a value indicative of the rate of energy expenditure, and may be expressed in various units such as kcal/h, or some other unit proportional to kcal/h. When the rate of energy expenditure is integrated over a period time, then EE may refer to a value indicative of the total energy expenditure over the period of time, and may be a value expressed in calories or some other unit proportional to calories.

Since direct measurements of aerobic activity parameters such as $VO_2$, $VO_2$ max, and EE are typically cumbersome uncomfortable procedures that need to be performed in controlled settings (e.g., running on a treadmill while wearing a mask that is used to collect and analyze exhaled breath), these values are often estimated based on various values that are correlated to some extent with the aerobic activity parameters. For example, various formulas and/or models were developed to estimate values of aerobic activity parameters from values such as heart rate (and changes from resting heart rate), activity level, and various statistics e.g., age, weight, height, gender, etc.)

Embodiments described herein utilize values indicative of the respiratory activity, such as $TH_{RBN}$ 683 and/or values derived from $TH_{RBN}$ 683 (e.g., respiration rate and/or respiration volume) in order to enhance the accuracy of the estimation of aerobic activity parameters. Respiration parameters such as the respiration rate and/or respiration volume are tightly related to parameters such as $VO_2$ and EE and thus provide additional information about these parameters. Additionally, respiration values can help reduce inaccuracies in estimation of aerobic activity parameters due to various artifacts. For example, during changes in body positions (e.g., postural hypotension), there are usually only minor changes in $VO_2$ and respiration but major changes in HR. In another example, a value such as the respiration rate can distinguish between non-metabolic (e.g. mental and non-exercise related physical stress) and metabolic (physical activity induced) increases in HR. Thus, for example, using respiration data in addition to other values (e.g., HR) may provide better estimations of the values of the aerobic activity parameters, compared to estimations that do not involve respiration data.

The computer 686 may utilize various approaches in order to estimate aerobic activity parameters based on data that includes $TH_{RBN}$ 683 and/or values derived from $TH_{RBN}$. In one embodiment, the computer 686 generates feature values based on data comprising $TH_{RBN}$, and utilizes a model 687 to calculate the aerobic activity parameter 688 based on the feature values. Optionally, the model 687 is trained based on data indicative of aerobic activity of multiple users (e.g., data that includes physiological signals such as respiratory rate, heart rate, etc., of the multiple users). Additionally or alternatively, the model 687 is trained based on data that includes previous $TH_{RBN}$ of the multiple users and values of the aerobic activity parameter of the multiple users corresponding to when the previous $TH_{RBN}$ were taken. For example, the training data includes samples, each sample comprising: (i) feature values were generated from certain pervious $TH_{RBN}$ of a certain user taken during certain period of time, and (ii) a label generated based on a measurement of the value of the aerobic activity parameter of the certain user during the certain period of time (i.e., the value of $VO_2$, $VO_2$ max, or EE, as measured during the certain period of time).

The computer 686 may generate various types of feature values that are used to estimate the value of the aerobic activity parameter 688. Optionally, the computer 686 generates one or more feature values, based on $TH_{RBN}$ 683, which may be any of the feature values described in this disclosure that are used to detect a physiological response, and in particular, the one or more feature values may be any of the feature values described in this disclosure as being pertinent to calculation of a respiratory parameter. Additionally or alternatively, feature values generated by the computer 686 may include: time series data comprising values measured by a CAM, average values of certain pixels of a CAM, and/or values measured at certain times by the certain pixels. Additionally or alternatively, at least some of the feature values generated by the computer 686 may include measurements of the environment in which the user is in and/or indications of confounding factors (e.g., indications of use of medication).

In some embodiments, feature values generated by the computer 686 may include values of one or more respiratory parameters calculated based on $TH_{RBN}$ 683. In one example, the feature values generated by the computer 686 include a feature value indicative of a ratio between an extent to which the user breathed via the mouth and an extent to which the user breathed via the nose. In another example, the feature values generated by the computer 686 include a feature value indicative of a ratio between durations of exhales of the user and duration of inhales of the user.

In some embodiment, the feature values generated by the computer 686 may include a feature value indicative of heart rate (HR) of the user while $TH_{RBN}$ 683 were taken. Additionally or alternatively, the feature values generated by the computer 686 include another feature value indicative of cardiac activity such as heart rate variability (HRV). For example, measurements indicative of HR and/or HRV may be obtained by a different sensor, which is not a CAM, such as a photoplethysmogram (PPG) sensor that is head-mounted (e.g., coupled to the temple of eyeglasses worn by the user), coupled to a wearable device such as a smartwatch, or embedded in a garment worn by the user, such as a smart shirt.

In addition to data describing physiological signals mentioned above, in some embodiments, data used to generate at least some of the feature values by the computer 686 may include various values describing the user, such as one or more of the following: age, gender, height, weight, type of body build, and body fat percentage. Additionally or alternatively, data used to generate at least some of the feature values by the computer 686 may include various values describing an activity of the user while $TH_{RBN}$ 683 of the user were taken. Optionally, data describing the activity is obtained by sensor 684. In one example, the sensor 684 comprises at least one of an accelerometer and a gyroscope, and the data describing the activity is indicative of at least one of the following: cadence, stride length, and/or type of movement (e.g., walking, running, rowing, cycling, etc.) In another example, the sensor 684 comprises a GPS receiver and/or some other sensor that may be used to determine the user's location. In this example, the data describing the activity may be indicative of one or more of the following: the speed of the user's movement, the distance of the user's movement, and/or changes in the user's elevation.

A person's baseline physiological signals, such as resting HR, respiration rate, or blood pressure may be indicative of the aerobic fitness of the person, and may provide useful information for calculation of an aerobic activity parameter. Thus, in some embodiments, the computer 686 may generate one or more feature values that are indicative of a baseline physiological signal of the user.

How a person's physiological signals change due to physical activity are indicative of the aerobic fitness of the person. Typically, the more fit an individual, the less dramatic the changes in the physiological signals for a certain type of activity. For example, a fit person's respiration rate will typically increase to a lesser extent after a few minutes of jogging compared to the increase in respiration that occurs to a less fit individual after performing the activity. To capture such aspects that may reflect on fitness, in some embodiments, the feature values generated by the computer 686 may include one or more feature values that reflect a change in the values of a physiological signal, before and after a certain extent of activity. For example, a feature value may be indicative of the change in the respiratory rate, change to the respiration volume, or respiration volume after conducting a certain activity (e.g., five minutes of moderate cycling). In another example, a feature value may be indicative of the change to the heart rate after running at a pace of 12 km/h for five minutes.

In other embodiments, the feature values generated by the computer 686 may include one or more feature values that are indicative of athletic performance of the user. For example, a feature value may be indicative of the time it took the user to complete a certain exercise such as running a mile as fast as the user is capable.

The model 687 is trained on data that includes previous $TH_{RBN}$ of the user and/or other users. Training the model 687 typically involves generating samples based on the previous $TH_{RBN}$ and corresponding labels indicative of values of the aerobic activity parameter when the previous $TH_{RBN}$ were taken. For example, each sample may comprise feature values generated based on at least some of the previous $TH_{RBN}$, and the sample's label represents the value of the aerobic activity parameter corresponding to when the at least some of the previous $TH_{RBN}$ were taken.

In some embodiments, the samples used to train the model 687 include data pertaining to a diverse set of users comprising users of different genders, ages, body builds, and athletic abilities. Optionally, the samples used to train the model 687 include samples generated based on $TH_{RBN}$ taken at different times of the day, while being at different locations, and/or while conducting different activities. In one example, at least some of the samples are generated based on $TH_{RBN}$ taken in the morning and $TH_{RBN}$ taken in the evening. In another example, at least some of the samples are generated based on $TH_{RBN}$ of a user taken while being indoors, and $TH_{RBN}$ of the user taken while being outdoors. In yet another example, at least some of the samples are generated based on $TH_{RBN}$ taken while a user was sitting down, and $TH_{RBN}$ taken while the user was walking, running, and/or engaging in physical exercise (e.g., dancing, biking, etc.). Additionally or alternatively, the samples used to train the model 687 may be generated based on $TH_{RBN}$ taken while various environmental conditions persisted. For example, the samples include first and second samples generated based on $TH_{RBN}$ taken while the environment had first and second temperatures, with the first temperature being at least 10° C., warmer than the second temperature. In another example, the samples include samples generated based on measurements taken while there were different extents of direct sunlight and/or different extents of wind blowing.

Various computational approaches may be utilized to train the model 687 based on the samples described above. In one example, a machine learning-based training algorithm may be utilized to train the model 687 based on the samples. Optionally, the model 687 includes parameters of at least one of the following types of models: a regression model, a neural network, a nearest neighbor model, a support vector machine, a support vector machine for regression, a naïve Bayes model, a Bayes network, and a decision tree.

In some embodiments, a deep learning algorithm may be used to train the model 687. In one example, the model 687 may include parameters describing multiple hidden layers of a neural network. In one embodiment, when $TH_{RBN}$ include measurements of multiple pixels, the model 687 may include a convolution neural network (CNN). In one example, the CNN may be utilized to identify certain patterns in the thermal images, such as patterns of temperatures in the region of the exhale stream that may be indicative of respiratory activity, which involve aspects such as the location, direction, size, and/or shape of an exhale stream from the nose and/or mouth. In another example, calculating a value of an aerobic activity parameter may be done based on multiple, possibly successive, thermal measurements. Optionally, calculating values of the aerobic activity parameter based on thermal measurements may involve retaining state information that is based on previous measurements. Optionally, the model 687 may include parameters that describe an architecture that supports such a capability. In one example, the model 687 may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using bidirectional recurrent neural network architecture (BRNN).

Monitoring a user over time can produce many observations indicative of the user's fitness. For example, the extent of increase in the user's respiration rate, change to respiration volume, and/or change in heart rate after moderate running of a few minutes, is indicative of the user's fitness, and can be measured multiple times. These multiple observations can be used to estimate the value of an aerobic activity parameter of the user such as $VO_2$ max (which is also indicative of the user's fitness) as follows. In one embodiment, the computer 686 calculates, based on $TH_{RBN}$ 683, n≥1 values $x_1, \ldots, x_u$, of observations of a parameter related to respiration such as the respiration rate, change to respiration rate, respiration volume, change to respiration volume, and the like. For example, $x_i$ may be the increase to the respiration rate observed after moderate running for a period (e.g., five minutes). In another example, $x_i$ may be the change to respiration volume and/or average respiration volume during a half hour of cycling.

The computer 686 may calculate an estimation of a value of the aerobic activity parameter (denoted $\theta^*$) utilizing one or more probability functions of the form $P(X=x|\theta)$, which is a conditional probability of a value of the parameter related to respiration given a value of the aerobic activity parameter is equal to $\theta$. Optionally, the computer 686 performs at least one of the following in order to calculate $\theta^*$ (the estimation value of the aerobic activity parameter): a maximum likelihood (ML) estimation, and a maximum a posteriori probability (MAP) estimation.

The one or more probability functions of the form $P(X=x|\theta)$ may be calculated based on data pertaining to a diverse set users comprising users of different genders, ages, body builds, and athletic abilities. Optionally, the data includes observations of a parameter related to respiration calculated based on $TH_{RBN}$ of the users. In one embodiment, a probability function of the form $P(X=x|\theta)$ may be a table describing the probability of observing different values of x given a certain value of $\theta$. For example, the table may describe an empirically observed probabilities for various increases in respiration (e.g., increases of 2, 4, 6, . . . , 40 breaths per minute) given different values of $\theta$, such as $VO_2$ max=10, 15, 20, . . . , 75, 80 mL/(kg·min). In another embodiment, a probability function of the form $P(X=x|\theta)$ may be described by a model that includes parameters of the distribution, where the parameters may be set using various approaches such as regression and/or maximum entropy approaches. Optionally, the parameters of the probability function describe a continuous exponential distribution.

A user interface 689 may be utilized to present the aerobic activity parameter 688 and/or present an alert related to the aerobic activity parameter 688. In one example, user interface 689 may be used to alert the user responsive to an indication that the aerobic activity parameter has fallen below a threshold (e.g., when the rate of energy expenditure falls below a threshold) or when the aerobic activity parameter reaches a certain threshold (e.g., when the total energy expenditure during a session reaches a certain caloric goal). Optionally, the user interface 689 includes a display, such as the display of a smart phone, a smartwatch, or a head-mounted augmented reality display. Optionally, the user interface 689 includes a speaker, such as a speaker of a smart phone, a smartwatch, or a head-mounted augmented reality display, or a speaker of a pair of headphones or an earbud.

As discussed herein, thermal measurements indicative of an exhale stream may be used by a computer to calculate various respiratory parameters, aerobic activity parameters, and coaching indications. In order to produce a better signal regarding the user's respiratory activity, in some embodiments, the computer 686 (or the computer 696 discussed below) may utilize additional input sources (besides thermal cameras).

In some embodiment, the additional input sources may include one or more visible-light cameras that capture images indicative of respiratory activity. In one example, the additional input sources include at least one inward-facing head-mounted visible-light camera (e.g., the camera 682), which is configured to take images of a region on the mouth ($IM_M$) of the user. In this example, $IM_M$ are indicative of whether the mouth is open or closed. In another example, the additional input sources include at least one inward-facing head-mounted visible-light camera configured to take images of a region on the nose ($IM_N$) of the user, in this example, $IM_N$ are indicative of movement of the nose while the user inhales (in this example, the camera 682 may be configured to take images of the nose in addition to, or instead of, the images of the mouth). Optionally, calculating various values (e.g., breathing rate, an aerobic activity parameters, or a coaching indication) based on $IM_M$ and/or $IM_N$ involves generating feature values based on $IM_M$ and/or $IM_N$ and using them in the calculation of said values (e.g., in addition to feature values generated based on $TH_{RBN}$). For example, feature values generated based on $IM_M$ and/or $IM_N$ involve using various image processing techniques and represent various low-level image properties. Some examples of such features may include features generated using Gabor filters, local binary patterns and their derivatives, features generated using algorithms such as SIFT, SURF, and/or ORB, and features generated using PCA or LDA. Optionally, $IM_M$ and/or $IM_N$ may be used to identify different states of the user (e.g., open vs, closed mouth or movement of the nostrils), and the information regarding the different states may be used as input (e.g., feature values) when calculating parameters such as the breathing rate.

In other embodiments, the additional input sources may include one or more microphones configured to record sounds made by the user's respiration. For example, the one or more sensors may include microphones in right and/or left in-the-ear earbuds, and feature values may be generated based on audio signal analysis of the recordings from the earbuds and utilized to calculating parameters such as the breathing rate, to detect inhaling/exhaling events, etc. Optionally, such in-ear measurements are used to calculate the user's breathing rate while the user was walking or running in an environment having ambient noise level above 50 dBA.

Other examples or sensors that may be used as additional input sources include sensors physically that are coupled to a garment worn over the user's torso and comprises at least one of the following: a pressure sensor, a stretch sensor, an electromechanical sensor, and a radio receiver. Optionally, these sensors are configured to measure movements of the chest due to respiration activity of the user, and these measurements are utilized to calculate various parameters such as the breathing rate.

The additional input sources described above may serve, in some embodiments, as complementary data that enhance accuracy of respiratory signals detected based on $TH_{RBN}$. For example, in some embodiments, exhaling air produces a stronger thermal signal than inhaling air. In these embodiments, detection of inhalation events can be assisted by images of the nostrils (which often show distinct movement when inhaling). In another example, there may be conditions in which exhaling may produce a relatively weak thermal signal, e.g., when exercising in warm environments in which the temperature of the exhaled air is close to the temperature in the environment. In such cases, additional data, such as data from sensors embedded in a garment or microphones in earbuds, may help and provide better indications of breathing.

The following is a description of another possible utilization of $TH_{RBN}$, which involves virtual coaching based on respiration data. FIG. 50B illustrates an embodiment of an athletic coaching system. The system includes at least one CAM (as described above) that is used to measure $TH_{RBN}$ 693 and a computer 696. Some embodiments of the system may optionally include additional elements, such as the frame 680, a head-mounted inward-facing video camera 692, a sensor 694, and a user interface 699.

The computer 696 is configured, in some embodiments to: receive measurements of movements ($M_{move}$ 695) involving the user; generate, based on $TH_{RBN}$ 693 and $M_{move}$ 695, a coaching indication 698; and present, via a user interface 699, the coaching indication 698 to the user. Various virtual coaching applications may be realized by analyzing $TH_{RBN}$ 693 and $M_{move}$ 695, and providing the user with insights and/or instructions based on the analysis. These insights and/or instructions may assist to improve the user's athletic performance in various ways.

One type of coaching application built on the system illustrated in FIG. 50B provides insights and/or instructions to a user performing an athletic activity that involves an aerobic exercise with repetitive motions such as running, rowing, or cycling. In one embodiment, the computer 696 generates the coaching indication 698, which is indicative of a change the user should make to one or more of the following: cadence of movements, stride length (if the user is running), breathing rate, breathing type (mouth or nasal), and duration of exhales. Optionally, responsive to a determination that the change is needed, the computer 696 provides, via the user interface 699, an indication to the user of this fact. For example, the user interface 699 may include a speaker (e.g., in earbuds) and the computer 696 generates an audio indication (e.g., a certain sound effect such as beeping at a certain frequency and/or speech conveying the coaching indication 698). In another example, the user interface may include a display and the coaching indication may be provided via visual cues (e.g., text, an image, or a light flashing at a certain frequency). The following are various examples of computations that may be performed by the computer 696 in order to generate the coaching indication 698.

In one embodiment, the computer 696 calculates the breathing rate of the user based on $TH_{RBN}$ 693 and then checks if it is in a desired range. Responsive to the breathing rate being below a first threshold, the computer 696 includes in the coaching indication 698, an instruction to increase the breathing rate. Additionally or alternatively, responsive to the breathing rate being above a second threshold (which is higher than the first threshold), the computer includes in the coaching indication 698 an instruction to decrease the breathing rate. Optionally, the first and/or second thresholds are calculated based on $M_{move}$ 695. For example, the first threshold (minimal desired breathing rate) and/or the second threshold (maximal desired breathing rate) are set according to the level of activity of the user. Optionally, "level of activity" may refer to one or more of the following: the speed of the user (e.g., when running or cycling), the cadence of the user's movement, a value of an aerobic activity parameter of the user (e.g., $VO_2$ or EE).

In another embodiment, the computer 696 calculates a value indicative of the cadence of the user based on $M_{move}$ 695. For example, the computer 696 may identify cyclic signals indicating movement such as pedaling, rowing, or strides. Optionally, the computer 696 utilizes a machine learning model to calculate the cadence based on $M_{move}$ 695, where the model is trained based on $M_{move}$ of other users. Optionally, responsive to the cadence being below a first threshold, the computer 696 includes in the coaching indication 698 an instruction to increase the cadence. Additionally or alternatively, responsive to the cadence being above a second threshold, the computer 696 includes in the coaching indication 698 an instruction to decrease the cadence. Optionally, the first and/or second thresholds are calculated according to $TH_{RBN}$ 693. For example, the first and/or second thresholds may correspond to a desired cadence that is appropriate for the breathing rate of the user, as determined based on $TH_{RBN}$ 693.

In yet another example, the computer 696 calculates a value indicative of exhale durations of the user based on $TH_{RBN}$ 693. Optionally, the computer 696 includes in the coaching indication 698 an instruction to increase the exhale durations responsive to determining that the exhale durations are below a threshold. Optionally, the threshold is calculated based on at least one of $M_{move}$ 695 and $TH_{RBN}$ 693. For example, the threshold may be set according to a predetermined function that assigns a minimal desired duration of exhales based on the cadence or speed of the user (e.g., as determined based on $M_{move}$ 695) and/or based on the breathing rate of the user (e.g., as determined based on $TH_{RBN}$ 693).

In still another embodiment, the computer 696 detects, based on $TH_{RBN}$ 693, whether the user is breathing through the mouth. Responsive to detecting that the user is breathing through the mouth, the computer 696 includes in the coaching indication 698 an instruction to the user to breathe through the nose.

The computer 69 may utilize a machine learning model 697 to generate the coaching indication 698. In some embodiments, the computer generates feature values based on $TH_{RBN}$ 693 and/or $M_{move}$ 695. For example, the feature values may include one or more of the feature values described above which are generated based on $TH_{RBN}$683 and/or measurements of the sensor 684 and are used to estimate the aerobic activity parameter 688. Optionally, the computer 696 utilizes the model 697 to calculate, based on the feature values generated based on $TH_{RBN}$ 693 and/or $M_{move}$ 695, a value indicative of whether the change is needed and/or what change in the user's activity should be indicated in the coaching indication 698.

The model 697 may be generated based on data comprising previously taken $TH_{RBN}$ and $M_{move}$ of the user and/or other users and indications of appropriate coaching instructions (and whether coaching instructions are needed) corresponding to the time previously taken $TH_{RBN}$ and $M_{move}$ were taken. For example, the previously taken $TH_{RBN}$ and $M_{move}$ may be used to generate samples, each sample comprising feature values generated based on $TH_{RBN}$ and $M_{move}$ taken during a certain period (the same type of feature values generate by the computer 696, as described above). The indications on appropriate coaching instructions may be used to create labels for the samples. In one example, the coaching instructions are provided by a human annotator (e.g., a human coach) that reviews the data and determines whether changes could be made to improve the athletic performance. In another example, the coaching instructions are provided by an expert system (e.g., a rule based system such as a decision tree), which is designed for this purpose.

In some embodiments, $M_{move}$ 695 are generated by a sensor 694, which may represent herein one or more of various types of sensors. In one embodiment, the sensor 694 is an accelerometer and/or gyroscope in a device carried or worn by the user. For example, the sensor 694 may be a movement sensor in a smartwatch or smart glasses worn by the user or a movement sensor in a smartphone carried by the user. Optionally, analysis of measurements of the sensor 694 provides information about one or more of the following: the types of movements the user is making (e.g., running, cycling, or rowing), the cadence of the user (e.g., number of steps per minute, number of revolutions per minute in cycling, or the number of strokes per minute), and/or the speed of the user. In another embodiment, the sensor 694 is a location identifying sensor, such as a GPS receiver. Optionally, analysis of measurements of the sensor 694 provides information on the speed of the user, the elevation and/or distance traveled, etc. In some embodiments, $M_{move}$ 695 may include information obtained from multiple movement sensors. In one example, information about the speed and/or distance traveled by the user, coupled with information about the cadence, is used in order to determine the length of the user's strides.

Another type of coaching application that may utilize $TH_{RBN}$ 693 and $M_{move}$ 695 provides the user with breathing cues (e.g., a breathing pacer application) in order to assist the user to breathe at a desired pace while conducting athletic activity. In one embodiment, the computer 696 calculates a target breathing rate based on data comprising at least one of $TH_{RUN}$ 693 and $M_{move}$ 695, and includes in the coaching indication breathing cues that correspond to the target breathing rate. Optionally, the computer 696 receives a value indicative of the heart rate (HR) of the user and uses HR to calculate the target breathing rate (in addition to utilizing at least one of $TH_{RBN}$ 693 and $M_{move}$ 695). In one example, $M_{move}$ 695 is utilized to calculate a value indicative of the speed of the user and/or the cadence of the user, and the computer 696 utilizes a predetermined function to select for the user the target breathing rate, based on the speed and/or the cadence. In another example, a current breathing rate of the user, which is calculated based on $TH_{RBN}$ 693, is used to select a target breathing rate that will match the cadence of the user (e.g., which is determined based on $M_{move}$ 695). In still another example, $TH_{RBN}$ 693 and $M_{move}$ 695 are used as input to a function that calculates the target breathing rate. For example, the computer 696 may generate feature values (e.g., as discussed above with respect to the coaching indication regarding an instruction to change an aspect of the user's activity) and utilize a certain model to calculate, based on these feature values, the target breathing rate. Optionally, the certain model is generated based on data comprising previously taken $TH_{RBN}$ and $M_{move}$ of the user and/or other users and indications of the appropriate breathing rate as determined by an expert (e.g., a human or an expert system). The various computational approaches described herein with respect to detecting a physiological response may be employed in order to calculate the target breathing rate (e.g., comparison to threshold, reference time series, and/or machine learning approaches described herein).

In one embodiment, the computer 696 calculates a current breathing rate based on $TH_{RBN}$ 693 and compares the current breathing rate to first and second thresholds, where the first threshold is below the target breathing rate and second threshold is above the target breathing rate. Responsive to the current breathing rate being below the first threshold or above the second threshold, the computer 696 instructs the user interface 699 to start providing the breathing cues or to increase intensity of provided breathing cues. Optionally, responsive to the current breathing rate being above the first threshold and below the second threshold, for at least a certain duration, the computer 696 instructs the user interface 699 to cease from providing the breathing cues or to provide weaker breathing cues.

Figure 50C:
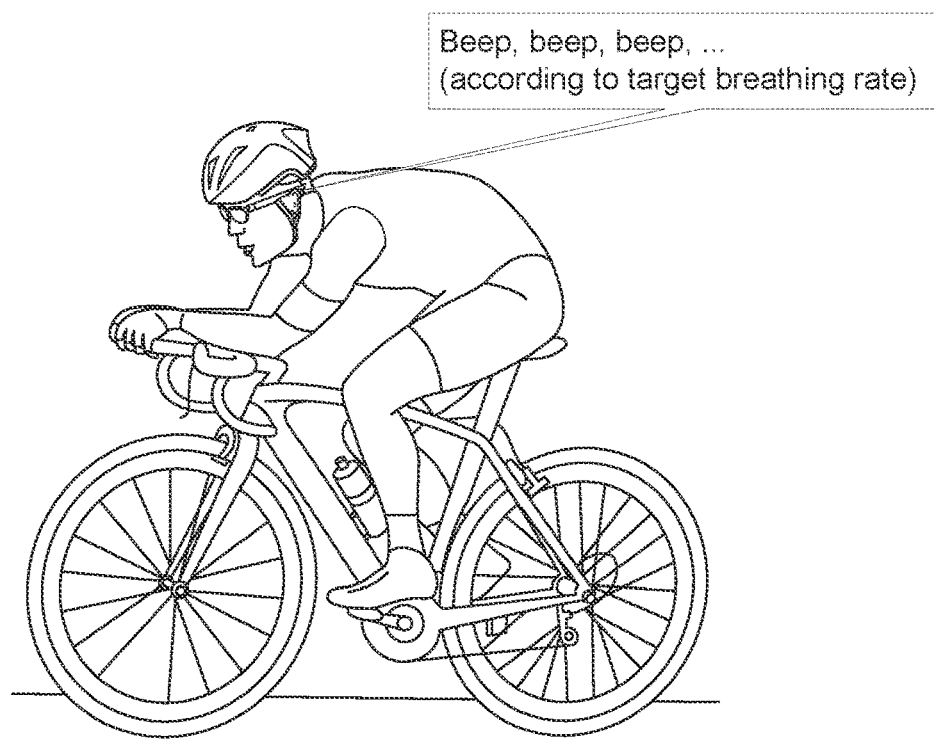
FIG. 50C illustrates a cycler who receives breathing cues via an earbud.

The breathing cues may be provided in various ways. In one example, the user interface 699 includes a speaker (e.g., in an earbud) and the breathing cues comprise auditory cues that have a frequency that corresponds to the target breathing rate (e.g., a beeping sound at the frequency or a music that has an underlying beat at the frequency). FIG. 50C illustrates a cycler who receives breathing cues via an earbud, which correspond to the target breathing rate. In another example, the user interface 699 includes a display (e.g., a display of augmented reality smart glasses, and the breathing cues comprise visual cues that have a frequency that corresponds to the target breathing rate (e.g., a flashing light or icon that changes its size at a frequency that corresponds to the target breathing rate).

Yet another type of coaching application that may utilize $TH_{RBN}$ 693 and $M_{move}$ 695 a coaching indication indicative synchronization of a breathing pattern of the user with a sequence of movements of the user. Optionally, the coaching indication 698 may be indicative of whether the breathing is synchronized with a sequence of movements (i.e., indicate to the user whether the user is breathing correctly when performing the sequence of movements). Additionally or alternatively, the coaching indication 698 may provide cues of the correct breathing pattern corresponding to the sequence of movements (i.e., provide cues that indicate to the user a synchronized breathing pattern). In one embodiment, the computer 696 provides the user, via the user interface 699, an indication indicative of whether the user's breathing is synchronized with the sequence of movements. Additionally or alternatively, the computer 696 determine whether the user did not breathe in an appropriate pattern while performing a sequences of movements. Responsive to determining that the user did not breathe in the appropriate pattern, the computer 696 notifies the user of this fact via a user interface 699.

A "correct" breathing pattern refers to a breathing pattern that is considered appropriate for the sequence of movements, and thus may be considered synchronized with the sequence of movements. Optionally, determining a breathing pattern that is correct for a sequence of movements may be done based on expert knowledge (e.g., coaches, experts in athletics and physiology, etc.) Additionally or alternatively, correct breathing patterns for a sequence of movements may be learned from observations. For example, performance of one or more users may be monitored while they breathe in various patterns while performing a certain sequence of movements, and the optimal breathing pattern (i.e., the breathing pattern that is synchronized with the certain sequence) may be determined based on detecting a breathing pattern for which the performance is maximized (e.g., farthest/most accurate driver hit).

The sequence of movements performed by the user may be, in some embodiments, sequences involved in performing a specific operation, such as swinging a bat, a racket or a golf club, lifting weights, performing a move in yoga, etc. In such cases, various sensors may be utilized in order to obtain $M_{move}$ 695, which provide indications of the type of movements the user is performing and/or how the user is manipulates objects (such as a bat, a racket, a golf club, a barbell, etc.). In some embodiments, the sensor 694 is a camera that takes images of the user, the user's limbs, and/or objects held by the user. In one example, the sensor 694 is an outward-facing head-mounted camera (e.g., a camera pointed outwards that is coupled to a frame worn on the user's head). In another example, the sensor 694 is an external camera, such as a camera in a laptop, smart TV, or a webcam. Optionally, the computer 696 performs image analysis of $M_{move}$ 695 that includes images taken by the sensor 694 in order to identify various movements of the user.

In some embodiments, the sensor 694 may include at least one of LiDAR system and a RADAR system. Optionally, the computer 696 analyzes $M_{move}$ 695 in order to identify movements of the user's limbs, changes to the user's pose, and/or the location of an object held by the user (e.g., a barbell, racket, golf club, etc.)

The following are examples of various sequences of movements and coaching indications that may be generated for them based on $TH_{RBN}$ 693 and $M_{move}$ 695.

In one embodiment, a sequence of movements of the user corresponds to a pressing motion of weights or a barbell, and the coaching indication 698 indicates to inhale in the concentric phase of the press and exhale in the eccentric phase of the press. In one example, the sensor 694 is a movement sensor (e.g., an accelerometer embedded in a garment worn by the user) and the computer 696 analyzes $M_{move}$ 695 to identify different movements involved in the pressing motion. In another example, the sensor 694 is an outward-facing head-mounted camera or a camera external to the user, and $M_{move}$ 695 include images of the user and/or of the weights or barbell. In this example, the computer 696 may utilize image analysis of $M_{move}$ 695 in order to identify different movements involved in the pressing motion. Optionally, the coaching indication 698 is provided to the user while the user performs the sequence of movements, such that when the computer 696 recognizes that the user is about push the weights or barbell, or starts to push (initiating the concentric phase), the user is instructed, in the coaching indication 698, to exhale.

In another embodiment, a sequence of movements of the user corresponds to swinging a racket in order to hit a ball with the racket (e.g., while playing tennis), and the coaching indication 698 indicates to exhale while hitting the ball. In one example, the sensor 694 is a movement sensor (e.g., an accelerometer) on the user's body, and the computer 696 analyzes $M_{move}$ 695 to identify movements that characterize a swinging motion. In another example, the sensor 694 comprises at least one of a LiDAR system and a RADAR system, and the computer 696 analyzes $M_{move}$ 695 to determine the location of the arms and/or the racket relative to the user's body in order to identify the swinging motion. Optionally, the coaching indication 698 is provided to the user while the user performs the sequence of movements, such that when the computer 696 recognizes that the user is about swing the racket, or starts to starts to swing the racket, the user is instructed, in the coaching indication 698, to exhale.

Figure 50D:
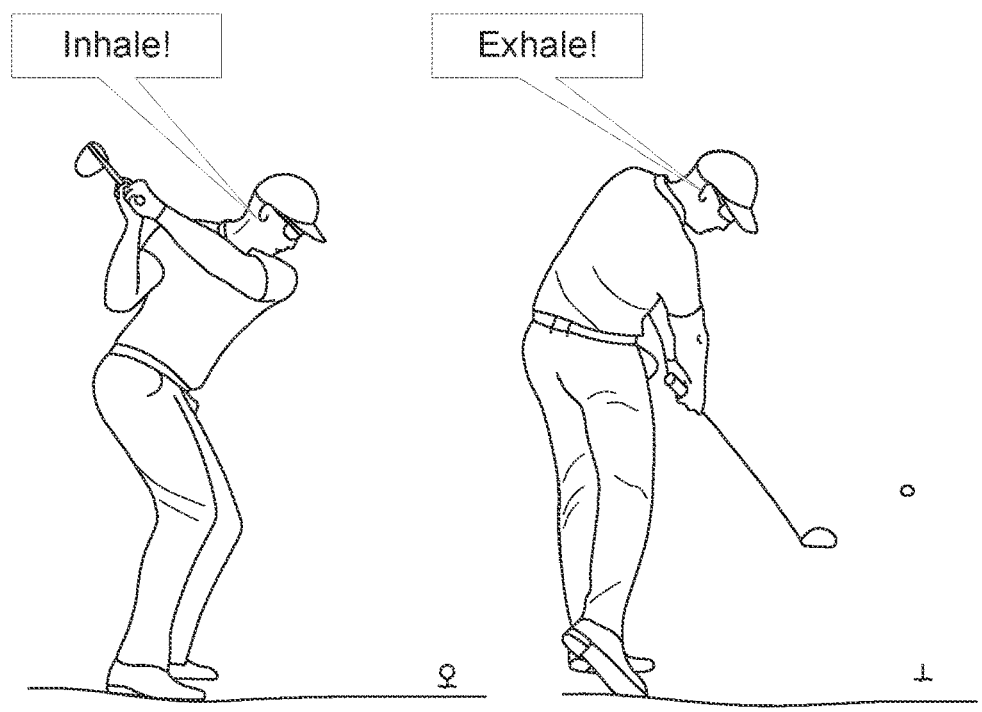
FIG. 50D illustrates a user receiving coaching instructions while hitting a driver in golf.

In yet another embodiment, a sequence of movements of the user corresponds to making a drive shot in golf, and the coaching indication 698 indicates to inhale during the backswing and exhale again on the downswing. Optionally, the coaching indication 698 also indicates to exhale at address. Optionally, the coaching indication 698 is provided to the user while the user performs the sequence of movements, such that when the computer 696 recognizes that the user is about to drive the shot (e.g., based on characteristic movements in the address), or starts the drive shot (e.g., by starting the backswing), the user is instructed, in the coaching indication 698, to exhale. FIG. 50D illustrates a user receiving coaching instructions while hitting a driver in golf; the figure illustrates the user receiving instructions (e.g., via an earbud) to inhale on the backswing and exhale of the downswing.

In still another embodiment, the computer 696: (i) receives from a fitness app (also known as a personal trainer app) an indication that the user should exhale while making a movement, (ii) determines, based on mm, 695, when the user is making the movement, and (iii) determines, based on $TH_{RBN}$ 693, whether the user exhaled while making the movement. Optionally, the computer 696 commands the user interface 699 to (i) play a positive feedback in response to determining that the user managed to exhale while making the physical effort, and/or (ii) play an alert and/or an explanation why the user should try next time to exhale while making the physical effort in response to determining that the user did not exhale while making the physical effort. FIG. 41A illustrates a fitness app running on smartphone 196, which instructs the user to exhale while bending down. CAM coupled to eyeglasses frame 181 measures the user breathing and is utilized by the fitness app that helps the user to exhale correctly. FIG. 41B illustrates inhaling while straightening up.

There are various ways in which the computer 696 may generate a coaching indication that is indicative of synchronization of a breathing pattern of the user with a sequence of movements of the user. In some embodiments, generating the coaching indication 698 involves identifying a breathing pattern based on $TH_{RHN}$ 693 and/or the sequence of movements based on $M_{move}$ 695. Additionally or alternatively, a machine learning model may be used to calculate, based on $TH_{RBN}$ 693 and $M_{move}$ 695, a value indicative of an extent to which the breathing pattern of the user is synchronized with the sequence of movements.

In some embodiments, a breathing pattern may refer to a description of characteristics of the user's breathes during a certain period of time. Optionally, the breathing pattern is determined by identifying, based on $TH_{RBN}$ 693, times at which the user inhaled or exhaled and/or by calculating, based on $TH_{RBN}$ 693, one or more of the various respiratory parameters described herein. Optionally, a breathing pattern may describe one or more of the following values: times at which the user inhaled, times at which the user exhaled, durations of inhales, durations of exhales, respiration volume (or changes to the respiration volume), indications of whether the user exhaled and/or inhaled from the mouth, and indications of whether the user exhaled and/or inhaled from the nose. Optionally, the values comprised in a breathing pattern include corresponding temporal values. For example, a breathing pattern may include the following: at time t=0 inhaling, at time t=1.5 exhaling, at time t=3 inhaling . . . , etc. Additionally or alternatively, a breathing pattern may include qualitative descriptors of respiration (determined based on $TH_{RBN}$ 693). For example, a breathing pattern may include the following descriptors: a regular inhaling followed by a short bursty exhaling (e.g., when hitting a ball).

In some embodiments, a sequence of movements of the user may refer to values describing movement of the user's body (changing location in the 3D space) and/or changes to pose and/or orientation of limbs. Optionally, the sequence of movements may be represented using descriptors that represent specific movements that are identified based on $M_{move}$ 695. For example, the sequence of movements describing a drive shot in golf may include descriptors such as: getting into position (address), a backswing, and a downswing. Optionally, the descriptors of movements in a sequence of movements may have associated temporal values describing properties such as when each of the movements started and/or how long each of the movements lasted.

In one embodiment, identifying a certain movement, from among the sequence of movements, is done using a machine learning-based model. $M_{move}$ 695 (or a portion thereof, e.g., a segment lasting a second) are converted into feature values representing values of $M_{move}$ (e.g., values of an accelerometer, low-level image features, etc.), using approaches described herein and/or approaches known in the art. A model is utilized to calculate, based on the feature values, a value indicative of whether the user performed the certain movement. Optionally, the model is trained on samples of one or more users, each comprising feature values generated based on $M_{move}$ of a user taken while said user performed the certain movement. Optionally, the model is trained on samples of one or more users, each comprising feature values generated based on $M_{move}$ of a user taken while said user did not perform the certain movement.

In one embodiment, identifying a certain movement, from among the sequence of movements, is done using similarity to reference $M_{move}$ taken while a certain user performed the certain movement. $M_{move}$ 695 (or a portion thereof, e.g., a segment lasting a second), is compared to the reference $M_{move}$ and if the similarity reaches a threshold, the user is considered to have performed the certain movement while $M_{move}$ 695 (or the portion thereof) were taken. In one example, the segments of $M_{move}$ being compared are treated as time series data, and one or more of the methods referenced herein with respect to determining similarity of time series are used to determine the similarity. In another example, the segments of $M_{move}$ being compared may be represented as points in a high dimensional space, and a distance function such as the Euclidian distance or some other distance function is used find the distance between the points. The threshold, to which the similarity is compared, may be determined experimentally and selected in order to achieve a desirable balance between specificity and sensitivity of identifications of the certain movement.

In order to determine to what extent the sequence of movements (determined based on $M_{move}$ 695) is synchronized with the breathing pattern (determined based on $TH_{RBN}$ 693) the computer 696 may align the sequence of movements and breathing pattern (e.g., by using temporal information associated with both). This alignment may be done in different ways. In one example, the alignment determines which respiratory actions were performed when different movements of the sequence of movements were performed. In this example, the computer 696 may utilized the alignment to determine whether the respiratory actions correspond to one or more predetermined breathing patterns appropriate for the certain movement sequence.

In another embodiment, feature values are generated based on the sequence of movements and the breathing pattern. For example, some of the feature values may describe which movements were performed, their relative order, and timing. Additionally some feature values may describe which respiratory activities were performed, their order/timing/duration, and other related properties described above. A model is used to calculate, based on the feature values, a value indicative of the extent to the breathing pattern is synchronized with the sequence of movements. Optionally, the model is trained based samples generated from $M_{move}$ and $TH_{RBN}$ of one or more users, which include samples generated based on $M_{move}$ and $TH_{RBN}$ taken while the sequence of movements was performed and a user was breathing in a breathing pattern that was synchronized with the sequence of movements. Additionally, the samples used to train the model may include samples generated based on $M_{move}$ and $TH_{RBN}$ taken while the sequence of movements was performed and a user was not breathing in a breathing pattern that was synchronized with the sequence of movements. Optionally, a breathing pattern is considered not to be synchronized with a sequence of movements if the extent of the synchronization between the two is below a predetermined threshold (and considered synchronized otherwise).

In yet another embodiment, a unified sequence is created from the breathing pattern and the sequence of movements, which describes both movements and respiration activities.

For example, the sequence of movements and the breathing pattern may be merged to a single sequence using temporal data. This unified sequence may then be evaluated to determine whether it corresponds to a breathing pattern that is synchronized to a sequence of movements based on similarity to a reference unified sequence and/or a machine learning-based model trained on samples generated based on unified sequences that are generated based on $M_{move}$ and $TH_{RBN}$ taken while the sequence of movements was performed and a user was breathing in a breathing pattern that was synchronized with the sequence of movements.

In some embodiments, determining whether a breathing pattern is synchronized with a sequence of movements of the user is done using a machine learning-based model. The computer 696 generates feature values based on $TH_{RBN}$ 693 (e.g., one or more feature values of types described herein which are used to calculate a respiratory parameter) and/or based on $M_{move}$ 695 (e.g., feature values described above which are used to identify certain movements). The computer 696 utilizes the machine learning-based model to calculate, based on the feature values, a value indicative of whether the breathing pattern was synchronized with the sequence of movements. Optionally, the model was trained based on data comprising: a first set of previous $TH_{RBN}$ and $M_{move}$ of one or more users, taken while performing the sequence of movements and breathing in a pattern that is synchronized with the sequence of movements, and a second set of previous $TH_{RBN}$ and $M_{move}$ of the one or more users taken while performing the sequence of movements and breathing in a pattern that is not synchronized with the sequence of movements.

One application for which thermal measurements of the face may be useful is to detect an allergic reaction. In one embodiment, a system configured to detect an allergic reaction of a user includes at least a CAM that takes thermal measurements of a region on the nose ($TH_N$) of the user, and a computer that detects an allergic reaction of the user based on $TH_N$. Optionally, an allergen may be any substance that causes the user to experience an allergic reaction due to the exposure of the user to the allergen (e.g., by consuming, inhaling, and/or coming into physical contact with the allergen). For example, an allergic reaction may be a reaction to a drug, peanuts, eggs, wheat, dairy products, seafood, pollen, dust, and/or perfume.

In one embodiment, CAM is physically coupled to a frame worn on the user's head (e.g., a frame of glasses or an augmented reality display). Optionally, CAM is located less than 15 cm from the user's face. Optionally, CAM weighs less than 10 g, 5 g or 1 g. Optionally, CAM uses a thermopile, a pyroelectric sensor, or a microbolometer sensor, which may be a focal-plane array sensor. For example, CAM may be the thermal cameras 48 and/or 49, which are illustrated in FIG. 16B, or the thermal camera 540 illustrated in FIG. 55.

Optionally, multiple CAMs may be utilized to obtain measurements of various ROIs such as different regions/sides of the nose, mouth and/or cheeks. For example, allergic reaction may cause red eyes, itchy eyes, tearing eyes, swollen eyelids, and/or burning eyes/eyelids. In some cases, a thermal camera that captures a region on the periorbital ($TH_{peri}$) around at least one of the eyes may detect an eye allergy symptom before the user is aware of the allergic reaction and/or used to assess the extent of the allergic reaction. As another example, allergic reaction may cause hives (urticaria) around the mouth and/or other parts of the face. In some cases, a thermal camera that captures the area around the mouth ($TH_{lips}$) may detect the hives around the mouth before the user is aware of the allergic reaction and/or used to assess the extent of the allergic reaction. In still some cases, thermal measurements of regions on the right and/or left cheeks ($TH_{ch}$) may help detecting the allergic reaction.

The computer is configured, in one embodiment, to detect the allergic reaction based on $TH_N$ and optionally other data, such as $TH_{CH}$, $TH_{peri}$, and/or $TH_{lips}$ mentioned above and/or other sources of information mentioned below. In one embodiment, detecting the allergic reaction may involve one or more of the following: determining whether the user is experiencing an allergic reaction, and/or determining the extent of the allergic reaction. Optionally, the extent of the allergic reaction may be indicative of the severity of the allergic reaction, and/or the duration of the allergic reaction (e.g., total time of the allergic reaction and/or the time remaining until the allergic reaction subsides).

In some cases, changes to temperatures at regions of the face (e.g., in the nasal area) occur quickly at the initial stages of an allergic reaction. Thus, the computer may detect the allergic reaction at its initial stages even before the user is aware of the allergic reaction. Thus, in some embodiments, detecting the allergic reaction involves detecting an onset of the allergic reaction, which may involve determining the time until the reaction reaches its peak severity (e.g., a rash, coughing, respiratory distress, sneezing) and/or determining the expected degree of severity (extent) of the allergic reaction.

In some cases, at the time the allergic reaction is identified, a user having the allergic reaction may not be aware of the allergic reaction, e.g., because the symptoms are not strong enough at the time. Thus, being notified about an allergic reaction before its full manifestation may have an advantage, in some embodiments, of allowing the user to take early action to alleviate and/or decrease the symptoms (e.g., take antihistamines) or seek medical attention.

In some allergic reactions, the nasal temperature can rise rapidly within minutes, before other more noticeable symptoms may manifest themselves (e.g., sneezing, itching, and/or respiratory problems). Thus, rising nasal temperatures may serve as an indication of an allergic reaction. For example, a fast increase due to an allergic reaction may correspond to an increase of more than 0.8° C., within a period of less than 10 minutes, or even less than 5 minutes.

FIG. 54A and FIG. 54B illustrate a scenario in which a user is alerted about an expected allergic reaction. In FIG. 54A, the user's nasal temperature is normal. At that time, a cat, to which the user is allergic, walks past the user. FIG. 54B illustrates the situation shortly after. The user's nasal temperature has increased, and based on thermal measurements of the nasal region, a computer issues an alert to the user about the expected allergic reaction. Note that at the time the alert is issued, the user may not be aware of any symptoms of the allergic reaction. Receiving an early warning in this case may enable the user to take measures to alleviate the effects of the allergic reaction, such as taking an antihistamine medicine.

In one embodiment, a system configured to alert about an allergic reaction includes at least CAM (which is discussed above) and a user interface (UI), such as UI 373. CAM is worn on a user's head and takes thermal measurements of a region on the user's nose ($TH_N$). Optionally, CAM weighs below 10 g, is physically coupled to a frame worn on the user's head, and is located less than 15 cm from the user's face. Optionally, the system includes a transmitter that may be used to transmit $TH_N$ to a computer that detects the allergic reaction based on $TH_N$. In one example, the computer may belong to a device of the user, such as a computer of an HMS of which CAM is part, or a computer belonging to a smartphone or a smartwatch carried by the user. In another example, the computer may be remote of the user, such as cloud-based server. Various approaches that may be utilized by the computer to detect the allergic reaction are discussed below. Optionally, responsive to detecting the allergic reaction (e.g., by calculating that an extent of the allergic reaction reaches a threshold), the computer commands the UT to provide the alert. For example, the computer may send a signal to a smartphone app, and/or to a software agent that has control of the UI, to provide the alert. In another example, the computer may send an instruction to the UT to provide the alert. Optionally, the alert is provided as text, image, sound, and/or haptic feedback.

There are various ways the computer may utilize $TH_N$ and possibly other thermal measurements such as $TH_{CH}$, $TH_{peri}$, and/or $TH_{lips}$, in order to detect the allergic reaction. In one embodiment, the computer may compare values derived from $TH_N$ (and/or from $TH_{CH}$, $TH_{peri}$, and/or $TH_{lips}$) to a certain threshold, and determine whether the threshold is reached (which is indicative of an occurrence of the allergic reaction). Optionally, the threshold is determined based on previous thermal measurements of the user. Optionally, the threshold is determined based on previous thermal measurements of other users. In another embodiment, the computer may determine a similarity between a reference time series corresponding to the allergic reaction and $TH_N$ and optionally the other thermal measurements (or a time series derived therefrom). Optionally, when a sufficiently high similarity is detected, the computer may interpret that as an indication of an occurrence of the allergic reaction. The reference time series may be generated based on previous thermal measurements of the user and/or of other users.

In yet another embodiment, the computer may generate feature values based on thermal measurements comprising $TH_N$ and optionally $TH_{CH}$, $TH_{peri}$, and/or $TH_{lips}$, and utilize a machine learning-based model to calculate, based on the feature values, a value indicative of whether the allergic reaction occurred and/or indicative of an extent of the allergic reaction (calculating the value be considered herein as "detecting the allergic reaction"). Optionally, the model was trained based on previous thermal measurements of the user. For example, the previous thermal measurements may include a first set of thermal measurements taken while the user had an allergic reaction, and a second set of thermal measurements taken while the user did not have an allergic reaction. In this example, the model may be considered a personalized model for the user. Additionally or alternatively, the model may be trained on thermal measurements of other users (e.g., a general model). Optionally, different models may be created to detect different types of allergic reactions, to detect allergic reactions to different allergens, and/or to detect different extents of an allergic reaction.

In one example, detection of the allergic reaction may involve the computer performing the following: (i) generating feature values based on thermal measurements comprising $TH_N$ and optionally $TH_{CH}$, $TH_{peri}$, and/or $TH_{lips}$; and (ii) utilizing a model to detect the allergic reaction based on the feature values. Optionally, the model was trained based on previous thermal measurements of the user comprising $TH_N$ and optionally $TH_{CH}$, $TH_{peri}$, and/or $TH_{lips}$, which were taken while the user had an allergic reaction. Alternatively, the model was trained based on a first set of previous thermal measurements of the user comprising $TH_N$ and optionally $TH_{CH}$, $TH_{peri}$, and/or $TH_{lips}$, which were taken while the user had an allergic reaction, and a second set of previous thermal measurements of the user comprising $TH_N$ and optionally $TH_{CH}$, $TH_{peri}$, and/or $TH_{lips}$, which were taken while the user did not have an allergic reaction.

In some embodiments, detecting the allergic reaction may involve utilizing baseline $TH_N$, most of which were taken when the user did not have an allergic reaction. Thus, detecting the allergic reaction may rely on observing a change relative to typical temperatures at the ROIs. In one example, the computer detects the allergic reaction based a difference between $TH_N$ and a baseline value determined based on a set of previous $TH_N$ taken with CAM. In this example, most of $TH_N$ belonging to the set were taken while the user had an allergic reaction, or within thirty minutes before or after the user had an allergic reaction.

Confounding factors such as extensive physical activity, touching the nose, and/or direct sunlight aimed at the nose may lead, in some embodiments, to less accurate detections of an allergic reaction (e.g., by increasing the frequency of false detections of the allergic reaction). In some embodiments, the system may include a sensor that takes additional measurements ($m_{conf}$) of the user, and/or of the environment in which the user was in while $TH_N$ were taken. Optionally, $m_{conf}$ are indicative of an extent to which a confounding factor occurred while $TH_N$ were taken. Another approach that may be utilized by the computer is to generate feature values based on $m_{conf}$ and to utilize these feature values in the detection of the allergic reaction.

Receiving early notice regarding an allergic reaction may be useful in some embodiments, since it may enable a user to take action in order to reduce the severity of the allergic reaction. For example, the user may attempt to reduce exposure to an allergen (e.g., leave an area that has a high concentration of pollen), take certain medication (e.g., antihistamines) to reduce the effects of the allergic reaction, and/or promptly seek medical attention (in anticipation of a more severe allergic reaction that is to come). However, providing such early indications may involve relaxing the conditions under which an allergic reaction is detected (e.g., lowering thresholds for $TH_N$). This can come at a cost of having more false positives in the detection of allergic reactions. Thus, in order to avoid excessive false positives the system may need to be judicious about when it employs more relaxed conditions for detecting an allergic reaction.

One way in which false positive allergic reaction detections may be reduced is to utilize knowledge of conditions and/or times in which it is more likely that the user may experience an allergic reaction. For example, if it is known with high probability that the user was exposed to an allergen to which the user is known, or suspected, to be allergic, then more relaxed conditions for detecting the allergic reaction may be employed. Optionally, if there is no reason to believe that the user was exposed to an allergen, then the more strict conditions may be employed for detecting the allergic reaction.

In some embodiments, the computer receives an indication of whether the user was exposed to an allergen and utilizes the indication in the process of detecting the allergic reactions. This indication may be utilized in various ways, which may depend on how the computer detects allergic reactions, as the following embodiments demonstrate.

In one embodiment, the computer compares $TH_N$ (or certain values computed based on $TH_N$) to a threshold, such that if $TH_N$ reach the threshold, this is indicative of a likely occurrence of the allergic reaction. In this embodiment, the threshold may be selected based on the indication that indicates exposure, or possible exposure, to the allergen. For example, responsive to receiving a first indication indicating that the user was exposed to the allergen, the computer selects a first threshold, and responsive to receiving a second indication indicating that the user was not exposed to the allergen, the computer selects a second threshold that is higher than the first threshold. Thus, the second threshold requires a greater change in $TH_N$ in order to detect the allergic reaction.

In another embodiment, the computer calculates a similarity between $TH_N$ and a reference time series comprising data indicative of temperatures at different points in time during an allergic reaction (e.g., time series of the user having the allergic reaction). When the similarity reaches a certain threshold, this is indicative of an occurrence of the allergic reaction. In this embodiment, the certain threshold may be selected based on the indication that indicates exposure, or possible exposure, to the allergen. For example, responsive to receiving a first indication indicating that the user was exposed to the allergen, the computer selects a first certain threshold, and responsive to receiving a second indication indicating that the user was not exposed to the allergen, the computer selects a second certain threshold that corresponds to a higher extent of similarity than the first certain threshold. Thus, the second certain threshold requires greater similarity to the reference time series in order to detect the allergic reaction.

In yet another embodiment, the computer utilizes $TH_N$ to generate feature values, and to utilize a model to calculate, based on the feature values, an extent of the allergic reaction. In this embodiment, the model is a machine learning-based model that is generated based on previous thermal measurements of regions on the noses of one or more users (which may include the user and/or other users). At least some of the feature values are generated based on the indication, and may describe various properties of the exposure to an allergen, such as the type of allergen, the duration of exposure, the extent of exposure (e.g., dosage), and/or the time that has elapsed since the exposure. Thus, the above factors may be taken into account by the model, which may increase the chances of detecting an allergic reaction when the features indicate sufficient exposure to certain allergens.

The indication that is indicative of exposure to the allergen may be received from various sources. In one embodiment, the indication may be self-reported by the user. For example, the user may provide information about the exposure through interaction with a device such as a smartphone or speaking with a software agent via a microphone. In another embodiment, various camera-based systems may be utilized to take images comprising the allergen or an object associated with the allergen, analyze the images, and generate the indication about the exposure based on the analysis. Such systems that monitor the environment the user is in and/or substances the user consumes are discussed in more detail below. In yet another embodiment, an external source may provide indication based on determining the location of the user. For example, the user's location may be determined based on GPS, cellphone transmissions, and/or Wi-Fi transmissions. Additionally, an external database that includes real-time data about the presence of various allergens (e.g., dust or pollen) may be queried in order to determine whether the user is likely exposed to a potential allergen substance.

Figure 52:
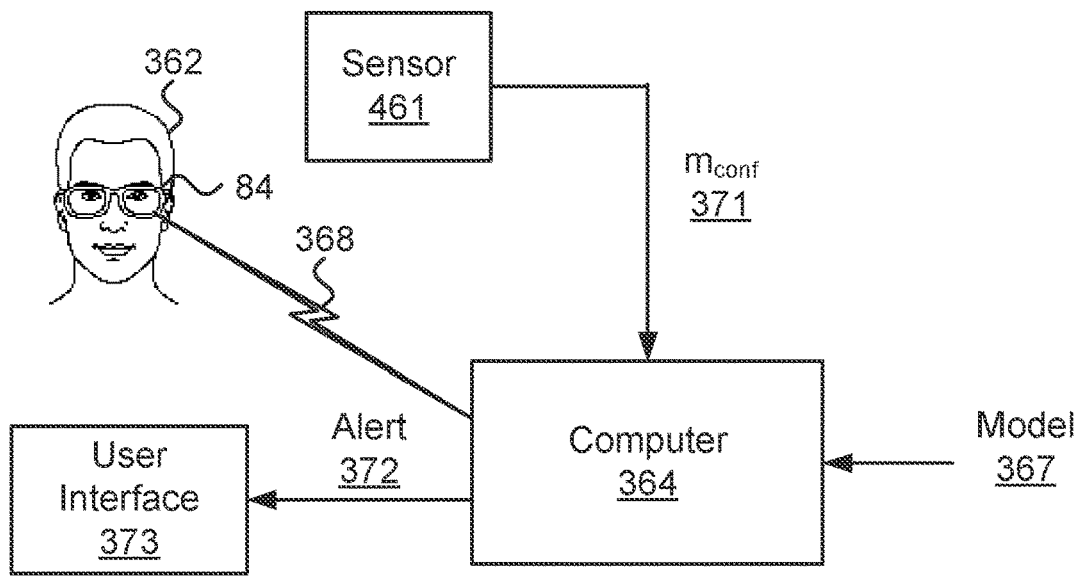
FIG. 52 illustrates an embodiment of a system configured to detect an allergic reaction.

The following method for detecting an allergic reaction of a user may be used, in some embodiments, by systems modeled according to FIG. 52. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, taking thermal measurements of a region on the nose ($TH_N$) of the user using an inward-facing head-mounted thermal camera.

In Step 2, training a model based on previous $TH_N$ taken during different days.

And in Step 3, detecting the allergic reaction based on $TH_N$ and the model. Optionally, the system detects and alerts about the allergic reaction before the user is aware of the symptom of the allergic reaction. Optionally, the alert is provided as text, image, sound, and/or haptic feedback. Optionally, detecting the allergic reaction involves generating feature values based on a subset of $TH_N$ comprising $TH_N$ taken during a window of a certain length, and utilizing a model to calculate, based on the feature values, a value indicative of the extent of allergic reaction. Optionally, the model may be personalized for the user. For example, the model was trained based on previous $TH_N$ of the user, taken during different days, which include: a first set of measurements taken while the user had an allergic reaction, and a second set of measurements taken while the user did not have an allergic reaction. Optionally, the model may be based on measurements of multiple users, taken during different days, which include: a first set of measurements taken while the users had an allergic reaction, and a second set of measurements taken while the users did not have an allergic reaction. The step of generating feature values and utilizing the model may be performed multiple times throughout the period of different days during which $TH_N$ were taken, each time utilizing a subset of $TH_N$ taken during a different window of a certain length; the alerting is done at a certain time for which an allergic reaction of at least a certain extent is detected (which warrants an alert).

Some of the embodiments described herein may be utilized to identify potential causes for the change (e.g., rise) of the temperature at an ROI. These causes may include inhaled allergens, food, drugs, and/or various chemicals which the user might have been exposed to (e.g., via ingestion, inhalation, and/or physical contact). In one embodiment, the computer may identify a potential allergen substance by estimating a time of exposure to the allergen from data indicative of a deviation over time of mean nasal temperature from a baseline and identifying the substances consumed by the user, and/or to which the user was exposed, around that time. For example, by identifying based on $TH_N$ when the nasal temperature started to rise, and taking into account the time required for the allergic reaction to be manifested via a temperature rise, a window of time can be determined during which the user was likely exposed to the allergen. Examining which substances the user was exposed to during the window can yield a list of one or more potential allergen substances. Optionally, the system alerts the user about the one or more potential allergen substances. Optionally, the system stores in a database potential allergen substances identified based on data indicative of a deviation over time of mean nasal temperature from baseline (such as allergens identified based on deviation over time of mean nasal temperature from baseline). In some embodiments, the system includes a camera that captures images of substances consumed by the user. Optionally, the camera is mounted to a frame worn on the user's head. Optionally, the system displays to the user an image of a substance associated with the potential allergen substance.

There are various known systems that may be utilized to monitor what substances a user was exposed to and/or what substances a user consumed. For example, systems that may be utilized to determine what the user ate or drank are described in US patent application 20110318717 (Personalized Food Identification and Nutrition Guidance System), in U.S. Pat. No. 9,053,483 (Personal audio/visual system providing allergy awareness), and in U.S. Pat. No. 9,189,021 (Wearable food nutrition feedback system). Additionally, obtaining indications of possible allergens to which the user was exposed is described in U.S. Pat. No. 9,000,933 (Automated allergy alerts). In one embodiment, upon identifying an increase in nasal temperature, the system can identify the potential cause to be one of the substances to which the user was exposed during a predetermined preceding duration, such as the preceding 20 min, 10 min, or 5 min.

Figure 55:
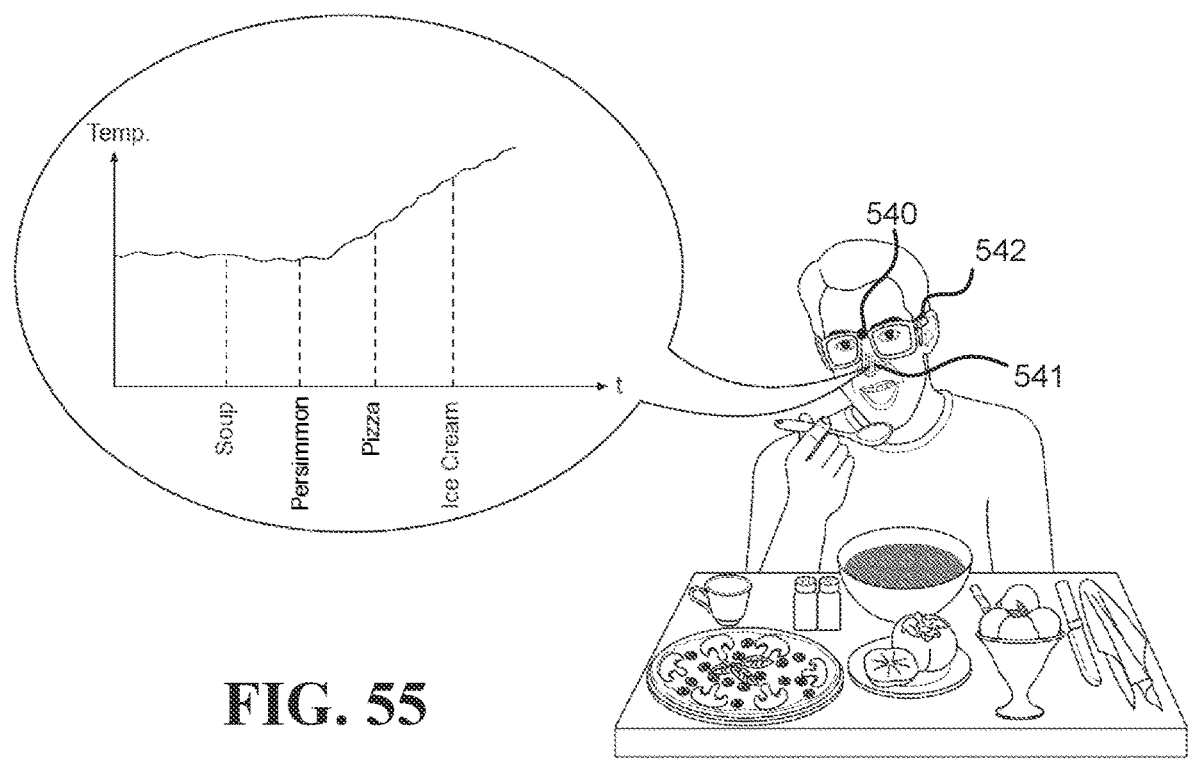
FIG. 55 illustrates how the system may be utilized to identify a trigger of an allergic reaction.

FIG. 55 illustrates how the system may be utilized to identify a trigger of an allergic reaction. CAM 540 is coupled to a frame of eyeglasses worn by the user and takes thermal measurements of a region on the user's nose 541, while the user eats different types of food. The dotted lines on the graph indicate when the user started eating each type of food. The nasal temperature increases shortly after starting eating the persimmon; however, it may reach a threshold indicating an allergic reaction only after some time, during which the user eats the pizza or the ice cream. Thus, in this case, the allergic reaction should likely be attributed to the persimmon or the soup, and not attributed to the pizza or the ice cream. Optionally, outward-facing head-mounted visible-light camera 542 takes images of the food the user eats, and the computer uses image processing to detect the types of food.

Another approach for identifying a cause of an allergic reaction (a "trigger" of an allergic reaction), involves analysis of potential triggers and the user's detected response when affected by the potential triggers. In one embodiment, the computer is further configured to: receive indications of times during which the user was exposed to potential triggers of the allergic reaction, and select a trigger, from among the potential triggers, based on the indications and extents of the allergic reaction detected based on $TH_N$. Optionally, during most of the time the user was affected by the trigger, an effect of the trigger, as manifested via changes to $TH_N$, was higher than effects of most of the potential triggers. Optionally, a camera is utilized to take images of the surroundings of the user, and the computer generates at least some of the indications based on analysis of the images. In one example, the exposure to the potential triggers involves consuming a certain drug and/or a certain food item. In another example, the exposure to the potential triggers involves being exposed to pollen, dust, and/or a certain cosmetics product. In still another example, the exposure to the potential triggers involves the user being at a certain location, and/or the user being in contact with a certain animal.

In some embodiments, determination of the extent of the allergic reaction may be utilized in the context of allergen challenge tests. For example, the system may receive an indication of when a non-invasive intranasal histamine and/or an allergen challenge is performed, and estimate effects of the histamine and/or allergen challenge in the tissues, based on an increase of nasal temperature as observed in $TH_N$. In one example, this involves utilizing a change in $TH_N$, induced by the histamine provocation (of the non-invasive intranasal histamine), as a marker of an intensity of the activity of the histamine in the nose. In another example, this may involve utilizing a change in $TH_N$, induced by the allergen challenge, as a marker of an intensity of the activity of the allergen in the nose.

Figure 51:
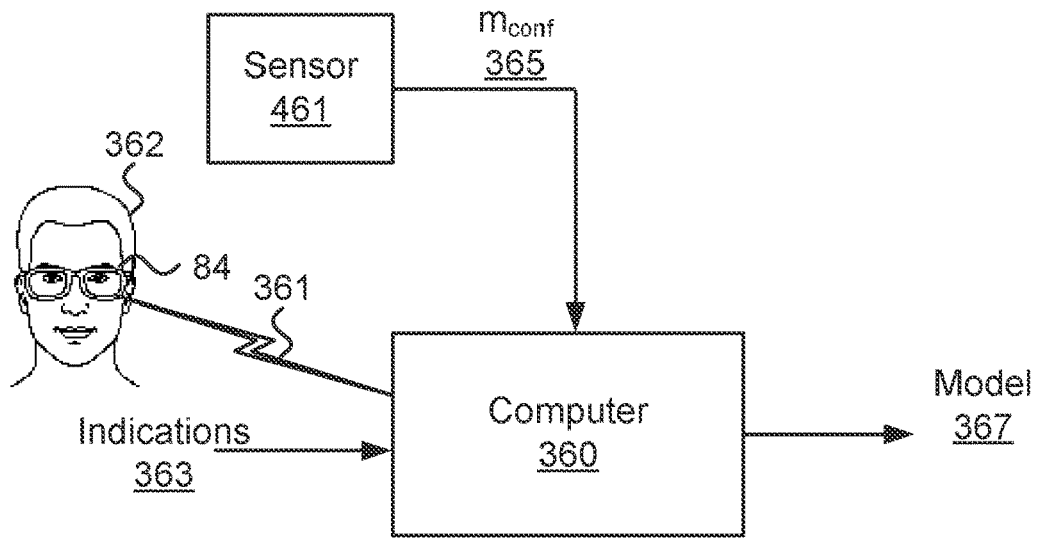
FIG. 51 illustrates an embodiment of a system that generates a model used to detect an allergic reaction.

FIG. 51 illustrates one embodiment of a system that generates a model to detect an allergic reaction. The system includes a CAM and a computer 360. Optionally, CAM is physically coupled to a frame worn on the head of a user 362. CAM takes measurements of a region on the nose ($TH_N$) 361 of the user. Optionally, CAM weighs below 10 g and is located less than 15 cm from the user's face.

In one embodiment, the computer 360 generates samples based on data comprising: (i) $TH_N$ 361, and (ii) indications 363, which correspond to different times, which are indicative of whether the user 362 experienced an allergic reaction at the different times. Optionally, each sample comprises: (i) feature values based on $TH_N$ taken during a certain period (which are from among $TH_N$ 361), and (ii) a label based on an indication from among the indications 363, which is indicative of whether the user 362 had an allergic reaction and/or to what extent the user 362 had the allergic reaction. Optionally, the label is indicative of the extent of the allergic reaction of the user 362 during the certain period and/or up to a certain time after the certain period (e.g., up to 30 minutes after the certain period). Optionally, at least some of the feature values in the sample may be generated based on other sources of information, as explained below. The computer 360 trains a model 367 based on the samples. Optionally, the computer 360 also provides the model 367 to be used by a system that detects an allergic reaction based on $TH_N$, such as the system illustrated in FIG. 52.

The indications 363 may be generated in different ways. In one embodiment, some of the indications 363 are generated by an entity that observes the user 362, such as a human observer or a software program (e.g., a software agent operating on behalf of the user). In another embodiment, some of the indications 363 are provided by the user 362. For example, the user may provide an indication via a smartphone app by pressing a certain button on a screen of a smartphone, and/or by speech that is interpreted by a software agent and/or a program with speech analysis capabilities. In yet another embodiment, some of the indications are determined based on analysis of the user's behavior. For example, monitoring the user using a camera and/or a microphone may indicate that the user is suffering from an allergic reaction by detecting coughing and/or sneezing. And in still another embodiment, some of the indications are determined based on physiological signals of the user, which are not thermal measurements of ROIs on the face, such as measurements of the user's heart rate and/or brainwave activity.

The following are some examples of feature values that may be generated for the samples used to train the model 367. The samples include feature values based on $TH_N$ of the user 362 (from among $TH_N$ 361), which were taken during a certain period, and possibly other information sources mentioned below. Additionally, the samples may include feature values generated based on $m_{conf}$ taken during the certain period (as discussed below).

In one embodiment, the computer 360 receives additional measurements of the user 362 taken during the certain period, and generates feature values based on the additional measurements. Optionally, the additional measurements are indicative of: a heart rate, heart rate variability, brainwave activity, galvanic skin response, muscle activity, and/or an extent of movement. In another embodiment, the computer 360 receives measurements of the environment in which the user 362 was in during the certain period and generates feature values based on the measurements of the environment. Optionally, each measurement of the environment is indicative of: a temperature of the environment, a humidity level of the environment, a noise level of the environment, air quality in the environment, a wind speed in the environment, an extent of precipitation in the environment, and/or an infrared radiation level in the environment.

In another embodiment, the computer 360 generates feature values based on values indicative of exposure of the user 362 to allergens during the certain period. Optionally, the values are indicative of: consumption of a certain drug, consumption of a certain food item, exposure to at least a certain concentration of pollen, exposure to at least a certain concentration of dust, exposure to a certain cosmetics product, and/or exposure to a certain aerosol.

In yet another embodiment, the computer 360 receives measurements (denoted $m_{conf}$ 365), which are indicative of at least one of the following confounding factors: a skin inflammation on the user's face, touching the user's face, a magnitude of thermal radiation directed at the user's face, and a magnitude of direct airflow on the user's face. Optionally, me g 365 are measured utilizing the sensor 461. Optionally, the computer 360 generates feature values based on me g, from among $m_{conf}$ 365, which were taken during the certain period.

The sensor 461 may involve different types of sensors in embodiments described herein. In one example, the sensor 461 is physically coupled to a frame worn on the head of the user 362. In another example, the sensor 461 is coupled to a device carried by the user 362, such as a smartphone, a smartwatch, and/or smart clothing (e.g., clothing embedded with sensors that can measure the user and/or the environment). In yet another example, the sensor 461 may be an external sensor that is not carried by the user 362. The following are some examples of specific types of sensors that the sensor 461 may include. In one example, the sensor 461 is a visible-light camera physically coupled to the frame, and configured to take images of a region on the user's face that includes at least 25% of the nose. Optionally, in this example, the confounding factor includes inflammation of the skin, skin blemishes, and/or touching the face. In another example, the sensor 461 includes a movement sensor that measures a movement of the user 362 and the confounding factor involves the user walking, running, exercising, bending over, and/or getting up from a sitting or lying position. And in yet another example, the sensor 461 measures at least one of the following environmental parameters: a temperature of the environment, a humidity level of the environment, a noise level of the environment, air quality in the environment, a wind speed in the environment, an extent of precipitation in the environment, and an infrared radiation level in the environment.

In one embodiment, the model 367 is trained on samples that were generated based on $TH_N$ taken while the user 362 had an allergic reaction, and samples that were generated based on $TH_N$ taken while the user 362 did not have an allergic reaction.

The samples utilized to train the model 367 may be generated based on feature values taken while user 362 was in different environments during first and second periods, optionally with different environmental conditions, such as (i) the environment temperature was at least 10° C., higher during the first period than during the second period; (ii) the humidity level in the environment during the first period was at least 30% higher than the humidity level during the second period, and (iii) the user was exposed to rain, hail, and/or snow during the first period, while the user was not exposed to any of rain, hail, and snow during the second period.

Additionally or alternatively, the samples utilized to train the model 367 may be generated based on feature values taken while the user 362 was in various situations during first and second periods, such as (i) the user 362 was sedentary during the first period, while the user 362 was walking, running, or biking during the second period; and/or (ii) the user 362 was indoors during the first period, while the user 362 was outdoors during the second period.

Additionally or alternatively, the samples utilized to train the model 367 may be based on $TH_N$ taken over a long period of time, such as more than a day, more than a week, more than a month, or more than a year.

Training the model 367 may involve various computational approaches. In one example, training the model 367 may involve selecting, based on the samples, a threshold; if a certain feature value reaches the threshold then an allergic reaction is detected. In another example, the computer 360 utilizes a machine learning-based training algorithm to train the model 367 based on the samples. Optionally, the model includes parameters of at least one of the following models: a regression model, a model utilized by a neural network, a nearest neighbor model, a model for a support vector machine for regression, and a model of a decision tree.

In some embodiments, the computer 360 may utilize deep learning algorithms to train the model 367. In one example, the model 367 may include parameters describing multiple hidden layers of a neural network. In one embodiment, when $TH_N$ include measurements of multiple pixels, such as when CAM includes a FPA, the model 367 may include parameters of a convolution neural network (CNN). In another embodiment, detecting the allergic reaction may be done based on multiple, possibly successive, measurements. For example, the allergic reaction may involve a progression of a state of the user (e.g., a gradual warming of the nose). In such cases, detecting the allergic reaction may involve retaining state information that is based on previous measurements. Optionally, the model 367 may include parameters that describe an architecture that supports such a capability. In one example, the model 367 may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

FIG. 52 illustrates one embodiment of a system configured to detect an allergic reaction. The system includes a CAM and a computer 364. CAM takes measurements of a region on the nose ($TH_N$) 368 of the user 362. Optionally, CAM weighs below 10 g and is located less than 15 cm from the user's face.

The computer 364 generates feature values and utilize the model 367 to detect an allergic reaction of the user 362 based on the feature values. Some feature values are generated based on $TH_N$ 368, and some feature values may be generated based on other data (as described below). Optionally, the model 367 was trained based on previous $TH_N$ of the user 362 (e.g., $TH_N$ 361). Optionally, the previous $TH_N$ of the user 362 were taken during different days and/or over more than a week. Optionally, the previous $TH_N$ include: a first set of $TH_N$ taken while the user had an allergic reaction, and a second set of $TH_N$ taken while the user did not have an allergic reaction.

The feature values generated by the computer 364 are similar in their nature to the feature values generated by the computer 360, which were discussed in more detail above. Optionally, the same modules and/or procedures are used by the computer 364 and the computer 360 to generate feature values based on $TH_N$ (and possibly other data). Some examples of feature values that may be generated by the computer 364 based on $TH_N$ 368 and possibly other data include: (i) values comprised in $TH_N$ 368 (optionally these values may undergo various forms of filtering and/or normalization), (ii) values of one or more respiratory parameters calculated based on $TH_N$368, (iii) values generated based on additional measurements of the user 362 (e.g., measurements of heart rate, heart rate variability, brainwave activity, galvanic skin response, muscle activity, and an extent of movement), and/or (iv) measurements of the environment in which the user 362 was in while $TH_N$ 368 were taken.

In one embodiment, the computer 364 may receive indications indicative of exposure of the user 362 to an allergen while $TH_N$ 368 were taken, or up to a predetermined duration before $TH_N$ 368 were taken (e.g., up to twelve hours before), and generate feature values based on the indications. Optionally, the indications are indicative of consumption of a certain drug, consumption of a certain food item, exposure to at least a certain concentration of pollen, exposure to at least a certain concentration of dust, exposure to a certain cosmetics product, and/or exposure to a certain aerosol. Optionally, determining exposure of the user 362 to the allergen may be done by analyzing images received from a camera that captures substances consumed by the user 362.

In another embodiment, the computer 364 may receive measurements ($m_{conf}$ 371), which are indicative of at least one of the following confounding factors: a skin inflammation on the user's face, touching the user's face, a magnitude of thermal radiation directed at the user's face, and/or a magnitude of direct airflow on the user's face. Optionally, $m_{conf}$ 371 are measured utilizing the sensor 461. In one embodiment, the computer 364 generates at least some of feature values based on $m_{conf}$ 371 and utilizes the at least some feature values to detect the allergic reaction.

In one embodiment, the computer 364 utilizes the model 367 to calculate, based on the feature values, a value indicative of the extent of an allergic reaction of the user 362. Optionally, the extent is presented to the user 362 via UI 373. Optionally, responsive to the extent reaching a threshold, the computer 364 generates an alert 372 that is presented to the user 362 via the UI 373.

In one embodiment, the extent of the allergic reaction may be indicative of whether there is an allergic reaction, the severity of the allergic reaction (e.g., a level of manifestation of symptoms on a scale of 1 to 10), and/or the duration of the allergic reaction (e.g., total time of the allergic reaction and/or time remaining until the allergic reaction subsides). Optionally, the extent may be indicative of the time until the allergic reaction reaches its peak severity (e.g., a rash, coughing, respiratory distress, sneezing), and/or the expected degree of severity of the allergic reaction.

In one embodiment, the computer 364 detects an early rise in nasal temperature of the user 362, which is detectable before the user 362 is aware of a manifestation of a symptom of the allergic reaction. Optionally, the UT 373 may present the user 362 with the alert 372 that is indicative of a possible allergic reaction, before the user 362 is aware of the symptom. In one example, an early rise in nasal temperature may involve a rise of at least 0.5° C. within less than 10 minutes and/or a rise of at least 0.75° C., within less than 20 minutes.

The system may optionally include additional CAMs, and thermal measurements of the additional CAMs may be used to generate feature values similarly to how $TH_N$ 368 are utilized. Optionally, the additional CAMs are physically coupled to a frame worn on the head of the user 362. For example, the system may include a second CAM, or second and third CAMs (CAM2 and CAM3, respectively), each of which weighs below 10 g and is located less than 15 cm from the user's face. CAM2 and CAM3 are located to the right and to the left of the vertical symmetry axis that divides the face of the user 362, respectively, and take thermal measurements of regions on the right and left checks ($TH_{ROI1}$ and $TH_{ROI2}$, respectively), respectively. Optionally, the computer 364 generates additional feature values based on $TH_{ROI1}$ and $TH_{ROI2}$, and utilizes the additional features values to detect the allergic reaction. In another example, the system includes a second CAM, or second and third CAMs (CAM2 and CAM3), each of which weighs below 10 g and is located less than 15 cm from the user's face. CAM2 and CAM3 are located to the right and to the left of the vertical symmetry axis, respectively, and take thermal measurements of regions on the right and left periorbital areas ($TH_{ROI1}$ and $TH_{ROI2}$, respectively). Optionally, the computer 364 generates additional feature values based on $TH_{ROI1}$ and $TH_{ROI2}$, and utilizes the additional feature values to detect the allergic reaction.

Analysis of detections of allergic reactions combined with information regarding potential triggers that affected the user at different times can reveal what are likely triggers of the allergic reaction. Some examples of potential triggers that may be considered triggers for certain users include ingested substances such as food (e.g., eggs, dairy, or peanuts) or certain drugs and chemicals and/or compounds to which the user may be exposed (e.g., pollen, dust, a certain cosmetics product, and a certain aerosol). Additionally, a trigger may be an indirect potential trigger that is correlated with allergic reactions of the user, such as being at a certain location, being in contact with a certain animal, conducting in a certain activity, and being in contact with a certain object.

FIG. 53 illustrates one embodiment of a system configured to select a trigger of an allergic reaction of a user. The system includes a CAM and a computer 376. The system may optionally include a frame 84, a camera 383, and/or a UI 385. CAM takes thermal measurements of a region on the nose ($TH_N$ 377) of the user.

In one embodiment, the thermal camera used to take $TH_N$ 377 is a head-mounted thermal camera. In another embodiment, the thermal camera used to take $TH_N$ 377 is not a head-mounted thermal camera. Examples of non-head-mounted thermal cameras include (i) thermal cameras embedded in a device such as a smartphone or a smartwatch, (ii) a thermal camera embedded in a device such as a laptop computer, a tablet, a television, or a gaming console, and/or (iii) a standalone thermal camera.

In some embodiments, multiple thermal cameras may be utilized to measure $TH_N$ 377. Additionally or alternatively, $TH_N$ 377 may include thermal measurements of multiple ROIs on the user's nose and/or thermal measurements of additional ROIs on other regions of the user's face (besides the nose).

$TH_N$ 377 are provided, in one embodiment, to the computer 376, which detects, based on $TH_N$ 377, extents of the allergic reaction of the user at different times. Optionally, the computer 376 employs a similar approach for detecting the extents of the allergic reaction to the approach described above involving the computer 364.

In some embodiments, detecting the extents of the allergic reaction of the user at different times may involve utilizing thermal measurements of other regions on the face, in addition to $TH_N$ 377.

In one example, the system includes second and third CAMs located to the right and to the left of the vertical symmetry axis that divides the user's face, which take thermal measurements of regions on the right and left cheeks ($TH_R$ and $TH_L$, respectively). Optionally, the computer 376 detects the extents of the allergic reaction also utilizing $TH_R$ and $TH_L$ (in addition to $TH_N$ 377).

In another example, the system includes second and third CAMs located to the right and left of a vertical symmetry axis that divides the user's face, respectively, which take thermal measurements of regions on the right and left periorbital areas ($TH_R$ and $TH_L$, respectively). Optionally, the computer 376 detects the extents of the allergic reaction also utilizing $TH_R$ and $TH_L$ (in addition to $TH_N$ 377).

The computer 376 is configured, in one embodiment, to receive indications 380 of potential triggers that affected the user at various times. Optionally, each of the indications 380 is indicative of a time during which the user was exposed to a certain potential trigger. Additionally or alternatively, each of the indications 380 may be indicative of a time during which the user was affected by a certain potential trigger. In some embodiments, at any given time, the user may be exposed to more than one of the potential triggers. Optionally, at least some of $TH_N$ 377, and optionally all of $TH_N$ 377, were taken while the user was exposed to two or more of the potential triggers.

The computer 376 selects a trigger 381, from among the potential triggers, based on the indications 380 and the extents of the allergic reaction. Optionally, an effect of a potential trigger is indicative how much the potential trigger influences the extent of the user's allergic reaction, which can range from no influence to a profound influence. Optionally, during most of the time the user is affected by the trigger 381, the effect of the trigger 381 on the extent of the allergic reaction of the user is higher than the effect of most of the other potential triggers on the allergic reaction of the user.

In one embodiment, the indications 380 include a list of periods of time during which various potential triggers affected the user. Optionally, the indications 380 are provided via a data structure and/or a queryable system that provides information for different points in time about which of the potential triggers affected the user at the points in time. Following are three examples of types of potential triggers that may be analyzed.

In a first example, some of the potential triggers relate to allergens in various foods, beverages, and/or other substances that may be consumed and digested by the user and may lead to an allergic reaction. For instance, the indications 380 may comprise a certain indication of a potential trigger that is indicative of the user consuming a certain drug and/or a certain food item.

In a second example, some of the potential triggers relate to allergens to which the user may be exposed in the environment. Optionally, an allergic reaction may occur after such an allergen is inhaled by the user and/or comes in contact with the user's skin. For instance, the indications 380 may comprise a certain indication of a potential trigger that is indicative of the user being exposed to pollen, dust, a certain cosmetics product, and/or a certain aerosol (e.g., a certain perfume fragrance).

In a third example, some of the potential triggers indirectly relate to the allergic reaction (e.g., they may be correlated with allergic reactions of the user). For instance, the indications 380 may include a certain indication of a potential trigger that is indicative of the user being at a certain location, the user being in contact with a certain animal, the user conducting in a certain activity, and/or the user being in contact with a certain object.

The extent of an allergic reaction may depend on quantitative aspects of the potential triggers. For example, a person who is allergic to dairy products may not have a noticeable allergic reaction following digestion of a small amount of dairy (e.g., adding milk to a cup of coffee), but may have a noticeable allergic reaction following a consumption of a larger amount of a dairy product (e.g., drinking a large milkshake). Thus, in some embodiments, the indications 380 include values that quantify how much at least some of the potential triggers affected the user. For example, these values may corresponds to amounts of substances consumed by the user, time spent by the user m certain environments, and/or values of environmental parameters (e.g., a concentration of pollen in the air).

The trigger 381 may be correlated with the occurrence of an allergic reaction of the user. Additionally, in some embodiments, the trigger 381 may be considered a direct cause of the allergic reaction (e.g., when the trigger 381 is a substance to which the user's immune system has an excessive reaction). Optionally, during most of the time the user was affected by the trigger 381, an effect of the trigger 381, as manifested via changes to $TH_N$, was higher than effects of most of the potential triggers. Optionally, the trigger 381 has a maximal effect (i.e., there is no other potential triggers that have a higher effect). Optionally, the trigger 381 has an effect that reaches a threshold, while the effect of most of the potential triggers does not reach the threshold.

In some embodiments, the effect of the trigger 381 is higher than the effect observed when the trigger 381 does not affect the user. For example, based on the values indicative of the extents of the allergic reaction and indications 380, an average extent of the allergic reaction of the user at a time $t+\Delta$ when the user was affected by the trigger 381 at some time during [t, t+Δ], is greater than an average extent of the allergic reaction of the user at a time t+Δ when the user was not affected by the trigger 381 at any time during [t, t+Δ]. Here Δ may be some predetermined period of time that is greater than five minutes, fifteen minutes, one hour, four hours, or twelve hours.

There are various ways in which the computer 376 may select, based on the indications 380 and the extents of the allergic reaction, the trigger 381 from among the multiple potential triggers being considered.

In some embodiments, the computer 376 performs a direct analysis of the effect of each of the potential triggers in order to identify which have a large effect (meaning they are likely to cause an allergic reaction with the user). Optionally, the effect of each potential trigger is calculated by determining, based on the indications 380, times at which the user was affected by each potential trigger, and observing the extent of the allergic reaction of the user at one or more times that are up to a certain period A later (where A may be for example a period of time up to 12 hours long or shorter, depending on the type of allergic reaction). In one example, an observed extent of the allergic reaction following being affected by a potential trigger is the maximum extent of the allergic reaction that is observed from the time t the user was affected by the potential trigger until the time t+Δ. In another example, the observed extent of the allergic reaction following being affected by a potential trigger is the extent of the allergic reaction that is observed at the time t+Δ (when the user was affected by the potential trigger at time t). Optionally, the observed extent of allergic reaction may be normalized based on a quantitative value representing how much the user was affected by the potential trigger (e.g., the observed extent may be normalized based on a dosage of a drug taken or the amount of time spent outdoors). Optionally, the effect of each potential trigger is calculated based on the observed extents of the allergic reactions following being affected by the potential trigger, as described above. In one example, the effect may be an average of the observed extents. In another example, the effect may be a value indicative of the proportion of the observed extents that reach a threshold. Following a calculation of the effects of the potential triggers, in one embodiment, the computer 376 selects the trigger 381 from among the potential triggers based on the effects.

In one embodiment, in order to increase confidence in the selection of the trigger 381, the trigger 381 is selected based on at least a certain number of times in which the user was affected by the trigger 381. For example, the certain number may be at least 3, 5, or 10 different times. Thus, in this embodiment, potential triggers that did not affect the user at least the certain number of times are not selected.

In some embodiments, the computer 376 generates a machine learning-based model based on the indications 380 and the extents of the allergic reaction, and selects the trigger 381 based on an analysis of the model. Optionally, the computer 376 generates samples used to train the model. In one embodiment, the samples may correspond to different times, with each sample corresponding to a time t+Δ including feature values and a label (target value) indicative of the extent of the allergic reaction of the user at the time t+Δ (where depending on the embodiment Δ may have a value between several minutes to 12 or even 24 hours). Optionally, Δ is at least one minute. Optionally, the label of each sample is determined based on values indicative of the extent of the allergic reaction at the time t+Δ or thereabouts (e.g., up to an hour before or after the time t+Δ). Optionally, the feature values are based on indications, from among the indications 380, which are indicative of the degree various potential trigger affected the user during a period [t, t+Δ]. Optionally, some of the feature values are indicative of how long before t+Δ some of the potential triggers affected the user and/or magnitudes of some of the potential triggers (e.g., amounts of food items consumed, dosages of drugs taken, etc.)

Each of the samples described above may be considered to represent a snapshot of potential triggers that affected the user during a certain period and a label that is indicative of the extent of the allergic reaction of the user following being affected by those potential triggers. Given multiple such samples, a machine learning training algorithm can be utilized to train a model for a predictor module that can predict the extent of the user's allergic reaction at a certain time based on feature values that describe the potential triggers that affected the user during a certain period of time leading up to the certain time. For example, if the model is a regression model, the predictor module may perform a dot product multiplication between a vector of regression coefficients (from the model) and a vector of the feature values in order to calculate a value corresponding to the predicted extent of the allergic reaction of the user at the certain time.

When such a predictor module is capable of predicting extents of the allergic reaction of the user based on the feature values described above, this may mean that the model captures, at least to some extent, the effects of at least some of the potential triggers on the extent of the allergic reaction of the user.

Training the model based on the samples described above may involve utilizing various training algorithms. Some examples of models that may be generated in order to be utilized by the predictor module described above include the following models: a regression model (e.g., a regression model), a naïve Bayes model, a Bayes network, a support vector machine for regression, a decision tree, and a neural network model, to name a few possibilities. There are various training algorithms known in the art for generating these models and other models with similar properties.

In some embodiments, the predictor module may be provided multiple inputs representing the potential triggers that affected the user at different points of time. For example, the predictor module may be provided with a series of vectors of feature values, each representing the potential triggers that affect the user during a period (e.g., during one minute, five minutes, thirty minutes, an hour, or six hours). In these embodiments, the predictor module may have a capability to store state information of previous inputs corresponding to earlier times when it comes to predict the extent of the allergic reaction of the user at a certain time. One example of a predictor module with such a capability is a predictor module that is based on a recurrent neural network.

Once the model is trained, it may be analyzed by the computer 376 to determine the effects of one or more of the potential triggers on the extent of the allergic reaction. Depending on the type of model that was trained, this analysis may be performed in different ways.

In one embodiment, the computer 376 performs the analysis of the model by evaluating parameters of the model that correspond to the potential triggers. Optionally, the computer 376 selects as the trigger 381 a certain potential trigger that has a corresponding parameter that is indicative of an effect that reaches a threshold while effects indicated in parameters corresponding to most of the potential triggers do not reach the threshold. In one example, the model may be a linear regression model in which each potential trigger corresponds to a regression variable. In this example, a magnitude of a value of a regression coefficient may be indicative of the magnitude of the effect of its corresponding potential trigger. In another example, the model may be a naïve Bayes model in which various classes correspond to extents of an allergic reaction (e.g., a binary classification model that is used to classify a vector of feature values to classes corresponding to allergic reaction vs, no allergic reaction). In this example, each feature value may correspond to a potential trigger, and the class conditional probabilities in the model are indicative of the magnitude of the effect of each of the potential triggers on the user.

In another embodiment, the computer 376 performs an analysis of the model, which may be characterized as "black box" analysis. In this approach, the predictor module is provided with various inputs that correspond to different potential triggers that affect the user, and calculates, based on the inputs and the model, various predicted extents of an allergic reaction of the user. The various inputs can be used to independently and individually increase the degree to which each of the potential triggers affects the user. This type of the model probing can help identify certain potential triggers that display an increase in the predicted extent of the allergic reaction, which corresponds to an increase in the degree to which the potential triggers affect the user (according to the model). Optionally, with the trigger 381 there is a positive correlation observed between increasing the degree to which the trigger 381 affects that user, and the predicted extent of the allergic reaction of the user. Optionally, the trigger 381 is selected from among the potential triggers, responsive to identifying that that: (i) based on a first subset of the various predicted extents of an allergic reaction of the user, an effect of the trigger 381 reaches a threshold, and (ii) based on a second subset of the various predicted extents of an allergic reaction of the user, effects of most of the potential triggers do not reach the threshold.

The indications 380 may be received from various sources. In one embodiment, the user may provide at least some of the indications 380 (e.g., by inputting data via an app and/or providing vocal annotations that are interpreted by a speech analysis software). In other embodiments, some indications 380 are provided by analysis of data sources. Optionally, the computer 376 generates some indications 380 based on the analysis of data obtained from the data sources. The following are some examples of data sources that may be utilized to identify potential triggers that affected the user at different times.

In a first example, a camera 383 captures images of the surroundings of the user. The camera 383 may be head-mounted or belong to a device of the user (e.g., a smartphone or a webcam). In one example, the camera 383 may belong to a camera-based systems such as OrCam (http://www.orcam.com/), which is utilized to identify various objects, products, faces, and/or recognize text. In another example, images captured by the camera 383 may be utilized to determine the nutritional composition of food a user consumes. Such an approach in which images of meals are utilized to generate estimates of food intake and meal composition, is described in Noronha, et al., "Platemate: crowdsourcing nutritional analysis from food photographs", Proceedings of the 24th annual ACM symposium on User interface software and technology, ACM, 2011.

In a second example, other sensors such as microphones, accelerometers, thermometers, pressure sensors, and/or barometers may be used to identify potential triggers that affect the user, by identifying what the user is doing (e.g., by analyzing movement patterns) and/or under what conditions (e.g., by analyzing ambient noise, temperature, and/or pressure).

In a third example, measurements of the environment that user is in are another source of information for determining potential stressor. The measurements may be received from a third party (e.g., a website that provides environmental information for various locations), and may indicate temperature, pressure, humidity, and/or particle counts for various types of chemicals or compounds (e.g. pollutants and/or allergens).

In a fourth example, Internet of Things (IoT) devices provide information when they are moved and/or utilized. Additionally or alternatively, communications of the user (e.g., email, text messages, voice conversations, and/or video conversations) may also be analyzed to provide context and/or to identify some potential stressors. Similarly, the user's calendar and/or schedule, as well as billing information, may provide information that may be used in some embodiments to identify potential stressors.

There are various approaches known in the art for identifying, indexing, and/or searching for potential triggers that may affect the user, which may be utilized in embodiments described herein. In one example, identifying potential triggers that may be done according to the teachings described in U.S. Pat. No. 9,087,058 titled "Method and apparatus for enabling a searchable history of real-world user experiences", which describes a searchable history of real-world user experiences of a user utilizing data captured by a mobile computing device. In another example, identifying potential triggers may be done according to the teachings described in U.S. Pat. No. 8,762,102 titled "Methods and systems for generation and rendering interactive events having combined activity and location information", which describes identification of events based on sensor data of mobile devices.

Knowledge of the trigger 381 may be utilized for various purposes. In one embodiment, the trigger 381 is utilized by a software agent operating on behalf of the user in order to better serve the user. For example, the software agent may ensure that food items that are ordered for the user do not include components that are known to trigger an allergic reaction (e.g., if the trigger 381 is a type of food). In another example, the software agent may plan routes for the user that do not include environments in which the trigger 381 may be present (e.g., if the trigger 381 is bloom).

In some embodiments, information about the trigger 381 is provided to the user via a UI 385. UI 385 may be utilized on a day-to-day basis to warn the user when the trigger 381 is detected. Optionally, a database may be consulted to determine whether the identified food items contain the trigger 381. If the trigger 381 is detected, the UI 385 may indicate that to the user.

Due to the mostly symmetric nature of the human body, when the face undergoes temperature changes, e.g., due to external factors such as the temperature in the environment or internal factors such as an activity-related rise in body temperature, the changes to the face are generally symmetric. That is, the temperature changes at a region of interest (ROI) on the left side of the face (e.g., the left side of the forehead) are similar to the temperature changes at the symmetric ROI on the right side of the face (e.g., the right side of the forehead). However, when the temperature on the face changes in an asymmetric way, this can be indicative of various physiological responses and/or undesirable phenomena. Some examples of phenomena that may be identified by detecting asymmetric thermal patterns ("thermal asymmetry") on a user's face include a headache, sinusitis, nerve damage, some types of strokes, orofacial pain, and Bell's palsy. Additionally, some forms of disorders such as Attention Deficit Hyperactivity Disorder (ADHD), stress, anxiety, and/or depression can also be identified based on thermal asymmetry of the forehead, and in some cases of other regions of the face.

In other cases, and sometime depending on personal characteristics of the user, certain physiological responses may manifest differently on different sides of the face. In particular, the temperatures at different positions on the right side of the face may not be a mirror image of the temperatures at the corresponding positions on the left side of the face. Thus, having two or more thermal cameras pointed at different areas of the face can, in some embodiments, help make more accurate detections of a physiological response. For example, stress may be manifested with some people by the cooling of an area on one side of the nose more than the symmetric area on the other side. Similarly, with some people, an allergic reaction may manifest by the nose heating to different extents on each of its sides. Thus, having, in this example, two or more thermal cameras pointed at different sides of the nose, may enable a more accurate detection of the physiological response.

Measuring and utilizing the asymmetric data also improves the robustness of the system against interferences that may cause an asymmetric thermal effect, such as an external heat source located to the user's side, a cooling air-conditioner that blows air from the top, touching and/or wiping one side of the face, and for some people also eating and/or conducting a physical activity. Therefore, utilizing thermal cameras pointed at symmetric ROIs may improve the system's ability to detect a physiological response compared to the case in which just one thermal camera is used.

In one embodiment, a system configured to collect thermal measurements indicative of thermal asymmetry on a user's face includes first and second inward-facing head-mounted thermal cameras (CAM1 and CAM2). Optionally, CAM1 and CAM2 are physically coupled to a frame worn on the user's head, and are located less than 15 cm, 5 cm, or 2 cm from the user's face. Optionally, CAM1 and CAM2 are located at least 0.5 cm to the right and to the left of the vertical symmetry axis that divides the face, respectively. Optionally, each of CAM1 and CAM2 weighs below 10 g, 5 g, or 1 g.

CAM1 and CAM2 take thermal measurements of regions on the right and left sides of the face ($TH_{ROI1}$ and $TH_{ROI2}$, respectively) of the user, and optionally do not occlude $ROI_1$ and $ROI_2$. Optionally, CAM1 and CAM2 are based on thermopile, microbolometer, or pyroelectric sensors, which may be focal-plane array sensors. Optionally, $ROI_1$ and $ROI_2$ have symmetric overlapping above 60%. In one example, CAM1 and CAM2 may be thermal cameras 120 and 122 in FIG. 25. In another example, CAM1 and CAM2 are thermal cameras 126 and 128 in FIG. 26.

The symmetric overlapping is considered with respect to the vertical symmetry axis that divides the face to the right and left portions. The symmetric overlapping between $ROI_1$ and $ROI_2$ may be observed by comparing the overlap between $ROI_1$ and a mirror image of $ROI_2$, where the mirror image is with respect to a mirror that is perpendicular to the front of the face and whose intersection with the face is along the vertical symmetry axis (which goes through the middle of the forehead and the middle of the nose). Depending on the application for which the thermal measurements are utilized, the ROIs may have different degrees of symmetric overlapping. In one example, the symmetric overlapping between $ROI_1$ and $ROI_2$ is above 80% of the smallest area from among the areas of $ROI_1$ and $ROI_2$. In another example, the overlap between $ROI_1$ and $ROI_2$ is above 25% and below 80% of the smallest area from among the areas of $ROI_1$ and $ROI_2$.

Depending on the locations of $ROI_1$ and $ROI_2$, in different embodiments, CAM1 and CAM2 may be located in specific locations on the frame and/or with respect to the face. In one example, $ROI_1$ and $ROI_2$ are on the nose and/or a region on the mouth, and CAM1 and CAM2 are located outside the exhale streams of the mouth and/or nostrils.

In one embodiment, each of CAM1 and CAM2 is located less than 10 cm from the face and there are angles greater than 20° between the Frankfort horizontal plane and the optical axes of CAM1 and CAM2.

Due to the angle between the optical axis of CAM1 and CAM2 and the Frankfort horizontal plane, in some embodiments, the Scheimpflug principle, may be employed in order to capture sharper images. For example, when the user wears the frame, CAM1 and/or CAM2 may have a certain tilt greater than 2° between their sensor and lens planes, in order to produce the sharper images.

In one embodiment, CAM1 and CAM2 utilize focal-plane array (FPA) sensors. Optionally, each FPA includes at least 6 or at least 12 sensing elements (pixels). Optionally, there are angles greater than 20° between the Frankfort horizontal plane and the optical axes of CAM1 and CAM2. Optionally, CAM1 is located to the right of the vertical symmetry axis and takes thermal measurements of a first region of interest ($TH_{ROI1}$), where $ROI_1$ covers more of the right side of the face than of the left side of the face; CAM2 is located to the left of the vertical symmetry axis and takes thermal measurements of a second region of interest ($TH_{ROI2}$), where $ROI_2$ covers more of the left side of the face than of the right side of the face. Optionally, the cameras do not occlude $ROI_1$ and $ROI_2$. Alternatively, the cameras occlude at least part of $ROI_1$ and $ROI_2$.

In some embodiments, the system for collecting thermal measurements indicative of thermal asymmetry on a user's face includes a computer. Optionally, the computer detects a physiological response based on the thermal measurements.

In one embodiment, the detection of the physiological response utilizes a personalized model of the user. Optionally, the computer (i) generates feature values based on $TH_{ROI1}$ and $TH_{ROI2}$, and (ii) utilizes a model to detect the physiological response based on the feature values. Optionally, at least some feature values used to detect the physiological response may be generated based on additional sources of information (other than CAM1 and CAM2), such as additional thermal cameras, additional sensors that measure physiological signals of the user (e.g., heart rate or galvanic skin response), and/or additional sensors that measure the environment. Optionally, the model is trained based on previous $TH_{ROI1}$ and $TH_{ROI2}$ taken while the user had the physiological response. Optionally, the physiological response involves the user experiencing stress, mental workload, fear, sexual arousal, anxiety, pain, a headache, dehydration, intoxication, and/or a stroke. Optionally, the physiological response is associated with facial thermal asymmetry, and the model was trained based on previous feature values taken during different days. Optionally, the previous feature values include: a first set of feature values generated based on $TH_{ROI1}$ and $TH_{ROI2}$ taken while the user had the physiological response, and a second set of feature values generated based on $TH_{ROI1}$ and $TH_{ROI2}$ taken while the user did not have the physiological response.

In different embodiments, the difference between $TH_{ROI1}$ and $TH_{ROI2}$ may be interpreted in different ways. In one embodiment, an extent of a physiological response may be proportional to the difference between $TH_{ROI1}$ and $TH_{ROI2}$ when the value of the difference is in a certain range. Optionally, when the value of the difference is outside of the range, this may be indicative of the occurrence of other phenomena (which are not the physiological response). In another embodiment, when the value of the difference between $TH_{ROI1}$ and $TH_{ROI2}$ reaches a threshold, that is indicative of an occurrence of the physiological response. In yet another embodiment, at least one feature value utilized by a predictor that predicts occurrences of the physiological response is based on the value of the difference between $TH_{ROI1}$ and $TH_{ROI2}$.

Often a change in the thermal asymmetry may be indicative of a physiological response. Optionally, the computer detects a change to thermal asymmetry on the face based on a change between thermal measurements taken at different times. The computer may further calculate the extent of the physiological response based on the change. This calculation can be performed in different ways, as described below.

In one embodiment, the computer calculates the change between the thermal measurements as follows: calculate a temperature difference between $ROI_1$ and $ROI_2$ at time x ($\Delta T_x$) based on [$TH_{ROI1}$, $TH_{ROI2}$] taken at time x, calculate a temperature difference between $ROI_1$ and $ROI_2$ at time y ($\Delta T_y$) based on [$TH_{ROI1}$, $TH_{ROI2}$] taken at time y, and calculate the output indicative of the change in the thermal asymmetry on the face based on a difference between $\Delta T_x$ and $\Delta T_y$.

The embodiment described above may optionally be implemented using a differential amplifier that receives $TH_{ROI1}$ and $TH_{ROI2}$ as inputs, and output the temperature difference between $ROI_1$ and $ROI_2$. Optionally, CAM1 and CAM2 are based on thermopile sensors. Alternatively, CAM1 and CAM2 are based on pyroelectric sensors. In one example, pairs of thermal sensor elements are wired as opposite inputs to a differential amplifier in order for the thermal measurements to cancel each other and thereby remove the average temperature of the field of view from the electrical signal. This allows CAM1 and CAM2 to be less prone to provide false indications of temperature changes in the event of being exposed to brief flashes of radiation or field-wide illumination. This embodiment may also minimize common-mode interference, and as a result improve the accuracy of the thermal cameras.

In another embodiment, the computer calculates the change between the thermal measurements as follows: calculate a temperature change between $TH_{ROI1}$ taken at times $t_1$ and $t_2$ ($\Delta TH_{ROI1}$), calculate a temperature change between $TH_{ROI2}$ taken at times $t_1$ and $t_2$ ($\Delta TH_{ROI2}$), and then calculate the output indicative of the thermal asymmetry on the face based on a difference between $\Delta TH_{ROI1}$ and $\Delta TH_{ROI2}$.

It is noted that sentences such as "calculate a difference between X and Y" or "detect a difference between X and Y" may be achieved by any function that is proportional to the difference between X and Y.

The computer may utilize the change in thermal asymmetry in order to detect a physiological response in various ways. For example, the change may be compared to a threshold, which if reached, is indicative of the occurrence of the physiological response. Optionally, the threshold needs to be reached a certain number of times and/or for a certain amount time, before it is assumed that the user experienced the physiological response. In another example, time series data that include changes to thermal asymmetry of the face may be compared to reference time series comprising changes in thermal asymmetry observed with the physiological response. In still another example, changes in thermal asymmetry may be utilized to generate feature values that are used along with a machine learning-based model to detect an occurrence of a physiological response (as discussed above).

Additional CAMs may be utilized to take thermal measurements used for detecting the physiological response. FIG. 24 illustrates one embodiment of a system that collects thermal measurements indicative of thermal asymmetry on a user's face, which involves additional CAMs. The system includes a frame 90, which has six CAMs coupled to it (some embedded in protruding arms). CAMs 91 and 92 are located on arms on the right and left sides of the top of the frame 90, respectively, and take thermal measurements of regions on the right and left sides of the forehead (97 and 98, respectively). CAMs 93 and 94 are located on the right and left sides of the frame 90 near the nose, respectively, and take thermal measurements of regions on the right and left periorbital areas (99 and 100), respectively. CAMs 95 and 96 are located on arms connected to the bottom of right and left rims, respectively, and take thermal measurements of right and left lower regions of the face (101 and 102, respectively). Optionally, some (or all) of the cameras contain multiple sensing elements.

In one embodiment, the system for collecting thermal measurements indicative of thermal asymmetry on a user's face further includes third and fourth CAMs (in addition to CAM1 and CAM2), each of which: weighs below 10 g, is physically coupled to the frame, and is located less than 15 cm from the face. The third and fourth CAMs take thermal measurements of regions on the right and left sides of the upper lip ($TH_{ROI3}$ and $TH_{ROI4}$, respectively) of the user, without occluding the upper lip. Optionally, the symmetric overlapping between the regions on the right and left sides of the upper lip is above 60%. Optionally, the system includes a computer that (i) generates feature values based on $TH_{ROI1}$, $TH_{ROI3}$, $TH_{ROI}$, and $TH_{ROI4}$, and (ii) utilizes a model to detect a physiological response based on the feature values. Optionally, the model was trained based on previous $TH_{ROI}$, $TH_{ROI2}$, $TH_{ROI3}$, and $TH_{ROI4}$ taken while the user had a physiological response associated with at least one of the following: stress, mental workload, fear, sexual arousal, anxiety, pain, a headache, dehydration, intoxication, and a stroke.

In another embodiment, $ROI_1$ and $ROI_2$ are on the right and left sides of the forehead, respectively, and the system further includes at least third and fourth CAMs, located less than 10 cm from the face, which take thermal measurements of regions on the right and left periorbital areas ($TH_{ROI3}$ and $TH_{ROI4}$, respectively). Optionally, the system includes a computer that utilizes a model to detect an emotional state and/or stress level based on $TH_{ROI1}$, $TH_{ROI2}$, $TH_{ROI3}$, and $TH_{ROI4}$. Optionally, the model was trained based on previous $TH_{ROI1}$, $TH_{ROI2}$, $TH_{ROI3}$, and $TH_{ROI4}$ taken during different days. Optionally, the system includes additional fifth and sixth CAMs, located less than 10 cm from the face, which take thermal measurements of regions on the right and left cheeks ($TH_{ROI5}$ and $TH_{ROI6}$, respectively). Optionally, the computer detects the physiological response also based on $TH_{ROI5}$ and $TH_{ROI6}$ (e.g., by generating based on $TH_{ROI5}$ and $TH_{ROI6}$ at least some of the feature values used to detect the physiological response).

In yet another embodiment, the system further includes third and fourth CAMs for taking thermal measurements of the environment to the right and to the left of the face ($TH_{ENV1}$ and $TH_{ENV2}$, respectively). The computer utilizes $TH_{ENV1}$ and $TH_{ENV2}$ to identify asymmetry resulting from the environment rather than from a physiological response. For example, the computer may generate feature values based on $TH_{ENV1}$ and $TH_{ENV2}$, and utilize these feature values, in addition to feature values generated based on thermal measurements of the ROIs on the face, in order to detect the physiological response. Optionally, the third and fourth CAMs are based on at least one of the following sensor types: a thermopile, a pyroelectric sensor, and a microbolometer. Optionally, the environmental cause of the asymmetry involves at least one of the following: sunlight, air blowing from an air-conditioner, radiation from a heater, and radiation from an oven.

The following examples of physiological responses may be identified utilizing embodiments of the system for collecting thermal measurements indicative of thermal asymmetry on a user's face.

There are various forms of sinusitis that may be detected utilizing different embodiments of the system. In one embodiment, $ROI_1$ and $ROI_2$ are on the right and left anterior sinuses, respectively. Optionally, the computer utilizes a model to detect sinusitis based on $TH_{ROI1}$ and $TH_{ROI2}$ (as described above). Optionally, the data used to train the model includes $TH_{ROI1}$ and $TH_{ROI2}$ taken from other users who suffer from maxillary sinusitis, frontal sinusitis, unilateral frontal sinusitis, and/or unilateral maxillary sinusitis. In a first example, $ROI_1$ and $ROI_2$ are on the right and left anterior sinus group, respectively. Optionally, the right/left anterior sinus group includes the right/left frontal sinus, the right/left maxillary sinus, and the right/left anterior ethmoid sinus. In a second example, $ROI_1$ and $ROI_2$ are on the user's right and left frontal sinuses, respectively, and the computer detects an occurrence of a unilateral frontal sinusitis. In a third example, $ROI_1$ and $ROI_2$ are on the user's right and left maxillary sinuses, respectively, and the computer detects an occurrence of a unilateral maxillary sinusitis.

Some forms of strokes may be detected using embodiments of the system. In a first example, $ROI_1$ and $ROI_2$ are on the right and left superficial temporal arteries. In a second example, each of $ROI_1$ and $ROI_2$ cover above 20%, or above 40%, of the right and left sides of the face that include exposed facial skin between the mouth level and the eyebrow level, respectively (e.g., the right and left cheeks and/or the right and left sides of the upper lip). Herein, "exposed facial skin" refers to facial skin that does not have excessive hair growth, such as a beard that usually damages the ability of CAM to measure the skin under the beard. In these two examples, a computer may detect whether the user has a stroke based on changes observed by comparing $TH_{ROI1}$ and $TH_{ROI2}$ taken from the user during different days. Optionally, if the probability that the user has a stroke reaches a certain threshold, such as at least 5%, 25%, or 50%, then the user and/or a third party are alerted about this finding so the user can receive immediate medical attention.

FIG. 34 illustrates a scenario in which an alert regarding a possible stroke is issued. The figure illustrates a user wearing a frame with at least two CAMs (562 and 563) for measuring ROIs on the right and left cheeks (ROIs 560 and 561, respectively). The measurements indicate that the left side of the face is colder than the right side of the face. Based on these measurements, and possibly additional data, the system detects the stroke and issues an alert. Optionally, the user's facial expression is slightly distorted and asymmetric, and a VCAM provides additional data in the form of images that may help detecting the stroke.

Various forms of nerve damage often cause detectable thermal differences on the face. At times, the thermal differences may manifest prior to changes to the appearance of the face. Thus, thermal measurements may be utilized for early detection of nerve damage, which may improve the outcome of a treatment. For example, in one embodiment, $ROI_1$ and $ROI_2$ may each be on the periorbital area around the eyes, the nose, and/or the mouth. Optionally, the computer may identify nerve damage based on changes observed by comparing $TH_{ROI1}$ and $TH_{ROI2}$ taken from the user during different days, and/or by using a model trained based on measurements of other users taken while they had nerve damages.

Headaches (which also include migraines), symptomatic behavior of Attention Deficit Hyperactivity Disorder (ADHD), and/or anger attacks are physiological responses that may also be detected by embodiments described herein. In one embodiment, detecting these physiological responses is done with a system in which $ROI_1$ and $ROI_2$ are on the right and left sides of the user's forehead. Alternatively, $ROI_1$ and $ROI_2$ may cover right and left regions on the periorbital areas, the nose, and/or the mouth. Optionally, the computer detects headaches utilizing a model that was trained based on previous $TH_{ROI1}$ and $TH_{ROI2}$ taken during different days, optionally including samples taken while the user had a headache and while the user did not have a headache.

Additionally, in some embodiments, a relationship between the stress the user feels and headache the user has may be studied. Optionally, the computer receive training data comprising physiological measurements indicative of levels of stress of the user, values indicative of durations during which the user felt stressed, and values indicative of durations during which the user had a headache. The computer utilizes a machine learning-based training algorithm to train the model based on the training data. The model may be used to detect a headache based on $TH_{ROI1}$ and $TH_{ROI2}$ and optionally, additional values indicative of stress the user felt.

Orofacial pain often results from dental causes (e.g., toothache caused by pulpitis or a dental abscess). Such pain may also be detected utilizing some embodiments of the system. In one embodiment, $ROI_1$ and $ROI_2$ are on the right and left sides of at least one of the jaws. Optionally, the computer detects orofacial pain based on $TH_{ROI1}$ and $TH_{ROI2}$ utilizing a model that was trained based on previous $TH_{ROI1}$ and $TH_{ROI2}$ taken during different days.

Bell's palsy is another medical disorder that may be identified based on thermal measurements. In one embodiment, the system includes a computer that detects Bell's palsy based on comparing $TH_{ROI1}$ and $TH_{ROI2}$ taken from the user during different days. Optionally, the system further includes a VCAM for taking photos of the face, and the computer analyzes the photos for asymmetry in order to improve the probability of identifying Bell's palsy. For example, the detection of Bell's palsy may be done based on feature values that include feature values generated based on the thermal measurements (e.g., corresponding to differences in values of thermal measurements at the same locations during different times), and feature values generated based on images taken by VCAM (e.g., corresponding to differences in facial features at the same locations during different times). Optionally, the system suggests the user to take a medical examination when the facial thermal asymmetry reaches a threshold for more than a predetermined duration (such as 1 minute, 5 minutes, or more than 30 minutes).

In one embodiment, a method for detecting a physiological response that causes a thermal asymmetry on a user's face includes the following steps: In step 1, taking, using first and second CAMs (CAM1 and CAM2), thermal measurements of regions on the right and left sides of the face ($TH_{ROI1}$ and $TH_{ROI2}$, respectively). The regions on the right and left sides of the face have a symmetric overlapping above 60%. CAM1 and CAM2 are less than 10 cm away from the face, and the angles between the Frankfort horizontal plane and the optical axes of CAM1 and CAM2 are greater than 20°. And in Step 2, detecting the physiological response based on $TH_{ROI1}$ and $TH_{ROI2}$.

In one embodiment, the method further includes the steps of (i) generating feature values based on $TH_{ROI1}$ and $TH_{ROI2}$, and (ii) utilizing a model to detect the physiological response based on the feature values. Optionally, the model was trained based on previous $TH_{ROI1}$ and $TH_{ROI2}$ taken while the user had a physiological response associated with stress, mental workload, fear, sexual arousal, anxiety, pain, a headache, dehydration, intoxication, and/or a stroke. Optionally, the previous $TH_{ROI1}$ and $TH_{ROI2}$ were taken on different days. Optionally, the method further alerts about the physiological response that causes the thermal asymmetry.

Some of the disclosed embodiments may be utilized to detect a stress level of a user based on thermal measurements of the user's face, such as the periorbital areas (i.e., areas around the eyes). In one embodiment, a system configured to detect a stress level includes a CAM and a computer.

CAM takes thermal measurements of a region on a periorbital area ($TH_{ROI1}$) of the user, and is located less than 10 cm from the user's head. The computer detects the stress level based on $TH_{ROI1}$.

In one embodiment, in which the region is on the periorbital area of the right eye, the system further includes a second inward-facing head-mounted thermal camera (CAM2), which is located less than 10 cm from the user's head and takes thermal measurements of a region on the periorbital area of the left eye ($TH_{ROI2}$). Optionally, the computer detects the stress level based on both $TH_{ROI1}$ and $TH_{ROI2}$. Optionally, CAM1 and CAM2 are located at least 0.5 cm to the right and to the left of the vertical symmetry axis (which goes through the middle of the forehead and the middle of the nose), respectively. Optionally, each of CAM1 and CAM2 weighs below 10 g and is based on a thermopile, a microbolometer, or a pyroelectric sensor, which may be a focal-plane array sensor.

It is to be noted that while various embodiments may utilize a single CAM, due to asymmetrical placement of blood vessels in the face, thermal emissions of faces of many people are asymmetric to a certain extent. That is, the pattern of thermal emission from the left side of the face may be different (possibly even noticeably different) from the pattern of thermal emission from the right side of the face. Thus, for example, the temperature changes at the periorbital areas, in response to experiencing at least a certain level of stress, may be asymmetric for some users. The fact that various embodiments described below may include two (or more) CAMs that take measurements of ROIs covering different sides of the face (referred to as $TH_{ROI1}$ and $TH_{ROI2}$) can enable the computer to account for the thermal asymmetry when detecting the stress level.

In some cases, interferences (such as an external heat source, touching one of the eyes, or an irritated eye) cause an asymmetric effect on the right and left periorbital areas. As a result, utilizing right and left CAMs, which are located in different angles relative to the interfering source, provides the computer additional data that can improve its performances. The following are some examples of various ways in which the computer may account for the asymmetry when detecting the stress level based on $TH_{ROI1}$ and $TH_{ROI2}$, which include measurements of the of regions on the periorbital areas of the right and left eyes of the user, respectively.

In one embodiment, when comparing $TH_{ROI1}$ and $TH_{ROI2}$ to thresholds, the computer may utilize different thresholds for $TH_{ROI1}$ and $TH_{ROI2}$, in order to determine whether the user experienced a certain level of stress. Optionally, the different thresholds may be learned based on previous $TH_{ROI1}$ and $TH_{ROI2}$, which were measured when the user experienced the certain level of stress and/or suffered from certain interferences.

In another embodiment, the computer may utilize different reference time series to which $TH_{ROI1}$ and $TH_{ROI2}$ are compared in order to determine whether the user experienced the certain level of stress. Optionally, accounting for the asymmetric manifestation of the stress is reflected in the fact that a reference time series to which $TH_{ROI1}$ is compared is different from a reference time series to which $TH_{ROI2}$ is compared.

In yet another embodiment, when the computer utilizes a model to calculate a stress level based on feature values generated based on $TH_{ROI1}$ and/or $TH_{ROI2}$. Optionally, the feature values include: (i) at least first and second feature values generated based on $TH_{ROI1}$ and $TH_{ROI2}$, respectively; and/or (ii) a third feature value indicative of the magnitude of a difference between $TH_{ROI1}$ and $TH_{ROI2}$. In this embodiment, the computer may provide different results for first and second events that involve the same average change in $TH_{ROI1}$ and $TH_{ROI2}$, but with different extents of asymmetry between $TH_{ROI1}$ and $TH_{ROI2}$, and/or different magnitudes of interferences on the right and left eyes.

In still another embodiment, the computer may utilize the fact that asymmetric temperature changes occur when the user experiences stress in order to distinguish between stress and other causes of temperature changes in the periorbital areas. For example, drinking a hot beverage or having a physical exercise may cause in some people a more symmetric warming pattern to the periorbital areas than stress. Thus, if such a more symmetric warming pattern is observed, the computer may refrain from identifying the temperature changes as being stress-related. However, if the warming pattern is asymmetric and corresponds to temperature changes in the periorbital areas of the user when the user experiences stress, then the computer may identify the changes in the temperatures being stress-related.

The computer may employ different approaches when detecting the stress level based on $TH_{ROI1}$ (and possibly other sources of data such as $TH_{ROI2}$). In one embodiment, the computer may compare $TH_{ROI1}$ (and possibly other data) to a threshold(s), which when reached would indicate a certain stress level. In another embodiment, the computer may generate feature values based on $TH_{ROI1}$ and $TH_{ROI2}$, and utilize a model (also referred to as a "machine learning-based model") to calculate a value indicative of the stress level based on the feature values (calculating the value indicative of the stress level may be considered herein as "detecting the stress level"). At least some of the feature values are generated based on $TH_{ROI1}$. Optionally, at least some of the feature values may be generated based on other sources of data, such as $TH_{ROI2}$ and/or $TH_{ROI3}$ (described below). Optionally, the model was trained based on samples comprising feature values generated based on previous $TH_{ROI1}$ (and possibly other data, as explained below), and corresponding labels indicative of a stress level of the user. Optionally, the data used to train the model includes previous $TH_{ROI1}$ taken while the user was under elevated stress, and other previous $TH_{ROI1}$ taken while the user was not under elevated stress. Optionally, "elevated stress" refers to a stress level that reaches a certain threshold, where the value of the threshold is set according to a predetermined stress scale (examples of stress scales are given further below). Optionally, "elevated stress" refers to a physiological state defined by certain threshold values of physiological signals (e.g., pulse, breathing rate, and/or concentration of cortisol in the blood).

In a first embodiment, when the stress level exceeds a certain value, $TH_{ROI1}$ reach a threshold, and when the stress level does not exceed the certain value, $TH_{ROI1}$ do not reach the threshold. Optionally, the stress level is proportional to the values of $TH_{ROI1}$ (which are thermal measurements of the region on the periorbital area), such that the higher $TH_{ROI1}$ and/or the higher the change to $TH_{ROI1}$ (e.g., with reference to a baseline), the higher the stress level.

In a second embodiment, the computer detects the stress level based on a difference between $TH_{ROI1}$ and a baseline value determined based on a set of previous measurements taken by CAM. Optionally, most of the measurements belonging to the set were taken while the user was not under elevated stress.

In a third embodiment, the stress level is detected using a model and feature values generated based on additional measurements ($m_{conf}$) of the user and/or of the environment in which the user was in while $TH_{ROI1}$ were taken, $m_{conf}$ may be taken by sensor 461. Optionally, $m_{conf}$ are indicative of an extent to which a confounding factor occurred while $TH_{ROI1}$ were taken. The following are some examples of sources of information for $m_{conf}$, which may be used to detect the stress level.

In a first example, $m_{conf}$ are physiological signals such as a heart rate, heart rate variability, galvanic skin response, a respiratory rate, and respiratory rate variability, which are taken using sensors such as PPG, ECG, EEG, GSR and/or a thermistor.

In a second example, $m_{conf}$ represent an environmental condition and/or a situation of the user that may be considered a confounding factor, such as an indication of whether the user touched at least one of the eyes, an indication of whether the user is engaged in physical activity (and possibly the type and/or extent of the physical activity), temperature, humidity, IR radiation level, and a noise level. Optionally, the one or more values are obtained based on using an accelerometer, a pedometer, a humidity sensor, a miniature radar (such as low-power radar operating in the range between 30 GHz and 3,000 GHz), a miniature active electro-optics distance measurement device (such as a miniature Lidar), an anemometer, an acoustic sensor, and/or a light meter.

In a third example, $m_{conf}$ represent properties describing the user, such as the user's age, gender, marital status, occupation, education level, health conditions, and/or mental health issues that the user may have.

Stress may be thought of as the body's method of reacting to a challenge. Optionally, stress may be considered a physiological reaction to a stressor. Some examples of stressors include mental stressors that may include, but are not limited to, disturbing thoughts, discontent with something, events, situations, individuals, comments, or anything a user may interpret as negative or threatening. Other examples of stressors include physical stressors that may put strain on the body (e.g., very cold/hot temperatures, injury, chronic illness, or pain). In one example, a (high) workload may be considered a stressor. The extent to which a user feels stressed is referred to herein as a "stress level" and being under a certain level of stress may be referred to herein as "experiencing a certain stress level". Depending on the embodiment, a stress level may be expressed via various types of values, such as a binary value (the user is "stressed" or "not stressed", or the user is under "elevated stress" or "not under elevated stress"), a categorial value (e.g., no stress/low stress/medium stress/high stress), and/or a numerical value (e.g., a value on a scale of 0 to 10). In some embodiments, a "stress level" may refer to a "fight or flight" reaction level.

Evaluation of stress typically involves determining an amount of stress a person may be feeling according to some standard scale. There are various approaches known in the literature that may be used for this task. One approach involves identifying various situations the person may be in, which are associated with certain predefined extents of stress (which are empirically derived based on observations). Example of popular approaches include the Holmes and Rahe stress scale, the Perceived Stress Scale, and the Standard Stress Scale (SSS). A common trait of many the various stress scales is that they require a manual evaluation of situations a user undergoes, and do not measure the actual physiological effects of stress.

In some embodiments, the computer may receive an indication of a type of stressor, and utilize the indication to detect the stress level. Optionally, the indication is indicative of a period and/or duration during which the user was affected by the stressor. In one example, the indication is utilized to select a certain threshold value, which is appropriate for the type of stressor, and to which $TH_{ROI1}$ may be compared in order to determine whether the user is experiencing a certain stress level. Optionally, the certain threshold is determined based on thermal measurements of the user when the user reacted to a stressor of the indicated type. In another example, the indication is utilized to select a certain reference time series, which corresponds to the type of stressor, and to which $TH_{ROI1}$ may be compared in order to determine whether the user is experiencing a certain stress level. Optionally, the certain time series is based on thermal measurements of the user taken when the user reacted to a stressor of the indicated type. In yet another example, the computer generates one or more feature values based on the indication, and the one or more feature values are utilized to detect the stress level using a model (in addition to feature values generated based on $TH_{ROI1}$). In still another example, the computer may select a window of time based on the indication, which corresponds to the expected duration of stress induced by the type of stressor indicated in the indication. In this example, in order to detect the stress level of the user, the computer evaluates thermal measurements from among $TH_{ROI1}$ that were taken at a time that falls in the window.

Additional CAMs may be utilized to detect the stress level. The thermal measurements of the additional CAMs, typically denoted $TH_{ROIi}$ below, may be utilized to generate one or more of the feature values that are used along with the machine learning-based model to detect the stress level.

In one embodiment, the system includes a second inward-facing head-mounted thermal camera (CAM2) that takes thermal measurements of an additional ROI on the face ($TH_{ROI2}$), such as the forehead, the nose, and/or a region below the nostrils. The region below the nostrils refer to one or more regions on the upper lip, the mouth, and/or air volume through which the exhale streams from the nose and/or mouth flow, and it's thermal measurements are indicative of the user's breathing.

Given $TH_{ROI2}$, the computer may generate feature values based on $TH_{ROI1}$ and $TH_{ROI2}$ (and possibly other sources of data) and utilizes a model to detect the stress level based on the feature values. Optionally, the model was trained based on previous $TH_{ROI1}$ and $TH_{ROI2}$ taken while the user had at least two different stress levels according to a predetermined stress scale. For example, a first set of previous $TH_{ROI1}$ and $TH_{ROI2}$ taken while the user was under elevated stress, and a second set of previous $TH_{ROI1}$ and $TH_{ROI2}$ taken while the user was not under elevated stress.

In another embodiment, the system further includes second and third CAMs that take thermal measurements of regions on the right and left cheeks, respectively. Optionally, the computer detects the stress level also based on the thermal measurements of the cheeks.

Figure 56:
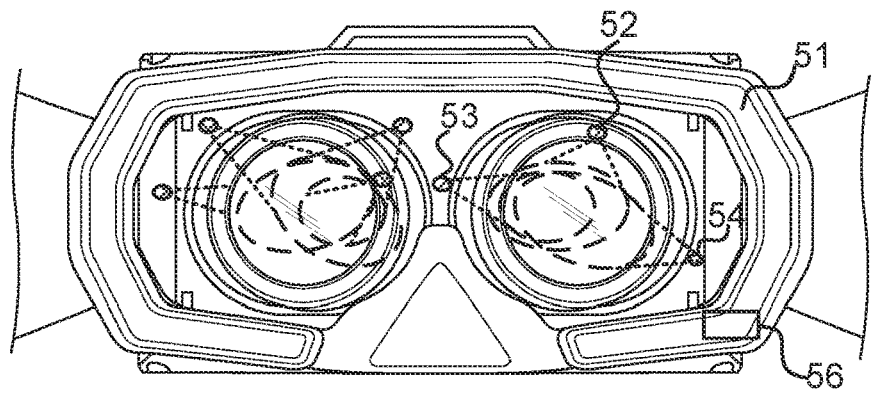
FIG. 56 illustrates an embodiment of an HMS able to measure stress level.

FIG. 56 illustrates one embodiment of an HMS able to measure stress level. The system includes a frame 51, CAMs (52, 53, 54), and a computer 56. CAMs are physically coupled to the frame and take thermal measurements of ROIs on the periorbital areas. Because CAMs are located close to their respective ROIs, they can be small, lightweight, and may be placed in many potential locations having line of sight to their respective ROIs. The computer 56, which may by located on the HMS, worn by the user, and/or remote such as in the cloud, detects the stress level based on changes to temperature of the periorbital areas received from the CAMs.

Due to the asymmetry of blood vessels in human faces and different shapes of human faces, having CAMs pointed at the right and left periorbital areas may enable a more accurate detection of physiological phenomena such as stress, and/or may enable detection of stress that is harder to detect based on measuring only a single periorbital area.

Figure 57:
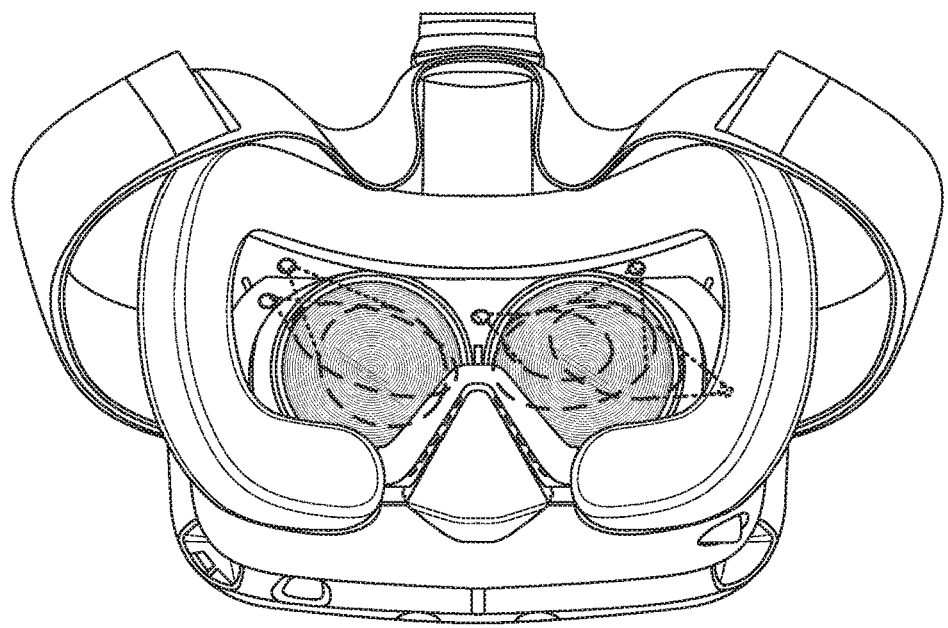
FIG. 57 illustrates examples of asymmetric locations of inward-facing head-mounted thermal cameras (CAMs) that measure the periorbital areas.
Figure 58:
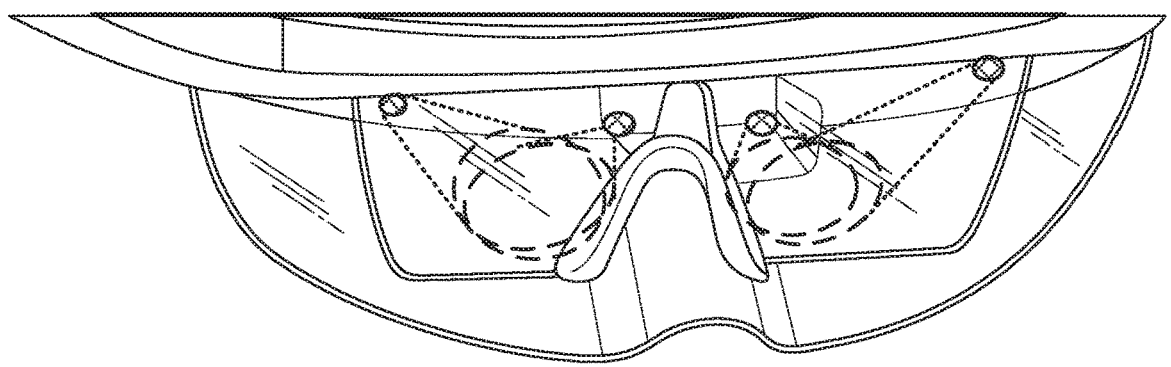
FIG. 58 illustrates an example of symmetric locations of the CAMs that measure the periorbital areas.

While FIG. 56 and FIG. 57 illustrate examples of asymmetric locations of CAMs that measure the right penorbital area relative to the locations of CAMs that measure the left periorbital area, FIG. 58 illustrates an example of symmetric locations of the CAMs that measure the right periorbital area relative to the locations of the CAMs that measure the left penorbital area. In some embodiments, using thermal measurements from both symmetric and asymmetric located CAMs may improve the system's adaptability to different faces having different proportions.

Figure 60A:
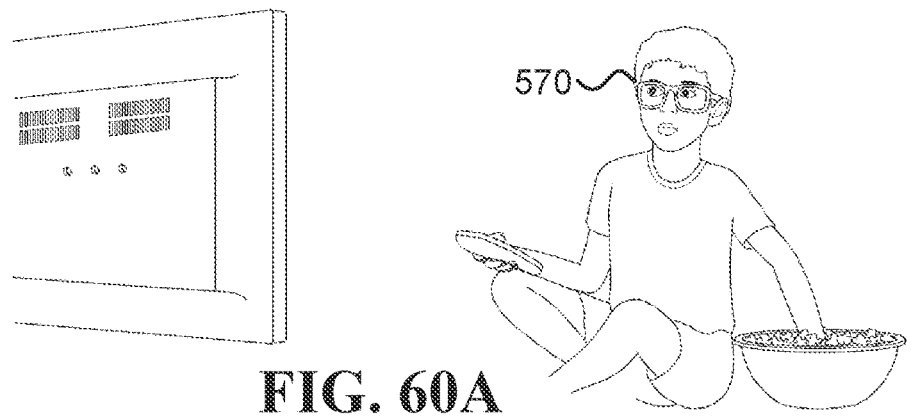
FIG. 60A illustrates a child watching a movie while wearing an eyeglasses frame with at least five CAMs.
Figure 60B:
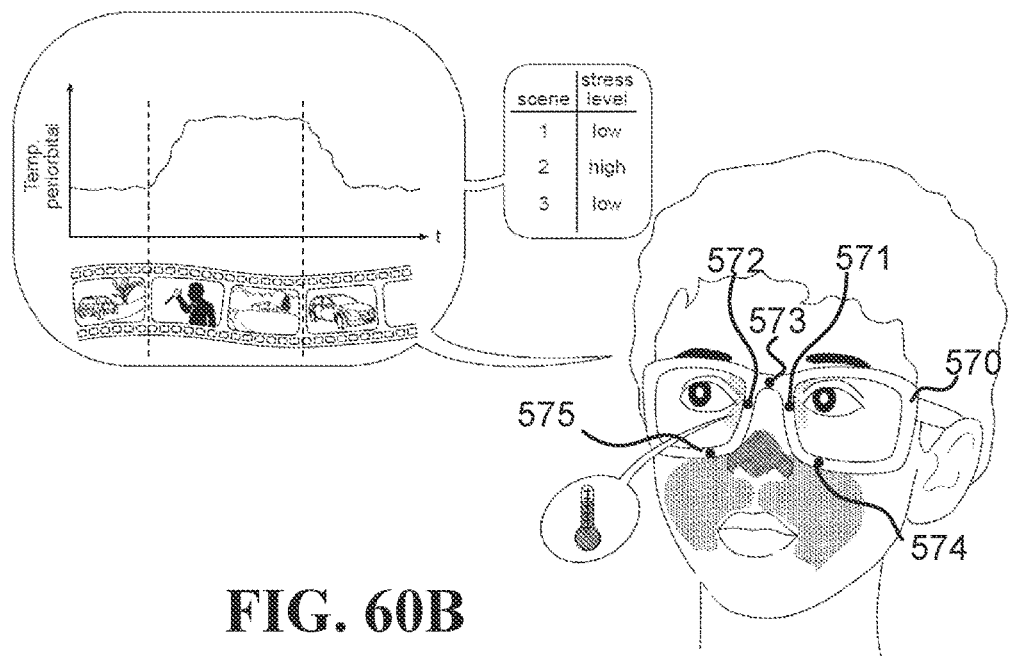
FIG. 60B illustrates generation of a graph of the stress level of the child detected at different times while different movie scenes were viewed.

FIG. 60A and FIG. 60B illustrate one scenario of detecting a user's stress level. FIG. 60A illustrates a child watching a movie while wearing an eyeglasses frame 570 with at least five CAMs. FIG. 60B illustrates the at least five CAMs 571, 572, 573, 574, and 575, which measure the right and left periorbital areas, the nose, and the right and left cheeks, respectively (the different ROIs are designated by different patterns). The figure further illustrates how the system produces a graph of the stress level detected at different times while different movie scenes were viewed.

In one embodiment, the system may include a head-mounted display (HMD) that presents digital content to the user and does not prevent CAM from measuring the ROI. In another embodiment, the system may include an eye tracker to track the user's gaze, and an optical see through HMD that operates in cooperation with the following components: a visible-light camera that captures images of objects the user is looking at, and a computer that matches the objects the user is looking at with the detected stress levels. Optionally, the eye tracker is coupled to a frame worn by the user. In yet another embodiment, the system may include a HMD that presents video comprising objects, and an eye tracker. The computer utilizes data generated by the eye tracker to match the objects the user is looking at with the detected stress levels. It is to be noted that there may be a delay between being affected by a stressor and a manifestation of stress as a reaction, and this delay may be taken into account when determining what objects caused the user stress.

Figure 62:
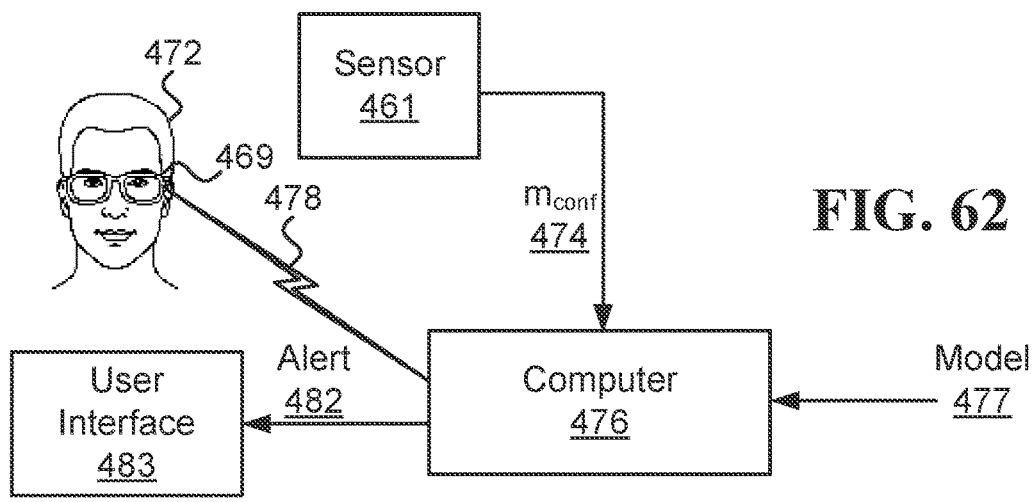
FIG. 62 illustrates an embodiment of a system that includes a user interface, which notifies a user when the stress level of the user reaches a predetermined threshold.

In one embodiment, the system further includes a user interface (UI), such as user interface 483 illustrated in FIG. 62, which notifies the user when the stress level reaches a predetermined threshold. Optionally, the UI notifies the user by an audio indication, a visual indication, and/or a haptic notification. Optionally, the greater the change to the temperature of the periorbital areas, the higher the detected stress level, and the indication is proportional to the stress level. Optionally, the UI also provides the user with encouragement not to engage in certain behavior that causes stress, such as displaying anger, screaming, denigrating others, lying, and/or cheating. In one example, the encouragement may include evidence based on detected stress levels of the user, which indicates that conducting in the certain behavior increases stress. In another example, the encouragement may include reminding the user that the certain behavior is against the user's beliefs and/or the certain behavior is contrary to the user's goals, interests, and/or resolutions.

In one embodiment, a system configured to alert about stress includes at least CAM1 and CAM2 located at least 0.5 cm to the right and to the left of the vertical symmetry axis that divides the user's face, respectively. CAM1 and CAM2 take thermal measurements of regions on the periorbital areas of the right and left eyes ($TH_{ROI1}$ and $TH_{ROI2}$, respectively) of the user. UI 483 provides an alert about a stress level reaching a threshold. Optionally, the system includes a frame that is worn on the user's head, CAM1 and CAM2 are physically coupled to the frame, weighs below 10 g each, and located less than 15 cm from the user's face. Optionally, the system includes a transmitter that may be used to transmit $TH_{ROI1}$ and $TH_{ROI2}$ to a computer that detects the stress level based on $TH_{ROI1}$ and $TH_{ROI2}$. Optionally, responsive to detecting a stress level that reaches a threshold, the computer commands the user interface to provide the alert. For example, the computer may send a signal to a smartphone app, and/or to a software agent that has control of the user interface, to provide the alert.

One embodiment of a method for alerting about stress includes at least the following steps: In Step 1, taking thermal measurements of regions on the periorbital areas of the right and left eyes ($TH_{ROI1}$ and $TH_{ROI2}$, respectively) of a user utilizing first and second CAMs worn on the user's head and located at least 0.5 cm to the right and to the left of the vertical symmetry axis that divides the users face, respectively. And in Step 2, alerting about a stress level that is detected based on $TH_{ROI1}$ and $TH_{ROI2}$. Optionally, the alert about the allergic reaction is provided as text, image, sound, and/or haptic feedback.

Optionally, the method further incudes generating feature values based on $TH_{ROI1}$ and $TH_{ROI2}$, and using a model for detecting the stress level based on the feature values. The model was trained based on previous $TH_{ROI1}$ and $TH_{ROI2}$ of the user, taken during different days, which include: a first set of measurements taken while the user had a first stress level according to a predetermined stress scale, and a second set of measurements taken while the user had a second stress level according to the predetermined stress scale.

Optionally, the method further incudes generating feature values based on $TH_{ROI1}$ and $TH_{ROI2}$, and using a model for detecting the stress level based on the feature values. The model was trained based on previous $TH_{ROI1}$ and $TH_{ROI2}$ of one or more users, taken during different days, which comprise: a first set of measurements taken while the one or more users had a first stress level according to a predetermined stress scale, and a second set of measurements taken while the one or more users had a second stress level according to the predetermined stress scale.

The above steps of generating the feature values and utilizing the model may be performed multiple times throughout the period of the different days during which $TH_{ROI1}$ and $TH_{ROI2}$ were taken, each time utilizing a subset of $TH_{ROI1}$ and $TH_{ROI2}$ taken during a different window of a certain length. In these embodiments, the alerting in Step 2 may be done at a certain time for which a certain stress level is detected (which warrants an alert).

Figure 59:
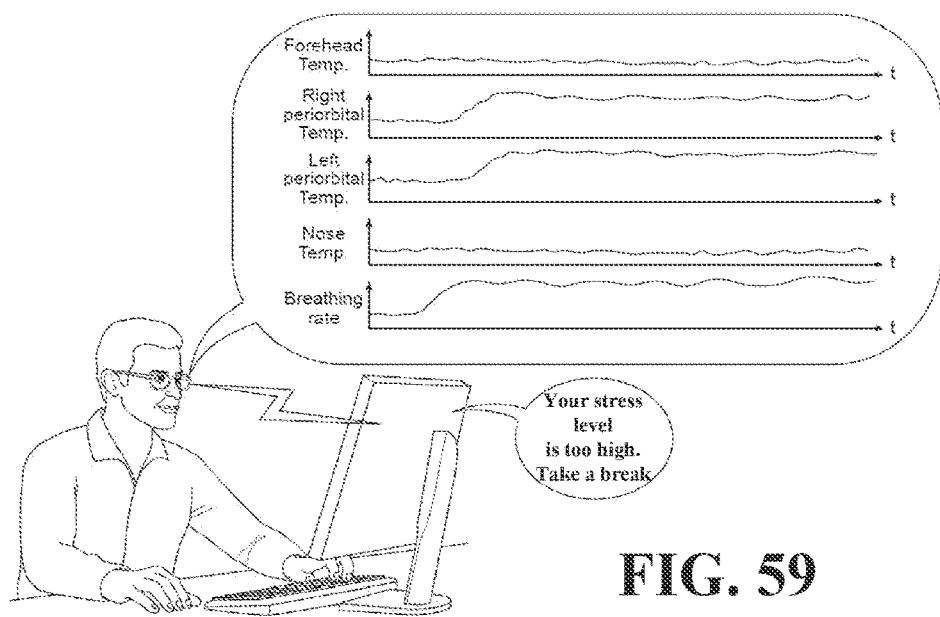
FIG. 59 illustrates a scenario in which a system suggests to the user to take a break in order to reduce the stress level.

FIG. 59 illustrates a scenario in which a system (which measures the forehead, right and left periorbital areas, nose, and below the nostrils) suggests to the user to take a break in order to reduce the stress level of the user. The system may suggest the user to partake in at least one of the following activities when the stress level reaches a first threshold: practice pranayama, physical exercise, listen to brainwave entrainment, and listen to positive loving statements. Optionally, the computer suggests to the user to stop the activity when the stress level gets below a second threshold. Optionally, the system shows the user video comprising objects, and the detected stress level associated with the objects.

Figure 61:
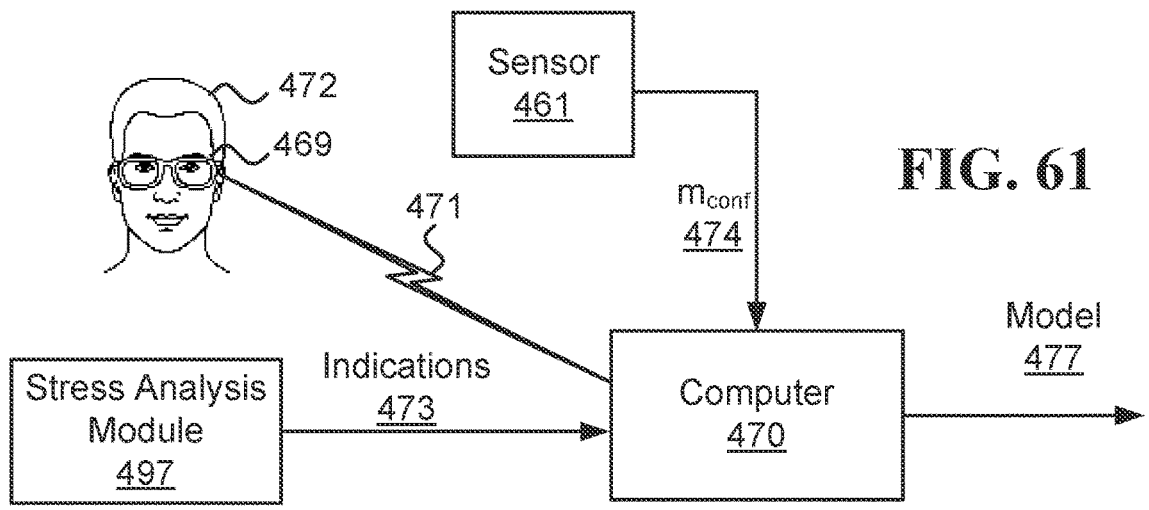
FIG. 61 illustrates an embodiment of a system that generates a personalized model for detecting stress based on thermal measurements of the face.

FIG. 61 illustrates one embodiment of a system configured to generate a personalized model for detecting stress based on thermal measurements of the face. The system includes a frame, first and second CAMs, and a computer 470. The first and second CAMs take thermal measurements 471 of regions on the periorbital areas of the right and left eyes ($TH_{ROI1}$ and $TH_{ROI2}$, respectively) of the user 472.

The computer 470 generates samples based on data comprising: (i) $TH_{ROI1}$ and $TH_{ROI2}$ 471, and (ii) indications 473 corresponding to different times, which are indicative of stress levels of the user at the different times. Optionally, each sample comprises: (i) feature values generated values based on $TH_{ROI1}$ and $TH_{ROI2}$ taken during a certain period, and (ii) a label indicative of a stress level of the user during the certain period. Optionally, at least one of the feature values in a sample may be generated based on other sources of information such as physiological measurements of the user 472 and/or measurements of the environment in which the user 472 was in when while $TH_{ROI1}$ and $TH_{ROI2}$ 471 were taken. Optionally, the stress levels indicated in the indications 473 correspond to levels of a known stress level scale. The computer 470 trains a model 477 based on the samples. Optionally, the computer 470 also provides the model 477 to be used by a system that detects stress based on $TH_{ROI1}$ and $TH_{ROI2}$.

The indications 473 may be generated in different ways, in different embodiments. One or more of the indications 473 may be (i) generated by an entity that observes the user 472, such as a human observer or a software program (e.g., a software agent operating on behalf of the user 472), (ii) provided by the user 472, such as via a smartphone app by pressing a certain button on a screen of a smartphone, and/or by speech that is interpreted by a software agent and/or a program with speech analysis capabilities, (iii) determined based on analysis of behavior of the user 472, such as by analyzing measurements of a camera and/or a microphone that indicate that the user 472 is experiencing a certain stress level, and (iv) determined based on physiological signals of the user 472 that are not thermal measurements of one or more ROIs on the face, such as measurements of the user's heart rate and/or brainwave activity.

Optional stress analysis module 497 receives descriptions of events corresponding to when at least some of $TH_{ROI1}$ and $TH_{ROI2}$ 471 were taken, and generates one or more of the indications 473 based on analyzing the descriptions. The stress analysis module 497 is implemented by the computer 470 or another computer. Optionally, all of the indications 473 are generated by the stress analysis module 497. Optionally, the stress analysis module 497 may be a module of a software agent operating on behalf of the user 472. The descriptions received by the stress analysis module 497 may include various forms of information. In one example, the descriptions include content of a communication of the user 472, and the stress analysis module 497 utilizes semantic analysis in order to determine whether the communication is indicative a stressful event for the user 472 (e.g., the communication is indicative of something going wrong at work). Optionally, the stress analysis module 497 utilizes a machine learning-based model to calculate based on features derived from the communication, a predicted stress level for the user 472. In another example, the stress analysis module 497 receives images of an event, such as images taken by an outward-facing head-mounted visible-light camera, utilizes image analysis to determine whether the event corresponds to a stressful event, and utilizes a machine learning-based model to calculate the predicted stress based on features derived from the images.

The model is trained on samples comprising feature values based on $TH_{ROI1}$ and $T_{ROI2}$, and additional feature values described in the following examples:

In a first example, the additional feature values include additional thermal measurements, taken with another CAM, of an ROI that includes the nasal and/or mouth regions.

In a second example, the additional feature values are indicative of one or more of the following signals of the user 472: a heart rate, heart rate variability, brainwave activity, galvanic skin response, muscle activity, and an extent of movement.

In a third example, the additional feature values are measurements ($m_{conf}$ 474) of the user 472 and/or of the environment in which the user 472 was in while $TH_{ROI1}$ and $TH_{ROI2}$ 471 were taken. Optionally, $m_{conf}$ 474 are taken by a sensor 461, which may be physically coupled to the frame. In another example, the sensor 461 is coupled to a device carried by the user, such as a smartphone, a smartwatch, and/or smart clothing (e.g., clothing embedded with sensors that can measure the user and/or the environment). In yet another example, the sensor 461 may be an external sensor that is not carried by the user. Optionally, the computer 470 is generates, based on $m_{conf}$ 474, one or more feature values of at least some of the samples, $m_{conf}$ 474 are indicative of an extent to which one or more confounding factors occurred while $TH_{ROI1}$ and $TH_{ROI2}$ 471 were taken.

In one embodiment, the sensor 461 is a visible-light camera physically coupled to the frame, which takes images of a region on the face of the user 472, which includes at least 25% of the $ROI_1$ and/or $ROI_2$. Optionally, the confounding factor in this embodiment involves inflammation of the skin, skin blemishes, food residues on the face, talking, eating, drinking, and/or touching the face. In another embodiment, the sensor 461 includes a movement sensor that measures a movement of the user 472. Optionally, the confounding factor in this embodiment involves the user 472 walking, running, exercising, bending over, and/or getting up from a sitting or lying position. In yet another embodiment, the sensor 461 measures at least one of the following environmental parameters: a temperature of the environment, a humidity level of the environment, a noise level of the environment, air quality in the environment, a wind speed in the environment, an extent of precipitation in the environment, and an infrared radiation level in the environment.

In some embodiments, the samples used to train the model 477 include samples that were generated based on $TH_{ROI1}$ and $TH_{ROI1}$ of the user 472 taken while the user 472 had different stress levels. In one embodiment, one or more samples that were generated based on $TH_{ROI1}$ and $TH_{ROI2}$ of the user 472 taken while a stress level of the user 472 reached a threshold. Optionally, the stress level is evaluated using one or more known stress level scales. Optionally, a user whose stress level reaches the threshold is considered "stressed". Additionally, in this embodiment, the samples include one or more samples that were generated based $TH_{ROI1}$ and $TH_{ROI2}$ of the user 472, which were taken while a stress level of the user 472 did not reach the threshold. Optionally, a user whose stress level does not reach the threshold is not considered "stressed". Thus, the samples may be utilized to train a model that can help distinguish between cases in which $TH_{ROI1}$ and $TH_{ROI2}$ of the user 472 are taken while the user 472 is stressed (and/or the user 472 has a certain stress level), and cases in which $TH_{ROI1}$ and $TH_{ROI2}$ of the user 472 are taken while the user 472 is not stressed (and/or the user 472 does not have a certain stress level).

The samples used to train the model 477 may include samples generated based on measurements taken while user 472 was in different environments. In one example, the samples comprise first and second samples that are based on $TH_{ROI1}$ and $TH_{ROI2}$ of the user 472 taken during first and second periods, respectively. Optionally, different environmental conditions prevailed during the first and second periods, which involved one or more of the following differences: (i) the temperature of the environment in which the user 472 was during the first period was at least 10° C., higher than the temperature of the environment in which the user 472 was during the second period; (ii) the humidity level in the environment in which the user 472 was during the first period was at least 30% higher than the humidity level in the environment in which the user 472 was during the second period; and (iii) the user 472 was exposed to rain, hail, and/or snow during the first period and the user was not exposed to any of rain, hail, and snow during the second period.

Additionally or alternatively, the samples utilized to train the model 477 may include samples generated based on measurements taken while the user 472 was in various situations. In one example, the samples comprise first and second samples that are based on $TH_{ROI1}$ and $TH_{ROI2}$ of the user 472 taken during first and second periods, respectively. Optionally, the user 472 was in different situations during the first and second periods, which involved one or more of the following differences: (i) the user 472 was sedentary during the first period, while the user 472 was walking, running, and/or biking during the second period; and (ii) the user 472 was indoors during the first period, while the user 472 was outdoors during the second.

Additionally or alternatively, the samples utilized to train the model 477 may be based on $TH_{ROI1}$ and $TH_{ROI2}$ taken during different days and/or over a long period, such as more than a week, more than a month, or more than a year.

Training the model 477 may involve one or more of the various computational approaches mentioned in this disclosure for training a model used to detect a physiological response. In one example, training the model 477 may involve selecting, based on the samples, a threshold; if a certain feature value reaches the threshold then a certain level of stress of the user is detected. In another example, the computer 470 utilizes a machine learning-based training algorithm to train the model 477 based on the samples. Optionally, the model comprises parameters of at least one of the following models: a regression model, a model utilized by a neural network, a nearest neighbor model, a model for a support vector machine for regression, and a model of a decision tree.

In some embodiments, the computer 470 may utilize deep learning algorithms to train the model 477. In one example, the model 477 may include parameters describing multiple hidden layers of a neural network. In one embodiment, when $TH_{ROI1}$ and $TH_{ROI2}$ include measurements of multiple pixels, such as when CAM includes a FPA, the model 477 may include parameters of a convolution neural network (CNN). In one example, a CNN may be utilized to identify certain patterns in the thermal images, such as patterns of temperatures on the forehead that may be indicative of a certain physiological response (e.g., a headache, stress, or anger). In another embodiment, detecting the stress level may be done based on multiple, possibly successive, measurements. For example, stress may involve a progression of a state of the user (e.g., a gradual warming of certain areas of the forehead). In such cases, detecting the stress level may involve retaining state information that is based on previous measurements. Optionally, the model 477 may include parameters that describe an architecture that supports such a capability. In one example, the model 477 may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

In one embodiment, training the model 477 involves altering parameters of another model, which is generated based on $TH_{ROI1}$ and $TH_{ROI2}$ of one or more other users. For example, the computer 470 may utilize the other model as an initial model. As the samples are acquired from measurements of the user 472, the computer 470 may update parameters of the initial model based on the samples. Thus, this process may be considered personalizing a general model according to measurements of the user 472.

Once the model 477 is generated, it may be utilized to detect stress of the user 472 based on other $TH_{ROI1}$ and $TH_{ROI2}$ of the user 472, which are not among $TH_{ROI1}$ and $TH_{ROI2}$ 471 that were used for training the model 477. Such utilization of the model 477 is illustrated in FIG. 62, which illustrates one embodiment of a system configured to perform personalized detection of stress based on thermal measurements of the periorbital area. One embodiment of the illustrated system includes a frame 469, first and second CAMs, and a computer 476.

The computer 476 is configured to: generate feature values based on $TH_{ROI1}$ and $TH_{ROI2}$ 478 and utilize the model 477 to detect the stress level of the user 472 based on the feature values. Optionally, the model 477 was trained based on previous $TH_{ROI1}$ and $TH_{ROI2}$ of the user 472 (e.g., $TH_{ROI1}$ and $TH_{ROI2}$ 471), which were taken during different days. The feature values generated based on $TH_{ROI1}$ and $TH_{ROI2}$ 478 are similar in their nature to the feature values generated based on $TH_{ROI1}$ and $TH_{ROI2}$ 471, which were discussed in more detail above. Optionally, the computer 476 and the computer 470 may utilize the same modules and/or procedures to generate feature values based on $TH_{ROI1}$ and $TH_{ROI2}$ (and possibly other data). Optionally, the computer 476 receives measurements $m_{conf}$ 474 indicative of an extent to which a confounding factor occurred while $TH_{ROI1}$ and $TH_{ROI2}$ 478 were taken, as discussed above.

Since the model 477 is personalized for the user 472, when such a model is trained for different users, it may lead to different detections of stress, even when provided with similar $TH_{ROI1}$ and $TH_{ROI2}$ of the users. In one example, first and second models are generated based on previous $TH_{ROI1}$ and $TH_{ROI2}$ of first and second different users, respectively. Responsive to utilizing the first model, a first value is detected based on first feature values generated based on $TH_{ROI1}$ and $TH_{ROI2}$ of the first user, which is indicative of a first stress level. Responsive to utilizing the second model, a second value is detected based on second feature values generated based on $TH_{ROI1}$ and $TH_{ROI1}$ of the second user, which is indicative of a second stress level. In this example, $TH_{ROI1}$ and $TH_{ROI2}$ of the first user indicate a greater temperature change at the periorbital areas of the first user compared to the change at the periorbital areas of the second user indicated by $TH_{ROI1}$ and $TH_{ROI2}$ of the second user. However, in this example, the first stress level is lower than the second stress level.

Some aspects of this disclosure involve monitoring a user over time with CAM that takes thermal measurements of a region on a periorbital area ($TH_{ROI1}$) of the user. One application for which $TH_{ROI1}$ may be useful is to detect the stress level of the user. Analysis of these detections combined with information regarding factors that affected the user at different times, which may be considered potential stressors, can reveal which of the factors may be stressor that increase the stress level of the user.

Some examples of factors that may be considered potential stressors for certain users include being in certain locations, interacting with certain entities, partaking in certain activities, or being exposed to certain content. Having knowledge of which potential stressor are likely to actually be stressors for a certain user can help that user avoid the stressors and/or take early measures to alleviate the effects of the stress they cause.

Figure 63:
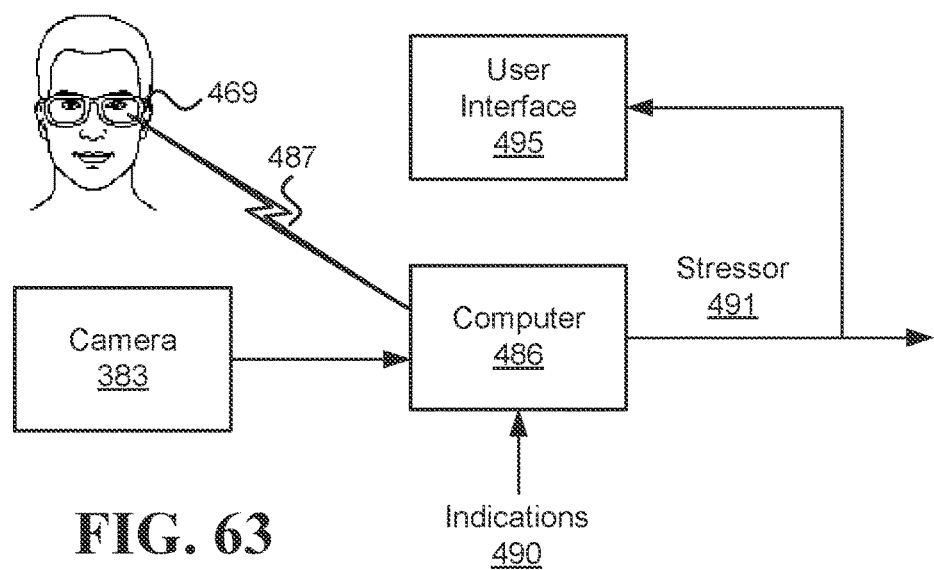
FIG. 63 illustrates an embodiment of a system that selects a stressor.

FIG. 63 illustrates one embodiment of a system configured to select a stressor. The system includes at least a computer 486 and CAM. The system may optionally include a frame 469, a camera 383, and/or a UI 495. In one example, CAM takes thermal measurements of the periorbital area of the right eye, and an additional CAM (CAM2) takes thermal measurements of a region on the periorbital area of the left eye ($TH_{ROI2}$) of the user.

In one embodiment, computer 486 calculates, based on the thermal measurements 487 (e.g., $TH_{ROI1}$ and $TH_{ROI2}$), values that are indicative of stress levels of the user at different times (i.e., detect the stress levels of the user at the different times). Optionally, $TH_{ROI1}$ and $TH_{ROI2}$ include thermal measurements taken while the user had at least two different stress levels according to a predetermined stress scale. Optionally, the thermal measurements 487 comprise thermal measurements taken during different days.

In some embodiments, the system that selects a stressor may include additional CAMs that take thermal measurements of one or more regions on the user's forehead, nose, and/or below the nostrils. Optionally, thermal measurements taken by the additional CAMs are utilized by the computer 486 when calculating the user's stress level.

Furthermore, the computer 486 may receive indications 490 of factors that affected the user at various times, which may be considered potential stressors. The computer 486 also selects a stressor 491, from among the potential stressors, based on the indications 490 and the values that are indicative of stress levels of the user at different times. Optionally, each of the indications 490 is indicative of a time during which the user was exposed to a potential stressor. Additionally or alternatively, each of the indications 490 may be indicative of a time during which the user was affected by a potential stressor. In some embodiments, at any given time, the user may be exposed to more than one of the potential stressors. Thus, in some embodiments, at least some of the thermal measurements 487, and optionally all of the thermal measurements 487, were taken while the user was exposed to two or more potential stressors.

In one embodiment, the indications 490 include a list of periods of time during which various potential stressors affected the user. Optionally, the indications 490 are provided via a data structure and/or a queryable system that provides information for different points in time about which of the potential stressors affected the user at the points in time. There are various types of potential stressors that may be indicated by the indications 490.

In one embodiment, one or more of the potential stressors may relate to various locations the user was at (e.g., work, school, doctor's office, in-laws house, etc.) and/or to various activities the user partakes in (e.g., driving, public speaking, operating machinery, caring for children, choosing clothes to wear, etc.)

In another embodiment, one or more of the potential stressors may relate to entities with which the user interacts. For example, an entity may be a certain person, a person with a certain role (e.g., a teacher, a police officer, a doctor, etc.), a certain software agent, and/or an avatar (representing a person or a software agent).

In yet another embodiment, one or more of the potential stressors may relate to situations in which the user is in, which can increase stress. For example, a situation may be being unemployed, having financial difficulties, being separated after being in a relationship with another person, being alone, or awaiting an important event (e.g., an exam, a job interview, or results of an important medical test). In another example, a situation may relate to a physical condition of the user, such as being sick or suffering from a certain chronic disease. Optionally, when the situations described above are applicable to another person who the user cares about (e.g., a spouse, child, parent, or close friend), then those situations, which relate to the other person, may be considered potential stressors that can lead to stress in the user.

In still another embodiment, one or more of the potential stressors may relate to the user's behavior. For example, behaving in a way that is argumentative, manipulative, deceptive, and/or untruthful may increase the stress level.

When a user is affected by one or more potential stressors, in some embodiments, the stress level of the user may depend on quantitative aspects of the potential stressors. In some examples, the degree to which a potential stressor affects the user's stress level may depend on the amount of time the potential stressor affected the user (e.g., the duration the user spent at a certain location) and/or the magnitude of the potential stressor (e.g., the extent to which an argument was heated—which may be expressed by the level of noise in peoples shouting). In some embodiments, the indications 490 include values that quantify how much at least some of the potential stressors affected the user.

The stressor 491 is a potential stressor that is correlated with an increase in the stress level of the user. Additionally, in some embodiments, the stressor 491 may be a potential stressor that may be considered a direct cause of the increase in the stress level of the user. When considering how being affected by the potential stressors relates to the stress level of the user, an effect of the stressor 491 is higher than effects of most of the potential stressors.

The effect of a potential stressor may be considered a measure of how much the potential stressor influences the stress level the user. This can range from no influence to a profound influence. More specifically, in one embodiment, the effect of a potential stressor is a value indicative of the average extent of change to the stress level of the user at a time t+Δ after being affected by the potential stressor at time t. Here, Δ corresponds to the typical time it may take the stress to manifest itself in the user after being affected by the potential stressor. This time may range from a short period e.g., several seconds or minutes, to hours.

There are various ways in which the computer 486 may select, based on the indications 490 and the thermal measurements 487, the stressor 491 from among the potential stressors being considered.

In some embodiments, the computer 486 performs a direct analysis of the effect of each of the potential stressors in order to identify which ones have a large effect on the user. Optionally, the effect of each potential stressor is indicative of the extent to which it increases the stress level of the user. Optionally, the effect of each potential stressor is calculated by determining, based on the indications 490, times at which the user was affected by the potential stressor, and observing the stress level of the user at one or more times that are up to a certain period Δ later (where Δ depends on the user and the type of stressor). In one example, Δ is ten seconds, thirty seconds, or one minute. In another example, Δ is one minute, ten minutes, or one hour.

In one embodiment, a stress level (or change to the stress level) following being affected by a potential stressor is the maximum stress level that is detected from the time t the user was affected by the potential stressor until the time t+Δ. In another example, the stress level (or change to the stress level) following being affected by the potential stressor is the extent of the stress level and/or change to the stress level that is detected at a time t+Δ (when the user was affected by the potential stressor at time t). Optionally, the extent may be normalized based on a quantitative value representing how much the user was affected by the potential stressor. Optionally, the stress level may be normalized with respect to a stress level detected prior to being affected by the potential stressor.

Following a calculation of the effects of the potential stressors, in one embodiment, the computer 486 selects the stressor 491 from among the potential stressors. Optionally, the stressor 491 is a potential stressor that has a maximal effect (i.e., there is no other potential stressor that has a higher effect). Optionally, the stressor 491 is a potential stressor that has an effect that reaches a threshold, while the effects of most of the potential stressors do not reach the threshold.

In one embodiment, in order to increase confidence in the selection of the stressor, the stressor 491 is selected based on at least a certain number of times in which the user was affected by the stressor 491. For example, the certain number may be at least 3 or 10 different times. Thus, in this embodiment, potential stressors that did not affect the user at least the certain number of times are not selected.

In some embodiments, the computer 486 generates a machine learning-based model based on the indications 490 and the values indicative of the stress levels of the user, and selects the stressor 491 based on an analysis of the model. Optionally, the computer 486 generates samples used to train the model. The samples used to train the model may correspond to different times, with each sample corresponding to a time t+Δ including feature values and a label indicative of the stress level of the user at the time t+Δ. Each sample may be considered to represent a snapshot of potential stressors that affected the user during a certain period, and a label that is indicative of the stress level of the user following being affected by those potential stressors. Given multiple such samples, a machine learning training algorithm can be utilized to train a model for a predictor module that can predict the stress level at a certain time based on feature values that describe potential stressors that affected the user during a certain period of time leading up to the certain time. For example, if the model is a regression model, the predictor module may perform a dot product multiplication between a vector of regression coefficients (from the model) and a vector of the feature values in order to calculate a value corresponding to the predicted stress level of the user at the certain time.

When such a predictor module is capable of predicting stress level of the user based on the feature values described above, this may mean that the model captures, at least to some extent, the effects of at least some of the potential stressors on the stress level of the user.

Training the model based on the samples described above may involve utilizing one or more of various training algorithms. Some examples of models that may be generated in order to be utilized by the predictor module described above include the following models: a regression model (e.g., a regression model), a naïve Bayes model, a Bayes network, a support vector machine for regression, a decision tree, and a neural network model, to name a few possibilities. There are various training algorithms known in the art for generating these models and other models with similar properties.

The predictor module may be provided multiple inputs representing the potential stressors that affected the user at different points of time, and have a capability to store state information of previous inputs corresponding to earlier times when it comes to predict the stress level of the user at a certain time. For example, the predictor module may be based on a recurrent neural network.

Once the model is trained, in some embodiments, it is analyzed by the computer 486 in order to determine the effects of one or more of the stressors on the stress level of the user. Depending on the type of model that was trained, this analysis may be performed in different ways.

In one embodiment, the computer 486 performs the analysis of the model by evaluating parameters of the model that correspond to the potential stressors. Optionally, the computer 486 selects as the stressor 491 a certain potential stressor that has a corresponding parameter that is indicative of an effect that reaches a threshold while effects indicated in parameters corresponding to most of the stressors do not reach the threshold. In one example, the model may be a linear regression model in which each potential stressor corresponds to a regression variable. In this example, a magnitude of a value of a regression coefficient may be indicative of the extent of the effect of its corresponding potential stressor. In another example, the model may be a naïve Bayes model in which various classes correspond to stress levels (e.g., a binary classification model that is used to classify a vector of feature values to classes corresponding to "stressed" vs. "not stressed"). In this example, each feature value may correspond to a potential stressor, and the class conditional probabilities in the model are indicative of the effect of each of the potential stressors on the user.

In another embodiment, the computer 486 performs an analysis of the model, which may be characterized as "black box" analysis. In this approach, the predictor module is provided with various inputs that correspond to different potential stressors that affect the user, and calculates, based on the inputs and the model, various predicted stress levels of the user. The various inputs can be used to independently and/or individually increase the extent to which each of the potential stressors affects the user. This type of the model probing can help identify certain potential stressors that display an increase in the predicted stress level, which corresponds to an increase in the extent to which the potential stressors affect the user (according to the model). Optionally, the stressor 491 is a potential stressor for which a positive correlation is observed between increasing the extent to which the potential stressor affects that user, and the predicted stress level of the user. Optionally, the stressor 491 is selected from among the potential stressors, responsive to identifying that: (i) based on a first subset of the various predicted stress levels of the user, an effect of the stressor 491 reaches a threshold, and (ii) based on a second subset of the various predicted stress levels of the user, effects of most of the potential stressors do not reach the threshold.

The indications 490 may be received from various sources. In one embodiment, the user may provide at least some of the indications 490 (e.g., by inputting data via an app and/or providing vocal annotations that are interpreted by a speech analysis software). In other embodiments, at least some of the indications 490 are provided by analysis of one or more sources of data. Optionally, the computer 486 generates one or more of the indications 490 based on an analysis of data obtained from the one or more sources. The following four examples, discussed herein in relation to allergy, arm also relevant as examples of sources of data that may be utilized to identify potential stressors that affected the user at different times: (i) a camera 383 captures images of the surroundings of the user, (ii) sensors such as microphones, accelerometers, thermometers, pressure sensors, and/or barometers may be used to identify potential stressors by identifying what the user is doing and/or under what conditions, (iii) measurements of the environment that user is in, and (iv) IoT devices, communications of the user, calendar, and/or billing information may provide information that may be used in some embodiments to identify potential stressors.

Knowledge of the stressor 491 may be utilized for various purposes. Optionally, the knowledge of the stressor 491 is utilized by a software agent operating on behalf of the user in order to better serve the user. In some embodiments, information about the stressor 491 is provided to the user via a UI 495, such as a smartphone, HMD, and/or an earphone).

UI 495 may be utilized on a day-to-day basis to warn the user when the stressor 491 is detected. For example, the computer 486 may provide real-time indications of potential stressors. Upon detecting that those potential stressors include the stressor 491, the UI notifies the user about the stressor in order for the user to take action, such as reducing exposure to the stressor (e.g., by leaving a certain location or ceasing a certain activity) and/or performing actions aimed at reducing stress (e.g., a breathing exercises).

In one embodiment, a software agent identifies that the user is going to be affected by the stressor 491 (e.g., by analyzing the user's calendar schedule and/or communications), and suggests the user, via UI 495, to perform various exercises (e.g., breathing exercises) and/or prepare himself for the stressor 491 in order to reduce its effect.

With little modifications, the system illustrated in FIG. 63 may be utilized to detect a calming factor that reduces the user's stress, rather than one that increases it. In particular, instead of selecting a stressor that has a large effect (or maximal effect) on the user, a factor that has a large negative effect on the stress level may be selected. Optionally, in the event that a high stress level of the user is detected, the calming factor may be suggested to the user (to reduce the user's stress level).

The following is a description of steps involved in one embodiment of a method for selecting a stressor. The steps described below may be used by systems modeled according to FIG. 63, and may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform operations of the method. In one embodiment, the method for alerting about stress includes at least the following steps:

In Step 1, taking, utilizing a CAM, thermal measurements of a region on a periorbital area ($TH_R(oi)$) of a user who wears CAM. Optionally, the region on the periorbital area is a region of the periorbital area of the right eye, and this step also involves taking, utilizing a second inward-facing head-mounted thermal camera (CAM2), thermal measurements of a region on the periorbital area of the lefteye ($TH_{ROI2}$).

In Step 2, detecting extents of stress based on $TH_{ROI1}$. Optionally, detecting the extents may be done utilizing the computer, as discussed above. Optionally, the extents are also detected based on $TH_{ROI1}$ (and/or other thermal measurements mentioned below).

In Step 3, receiving indications of times during which the user was exposed to potential stressors.

And in Step 4, selecting the stressor, from among the potential stressors, based on the indications and the extents. Optionally, during most of the time the user was affected by the stressor, an effect of the stressor, as manifested via changes to $TH_{ROI1}$, was higher than effects of most of the potential stressors.

In one embodiment, the method may optionally include a step of taking images of the surroundings of the user and generating at least some of the indications based on analysis of the images. Optionally, the images are taken with the camera 383, as discussed above.

In one embodiment, selecting the stressor is done by generating a machine learning-based model based on the indications and extents, and selecting the stressor based on an analysis of the model. In one example, performing the analysis of the model involves evaluating parameters of the model that correspond to the potential stressors. In this example, a certain potential stressor is selected as a stress. The certain potential stressor has a corresponding parameter in the model that is indicative of an effect that reaches a threshold, while effects indicated in parameters corresponding to most of the other potential stressors do not reach the threshold. In another example, performing the analysis of the model involves: (i) providing a predictor module with various inputs that correspond to different potential stressors that affect the user, (ii) calculating, based on the inputs and the model, various predicted stress levels; (iii) determining, based on the various predicted stress levels, effects of the potential stressors; and (iv) selecting the stressor based on the effects. In this example, the effect of the stressor reaches a threshold, while effects of most of the other potential stressors do not reach the threshold.

In one embodiment, a system configured to detect an irregular physiological response of a user while the user is exposed to sensitive data includes at least a head-mounted display (HMD), a CAM, and a computer. Optionally, CAM is coupled to the HMD (e.g., they are both components of an HMS). The HMD exposes sensitive data to a user who wears the HMD. For example, the HMD may display text, images, and/or video. Optionally, the HMD may be a virtual reality display or an augmented reality display. Optionally, the HMD is designed such that only the user who wears the HMD can view the sensitive data displayed on the HMD. CAM takes thermal measurements of an ROI ($TH_{ROI}$) on the user's face while the user is exposed to the sensitive data, and is optionally located less than 15 cm from the face. In some embodiments, the system may include additional CAMs that take thermal measurements of additional ROIs on the user's face. In some embodiments, CAM may weigh below 5 g and/or CAM may be located less than 5 cm from the user's face.

The computer detects, based on certain $TH_{ROI}$ taken while the user is exposed to certain sensitive data, whether the user experienced the irregular physiological response while being exposed to the certain sensitive data.

In one embodiment, the certain $TH_{ROI}$ are taken during a certain window of time that depends on the type of the irregular physiological response (e.g., a certain stress level and/or a certain emotional response). Optionally, the window is at least five seconds long, at least thirty seconds long, at least two minutes long, at least five minutes long, at least fifteen minutes long, at least one hour long, or is some other window that is longer than one second. Optionally, during the time the user is exposed to sensitive data, $TH_{ROI}$ from multiple windows may be evaluated (e.g., using a sliding window approach), which include a window that contains a period during which the certain $TH_{ROI}$ were taken.

In some embodiments, detecting the irregular physiological response is done based on additional inputs such as thermal measurements taken by additional CAMs (which may cover additional ROIs), and/or values of physiological signals and/or behavioral cues of the user such as heart rate, breathing rate, galvanic skin response, movements, facial expressions, and/or brainwave activity. Optionally, the values of physiological signals and/or behavioral cues are obtained utilizing sensors other than CAMs.

What corresponds to an "irregular physiological response" may vary between different embodiments. The following are some examples of criteria and/or ways of determining whether a physiological response is considered an "irregular physiological response". In one example, the irregular physiological response involves the user experiencing stress that reaches a certain threshold. Optionally, for most of the time the user wears the HMD, the stress level detected for the user does not reach the certain threshold. In another example, the irregular physiological response involves the user experiencing at least a certain level of one or more of the following emotions: anxiety, fear, and anger. Optionally, for most of the time the user wears the HMD, the extent to which the user experiences the one or more emotions does not reach the certain level. In yet another example, an irregular physiological response corresponds to atypical measurement values. For example, if a probability density function is generated based on previously taken $TH_{ROI1}$ of the user, values with a low probability, such as a probability value that is lower than the probability of 97% of the previously taken $TH_{ROI}$, may be considered atypical.

In order to detect the irregular physiological response, the computer may utilize $TH_{ROI}$ in various ways, as described below. Optionally, detection of the irregular physiological response is done while taking into account various factors that may influence the user's measured physiological responses, such as the user's emotional state (e.g., whether the user is anxious, distraught, or calm), the environmental conditions (e.g., the temperature, humidity level, and/or level of oxygen in the air), and/or the type of sensitive data that the user accesses.

In one embodiment, the computer compares one or more values derived from the certain $TH_{ROI}$ to a certain threshold, and determines whether the threshold is reached (which is indicative of an occurrence of the irregular physiological response). Optionally, the threshold is determined based on previously taken $TH_{ROI}$ of the user (e.g., taken when the user had an irregular physiological response). Optionally, the threshold is determined based on baseline thermal measurements of the user, and the threshold represents a difference of a certain magnitude relative to the baseline measurements. Optionally, different thresholds may be utilized to detect different types of irregular physiological responses, to detect irregular physiological responses to different types of sensitive data, and/or to detect irregular physiological responses when the user is in certain emotional states and/or under certain environmental conditions.

In another embodiment, the computer generates feature values and utilizes a machine learning-based model to detect, based on the feature values, whether the user had an irregular physiological response. One or more of the feature values are generated based on the certain $TH_{ROI}$. Optionally, at least one of the feature values is generated based on the sensitive data, e.g., the at least one of the feature values may describe properties of the sensitive data. In one example, the model may be generated based on previous $TH_{ROI}$ of the user. In another example, the model may be generated based on previous $TH_{ROI}$ of other users.

The emotional state of the user, while accessing the certain sensitive data, may influence the user's physiological response, and thus may play a role in determining whether the user had an irregular physiological response. Similarly, the environmental conditions that prevail when the user accesses the certain sensitive data, and also the type of sensitive data being accessed, may influence the user's physiological response and thus may have a bearing on whether the user's physiological response should be considered irregular or not. Addressing these factors may be done in different ways.

In one embodiment, multiple machine learning-based models may be generated utilizing different training sets of data. For example, different models may be created to detect different types of irregular physiological responses, to detect irregular physiological responses to different types of sensitive data, and/or to detect irregular physiological responses when the user is in a certain emotional state and/or under certain environmental conditions.

In another embodiment, the feature values generated by the computer may include feature values that describe one or more of the following factors: an emotional state of the user while accessing the certain sensitive data, a condition of the environment in which the user accessed the certain sensitive data, and the type of the certain sensitive data. Thus, the factors mentioned above may be considered when the determination is made regarding whether the user experienced an irregular physiological response. In one example, the computer receives values indicative of the user's emotional state while being exposed to the certain sensitive data, and utilizes a machine learning-based model to detect whether the user experienced the irregular physiological response based on the certain $TH_{ROI}$. Optionally, in this example, the machine learning-based model was trained based on previous $TH_{ROI}$ taken while the user was in a similar emotional state. In another example, the computer is receives values indicative of the environment the user was in while being exposed to the certain sensitive data (e.g., temperature and/or humidity level), and utilizes a machine learning-based model to detect whether the user experienced the irregular physiological response based on the certain $TH_{ROI}$. Optionally, in this example, the machine learning-based model was trained based on previous $TH_{ROI}$ taken while the user was in a similar environment.

Determining what constitutes a certain type of sensitive data may be done according to various criteria. In one example, different types of sensitive data involve data with different classes of content (e.g., intelligence reports vs, billing statements). In another example, different types of sensitive data involve data with different levels of sensitivity (e.g., involve different levels of security clearance). In yet another example, different types of sensitive data come from different sources. In another example, different types of sensitive data involve different types of media (e.g., text information vs, video). In still another example, different types of sensitive data may correspond to the relationship of the sensitive data to the user (e.g., data that involves someone close to the user vs, data that involves a stranger).

The following describes how the system may utilize information about the type of sensitive data the user is exposed to in order to improve the detection of an irregular physiological response during exposure to that data. In one example, certain sensitive data is associated with a first type of sensitive data, and the computer detects the irregular physiological response when the certain $TH_{ROI}$ reach a first threshold. Optionally, the first threshold is calculated based on other $TH_{ROI}$ taken while the user was exposed to sensitive data associated with the first type of sensitive data. Additionally, the user is exposed to second certain sensitive data, which is associated with a second type of sensitive data. In this case, the computer detects the irregular physiological response when second certain $TH_{ROI}$ reach a second threshold. The second certain $TH_{ROI}$ are taken while the user is exposed to the second certain sensitive data, the second threshold is calculated based on other $TH_{ROI}$ taken while the user was exposed to sensitive data associated with the second type of sensitive data. In this example, the second threshold is different from the first threshold.

In one embodiment, the sensitive data is associated with a type of data that belongs to a set that includes at least first and second types of sensitive data. The computer utilizes $TH_{ROI}$ to generate feature values, and utilizes a model to calculate, based on the feature values, an extent of the irregular physiological response. Optionally, at least one of the feature values indicates the type of sensitive data to which the user was exposed. Optionally, the model was trained based on previous $TH_{ROI}$ of one or more users and indications of the type of sensitive data to which each of the one or more users was exposed. Optionally, the previous $TH_{ROI}$ comprise at least some measurements taken while the one or more users were exposed to the first type of sensitive data and at least some measurements taken while the one or more users were exposed to the second type of sensitive data.

Detecting the irregular physiological response may involve utilization of one or more baselines. Optionally, a baseline may be indicative of typical values for the user, such as typical thermal measurements when exposed to sensitive data, the extent to which a user is typically stressed when exposed to sensitive data, and/or the extent the user typically expresses one or more of the following emotions when exposed to sensitive data: anxiety, fear, and anger. Optionally, a baseline may correspond to the user, i.e., it may represent expected values of the user. Additionally or alternatively, a baseline may correspond to multiple users, and represent expected values of other users (e.g., a general response).

In some embodiments, a baseline may be determined based on previous thermal measurements. In one example, the previous thermal measurements comprise thermal measurements of the user. In another example, the previous thermal measurements comprise thermal measurements of other users. Optionally, the previous thermal measurements are taken while being exposed to baseline sensitive data. Optionally, the baseline sensitive data may be of the same type as the certain sensitive data. Optionally, the previous thermal measurements are taken with essentially the same system as the certain $TH_{ROI}$ (e.g., the same headset or a headset with a similar positioning of CAM).

In some embodiments, multiple baselines may be generated, corresponding to different types of sensitive data, different environmental conditions, and/or different emotional states of the user. Optionally, the multiple baselines are each generated based on corresponding thermal measurements, such as thermal measurements taken while the person being measured (e.g., the user or some other user) was exposed to a certain type of sensitive data, in a certain type of environment, and/or while in a certain emotional state.

In some cases, it may be useful to generate a baseline based on measurements taken in temporal proximity to when the user is exposed to the certain sensitive data. Comparing close events may be beneficial because the shorter the time between being exposed to baseline sensitive data and being exposed to the certain sensitive data, the smaller the effect of environmental changes and/or normal physiological changes may be. In one example, the user is exposed to the certain sensitive data immediately before and/or after being exposed to the baseline sensitive data. In another example, the user is exposed to the certain sensitive data within less than 5 minutes before and/or after being exposed to the baseline sensitive data. In still another example, the user exposed to the certain sensitive data within less than 15 minutes before or after being exposed to the baseline sensitive data.

In some embodiments, a baseline may be calculated utilizing a predictor, which receives input comprising feature values describing various values such as characteristics of user (e.g., age, gender, weight, occupation), the sensitive data, the environment in which the user is in, and/or the emotional state of the user. The predictor utilizes a machine learning-based model to calculate, based on the feature values, the baseline which may be, for example, a value of thermal measurements, a stress level, or an extent of expressing a certain emotion. Optionally, the model was trained based on measurements of the user. Optionally, the model was trained based on measurements of other users.

Baseline values may be utilized by the computer in various ways. For example, thermal measurements may be normalized with respect to a baseline in order to help identify when the thermal measurements deviate from the expected values (which may be indicative of the irregular physiological response). In another example, a threshold to which the computer compares the certain $TH_{ROI}$ may be a value that is defined relative to the baseline. In yet another example, a reference time series may be selected based on a corresponding baseline (i.e., a reference time series may correspond to an irregular physiological response that occurs when the user is in a certain baseline state). In still another example, one or more feature values utilized to detect a physiological response may be generated based on a baseline value (i.e., the baseline may be one of the inputs for detecting the physiological response).

In one embodiment, $TH_{ROI}$ express temperature at the ROI, and the baseline expresses ordinary temperature at the ROI while the user is exposed to sensitive data. In another embodiment, $TH_{ROI}$ express temperature change at the ROI, and the baseline expresses ordinary temperature changes at the ROI around the time of switching from being exposed to non-sensitive data to being exposed to sensitive data. In still another embodiment, $TH_{ROI}$ express temperature change at the ROI, and the baseline expresses ordinary temperature changes at the ROI around the time of switching from being exposed to sensitive data to being exposed to non-sensitive data.

It is noted that when the user is exposed to data over a period of time, in some embodiments, each segment of data (e.g., data watched during a certain span of a few minutes) may serve both as a baseline sensitive data and/or as the certain sensitive data.

In one embodiment, the certain sensitive data is associated with a first type of sensitive data, and the computer detects the irregular physiological response when a difference between the certain $TH_{ROI}$ and a first baseline reaches a first threshold. Optionally, the first baseline is calculated based on other $TH_{ROI}$ taken while the user was exposed to sensitive data associated with the first type of sensitive data. Additionally, the user is exposed to a second certain sensitive data that is associated with a second type of sensitive data, and the computer detects the irregular physiological response while being exposed to the second certain sensitive data when a difference between second certain $TH_{ROI}$ and a second baseline reaches a second threshold. Here, the second certain $TH_{ROI}$ are taken while the user is exposed to the second certain sensitive data, the second baseline is calculated based on other $TH_{ROI}$ taken while the user was exposed to sensitive data associated with the second type of sensitive data. In this embodiment, the second threshold is different from the first threshold. Optionally, the system estimates job burnout; the greater the differences between $TH_{ROI}$ and their associated baselines, the worse is the job burnout.

In different embodiments of the system configured to detect an irregular physiological response of a user while the user is exposed to sensitive data, the ROI may comprise different regions of the face and/or the system may involve various hardware configurations (e.g., certain types of CAMs and/or additional CAMs). Optionally, measurements taken by an additional CAM are utilized to generate one or more of the feature values utilized by the computer to detect the irregular physiological response.

In one embodiment, the ROI is on periorbital area of the user and CAM includes an uncooled thermal sensor. Optionally, the ROI is on the periorbital area of the right eye, and the system includes a second CAM that takes thermal measurements of a region on the penorbital area of the left eye. Optionally, the computer detects the irregular physiological response based on the measurements of the penorbital areas of the right and left eyes.

In another embodiment, the ROI is on the user's nose and CAM includes an uncooled thermal sensor. Optionally, the ROI is on the right side of the user's nose and the system includes a second CAM that takes thermal measurements of a region on the left side of the nose. Optionally, the computer detects the irregular physiological response based on the measurements of the regions on the left and right sides of the nose.

In yet another embodiment, the ROI is on the user's forehead. Optionally, the ROI is on the right side of the user's forehead, and the system includes a second CAM that takes thermal measurements of the left side of the user's forehead. Optionally, the computer detects the irregular physiological response based on the measurements of the regions on the left and right sides of the forehead.

Figure 64:
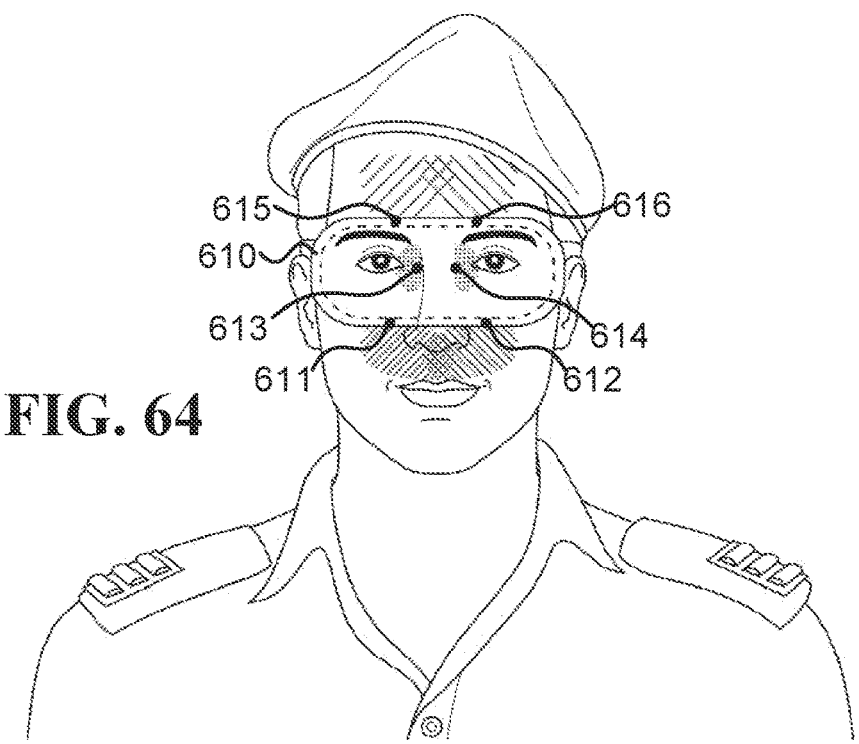
FIG. 64 illustrates an embodiment of a system that detects an irregular physiological response of a user while the user is exposed to sensitive data.

FIG. 64 illustrates one embodiment of a system configured to detect an irregular physiological response of a user while the user is exposed to sensitive data. The system includes head-mounted system HMS 610, which includes a head-mounted display (HMD) for exposing the user to sensitive data (not depicted in the figure) and six CAMs coupled to the frame of the HMS 610, which are 611 and 612 on the bottom of the frame to measure the upper lip and nose, 613 and 614 inside the HMS to measure the periorbital areas, and 615 and 616 on the top of the frame to measure the forehead (the measured regions on the face are illustrated as shaded areas). It is to be noted that though the user's eyes are visible in the figure, the front of the HMS may be opaque as is common with virtual reality headsets.

Figure 65:
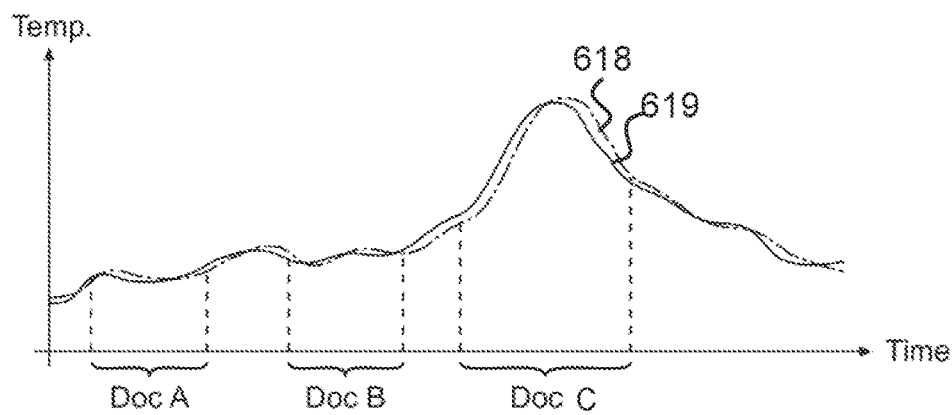
FIG. 65 illustrates detection of an irregular physiological response.

FIG. 65 illustrates detection of an irregular physiological response. The figure depicts a graph displaying temperatures at the right and left periorbital areas (lines 618 and 619 in the figure). The user is exposed to three documents via a HMD, "doc A", "doc B", and "doc C". With the first two documents ("doc A" and "doc B"), the temperatures remain low, but when the user is exposed to "doc C" the temperature rises dramatically, which in this exemplary figure may constitute an irregular physiological response.

In order to avoid detection of an irregular physiological response, a user exposed to sensitive data via the HMD may attempt to take evasive measures such as touching the face, moving the HMD, and/or occluding the sensors (e.g., in order to disrupt sensor measurements). An example of such behavior is illustrated in FIG. 67 in which the user moves the HMD a bit and touches a CAM, which triggers an alert.

In one embodiment, the system may detect whether the user moves the HMD relative to the face while being exposed to the certain sensitive data, based on measurements of an additional sensor (e.g., a sensor that measures a confounding factor). Optionally, the computer takes one or more security-related measures responsive to detecting that the user moved the HMD relative to the face while being exposed to the certain sensitive data. Optionally, the system identifies moving the HMD relative to the face based on one or more of the following: (i) analysis of images taken by an optical sensor physically coupled to the HMD, such as a CAM, an active near-IR camera physically coupled to the HMD, and/or a visible-light camera physically coupled to the HMD, (ii) analysis of images taken by an optical sensor that captures the user's face without being physically coupled to the HMD, such as a 2D or a 3D camera located in a position that faces the user or located on a smartwatch or a smart-shirt, and/or (iii) analysis of measurements of a non-optical sensor physically coupled to the HMD, such as a movement sensor, a miniature radar operating in the Extremely High Frequency (EHF) band, an acoustic sensor, an electroencephalogram sensor, an electromyogram sensor, a piezoelectric sensor, and/or strain gauges, as mentioned for example in the reference Li, Hao, et al. "Facial performance sensing head-mounted display" ACM Transactions on Graphics 2015, and (iv) analysis of measurements of a non-optical sensor physically coupled to the user's body, such as a movement sensor embedded in a wrist band or embedded in a smart-shirt.

It is noted that sentences such as "while being exposed to the certain sensitive data" does not include removing the HMD off the face, because after removing the HMD off the face the user is not exposed to the certain sensitive data. In one example, moving the HMD relative to the face refers to a relative movement above a minimum threshold (e.g., moving the frame to a distance that is greater than 1 cm). In another example, making facial expressions does not cause the system to detect that the user is moving the HMD relative to the face.

Some non-limiting examples of the security-related measures that the system may take include performing one or more of the following: storing in a database an indication that the user made a suspicious action (like moving the HMD relative to the face while being exposed to the certain sensitive data at a certain point in time), ceasing from exposing the user to the certain sensitive data, not allowing the user to perform a certain transaction related to the certain sensitive data, blocking the user's access to the certain sensitive data, issuing an alert, marking as suspicious the relationship between the user and the certain sensitive data, tightening the security restrictions for the user for accessing sensitive data on the system, providing the user a canary trap, and providing the user a barium meal test.

A "canary trap" refers to a practice of providing the user with a version of the sensitive data that contains certain indicators (e.g., small variations) that are unique to the version provided to the user. Thus, if the sensitive data is leaked, the user may be identified as the source based on detecting the small variations in the leaked data. A "barium meal test" refers to a practice of including in the sensitive data certain information; when the certain information reaches an entity it causes the entity to take a certain action (e.g., visit a certain website it would not ordinarily visit). Thus, detecting the certain action is indicative of the sensitive data (to which the user was exposed) being passed on to the entity.

In another embodiment, the system includes a sensor that provides measurements indicative of times at which the user touches the ROI. Optionally, touching the ROI is expected to influence $TH_{ROI}$ and/or disrupt the ability to detect the irregular physiological response. The user may touch the ROI using a finger, the palm, a tissue or a towel held by the user, a makeup-related item held by the user, a material that is expected to cool the ROI (such as a metal that is colder than the skin), and/or a material that is transparent in the visible spectrum (such as a transparent glass that is colder than the skin). Optionally, responsive to detecting that the user touched the ROI while being exposed to the certain sensitive data, the computer stores in a database an indication thereof, and/or the system may perform at least one of the aforementioned security-related measures.

In yet another embodiment, the system detects occlusion of CAM based on identifying a sudden change of more than 2° C., in $TH_{ROI}$ and/or utilizing a sensor that generates a signal indicative of whether a solid object is located between CAM and the ROI. Optionally, responsive to detecting that the user occluded CAM while being exposed to the certain sensitive data, the computer stores in a database an indication thereof and/or the system may perform at least one of the aforementioned security-related measures.

In one embodiment, the computer tightens security restrictions for the user responsive to detecting multiple occurrences possibly evasive measures such as touching the ROI, moving the HMD, and/or occluding the ROI. Optionally, the multiple occurrences are detected while the user is exposed to sensitive data that is of the same type as the certain sensitive data. Optionally, tightening security restrictions for the user involves restricting the user from performing a certain transaction related to the sensitive data. In one example, the certain transaction comprises copying, reading, and/or modifying the certain sensitive data. In another example, the certain sensitive data relates to money, and the certain transaction comprises an electronic funds transfer from one person or entity to another person or entity.

In some embodiments, responsive to a detection of the irregular physiological response, the system initiates a process to detect an illegal activity. Optionally, the process is initiated within less than two minutes after detecting the irregular physiological response. Optionally, the sensitive data belongs to an organization, the user is an employee of the organization, and the system helps in preventing illegal activities of employees related to sensitive data.

Some embodiments of the system configured to detect an irregular physiological response while being exposed to sensitive data include added security measures such as encryption of the sensitive data. Optionally, the system receives the certain sensitive data in an encrypted form, and the computer decrypts the certain sensitive data before presentation via the HMD. The decryption may involve hardware-based decryption, requesting a password from the user, and/or measuring the user with a sensor (e.g., an iris scan), and/or multi-factor authentication.

Another security measure that may be included in some embodiments of the system involves biometric identification of the user. In these embodiments, the system may include a biometric identification device, which is physically coupled to the HMD, and identifies the user while the user wears the HMD. Optionally, the computer exposes the user to the sensitive data responsive to receiving an indication that confirms the user's identity. Optionally, the biometric identification device performs one or more of the following operations: an iris scan, detection of brainwave patterns, detection of a cardiac activity pattern, and detection of thermal patterns on the user's face. Optionally, the biometric identification device performs a fingerprint-based identification of the user.

Figure 66:
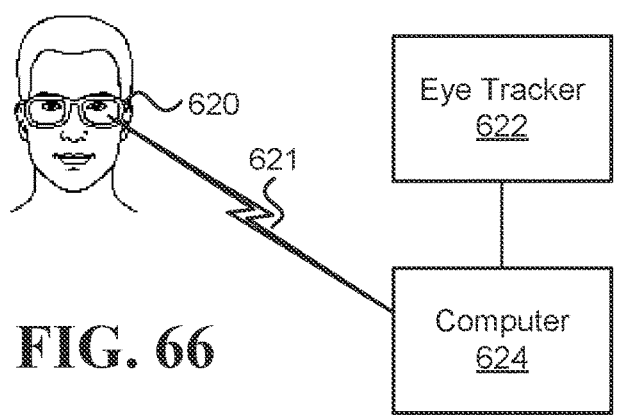
FIG. 66 is a schematic illustration of a system that includes a frame, CAM, a computer, and an eye tracker.

In one embodiment, a system that identifies whether a visual content (such as a video) includes an item that agitates a user includes an eye tracker, CAM, and a computer. The system may optionally include other components, such as a frame that is worn on the user's head (to which CAM, the eye tracker, and/or other components may be physically coupled). Additionally, the system may optionally include one or more additional CAMs and one or more sensors (which are not CAMs). The system may also include a head-mounted display (HMD) to display video to the user. FIG. 66 is a schematic illustration of such a system that includes frame 620 with CAM coupled to it, a computer 624, and an eye tracker 622.

CAM takes thermal measurements of an ROI ($TH_{ROI}$) on the user's face. Optionally, CAM is located less than 15 cm from the user's face. Optionally, CAM weighs less than 10 g. The ROI exhibits a change in temperature when the user experiences stress, such as the periorbital areas around the eyes, the nose, and/or the forehead.

In one embodiment, $TH_{ROI}$ are taken during a window of time that lasts between a second to a few minutes during which the user views a visual content that depicts items. Optionally, the window is at least five seconds long, at least thirty seconds long, at least two minutes long, at least five minutes long, at least fifteen minutes long, at least one hour long, or is some other window that is longer than one second. Optionally, during the time the user is exposed to the visual content, $TH_{ROI}$ from multiple windows may be evaluated (e.g., using a sliding window approach).

The eye tracker tracks the user's gaze while watching the video that depicts items. Optionally, the user's gaze is indicative of attention the user paid to the items. Optionally, data generated by the eye tracker is indicative of attention the user paid to each of the items. The eye tracker may be head-mounted or non-head-mounted.

The data generated by the eye tracker describes the gaze of the user. For example, the data may be indicative of the coordinates, on a display displaying the visual content (e.g., video), on which the user focused during various times while watching the video. Optionally, the coordinates represent certain pixels and/or sets of pixels. This information may be analyzed along with information that describes the boundaries (e.g., coordinates) of the items in the video at different times during its presentation in order to determine when the user focuses on each item. Optionally, determining which items were presented in the video may involve utilizing various image processing algorithms, which can identify items (e.g., objects and/or people) in the video and/or define the boundaries of the items in the video at various times. Thus, using the data generated by the eye tracker, attention levels of the user in at least some of the items can be determined (e.g., by the computer). In one example, an attention level of the user in an item is indicative of the amount of time the user spent focusing on the item (e.g., before moving to another item). In another example, the attention level of the user in an item is indicative of the number of times the user's sight was focused on the item during certain duration. In still another example, the attention level of the user is a relative value, which indicates whether the user paid more attention or less attention to the item compared to the other items in the video.

The computer is configured, in some embodiments, to detect, based on $TH_{ROI}$ taken while the user views the video, a stress level of the user. Additionally, the computer is configured to calculate an extent of discordance between the attention the user paid to the items and expected attention levels in the items. These two values (the stress level and extent of discordance) are utilized by the computer to determine whether at least one of the items agitated the user. In one embodiment, if the stress level reaches a first threshold and the extent of discordance reaches a second threshold, the computer makes a determination that at least one of the items in the video agitated the user. In another embodiment, the computer calculates, based on the stress level and the extent of discordance, a value indicative of a probability that the items include an item that agitates the user. Optionally, if the value indicates a probability above a third threshold, the computer makes a determination that at least one of the items in the video agitated the user.

The value indicative of the probability that the items include an item that agitates the user is, in some embodiments, proportional to a product of the stress level and the extent of the discordance. That is, in most scenarios, the larger one or both of these values (the stress level and the extent of the discordance), the larger probability that the items include an item that agitates the user. In one example, the value is indicative of negative feelings related to an item and/or a situation presented in the video (the larger the value the likelier it is that the user harbors such negative feelings). In another example, the value is indicative of an extent to which it is likely that the user is concealing something related to the content of the video.

In one embodiment, the computer may utilize the stress levels and the information of the user's gaze to select the item, from among the items depicted in the video, which agitates the user. Optionally, agitation due to the item may be manifested by an increase of at least a certain level in the stress of the user and/or by the user having an atypical gaze pattern in which the user pays significantly less attention or significantly more attention to the item than expected. In one example, "significantly more attention" refers to staring at the item at least double the expected time, and "significantly less attention" refers to staring at the item less than half the expected time.

The expected attention levels in the items may be based, in some embodiments, on tracking gazes during previous viewings of the video and/or previous viewings of similar videos in order to determine attention in the items. In one embodiment, the attention levels in the items are based on attention levels detected when the same video was viewed by other people. For example, the attention levels may represent the average attention paid by the other users to each item. In another embodiment, the attention levels in the items are based on attention levels of the user to items in similar videos. For example, if the video depicts a scene (e.g., a person filling out a loan application), then a similar video may include the same scene, possibly with slightly different items (e.g., a different person filling out a loan application).

In some embodiments, determining the expected attention levels in the items may involve utilizing a model. Optionally, the model is trained based on previous tracking of the user's gaze when observing other videos. Additionally or alternatively, the model is trained based on tracking of other users' gaze when observing other videos. Optionally, the model may be generated using one or more of the various attention modelling algorithms known in the art (such algorithms may also be referred to as saliency mapping algorithms). Some of the many algorithms that may be utilized are surveyed in A. Borji, L. Itti, "State-of-the-Art in Visual Attention Modeling", IEEE Transactions on Pattern Analysis & Machine Intelligence vol. 35(1), p. 185-207, 2013.

In one embodiment, a model for attention in visual items may be generated by creating a training set of samples. Where each sample corresponds to an item in a video and includes features values and a label describing the extent of attention in the item. Various feature values may be included in each sample. For example, some feature values may be generated using various image processing techniques and represent various low-level image properties. Some examples of such features may include features generated using Gabor filters, local binary patterns and their derivatives, features generated using algorithms such as SIFT, SURF, and/or ORB, and features generated using PCA or LDA. In another example, at least some feature values may include higher-level description of the items (e.g., after identification of the items and/or actions depicted in the video). In yet another example, some feature values may describe the user viewing the video (e.g., demographic information about the user and/or data related to the user's physiological state). A collection of samples, such as the ones described above, may be provided to a machine learning-based training algorithm in order to train the model. Some examples of the types of models that may be generated include support vector machines (SVMs) and neural networks.

Obtaining the expected attention levels may be done in various ways. In one embodiment, values of the attention levels are determined based on tracking the gaze of the user (and/or other users) in previous viewing the video and/or similar videos, the attention levels determined in this tracking may be used as the expected attention levels in the items displayed in the video while $TH_{ROI}$ are taken. In another embodiment, feature values are generated based on the video and/or a description of the user, and the expected attention values are calculated based on the feature values utilizing a model for attention in visual items, as described above.

In one embodiment, the expected attention levels comprise values of attention in two or more of the items. Additionally, the attention the user paid to the two or more items is determined based on the gaze of the user. These two sets of values may be compared in order to calculate the extent of the discordance between the attention the user paid to the items and expected attention levels in the items. In one example, a divergence metric, such as the Kullback-Leibler divergence may be used to calculate the discordance between the two sets of values. In another example, a distance metric, such as a vector dot product may be used to calculate the discordance between the two sets of values.

In another embodiment, the expected attention levels comprise an indication of a subset comprising one or more of the items to which the user is expected to pay at least a certain amount of attention or one or more of the items to which the user is expected to pay at most a certain amount of attention. Additionally, a subset of the items to which the user paid at least the certain amount of attention (or at most the certain amount of attention), is determined based on the gaze of the user. In this embodiment, a comparison between the subset of items selected based on expected attention levels and the subset selected based on the gaze of the user may be done in order to calculate the extent of the discordance between the attention the user paid to the items and expected attention levels in the items. In one example, the extent of the discordance is proportional to the size of the symmetric difference between the two subsets.

In one embodiment, the stress level is calculated by comparing one or more values derived from $TH_{ROI}$ to a certain threshold, and determining whether the threshold is reached (which is indicative of an occurrence of at least a certain amount of stress). Optionally, the certain threshold is determined based on previous thermal measurements of the user taken with CAM. Optionally, most of the previous measurements were taken while the user was not under elevated stress. Alternatively, most of the previous measurements were taken while the user was under elevated stress. Optionally, the certain threshold is determined based on baseline thermal measurements of the user, and the certain threshold represents a difference of a certain magnitude relative to the baseline measurements. Optionally, different thresholds may be utilized to detect the stress level when the user is in a certain emotional state and/or is in an environment characterized by certain environmental conditions.

In another embodiment, the stress level is calculated by generating feature values based on $TH_{ROI}$ and utilizing a machine learning-based model to calculate, based on the feature values, a stress level experienced by the user. Optionally, at least some of the feature values are generated based on the video, e.g., the at least some of the feature values describe properties of the items depicted in the video. In one example, the model is trained based on pervious $TH_{ROI}$ taken while the user had at least two different stress levels according to a predetermined stress scale. In another example, the model is trained based on thermal measurements of other users (e.g., the model is a general model). Optionally, at least some of the feature values describe the emotional state of the user and/or environmental conditions corresponding to when $TH_{ROI}$ were taken. Optionally, at least some of the feature values are generated based on previous $TH_{ROI}$ taken before the user viewed the video (e.g., up to 15 minutes before); thus, when determining the extent of stress the user experienced, the computer can account for the user's baseline stress level.

In some embodiments, at least some feature values utilized to calculate the stress level may be based on thermal measurements obtained with other thermal cameras. In one embodiment, the ROI is on a periorbital area, and the system includes second and third CAMs configured to take thermal measurements of a region on the forehead ($TH_{ROI2}$) of the user and thermal measurements of a region on the nose ($TH_{ROI3}$) of the user, respectively. Optionally, the computer detects the stress level also based on $TH_{ROI2}$ and/or $TH_{ROI3}$. In one example, the computer generates feature values based on $TH_{ROI}$ and on $TH_{ROI2}$ and/or $TH_{ROI3}$, and utilizes a certain model to calculate, based on the feature values, the stress level of the user. In this example, the certain model is trained based on previous $TH_{ROI1}$ and $TH_{ROI2}$ and/or $TH_{ROI3}$ taken while the user had at least two different stress levels according to a predetermined stress scale.

There are various ways in which the computer may calculate, based on the stress level and the extent of discordance, a value indicative of a probability that the items include an item that agitates the user.

In one embodiment, the value indicative of the probability is calculated by comparing the stress level and the extent of discordance to corresponding thresholds. For example, when the stress level reaches at least a certain level and the discordance is at least a certain extent, that is indicative that there is at least a certain probability that that the items include an item that agitates the user. Optionally, calculating the probability involves utilizing a table that includes probability values for different combinations of thresholds (i.e., for different combinations of minimal stress levels and extents of discordance). Optionally, the table is generated based on observations of events in which the extent of stress of users was measured along with the extent of discordance based on their gaze, along with indications of whether the events involved a video that includes an item that agitated the viewer.

In another embodiment, the computer generates feature values based on the stress level and the extent of discordance and utilizes a machine learning-based model to calculate, based on the feature values, the probability that the items include an item that agitates the user. It is to be noted that this machine learning-based model is a different model than the one used in the embodiment described further above to detect the stress level. Optionally, the feature values include at least some features values indicative of the value of the stress level and/or the extent of discordance. Optionally, the feature values include at least one feature value indicative of a difference between the stress level and a baseline stress level of the user. Optionally, the feature values include at least one feature value that describes the video. For example, the at least one feature values may be indicative of what types of items are presented in the video. Optionally, the feature values include at least one feature value describing the user (e.g., the at least one feature value may be indicative of values such as the user's, the user's gender, the user's occupation, etc.) Optionally, the machine learning-based model is trained based on samples generated from previous events in which the extent of stress of users was measured along with the extent of discordance based on their gaze, along with indications of whether the events involved a video that includes an item that agitated the viewer.

When utilizing feature values along with a machine learning-based model, such as the model used to detect the stress level or the model used to calculate the value indicative of the probability that the items in the video include an item that agitates the user, in some embodiments, the feature values may include values based on additional inputs. In one example, the computer (i) receives one or more values indicative of at least one of the following parameters of the user heart rate, heart rate variability, galvanic skin response, respiratory rate, and respiratory rate variability, and (ii) generates one or more of the feature values based on the one or more values. In another example, the computer (i) receives one or more values measured by at least one of the following sensors coupled to the user: a photoplethysmogram (PPG) sensor, an electrocardiogram (ECG) sensor, an electroencephalography (EEG) sensor, a galvanic skin response (GSR) sensor, and a thermistor, and (ii) generates one or more of the feature values based on the one or more values. In yet another example, the computer (i) receives one or more values indicative of whether the user touched at least one of the eyes, whether the user is engaged in physical activity, and/or an environmental parameter, and (ii) generates one or more of the feature values based on the one or more values. In still another example, the computer (i) receives one or more values measured by an accelerometer, a pedometer, a humidity sensor, a miniature radar, a miniature active electro-optics distance measurement device, an anemometer, an acoustic sensor, and/or a light meter, and (ii) generates one or more of the feature values based on the one or more values. And in another example, the computer (i) receives values indicative of at least one of the following properties describing the user: age, gender, weight, height, health problems, mental health problems, occupation, education level, marital status, and (ii) generates one or more of the feature values based on the one or more values.

FIG. 68 illustrates a scenario in which an embodiment of a system described above is utilized to identify that a user is agitated (stressed) from viewing a video. In this scenario, a user is measured with CAMs coupled to a frame worn on the user's head while viewing an image of an accident scene. Eye tracking reveals that the user is avoiding a region that corresponds to the accident and the thermal measurements indicate an elevated stress level. Thus, the system may indicate that there is a high probability that the scene includes something that particularly agitates the user.

In one embodiment, a system configured to identify whether a visual content includes an item that agitates a user, includes: an eye tracker configured to track the user's gaze while watching a visual content depicting items; where the user's gaze is indicative of attention the user paid to the items; an inward-facing head-mounted thermal camera (CAM) configured to take thermal measurements of a region of interest on the face ($TH_{ROI}$) of the user, and a computer configured to: calculate stress levels based on $TH_{ROI}$, calculate an extent of discordance between the attention the user paid to the items and expected attention levels in the items, and determine, based on the stress level and the extent of discordance, whether at least one of the items agitated the user.

The following is a description of steps involved in one embodiment of a method for identifying when video includes an item that agitates a user. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform operations of the method. In one embodiment, the method includes at least the following steps:

In Step 1, tracking the user's gaze while the user watches a video depicting items. Optionally, the user's gaze is indicative of attention the user paid to the items. Optionally, tracking the user's gaze is performed by an eye tracker.

In Step 2, taking thermal measurements of a region of interest on the face ($TH_{ROI}$) of the user, while the user watches the video, with an inward-facing head-mounted thermal camera.

In Step 3, calculating stress levels based on $TH_{ROI}$.

In Step 4, calculating an extent of discordance between the attention the user paid to the items and expected attention levels in the items.

And in Step 5, calculating, based on the stress level and the extent of discordance, a value indicative of a probability that the items include an item that agitates the user.

In one embodiment, the method may optionally include a step involving calculating the expected attention levels in the items utilizing a model of the user. Optionally, the model used in this step was trained based on previous tracking of the user's gaze when observing other videos. Additionally or alternatively, calculating the expected attention levels in the items using a saliency mapping algorithm.

In another embodiment, the method may optionally include a step involving calculating, based on $TH_{ROI}$, stress levels corresponding to different times, and utilizing tracking of the user's gaze to assign stress levels to different items.

In yet another embodiment, the method may optionally include a step involving identifying that an item from among the items is a suspicious item based on the stress level reaching a first threshold and a difference between the attention the user paid to the item and the expected attention to the item reaching a second threshold.

Some aspects of this disclosure involve monitoring a user while performing his or her job in order to create a model of the user's typical behavior. This monitoring may involve determining the typical stress levels of the user and gaze patterns (e.g., what the user typically pays attention too when performing the usual activities on the job). When the user exhibits atypical behavior while performing a job, it may be an indication that something illicit and/or illegal is being performed. For example, a bank loan officer knowingly approving a faulty loan may exhibit higher stress levels while evaluating the loan forms and may also have a significantly different gaze pattern compared to when working on a usual loan application. In another example, a doctor examining a patient in order to assist in a faulty insurance claim may also be more stressed and/or have a different gaze pattern. In yet another example, a customs official "looking the other way" when an accomplice smuggles contraband is also expected to have elevated stress levels and a different gaze pattern than ordinarily observed on the job. When atypical behavior is detected, it can be noted in order to have the event to which it corresponds inspected more thoroughly by other parties (e.g., a supervisor).

FIG. 69A and FIG. 69B illustrate a scenario in which stress levels and gaze patterns may be utilized do detect atypical user behavior. FIG. 69A illustrates a typical gaze pattern of the user shown as dashed-line closed-shapes on screen 631 (obtained using eye tracking), while the user performs his job at a computer terminal. Thermal measurements of the user 630 indicate that the user is not stressed. FIG. 69B illustrates an instance in which the user has an atypical gaze pattern shown as dashed-line closed-shapes on screen 633, and in addition, the thermal measurements of the user 632 indicate that the user is stressed. Embodiments of the system described below can identify the atypical gaze pattern and the user elevated stress level, and generate an indication that the user is behaving atypically.

In one embodiment, a system configured to identify atypical behavior of a user includes an eye tracker, a CAM, and a computer. CAM takes thermal measurements of a region of interest ($TH_{ROI}$) on the user's face. Optionally, CAM is located less than 15 cm from the face. Optionally, the ROI is on a periorbital area. Optionally, the system also includes a head-mounted display (HMD), which displays video to the user. The system may optionally include a frame which is worn on the user's head, and one or more of the following components are physically coupled to the frame: the HMD, CAM, the eye tracker, and the computer.

The eye tracker tracks the user's gaze while viewing items. Optionally, the user's gaze is indicative of attention of the user in the items. Optionally, the user's gaze is indicative of attention the user paid to each of the items. In one embodiment, the user's gaze is tracked while the user performs some work related task, such as performing office work (e.g., if the user is a clerk) or examining a patient (e.g., if the user is a doctor). Optionally, the user's gaze is tracked while the user views video related to the task the user is performing. In one example, the video is presented via the HMD, which may be a virtual reality display or an augmented reality display.

In some embodiments, the computer generates features values and utilizes a model to identify, based on the feature values, whether the user's behavior while viewing the items was atypical. Optionally, the feature values include feature values generated based on $TH_{ROI}$ taken while the user viewed the items and a set of feature values generated based on tracking the user's gaze. Optionally, the feature values generated based on the eye tracking are indicative of the attention of the user in the items. Optionally, the feature values may include at least some feature values indicative of expected attention levels in the items.

In one embodiment, the system configured to identify atypical behavior includes a second inward-facing head-mounted thermal camera that takes measurements of a second region on the face ($TH_{ROI2}$). Optionally, the computer generates one or more of the feature values used to detect the atypical behavior based on $TH_{ROI2}$. In one example, the second region is on the forehead. In another example, the second region is on the nose.

In another embodiment, the computer generates one or more of the feature values based on a difference between $TH_{ROI}$ and a baseline value determined based on a set of previous measurements taken by CAM. Optionally, most of the measurements belonging to the set were taken while the behavior of the user was not considered atypical according to the model.

In one embodiment, the model used to identify whether the user's behavior was atypical is generated based on previous tracking of the user's gaze while viewing other items and previous $TH_{ROI}$ taken during the viewing of the other items. Optionally, the user's behavior during most of the viewing of the other items was typical (i.e., it was not considered atypical). Optionally, the viewing of the previous items was done while the user was performing a similar activity to one performed by the user while $TH_{ROI}$ were taken. Optionally, the previous $TH_{ROI}$ were taken on different days. Optionally, the previous $TH_{ROI}$ were taken in different situations that include first $TH_{ROI}$ taken at most one hour before having a meal and second $TH_{ROI}$ taken at most one hour after having a meal. Optionally, the model is trained based on training samples, with each training sample corresponding to an event in which the user was monitored with the eye tracker and CAM, and each training sample comprising feature values generated based on a tracking of the user's gaze and $TH_{ROI}$ taken during the event.

In one embodiment, the model is indicative of a probability density function (pdf) of values derived from $TH_{ROI}$ and/or values derived from tracking the gaze of the user. For example, the model may be a regression model (e.g., a maximum entropy model) generated based on the training samples described above. Optionally, if the value calculated by the computer represents a probability that is below a threshold, the behavior of the user is considered atypical.

In another embodiment, the model describes one or more thresholds derived from $TH_{ROI}$ and/or values derived from tracking the gaze of the user. For example, the model may include typical ranges for $TH_{ROI}$, which are indicative of typical stress levels, and/or typical gaze patterns of the user, which are indicative of how much attention the user pays to different items. Optionally, if the user exhibits behavior that does not correspond to values in the ranges that appear in the model, that is indicative that the user's behavior while viewing the items was atypical.

The computer may calculate, based on $TH_{ROI}$ a value describing a stress level of the user. Additionally or alternatively, the computer may calculate an extent of discordance between the attention the user paid to the items and expected attention levels in the items. Optionally, the stress level and/or the extent of discordance are utilized by the computer to identify whether the user's behavior while viewing the items was atypical. For example, one or more of the feature values may be generated based on the stress level and/or one or more of the feature values may be generated based on the extent of the discordance.

In some embodiments, when the user's behavior while viewing the items was atypical, a stress level of the user during the viewing, which is calculated based on $TH_{ROI}$, reaches a threshold. The stress levels of the user during most of the time spent viewing the other items, as calculated based on the previous $TH_{ROI}$, do not reach the threshold. As discussed in more detail further above, there are various ways in which the computer may detect the stress level based on $TH_{ROI}$. In one embodiment, the stress level is calculated by comparing one or more values derived from $TH_{ROI}$ to a certain threshold, and determining whether the threshold is reached (which is indicative of an occurrence of at least a certain amount of stress). Optionally, the certain threshold is determined based on thermal measurements of the user (e.g., thermal measurements taken when the user was stressed). In another embodiment, the stress level is calculated by generating certain feature values based on $TH_{ROI}$ and utilizing a certain machine learning-based model to calculate, based on the certain feature values, the stress level experienced by the user.

In some embodiments, when the user's behavior while viewing the items was atypical, a divergence between the attention of the user in the items and expected attention of the user in the items is above a certain value. During most of the time spent viewing of the other items, divergences between the attention of the user in the other items and expected attention of the user in the other items were below the threshold. As discussed in more detail above, expected attention levels may be obtained in various ways. In one example, the expected attention levels in the other items are calculated utilizing a certain model of the user, which is trained based on previous tracking of the user's gaze. In another example, the expected attention levels in the other items are calculated utilizing a certain model that is trained based on tracking of other users' gaze. In yet another example, the expected attention levels in the other items are calculated using a saliency mapping algorithm.

When utilizing feature values along with a model, such as the certain model used to detect the stress level and/or the model used to identify whether the user's behavior was atypical, in some embodiments, the feature values may include values based on additional inputs (beyond $TH_{ROI}$), which are also utilized to detect the stress level. In one example, the computer (i) receives one or more values indicative of at least one of the following parameters of the user: heart rate, heart rate variability, galvanic skin response, respiratory rate, and respiratory rate variability, and (ii) generates one or more of the feature values based on the one or more values. In another example, the computer (i) receives one or more values measured by at least one of the following sensors coupled to the user a photoplethysmogram (PPG) sensor, an electrocardiogram (ECG) sensor, an electroencephalography (EEG) sensor, a galvanic skin response (GSR) sensor, and a thermistor, and (ii) generates one or more of the feature values based on the one or more values. In yet another example, the computer (i) receives one or more values indicative of whether the user touched at least one of the eyes, whether the user is engaged in physical activity, aid/or an environmental parameter, and (ii) generates one or more of the feature values based on the one or more values. In still another example, the computer (i) receives one or more values measured by an accelerometer, a pedometer, a humidity sensor, a miniature radar, a miniature active electro-optics distance measurement device, an anemometer, an acoustic sensor, and/or a light meter, and (ii) generates one or more of the feature values based on the one or more values. And in another example, the computer (i) receives values indicative of at least one of the following properties describing the user: age, gender, weight, height, health problems, mental health problems, occupation, education level, marital status, and (ii) generates one or more of the feature values based on the one or more values.

The following is a description of steps involved in one embodiment of a method for identifying atypical behavior. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform operations of the method. In one embodiment, the method includes at least the following steps:

In Step 1, tracking the user's gaze while the user views items. Optionally, the user's gaze is indicative of attention the user paid to the items. Optionally, tracking the user's gaze is performed by the eye tracker described above.

In Step 2, taking thermal measurements of a region of interest ($TH_{ROI}$) on the user's face, while the user views the items, with an inward-facing head-mounted thermal camera.

In Step 3, generating feature values. Optionally, the generated feature values include feature values generated based on $TH_{ROI}$ and feature values based on the tracking in Step 1.

And in Step 4, utilizing a model to identify, based on the feature values generated in Step 3, whether the user's behavior, while viewing the items, was atypical. Optionally, the model was trained based on previous tracking of the user's gaze while viewing other items and previous $TH_{ROI}$ taken during the viewing of the other items.

In one embodiment, the method may optionally involve a step of calculating expected attention of the user in the items and generating at least some of the feature values based on the expected attention of the user in the items. Optionally, the user's gaze is indicative of attention of the user in the items, and when the user's behavior while viewing the items is atypical, a divergence between the attention of the user in the items and the expected attention of the user in the items is above a certain value.

In one embodiment, the method may optionally include steps that involve: taking, using a second inward-facing head-mounted thermal camera, additional thermal measurements of a region on the forehead, and generating one or more of the feature values used in Step 4, based on the additional thermal measurements.

In another embodiment, the method may optionally include steps that involve: taking, using a second inward-facing head-mounted thermal camera, additional thermal measurements of a region on the nose, and generating one or more of the feature values used in Step 4, based on the additional thermal measurements.

Normally, the lens plane and the sensor plane of a camera are parallel, and the plane of focus (PoF) is parallel to the lens and sensor planes. If a planar object is also parallel to the sensor plane, it can coincide with the PoF, and the entire object can be captured sharply. If the lens plane is tilted (not parallel) relative to the sensor plane, it will be in focus along a line where it intersects the PoF. The Scheimpflug principle is a known geometric rule that describes the orientation of the plane of focus of a camera when the lens plane is tilted relative to the sensor plane.

Figure 35A:
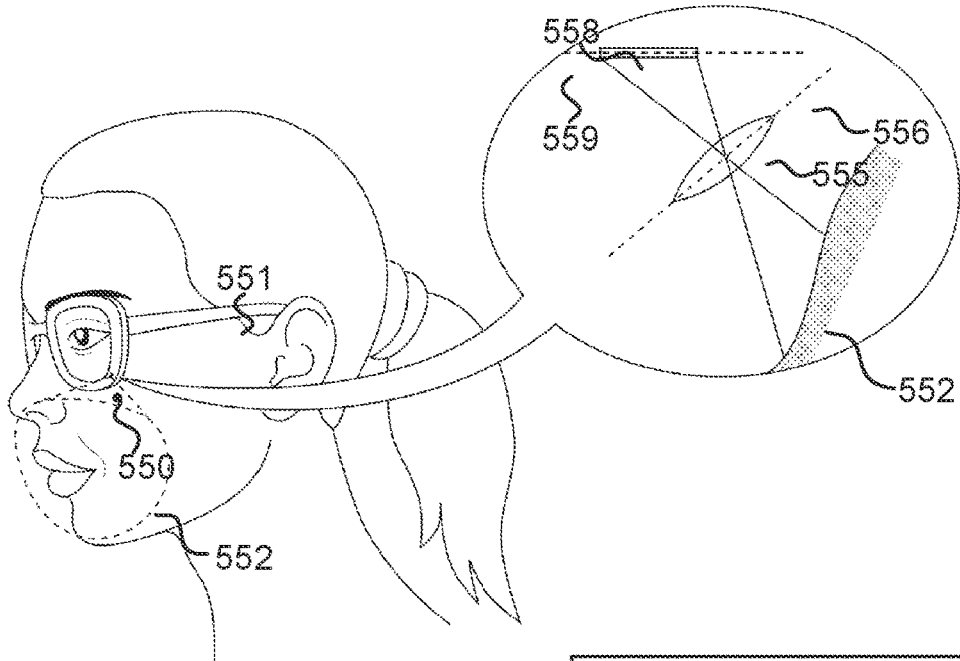
FIG. 35A is a schematic illustration of an inward-facing head-mounted camera embedded in an eyeglasses frame, which utilizes the Scheimpflug principle.

FIG. 35A is a schematic illustration of an inward-facing head-mounted camera 550 embedded in an eyeglasses frame 551, which utilizes the Scheimpflug principle to improve the sharpness of the image taken by the camera 550. The camera 550 includes a sensor 558 and a lens 555. The tilt of the lens 555 relative to sensor 558, which may also be considered as the angle between the lens plane 555 and the sensor plane 559, is determined according to the expected position of the camera 550 relative to the ROI 552 when the user wears the eyeglasses. For a refractive optical lens, the "lens plane" 556 refers to a plane that is perpendicular to the optical axis of the lens 555. Herein, the singular also includes the plural, and the term "lens" refers to one or more lenses. When "lens" refers to multiple lenses (which is usually the case in most modern cameras having a lens module with multiple lenses), then the "lens plane" refers to a plane that is perpendicular to the optical axis of the lens module.

Figure 35B:
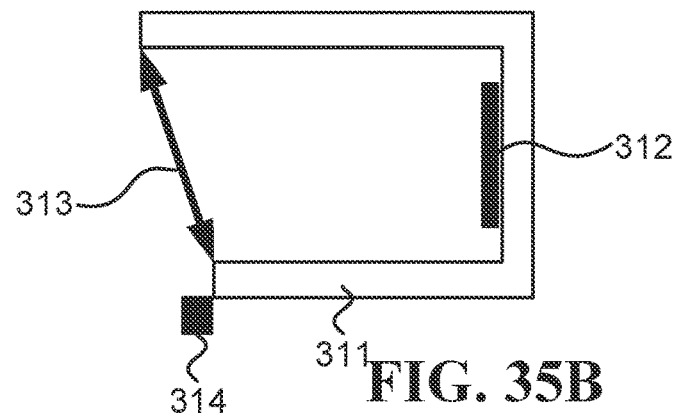
FIG. 35B is a schematic illustration of a camera that is able to change the relative tilt between its lens and sensor planes according to the Scheimpflug principle.

The Scheimpflug principle may be used for both thermal cameras (based on lenses and sensors for wavelengths longer than 2500 nm) and visible-light and/or near-IR cameras (based on lenses and sensors for wavelengths between 400-900 nm). FIG. 35B is a schematic illustration of a camera that is able to change the relative tilt between its lens and sensor planes according to the Scheimpflug principle. Housing 311 mounts a sensor 312 and lens 313. The lens 313 is tilted relative to the sensor 312. The tilt may be fixed according to the expected position of the camera relative to the ROI when the user wears the HMS, or may be adjusted using motor 314. The motor 314 may move the lens 313 and/or the sensor 312.

In one embodiment, an HMS device includes a frame configured to be worn on a user's head, and an inward-facing camera physically coupled to the frame. The inward-facing camera may assume one of two configurations: (i) the inward-facing camera is oriented such that the optical axis of the camera is above the Frankfort horizontal plane and pointed upward to capture an image of a region of interest (ROI) above the user's eyes, or (ii) the inward-facing camera is oriented such that the optical axis is below the Frankfort horizontal plane and pointed downward to capture an image of an ROI below the user's eyes. The inward-facing camera includes a sensor and a lens. The sensor plane is tilted by more than 2° relative to the lens plane according to the Scheimpflug principle in order to capture a sharper image.

In another embodiment, an HMS includes an inward-facing head-mounted camera that captures an image of an ROI on a user's face, when worn on the user's head. The ROI is on the user's forehead, nose, upper lip, cheek, and/or lips. The camera includes a sensor and a lens. And the sensor plane is tilted by more than 2° relative to the lens plane according to the Scheimpflug principle in order to capture a sharper image.

Because the face is not planar and the inward-facing head-mounted camera is located close to the face, an image captured by a camera having a wide field of view (FOV) and a low f-number may not be perfectly sharp, even after applying the Scheimpflug principle. Therefore, in some embodiments, the tilt between the lens plane and the sensor plane is selected such as to adjust the sharpness of the various areas covered in the ROI according to their importance for detecting the user's physiological response (which may be the user's emotional response in some cases). In one embodiment, the ROI covers first and second areas, where the first area includes finer details and/or is more important for detecting the physiological response than the second area. Therefore, the tilt between the lens and sensor planes is adjusted such that the image of the first area is shaper than the image of the second area.

In another embodiment, the ROI covers both a first area on the upper lip and a second area on a cheek, and the tilt is adjusted such that the image of the first area is shaper than the image of the second area, possibly because the upper lip usually provides more information and has more details relative to the cheek.

In still another embodiment, the ROI covers both a first area on the upper lip and a second area on the nose, and the tilt is adjusted such that the image of the first area is shaper than the image of the second area, possibly because the upper lip usually provides more information relative to the nose.

In still another embodiment, the ROI covers a first area on the cheek straight above the upper lip, a second area on the cheek from the edge of the upper lip towards the ear, and a third area on the nose. And the tilt between the lens plane and the sensor plane is adjusted such that the image of the first area is shaper than both the images of the second and third areas.

In still another embodiment, the ROI covers both a first area on the lips and a second area on the chin, and the tilt is adjusted such that the image of the first area is shaper than the image of the second area, possibly because the lips usually provides more information than the chin.

In still another embodiment, the camera is a visible-light camera, and the ROI covers both a first area on the lower forehead (including an eyebrow) and a second area on the upper forehead, and the tilt is adjusted such that the image of the first area is shaper than the image of the second area, possibly because the eyebrow provides more information about the user's emotional response than the upper forehead.

In still another embodiment, the camera is a thermal camera, and the ROI covers an area on the forehead, and the tilt is adjusted such that the image of a portion of the middle and upper part of the forehead (below the hair line) is shaper than the image of a portion of the lower part of the forehead, possibly because the middle and upper parts of the forehead are more indicative of prefrontal cortex activity than the lower part of the forehead, and movements of the eyebrows disturb the thermal measurements of the lower part of the forehead.

In one embodiment, the tilt between the lens plane and sensor plane is fixed. The fixed tilt is selected according to an expected orientation between the camera and the ROI when a user wears the frame. Having a fixed tilt between the lens and sensor planes may eliminate the need for an adjustable electromechanical tilting mechanism. As a result, a fixed tilt may reduce the weight and cost of the camera, while still providing a sharper image than an image that would be obtained from a similar camera in which the lens and sensor planes are parallel. The magnitude of the fixed tilt may be selected according to facial dimensions of an average user expected to wear the system, or according to a model of the specific user expected to wear the system in order to obtain the sharpest image.

In another embodiment, the system includes an adjustable electromechanical tilting mechanism configured to change the tilt between the lens and sensor planes according to the Scheimpflug principle based on the orientation between the camera and the ROI when the frame is worn by the user. The tilt may be achieved using at least one motor, such as a brushless DC motor, a stepper motor (without a feedback sensor), a brushed DC electric motor, a piezoelectric motor, and/or a micro-motion motor.

The adjustable electromechanical tilting mechanism configured to change the tilt between the lens and sensor planes may include one or more of the following mechanisms: (i) a mirror that changes its angle; (ii) a device that changes the angle of the lens relative to the sensor, and/or (iii) a device that changes the angle of the sensor relative to the lens. In one embodiment, the camera, including the adjustable electromechanical tilting mechanism, weighs less than 10 g, and the adjustable electromechanical tilting mechanism is able to change the tilt in a limited range below 30° between the two utmost orientations between the lens and sensor planes. Optionally, the adjustable electromechanical tilting mechanism is able to change the tilt in a limited range below 20° between the two utmost orientations between the lens and sensor planes. In another embodiment, the adjustable electromechanical tilting mechanism is able to change the tilt in a limited range below 10°. In some embodiments, being able to change the tilt in a limited range reduces at least one of the weight, cost, and size of the camera, which is advantageous for a wearable device. In one example, the camera is manufactured with a fixed predetermined tilt between the lens and sensor planes, which is in addition to the tilt provided by the adjustable electromechanical tilting mechanism. The fixed predetermined orientation may be determined according to the expected orientation between the camera and the ROI for an average user, such that the adjustable electromechanical tilting mechanism is used to fine-tune the tilt between the lens and sensor planes for the specific user who wears the frame and has facial dimensions that are different from the average user.

Various types of cameras may be utilized in different embodiments described herein. In one embodiment, the camera is a thermal camera that takes thermal measurements of the ROI with a focal plane array thermal sensor having an angle above 2° between the lens and sensor planes. Optionally, the thermal camera weighs below 10 g, is located less than 10 cm from the user's face, and the tilt of the lens plane relative to the sensor plane is fixed. The fixed tilt is selected according to an expected orientation between the camera and the ROI when the user wears the frame. Optionally, the system includes a computer to detect a physiological response based on the thermal measurements. Optionally, the computer processes time series measurements of each sensing element individually to detect the physiological response.

In another embodiment, the camera is a visible-light camera that takes visible-light images of the ROI, and a computer generates an avatar for the user based on the visible-light images. Some of the various approaches that may be utilized to generate the avatar based on the visible-light images are described in co-pending US patent publication 2016/0360970. Additionally or alternatively, the computer may detect an emotional response of the user based on (i) facial expressions in the visible-light images utilizing image processing, and/or (ii) facial skin color changes (FSCC), which result from concentration changes of hemoglobin and/or oxygenation.

It is to be noted that there are various approaches known in the art for identifying facial expressions from images. While many of these approaches were originally designed for full-face frontal images, those skilled in the art will recognize that algorithms designed for full-face frontal images may be easily adapted to be used with images obtained using the inward-facing head-mounted visible-light cameras disclosed herein. For example, the various machine learning techniques described in prior art references may be applied to feature values extracted from images that include portions of the face from orientations that are not directly in front of the user. Furthermore, due to the closeness of the visible-light cameras to the face, facial features are typically larger in images obtained by the systems described herein. Moreover, challenges such as image registration and face tracking are vastly simplified and possibly non-existent when using inward-facing head-mounted cameras. The reference Zeng, Zhihong, et al. "A survey of affect recognition methods: Audio, visual, and spontaneous expressions." IEEE transactions on pattern analysis and machine intelligence 31.1 (2009): 39-58, describes some of the algorithmic approaches that may be used for this task. The following references discuss detection of emotional responses based on FSCC: (i) Ramirez, Geovany A., et al. "Color analysis of facial skin: Detection of emotional state" in Proceedings of the IEEE Conference on Computer Vision and Pattern Recognition Workshops, 2014; and (ii) Wang, Su-Jing, et al. "Micro-expression recognition using color spaces", in IEEE Transactions on Image Processing 24.12 (2015): 6034-6047.

In still another embodiment, the camera is a light field camera that implements a predetermined blurring at a certain Scheimpflug angle, and decodes the predetermined blurring as function of the certain Scheimpflug angle. The light field camera may include an autofocusing of the image obtained using the tilting mechanism based on the principle that scene points that are not in focus are blurred while scene points in focus are sharp. The autofocusing may study a small region around a given pixel; the region is expected to get sharper as the Scheimpflug adjustment gets better, and vice versa. Additionally or alternatively, the autofocusing may use the variance of the neighborhood around each pixel as a measure of sharpness, where a proper Scheimpflug adjustment should increase the variance.

FIG. 70A and FIG. 70B are schematic illustrations of possible embodiments for computers (400, 410) that are able to realize one or more of the embodiments discussed herein that include a "computer". The computer (400, 410) may be implemented in various ways, such as, but not limited to, a microcontroller, a computer on a chip, a system-on-chip (SoC), a system-on-module (SoM), a processor with its required peripherals, a server computer, a client computer, a personal computer, a cloud computer, a network device, a handheld device (e.g., a smartphone), an head-mounted system (such as smartglasses, an augmented reality system, a virtual reality system, and/or a smart-helmet), a computing device embedded in a wearable device (e.g., a smartwatch or a computer embedded in clothing), a computing device implanted in the human body, and/or any other computer form capable of executing a set of computer instructions. Further, references to a computer or a processor include any collection of one or more computers and/or processors (which may be at different locations) that individually or jointly execute one or more sets of computer instructions. This means that the singular term "computer" is intended to imply one or more computers, which jointly perform the functions attributed to "the computer". In particular, some functions attributed to the computer may be performed by a computer on a wearable device (e.g., smartglasses) and/or a computer of the user (e.g., smartphone), while other functions may be performed on a remote computer, such as a cloud-based server.

The computer 400 includes one or more of the following components: processor 401, memory 402, computer readable medium 403, user interface 404, communication interface 405, and bus 406. The computer 410 includes one or more of the following components: processor 411, memory 412, and communication interface 413.

Thermal measurements that are forwarded to a processor/computer may include "raw" values that are essentially the same as the values measured by thermal cameras, and/or processed values that are the result of applying some form of preprocessing and/or analysis to the raw values. Examples of methods that may be used to process the raw values include analog signal processing, digital signal processing, and various forms of normalization, noise cancellation, and/or feature extraction.

Functionality of various embodiments may be implemented in hardware, software, firmware, or an combination thereof. If implemented at least in part in software, implementing the functionality may involve a computer program that includes one or more instructions or code stored or transmitted on a computer-readable medium and executed by one or more processors. Computer-readable media may include computer-readable storage media, which corresponds to a tangible medium such as data storage media, or communication media including any medium that facilitates transfer of a computer program from one place to another. Computer-readable medium may be any media that can be accessed by one or more computers to retrieve instructions, code, data, and/or data structures for implementation of the described embodiments. A computer program product may include a computer-readable medium. In one example, the computer-readable medium 403 may include one or more of the following: RAM, ROM, EEPROM, optical storage, magnetic storage, biologic storage, flash memory, or any other medium that can store computer readable data.

A computer program (also known as a program, software, software application, script, program code, or code) can be written in any form of programming language, including compiled or interpreted languages, declarative or procedural languages. The program can be deployed in any form, including as a standalone program or as a module, component, subroutine, object, or another unit suitable for use in a computing environment A computer program may correspond to a file in a file system, may be stored in a portion of a file that holds other programs or data, and/or may be stored in one or more files that may be dedicated to the program. A computer program may be deployed to be executed on one or more computers that are located at one or more sites that may be interconnected by a communication network.

Computer-readable medium may include a single medium and/or multiple media (e.g., a centralized or distributed database, and/or associated caches and servers) that store one or more sets of instructions. In various embodiments, a computer program, and/or portions of a computer program, may be stored on a non-transitory computer-readable medium, and may be updated and/or downloaded via a communication network, such as the Internet. Optionally, the computer program may be downloaded from a central repository, such as Apple App Store and/or Google Play.

Optionally, the computer program may be downloaded from a repository, such as an open source and/or community run repository (e.g., GitHub).

At least some of the methods described herein are "computer-implemented methods" that are implemented on a computer, such as the computer (400, 410), by executing instructions on the processor (401, 411). Additionally, at least some of these instructions may be stored on a non-transitory computer-readable medium.

Herein, a direction of the optical axis of a VCAM or a CAM that has focusing optics is determined by the focusing optics, while the direction of the optical axis of a CAM without focusing optics (such as a single pixel thermopile) is determined by the angle of maximum responsivity of its sensor. When optics are utilized to take measurements with a CAM, then the term CAM includes the optics (e.g., one or more lenses). In some embodiments, the optics of a CAM may include one or more lenses made of a material suitable for the required wavelength, such as one or more of the following materials: Calcium Fluoride, Gallium Arsenide, Germanium, Potassium Bromide, Sapphire, Silicon, Sodium Chloride, and Zinc Sulfide. In other embodiments, the CAM optics may include one or more diffractive optical elements, and/or or a combination of one or more diffractive optical elements and one or more refractive optical elements.

When CAM includes an optical limiter/field limiter/FOV limiter (such as a thermopile sensor inside a standard TO-39 package with a window, or a thermopile sensor with a polished metal field limiter), then the term CAM may also refer to the optical limiter. Depending on the context, the term CAM may also refer to a readout circuit adjacent to CAM, and/or to the housing that holds CAM.

Herein, references to thermal measurements in the context of calculating values based on thermal measurements, generating feature values based on thermal measurements, or comparison of thermal measurements, relate to the values of the thermal measurements (which are values of temperature or values of temperature changes). Thus, a sentence in the form of "calculating based on $TH_{ROI1}$" may be interpreted as "calculating based on the values of $TH_{ROI1}$", and a sentence in the form of "comparing $TH_{ROI1}$ and $TH_{ROI2}$" may be interpreted as "comparing values of $TH_{ROI1}$ and values of $TH_{ROI2}$".

Depending on the embodiment, thermal measurements of an ROI (usually denoted $TH_{ROI}$ or using a similar notation) may have various forms, such as time series, measurements taken according to a varying sampling frequency, and/or measurements taken at irregular intervals. In some embodiments, thermal measurements may include various statistics of the temperature measurements (T) and/or the changes to temperature measurements ($\Delta T$), such as minimum, maximum, and/or average values. Thermal measurements may be raw and/or processed values. When a thermal camera has multiple sensing elements (pixels), the thermal measurements may include values corresponding to each of the pixels, and/or include values representing processing of the values of the pixels. The thermal measurements may be normalized, such as normalized with respect to a baseline (which is based on earlier thermal measurements), time of day, day in the month, type of activity being conducted by the user, and/or various environmental parameters (e.g., the environment's temperature, humidity, radiation level, etc.).

As used herein, references to "one embodiment" (and its variations) mean that the feature being referred to may be included in at least one embodiment of the invention. Moreover, separate references to "one embodiment", "some embodiments", "another embodiment", "still another embodiment", etc., may refer to the same embodiment, may illustrate different aspects of an embodiment, and/or may refer to different embodiments.

Some embodiments may be described using the verb "indicating", the adjective "indicative", and/or using variations thereof. Herein, sentences in the form of "X is indicative of Y" mean that X includes information correlated with Y, up to the case where X equals Y. For example, sentences in the form of "thermal measurements indicative of a physiological response" mean that the thermal measurements include information from which it is possible to infer the physiological response. Stating that "X indicates Y" or "X indicating Y" may be interpreted as "X being indicative of Y". Additionally, sentences in the form of "provide/receive an indication indicating whether X happened" may refer herein to any indication method, including but not limited to: sending/receiving a signal when X happened and not sending/receiving a signal when X did not happen, not sending/receiving a signal when X happened and sending/receiving a signal when X did not happen, and/or sending/receiving a first signal when X happened and sending/receiving a second signal X did not happen.

Herein, "most" of something is defined as above 51% of the something (including 100% of the something). Both a "portion" of something and a "region" of something refer herein to a value between a fraction of the something and 100% of the something. For example, sentences in the form of a "portion of an area" may cover between 0.1% and 100% of the area. As another example, sentences in the form of a "region on the user's forehead" may cover between the smallest area captured by a single pixel (such as 0.1% or 5% of the forehead) and 100% of the forehead. The word "region" refers to an open-ended claim language, and a camera said to capture a specific region on the face may capture just a small part of the specific region, the entire specific region, and/or a portion of the specific region together with additional region(s).

Sentences in the form of "angle greater than 20°" refer to absolute values (which may be +20° or −20° in this example), unless specifically indicated, such as in a phrase having the form of "the optical axis of CAM is 20° above/below the Frankfort horizontal plane" where it is clearly indicated that the CAM is pointed upwards/downwards. The Frankfort horizontal plane is created by two lines from the superior aspects of the right/left external auditory canal to the most inferior point of the right/left orbital rims.

The terms "comprises," "comprising," "includes." "including," "has," "having", or any other variation thereof, indicate an open-ended claim language that does not exclude additional limitations. The "a" or "an" is employed to describe one or more, and the singular also includes the plural unless it is obvious that it is meant otherwise; for example, sentences in the form of "a CAM configured to take thermal measurements of a region ($TH_{ROI}$)" refers to one or more CAMs that take thermal measurements of one or more regions, including one CAM that takes thermal measurements of multiple regions; as another example, "a computer" refers to one or more computers, such as a combination of a wearable computer that operates together with a cloud computer.

The phrase "based on" is intended to mean "based, at least in part, on". Additionally, stating that a value is calculated "based on X" and following that, in a certain embodiment, that the value is calculated "also based on Y", means that in the certain embodiment, the value is calculated based on X and Y.

The terms "first", "second" and so forth are to be interpreted merely as ordinal designations, and shall not be limited in themselves. A predetermined value is a fixed value and/or a value determined any time before performing a calculation that compares a certain value with the predetermined value. A value is also considered to be a predetermined value when the logic, used to determine whether a threshold that utilizes the value is reached, is known before start performing computations to determine whether the threshold is reached.

The embodiments of the invention may include any variety of combinations and/or integrations of the features of the embodiments described herein. Although some embodiments may depict serial operations, the embodiments may perform certain operations in parallel and/or in different orders from those depicted. Moreover, the use of repeated reference numerals and/or letters in the text and/or drawings is for the purpose of simplicity and clarity and does not in itself dictate a relationship between the various embodiments and/or configurations discussed. The embodiments are not limited in their applications to the order of steps of the methods, or to details of implementation of the devices, set in the description, drawings, or examples. Moreover, individual blocks illustrated in the figures may be functional in nature and therefore may not necessarily correspond to discrete hardware elements.

Certain features of the embodiments, which may have been, for clarity, described in the context of separate embodiments, may also be provided in various combinations in a single embodiment. Conversely, various features of the embodiments, which may have been, for brevity, described in the context of a single embodiment, may also be provided separately or in any suitable sub-combination. Embodiments described in conjunction with specific examples are presented by way of example, and not limitation. Moreover, it is evident that many alternatives, modifications, and variations will be apparent to those skilled in the art. It is to be understood that other embodiments may be utilized and structural changes may be made without departing from the scope of the embodiments. Accordingly, this disclosure is intended to embrace all such alternatives, modifications, and variations that fall within the spirit and scope of the appended claims and their equivalents.

We claim:

1. A system configured to grant passage through a doorway based on health state, comprising:
   a wearable device comprising: a first sensor configured to measure a signal indicative of a photoplethysmogram signal (PPG signal) of a user, and a second sensor configured to measure a temperature of the user, and
   a computer configured to:
   receive current measurements of the user, taken with the wearable device;
   receive baseline measurements of the user, taken with the wearable device on one or more earlier days;
   calculate a health score based on a difference between the baseline measurements and the current measurements;
   calculate an extent of similarity between characteristics of the PPG signal in the current measurements and characteristics of the PPG signal in the baseline measurements; and
   transmit an authorization signal responsive to the health score reaching a first threshold and the extent of the similarity reaching a second threshold; whereby transmission of the authorization signal indicates a health state of the user permits passage through the doorway.

2. The system of claim 1, further comprising a controller configured to command an automatic door to open and/or unlock, permitting the passage through the doorway, responsive to receiving the authorization signal; wherein the automatic door comprises a barrier that restricts the passage through the doorway when the automatic door is in a closed and/or locked position.

3. The system of claim 2, wherein the controller is further configured to command the automatic door to close and/or remain shut, thereby restricting the passage through the doorway, responsive to detecting that the user has passed through the doorway and/or not receiving an additional transmission of the authorization signal within a predetermined time.

4. The system of claim 2, wherein the automatic door belongs to a vehicle, and commanding the automatic door to open unlocks the door and/or moves the door to an open position, enabling the user to enter the cabin of the vehicle.

5. The system of claim 2, wherein the automatic door is an entrance door to a room and/or building, and commanding the automatic door to open unlocks the door and/or moves the door to an open position, enabling the user to enter the interior of the room and/or building.

6. The system of claim 2, wherein the automatic door is a gate comprising a turnstile or a revolving door, and commanding the automatic door to open enables the turnstile or the revolving door to revolve and/or revolving the turnstile or the revolving door, enabling the user to pass through the gate.

7. The system of claim 1, wherein the computer is further configured to transmit a second signal responsive to the health score not reaching the first threshold and/or the extent of the similarity not reaching the second threshold.

8. The system of claim 7, further comprising a controller configured to command an automatic door to close and/or remain shut, thereby restricting the passage through the doorway, responsive to receiving the second signal.

9. The system of claim 1, wherein the authorization signal does not include information identifying the user.

10. The system of claim 1, wherein the current measurements are taken over a duration of at least five minutes.

11. The system of claim 1, wherein calculation of the health score by the computer comprises: calculating, based on the baseline measurements, an expected value of a physiological signal of the user; calculating, based on the current measurements, a current value of the physiological signal; and calculating the health score based on a difference between the expected value and the current value.

12. The system of claim 11, wherein the physiological signal is body temperature, and the calculating of the health score utilizes a function that returns a value that is below the first threshold when a current body temperature is greater than an expected body temperature by at least a certain margin; and wherein the certain margin is at least 0.4° C.

13. The system of claim 11, wherein calculating the current value of the physiological signal comprises: generating feature values based on the current measurements, and utilizing a model to calculate, based on the feature values, the current value of the physiological signal; and wherein the model was generated from training data comprising: previous measurements of the user taken with the wearable device, and values of the physiological signal obtained utilizing a sensor that is not part of the wearable device.

14. The system of claim 11, further comprising a movement sensor, physically coupled to the wearable device, configured to measure a signal indicative of movements of the user; wherein calculating the current value of the physiological signal comprises: generating feature values based on the current measurements and the signal indicative of movements of the user, and utilizing a model to calculate the current value of the physiological signal; and wherein one or more of the feature values are indicative of an extent of movements of the user while the current measurements were taken.

15. The system of claim 1, wherein the computer is further configured to: determine, based on the measurements taken with the wearable device, whether the wearable device was removed from the user's body while the current measurements were taken or after the current measurements were taken, and responsive to making a determination that he wearable device has been removed, to refrain from transmitting the authorization signal.

16. The system of claim 15, wherein the computer is further configured to perform the following steps responsive to making the determination that the wearable device was removed:
receive additional measurements of the user, taken at most three hours after the current measurements were taken;
calculate an additional similarity between characteristics of the PPG signal in the current measurements and characteristics of the PPG signal in the additional measurements; and
transmit the authorization signal responsive to the health score reaching the first threshold and the additional similarity reaching the second threshold; whereby the additional similarity reaching the second threshold is indicative of a probability that the current measurements and the additional measurements are of the same person is above a predetermined threshold.

17. The system of claim 1, wherein the computer is further configured to:
receive additional measurements of the user;
calculate an additional extent of similarity between characteristics of the PPG signal in the additional measurements and characteristics of the PPG signal in the baseline measurements;
calculate an additional health score based on a difference between the baseline measurements and the additional measurements; and
responsive to the extent of similarity reaching the second threshold, report the additional health score to the user and/or providing the user with an indication of whether the health state of the user permits passage through the doorway.

18. The system of claim 1, wherein the computer is further configured to: generate feature values based on data comprising the current measurements and the baseline measurements, and utilize a model to calculate, based on the feature values, the health score; and wherein the model is generated based on training data comprising a first set of training measurements of a plurality of users taken while the plurality of users were healthy and a second set of training measurements of the plurality of users taken while the plurality of users were not healthy.

19. The system of claim 18, further comprising a temperature sensor configured to measure temperature of the environment ($T_{env}$); wherein the computer is further configured to generate one or more of the feature values based on first and second values of Ten measured while the baseline measurements and the current measurements were taken, respectively, and to utilize the one or more of the feature values to calculate the health score; whereby the one or more of the feature values are indicative of a change to $T_{env}$ between when the baseline measurements were taken and when the current measurements were taken.

20. The system of claim 1, wherein the first sensor is a video camera configured to capture images of a skin region on the user's head, and calculating the extent of similarity between the characteristics of the PPG signal in the current measurements and the characteristics of the PPG signal in the baseline measurements comprises calculating an extent of similarity between imaging photoplethysmography signals recognizable in images belonging to the current measurements and imaging photoplethysmography signals recognizable in images belonging to the baseline measurements.

* * * * *

UNITED STATES PATENT AND TRADEMARK OFFICE
CERTIFICATE OF CORRECTION

| | | |
|---|---|---|
| PATENT NO. | : 11,903,680 B2 | Page 1 of 1 |
| APPLICATION NO. | : 17/319634 | |
| DATED | : February 20, 2024 | |
| INVENTOR(S) | : Ari M Frank et al. | |

It is certified that error appears in the above-identified patent and that said Letters Patent is hereby corrected as shown below:

In the Claims

Claim 19, Column 188, Line 22, please delete "Ten" and insert --Tenv--, therefor.

Signed and Sealed this
Second Day of April, 2024

Katherine Kelly Vidal
*Director of the United States Patent and Trademark Office*